US 8,778,941 B2

(12) United States Patent
Brown et al.

(10) Patent No.: US 8,778,941 B2
(45) Date of Patent: Jul. 15, 2014

(54) TRPM8 ANTAGONISTS AND THEIR USE IN TREATMENTS

(75) Inventors: James Brown, Moorpark, CA (US);
Jian J. Chen, Camarillo, CA (US);
Vijay Keshav Gore, Irvine, CA (US);
Scott Harried, Pittsburgh, PA (US);
Daniel B. Horne, Simi Valley, CA (US);
Matthew R. Kaller, Ventura, CA (US);
Qingyian Liu, Camarillo, CA (US);
Holger Monenschein, Jupiter, FL (US);
Thomas T. Nguyen, Newbury Park, CA (US); Nobuko Nishimura, West Hills, CA (US); Wenge Zhong, Thousand Oaks, CA (US)

(73) Assignee: AMGEN Inc., Thousand Oaks, CA (US)

( * ) Notice: Subject to any disclaimer, the term of this patent is extended or adjusted under 35 U.S.C. 154(b) by 0 days.

(21) Appl. No.: 13/529,880

(22) Filed: Jun. 21, 2012

(65) Prior Publication Data
US 2013/0158034 A1    Jun. 20, 2013

Related U.S. Application Data

(60) Provisional application No. 61/500,835, filed on Jun. 24, 2011.

(51) Int. Cl.
*C07D 401/14* (2006.01)
*C07D 213/75* (2006.01)
*C07D 213/40* (2006.01)
*C07D 405/12* (2006.01)
*C07D 413/12* (2006.01)

(52) U.S. Cl.
USPC ...................................... 514/237.2

(58) Field of Classification Search
None
See application file for complete search history.

(56) References Cited

U.S. PATENT DOCUMENTS

| | | | |
|---|---|---|---|
| 2,483,250 A | 9/1949 | Suter | |
| 3,995,044 A | 11/1976 | Kabbe et al. | |
| 4,006,239 A | 2/1977 | Mayer et al. | |
| 5,081,131 A | 1/1992 | Tomcufcik et al. | |
| 5,223,499 A | 6/1993 | Greenlee et al. | |
| 5,296,495 A | 3/1994 | Matsuo et al. | |
| 5,344,813 A | 9/1994 | Theobald et al. | |
| 5,380,721 A | 1/1995 | Johnson et al. | |
| 5,395,840 A | 3/1995 | Miiller et al. | |
| 5,468,882 A | 11/1995 | Schohe-Loop et al. | |
| 5,698,554 A | 12/1997 | Ishida et al. | |
| 5,728,699 A | 3/1998 | Toriyabe et al. | |
| 5,817,677 A | 10/1998 | Linz et al. | |
| 5,891,872 A | 4/1999 | Doll et al. | |
| 5,892,030 A | 4/1999 | Alig | |
| 5,910,595 A | 6/1999 | Durrwachter | |
| 5,916,906 A | 6/1999 | Shaskan | |
| 5,977,090 A | 11/1999 | Slusher et al. | |
| 6,075,029 A | 6/2000 | Klein et al. | |
| 6,200,993 B1 | 3/2001 | Cote et al. | |
| 6,268,384 B1 | 7/2001 | Novak et al. | |
| 6,302,921 B1 | 10/2001 | Delroisse et al. | |
| 6,329,405 B1 | 12/2001 | Kurata et al. | |
| 6,369,227 B1 | 4/2002 | Lam et al. | |
| 6,413,979 B1 | 7/2002 | Hayama et al. | |
| 6,448,281 B1 | 9/2002 | Beaulieu et al. | |
| 6,451,752 B1 | 9/2002 | Delroisse et al. | |
| 6,555,561 B2 | 4/2003 | Bloom et al. | |
| 6,617,351 B1 | 9/2003 | Arnold et al. | |
| 6,630,495 B1 | 10/2003 | Cooke et al. | |
| 6,630,509 B2 | 10/2003 | Fagerhag et al. | |
| 6,696,467 B2 | 2/2004 | Mattei et al. | |
| 6,903,128 B2 | 6/2005 | Duplantier et al. | |
| 7,087,617 B2 | 8/2006 | Corbett et al. | |

(Continued)

FOREIGN PATENT DOCUMENTS

| | | |
|---|---|---|
| CA | 2135536 A1 | 5/1995 |
| CA | 2761639 A1 | 12/2010 |

(Continued)

OTHER PUBLICATIONS

Steffen G. et al. Trends in Active Pharmaceutical Ingredient Salt Selection based on Analysis of the Orange Book Database. J. Med Chem 2007, vol. 50, pp. 6665-6672.*
Patani et al. Bioisosterism: A Rational Approach in Drug Delivery. Chem. Rev. 1996, vol. 96, pp. 3147-3176.*
International Search Report for analogous PCT Application No. PCT/US2012/043569, mailed on Sep. 24, 2012.
International Search Report and Written Opinion for PCT Application No. PCT/US2012/043566, mailed on Feb. 18, 2013.
Albrecht, W. L. et al, "3-Substituted Imidazo[1,5-a]pyridines," *Journal of Heterocyclic Chemistry*, 16(7), pp. 1349-1351 (1979).
Bensel, N. et al, "BensenelStraightforward Synthesis of N-Protected Benzylic Amines by Carbamoalkylation of Aromatic Compounds," *Tetrahedron Letters*, 40, pp. 879-882 (1999).
Boyer, J. H. et al, "Diazotization of 2-Pyridylmethylamine," *Journal of Organic Chemistry*, 23, pp. 1053-1054 (1958).
Childers, W. E. et al., "Advances in the Development of Novel Analgesics," *Expert Opinion on Therapeutic Patents*, 18(8), pp. 1027-1067 (2008).

(Continued)

*Primary Examiner* — Leslie A. Royds Draper
*Assistant Examiner* — Taina D Matos Negron
(74) *Attorney, Agent, or Firm* — Bernard P. Friedrichsen

(57) ABSTRACT

Compounds of Formula I are useful as antagonists of TRPM8. Such compounds are useful in treating a number of TRPM8 mediated disorders and conditions and may be used to prepare medicaments and pharmaceutical compositions useful for treating such disorders and conditions. Examples of such disorders include, but are not limited to, migraines and neuropathic pain. Compounds of Formula I have the following structure:

where the definitions of the variables are provided herein.

33 Claims, No Drawings

(56) References Cited

U.S. PATENT DOCUMENTS

| | | |
|---|---|---|
| 7,091,371 B2 | 8/2006 | Ducray et al. |
| 7,179,823 B1 | 2/2007 | Momose et al. |
| 7,273,856 B2 | 9/2007 | Sisto et al. |
| 7,291,641 B2 | 11/2007 | Chabrier De Lassauniere et al. |
| 7,351,713 B2 | 4/2008 | Chan Chun Kong et al. |
| 7,375,093 B2 | 5/2008 | Tice et al. |
| 7,405,221 B2 | 7/2008 | Kopka et al. |
| 7,550,499 B2 | 6/2009 | Tuerdi et al. |
| 7,601,868 B2 | 10/2009 | Ishihara et al. |
| 7,618,959 B2 | 11/2009 | Axten et al. |
| 7,625,937 B2 | 12/2009 | Ali et al. |
| 7,834,023 B2 | 11/2010 | Scarborough et al. |
| 7,888,376 B2 | 2/2011 | Salvati et al. |
| 7,947,718 B2 | 5/2011 | Carruthers et al. |
| 7,964,204 B2 | 6/2011 | Lahm et al. |
| 7,968,542 B2 | 6/2011 | Miyaji et al. |
| 8,017,635 B2 | 9/2011 | Lyga et al. |
| 8,268,754 B2 | 9/2012 | Mita et al. |
| 2002/0019527 A1 | 2/2002 | Wang et al. |
| 2002/0042516 A1 | 4/2002 | Tom et al. |
| 2003/0050211 A1 | 3/2003 | Hage et al. |
| 2003/0195212 A1 | 10/2003 | Lundstedt et al. |
| 2005/0026991 A1 | 2/2005 | Cholody et al. |
| 2005/0038035 A1 | 2/2005 | Takasugi et al. |
| 2005/0159450 A1 | 7/2005 | Dargazanli et al. |
| 2006/0063775 A1 | 3/2006 | Pajouhesh et al. |
| 2006/0117994 A1 | 6/2006 | Ryu et al. |
| 2006/0173183 A1 | 8/2006 | Powers et al. |
| 2007/0066604 A1 | 3/2007 | Herold et al. |
| 2007/0155738 A1 | 7/2007 | Steeneck et al. |
| 2007/0185152 A1 | 8/2007 | Yamashita et al. |
| 2008/0045589 A1 | 2/2008 | Kelley |
| 2008/0051418 A1 | 2/2008 | Maekawa et al. |
| 2008/0146612 A1 | 6/2008 | Thompson et al. |
| 2008/0214552 A1 | 9/2008 | Fischer et al. |
| 2008/0293674 A1 | 11/2008 | Schwarz et al. |
| 2008/0293687 A1 | 11/2008 | Gibson et al. |
| 2008/0312278 A1 | 12/2008 | Schadt et al. |
| 2009/0069320 A1 | 3/2009 | Reich et al. |
| 2009/0082358 A1 | 3/2009 | Nishimura et al. |
| 2009/0239876 A1 | 9/2009 | Clements et al. |
| 2009/0286765 A1 | 11/2009 | Blackaby et al. |
| 2010/0063100 A1 | 3/2010 | Chen et al. |
| 2010/0125062 A1 | 5/2010 | Allen et al. |
| 2010/0179166 A1 | 7/2010 | Bell et al. |
| 2010/0261723 A1 | 10/2010 | Finlay |
| 2010/0261728 A1 | 10/2010 | Norman et al. |
| 2010/0292263 A1 | 11/2010 | Wood |
| 2011/0028507 A1 | 2/2011 | Kim et al. |
| 2011/0028509 A1 | 2/2011 | Crosignani et al. |
| 2011/0105532 A1 | 5/2011 | Heil et al. |
| 2011/0105549 A1 | 5/2011 | Wood et al. |
| 2011/0212969 A1 | 9/2011 | Blackburn et al. |
| 2011/0269761 A1 | 11/2011 | Langkopf et al. |
| 2011/0301193 A1 | 12/2011 | Errico et al. |
| 2012/0004198 A1 | 1/2012 | Liao et al. |

FOREIGN PATENT DOCUMENTS

| | | |
|---|---|---|
| CN | 1733708 | 2/2006 |
| CN | 101343313 | 6/2009 |
| EP | 0459730 A2 | 12/1991 |
| EP | 528172 A1 | 1/1993 |
| EP | 1099442 A2 | 5/2001 |
| EP | 1099701 A1 | 5/2001 |
| EP | 1500650 A1 | 1/2005 |
| EP | 2272841 A1 | 1/2011 |
| FR | 2692895 A1 | 6/1992 |
| JP | 53141271 A1 | 12/1978 |
| JP | 07285962 A1 | 10/1995 |
| JP | 2001354563 A1 | 12/2001 |
| JP | 2002302439 A1 | 10/2002 |
| JP | 2004115450 A1 | 4/2004 |
| JP | 2004175872 A1 | 6/2004 |
| JP | 2004203871 A1 | 7/2004 |
| JP | 2007091708 A1 | 8/2007 |
| WO | WO 9212973 | 1/1992 |
| WO | WO 9312796 A1 | 7/1993 |
| WO | WO 9701546 A1 | 1/1996 |
| WO | WO 9620173 A1 | 7/1996 |
| WO | WO 9710219 A1 | 3/1997 |
| WO | WO 9715567 A1 | 5/1997 |
| WO | WO 9722588 A1 | 6/1997 |
| WO | WO 9962486 A1 | 12/1999 |
| WO | WO 0035889 A1 | 6/2000 |
| WO | WO 0116271 A1 | 3/2001 |
| WO | WO 0158869 A2 | 8/2001 |
| WO | WO 0181316 A2 | 11/2001 |
| WO | WO 02051396 A1 | 7/2002 |
| WO | WO 02079189 A2 | 10/2002 |
| WO | WO 02088073 A1 | 11/2002 |
| WO | WO 03045385 A1 | 6/2003 |
| WO | WO 03051275 A2 | 6/2003 |
| WO | WO 03082278 A1 | 10/2003 |
| WO | WO 2004013100 A2 | 2/2004 |
| WO | WO 2004/026840 A1 | 4/2004 |
| WO | WO 2004039795 A2 | 5/2004 |
| WO | WO 2004058755 A2 | 7/2004 |
| WO | WO 2005005392 A1 | 1/2005 |
| WO | WO 2005007656 A1 | 1/2005 |
| WO | WO 2005021545 A1 | 3/2005 |
| WO | WO 2005023794 A2 | 3/2005 |
| WO | WO 2005/046683 | 5/2005 |
| WO | WO 2005042524 A1 | 5/2005 |
| WO | WO 2005080373 A1 | 9/2005 |
| WO | WO 2005080390 A1 | 9/2005 |
| WO | WO 2005113553 A2 | 12/2005 |
| WO | WO 2005115374 A1 | 12/2005 |
| WO | WO 2006002383 A2 | 1/2006 |
| WO | WO 2006068594 A1 | 6/2006 |
| WO | WO 2006094246 A2 | 9/2006 |
| WO | WO 2007002559 A1 | 1/2007 |
| WO | WO 2007/017093 A1 | 2/2007 |
| WO | WO 2007054215 A1 | 5/2007 |
| WO | WO 2007054302 A1 | 5/2007 |
| WO | WO 2007060028 A1 | 5/2007 |
| WO | WO 2007062314 A2 | 5/2007 |
| WO | WO 2007068381 A1 | 6/2007 |
| WO | WO 2007068383 A1 | 6/2007 |
| WO | WO 2007086799 A1 | 8/2007 |
| WO | WO 2007097470 A2 | 8/2007 |
| WO | WO 2007141504 A1 | 12/2007 |
| WO | WO 2008003746 A1 | 1/2008 |
| WO | WO 2008/022938 | 2/2008 |
| WO | WO 2008014602 A1 | 2/2008 |
| WO | WO 2008056687 A1 | 5/2008 |
| WO | WO 2008063667 A1 | 5/2008 |
| WO | WO 2008063670 A1 | 5/2008 |
| WO | WO 2008073825 A1 | 6/2008 |
| WO | WO 2008080015 A2 | 7/2008 |
| WO | WO 2008112156 A1 | 9/2008 |
| WO | WO 2009023179 A2 | 2/2009 |
| WO | WO 2009117269 A1 | 9/2009 |
| WO | WO 2009156089 A1 | 12/2009 |
| WO | WO 2010027236 A2 | 3/2010 |
| WO | WO 2010046780 A2 | 4/2010 |
| WO | WO 2010114471 A1 | 10/2010 |
| WO | WO 2010137351 A1 | 12/2010 |
| WO | WO 2010141330 A1 | 12/2010 |
| WO | WO 2011014649 A1 | 2/2011 |
| WO | WO 2011023703 A1 | 3/2011 |
| WO | WO 2011054436 A2 | 5/2011 |
| WO | WO 2011085126 A2 | 7/2011 |
| WO | WO 2011106632 A1 | 9/2011 |
| WO | WO 2011142359 A1 | 11/2011 |
| WO | WO 2011146300 A1 | 11/2011 |
| WO | WO 2011147765 A1 | 12/2011 |
| WO | WO 2012052540 A1 | 4/2012 |
| WO | WO 2012061698 A2 | 5/2012 |
| WO | WO 2012078855 A1 | 6/2012 |
| WO | WO 2012079624 A1 | 6/2012 |
| WO | WO 2012082862 A2 | 6/2012 |

(56) References Cited

FOREIGN PATENT DOCUMENTS

| WO | WO 2012083190 A1 | 6/2012 |
|---|---|---|
| WO | WO 2012118850 A1 | 9/2012 |
| WO | WO 2012120398 A1 | 9/2012 |

OTHER PUBLICATIONS

Chung, J.-U. et al, "α-Substituted N-(4-tert-Butylbenzyl)-N'-[4-(methylsulfonylamino)-benzyl]thiourea Analogues as Potent and StereospecificTRPV1 Antagonists," *Bioorganic & Medicinal Chemistry*, 15, pp. 6043-6053 (2007).

DeFalco, J. et al., "TRPM8 Biology and Medicinal Chemistry," *Current Topics in Medicinal Chemistry*, 11(17), pp. 2237-2252 (2011).

Dou, X.-Y. et al, "Rhodium-Catalyzed Arylation of α-Amido Sulfones with Arylboronic Acids in a Water-Toluene Biphasic System," *Inorganica Chimica Acta*, 369, pp. 284-287 (2011).

Gomtsyan, A. et al, "α-Methylation at Benzylic Fragment of N-Aryl-N'-benzyl Ureas provides TRPV1 antagonists with better pharmacokinetic properties and higher efficacy in inflammatory pain model," *Bioorganic & Medicinal Chemistry Letters*, 17, pp. 3894-3899 (2007).

Heymans, F. et al., "Quantitative Structure-Activity Relationships for N-[(N',N'-Disubstituted-amino)acetyl]arylamines for Local Anesthetic Activity and Acute Toxicity," *Journal of Medicinal Chemistry*, 23(2), pp. 184-193 (1980).

Hou, G. et al., "Iridium,-Monodentate Phophoramidite-Catalyzed Asymmetric Hydrogenation of Substituted Benzophenone N—H Imines," *Journal of the American Chemical Society*, 132(7) pp. 2124-2125 and S1-S52 (2010).

Kovtun, Y. P. et al, "Improved Method for the Preparation of 3-Aryl- and 3-Styrylimidazo[1,5-a]pyridines," *Chemistry of Heterocyclic Compounds* (New York) (Translation of Khimiya Geterotsiklicheskikh Soedinenii), 36(5), pp. 557-559 (2000).

Kraznov, V. A. et al., "Synthesis and Anticonvulsive Activity of Fluorine-Substituted Benzyhydrylamides," Pharmaceutical Chemistry Journal, 31(7), pp. 368-369 (1997).

Laurent, M. et al, "A Practical Synthesis of para Di- and Mono-Substituted Benzhydrylamines from Benzhydrol Precursors," *Synthesis*, 5, pp. 667-672 (2000).

Lespagnol, A. et al, "Amides with a papaverine structure." *Bulletin de la Societe Chimique de France*, (2), pp. 699-702, (1972).

Liu, Z. et al, "Catalytic Asymmetric Addition of Arylboronic acids to N-Boc Imines Generated in situ using C2-Symmetric Cationic N-Heterocyclic Carbenes (NHCs) Pd2b diaquo complexes," *Tetrahedron*, 66, pp. 2619-2623 (2010).

Maki, T. et al., "4,5,6,7-Tetrachlorobenzo[d][1,3,2]dioxaboro]-2-ol as an Effective Catalyst for the Amide Condensation of Sterically Demanding Carboxylic Acids," *Organic Letters*, 8(7), pp. 1431-1434 and S1-S29 (2006).

Metzger, F. et al. "Sulphonylurea Binding in Rat Isolated Glomeruli: Pharmacological Characterization and Dependence on Cell Metabolism and Cytoskeleton," *Nauyn-Schmiedberg's Archives of Pharmacology*, 355(2), pp. 141-149 (1997).

Muccioli, G.G. et al, "1-Benzhydryl-3-phenylurea and 1-Benzhydryl-3-phenylthiourea Derivatives: New Templates among the CB1 Cannabinoid Receptor Inverse Agonists," *Journal of Medicinal Chemistry*, 48, pp. 7486-7490 (2005).

Pacchiano, F. et al, "Ureido-Substituted Benzenesulfonamides Potently Inhibit Carbonic Anhydrase IX and Show Antimetastatic Activity in a Model of Breast Cancer Metastasis," *Journal of Medicinal Chemistry*, 54, pp. 1896-1902 (2011).

Raja, E. K. et al., "Superelectrophilic Chemistry of Amino-Nitriles and Related Substrates," *Tetrahedron*, 67(25), pp. 4494-4497 (2011).

Sasse, A. et al, "(Partial) Agonist/Antagonist Properties of Novel Diarylalkyl Carbamates on Histamine H3 Receptors," *Bioorganic & Medicinal Chemistry*, 8, pp. 1139-1149 (2000).

Trivedi, B.K. et al, "Inhibitors of Acyl-CoA:Cholesterol Acyltransferase. 4. A Novel Series of Urea ACAT Inhibitors as Potential Hypocholesterolemic Agents," *Journal of Medicinal Chemistry*, 36(22), pp. 3300-3307 (1993).

Weil, A, "Conservation of Functional and Pharmacological Properties in the Distantly Related Temperature Sensors TRPV1 and TRPM8," *Molecular Pharmacology*, 68(2), pp. 518-527 (2005).

Wrobleski, S.T. et al.,"Rational Design and Synthesis of an Orally Active Indolopyridone as a Novel Conformationally Constrained Cannabinoid Ligand Possessing Antiinflammatory Properties," *Journal of Medicinal Chemistry*, 46(11), pp. 2110-2116 (2003).

XP002690876, Database PubChem Compound [Online]"ACIM78XL-Compound Summary" Database Accession No. CID2437712 (Jul. 15, 2005) (Cited in International Search Report for PCT Application No. PCT/US2012/043566).

XP002690877, Database Registry [Online] Chemical Abstracts Service, Columbus, Ohio, US "6-Methoxy-N-[phenyl(pyridin-2-yl)methyl]quinoline-2-carboxamide," Database Accession No. 1241062-82-7 (Sep. 15, 2010) (Cited in International Search Report for PCT Application No. PCT/US2012/043566).

XP002691556, Database PubChem Compound [Online] "Zinc58157967-Compound Summary"Database Accession No. CID52501511 (May 20, 2011) (Cited in International Search Report for PCT Application No. PCT/US2012/043566).

XP002690878, Database Registry [Online] Chemical Abstracts Service, Columbus, Ohio, US "1,6-Dihydro-1-methyl-6-oxo-N-(phenyl-2-pyridinylmethyl)-3-pyridinecarboxamide," Database Accession No. 1280882-39-4 (Apr. 17, 2011) (Cited in International Search Report for PCT Application No. PCT/US2012/043566).

XP002690879, Database Registry [Online] Chemical Abstracts Service, Columbus, Ohio, US "2-Methyl-N-(phenyl-3-pyridinylmethyl)-1H-benzimidazole-6-carboxamide," Database Accession No. 1214549-94-6 (Mar. 25, 2010) (Cited in International Search Report for PCT Application No. PCT/US2012/043566).

U.S. Appl. No. 13/529,860, filed Jun. 21, 2012, Amgen Inc.

\* cited by examiner

TRPM8 ANTAGONISTS AND THEIR USE IN TREATMENTS

CROSS REFERENCES TO RELATED APPLICATIONS

This application claims the benefit of U.S. Provisional Application No. 61/500,835, filed on Jun. 24, 2011, which is hereby incorporated by reference in its entirety and for all purposes as if fully set forth herein.

FIELD OF THE INVENTION

The present invention relates to compounds that have TRPM8 antagonist properties and are useful in preparing medicaments and compositions and in treating diseases and conditions such as those mediated by TRPM8. The compounds and compositions may be used to treat various diseases or conditions modulated by TRPM8 such as, but not limited to, migraines and neuropathic pain.

BACKGROUND OF THE INVENTION

Cold sensation is derived from activation of the somatosensory system by a cold stimulus. Calcium imaging and patch clamp experiments in dissociated trigeminal and dorsal root ganglia neurons have revealed cold stimuli induced calcium influx, suggesting the direct opening of a calcium-permeable ion channels by cold (Thut et al., 2003; Reid, 2005). A recently cloned non-selective cation channel, TRPM8 (transient receptor potential melastatin 8) or trp-p8 (identified as a prostate-specific gene, up-regulated in prostate cancer and other malignancies, (Tsavaler et al., 2001)) is activated by cold stimulus of 10 to 24° C. temperature (McKemy et al., 2002; Peier et al., 2002). In addition, TRPM8 is also activated by compounds that elicit cool sensation such as menthol, icilin (AG-3-5) (McKemy et al., 2002), and the endogenous lipid $PIP_2$ (Rohacs et al., 2005). Correlating with the cold sensitivity of both A delta and C-fibers, TRPM8 is highly expressed in sensory neurons of the trigeminal and dorsal root ganglia (McKemy et al., 2002; Peier et al., 2002; Thut et al., 2003). TRPM8 is also expressed in nerve fibers innervating urinary bladder in guinea pigs (Tsukimi et al., 2005) and humans (Mukerji et al., 2006) and believed to contribute to the bladder hypersensitivity.

Activation mechanism of TRPM8 by menthol and icilin appears to differ. Icilin requires calcium for robust activation of TRPM8, whereas menthol and cold do not (Chuang et al., 2004). Typically, activation by all these agonists follows a period of calcium-dependent desensitization. The domain swap analysis of chicken and rat TRPM8 and further mutational studies revealed that determinants of icilin sensitivity map to a region of TRPM8 that corresponds to the capsaicin binding site in TRPV1 transmembrane domain 3 to 4 region (Chuang et al., 2004).

Cold allodynia and mechanical hyperalgesia are associated with neuropathic pain in humans and in rodent models of neuropathic and chemotherapy-induced pain. TRPM8 is shown to mediate the analgesia by agonists such as menthol and icilin (by desensitization of the receptor) during experimental neuropathic pain in rodents (Proudfoot et al., 2006). Further, attenuation of cold sensation and cold allodynia after chronic constriction injury model of neuropathic pain in TRPM8 knockout mice (Colburn et al., 2007; Dhaka et al., 2007) suggests that antagonists of TRPM8 may be considered as pain therapeutics for chemotherapy-induced pain, neuropathic pain and bladder disorders.

Mint oil that contains menthol, an agonist of TRPM8 has been reported to alleviate pain in post-herpetic neuralgia (Davies et al., 2002), a neuropathic pain condition. Furthermore, oral or intracerebroventricular injection of menthol decreased nociceptive responses to hot-plate test and acetic acid-induced writhing in mice (Galeotti et al., 2002). These responses are believed to be mediated by the activation and desensitization of the TRPM8. These observations and the knockout mice studies indicate that TRPM8 modulation by antagonists might be beneficial for patients experiencing neuropathic pain.

A need exists for TRPM8 antagonist compounds that can be used to treat diseases and conditions mediated by TRPM8 such as, but not limited to, migraines and neuropathic pain and those other conditions described herein.

SUMMARY OF THE INVENTION

The present invention comprises a new class of compounds useful in the treatment of diseases, such as TRPM8-mediated diseases and other maladies, such as inflammatory or neuropathic pain and diseases involving sensory nerve function such as asthma, rheumatoid arthritis, osteoarthritis, inflammatory bowel disorders, urinary incontinence, migraine and psoriasis. In particular, the compounds of the invention are useful for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, anxiety, depression, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders. Accordingly, the invention also comprises pharmaceutical compositions comprising the compounds, methods for the treatment of TRPM8-receptor-mediated diseases, such as inflammatory or neuropathic pain, asthma, rheumatoid arthritis, osteoarthritis, inflammatory bowel disorders, urinary incontinence, migraine and psoriasis diseases, using the compounds and compositions of the invention, and intermediates and processes useful for the preparation of the compounds of the invention.

The compounds of the invention are represented by the following general structure:

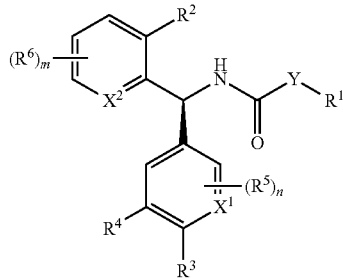

or a pharmaceutically acceptable salt thereof, wherein $R^1$, $R^2$, $R^3$, $R^4$, $R^5$, $R^6$, Y, $X^1$, $X^2$, m and n are defined below.

In one aspect, the invention provides a compound of Formula I having the structure:

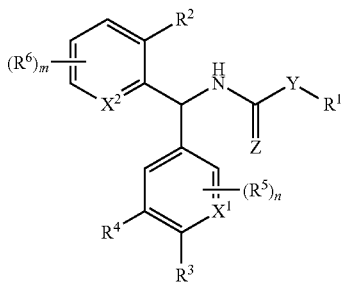

I or a pharmaceutically-acceptable salt thereof, a tautomer thereof, a pharmaceutically-acceptable salt of the tautomer, a stereoisomer thereof, or a mixture thereof, wherein:

m is 0, 1, 2 or 3;
n is 0 or 1;
$X^1$ is $C(R^4)$ or N;
$X^2$ is CH or N;
Y is NH, $NR^{1a}$, or O;
Z is O or S;
$R^1$ is $C_{1-6}$alk, —(C=O)—O—$C_{1-6}$alk, or a direct-bonded, $C_{1-6}$alk-linked, $C_{1-2}$alkO-linked, —C(=O)—O linked, —C(=O)— linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 heteroatoms selected from N, O and S, the $C_{1-6}$alk, the $C_{1-6}$alk of the $C_{1-6}$alk-link, and the monocyclic or bicyclic ring being substituted by 0, 1, 2 or 3 substituents independently selected from halo, oxo, $C_{1-6}$alk, $C_{1-6}$alkOH, $C_{1-6}$alk-C(=O)$R^a$, $C_{1-6}$alk-C(=O)O$R^a$, $C_{1-4}$haloalk, cyano, nitro, —C(=O)$R^a$, —C(=O)O$R^a$, —C(=O)$NR^aR^a$, —C(=$NR^a$)$NR^aR^a$, —O$R^a$, —OC(=O)$R^a$, —OC(=O)$NR^aR^a$, —OC(=O)N($R^a$)S(=O)$_2R^a$, —O$C_{2-6}$alk$NR^aR^a$, —O$C_{2-6}$alkO$R^a$, —S$R^a$, =S, —S(=O)$R^a$, —S(=O)$_2R^a$, —S(=O)$_2NR^aR^a$, —S(=O)$_2$N($R^a$)C(=O)$R^a$, —S(=O)$_2$N($R^a$)C(=O)O$R^a$, —S(=O)$_2$N($R^a$)C(=O)$NR^aR^a$, —$NR^aR^a$, —N($R^a$)C(=O)$R^a$, —N($R^a$)C(=O)O$R^a$, —N($R^a$)C(=O)$NR^aR^a$, —N($R^a$)C(=$NR^a$)$NR^aR^a$, —N($R^a$)S(=O)$_2R^a$, —N($R^a$)S(=O)$_2NR^aR^a$, —$NR^aC_{2-6}$alk$NR^aR^a$ and —$NR^aC_{1-6}$alkO$R^a$, wherein the ring is additionally substituted by 0 or 1 directly bonded, $SO_2$ linked, C(=O) linked or $CH_2$ linked saturated, partially-saturated or unsaturated 3-, 4-, 5-, 6- or 7-membered monocyclic ring containing 0, 1, 2, 3 or 4 heteroatoms selected from N, O and S, and substituted by 0, 1, 2 or 3 groups selected from halo, $C_{1-6}$alk, $C_{1-4}$haloalk, cyano, oxo, nitro, —C(=O)$R^a$, —C(=O)O$R^a$, —C(=O)$NR^aR^a$, —C(=$NR^a$)$NR^aR^a$, —O$R^a$, —OC(=O)$R^a$, —S$R^a$, —S(=O)$R^a$, —S(=O)$_2R^a$, —S(=O)$_2NR^aR^a$, —$NR^aR^a$, and —N($R^a$)C(=O)$R^a$; or $R^{1a}$ and $R^1$, together with the N atom to which they are attached, form a saturated, partially-saturated or unsaturated 4-, 5-, 6-, or 7-membered monocyclic or a 9- or 10-membered bicyclic ring containing 0, 1, or 2 additional heteroatoms independently selected from N, O, and S, wherein the ring formed by $R^{1a}$ and $R^1$ is substituted with 0, 1, or 2 substituents independently selected from halo, oxo, $C_{1-6}$alk, $C_{1-6}$alkOH, $C_{1-6}$alk-C(=O)$R^a$, $C_{1-6}$alk-C(=O)O$R^a$, $C_{1-4}$haloalk, cyano, nitro, —C(=O)$R^a$, —C(=O)O$R^a$, or —C(=O)$NR^aR^a$;

$R^2$ is H, halo, cyano, $R^c$, —C(=O)$R^b$, —C(=O)O$R^b$, —C(=O)$NR^aR^a$, —C(=$NR^a$)$NR^aR^a$, —O$R^a$, —OC(=O)$R^b$, —OC(=O)$NR^aR^a$, —O$C_{2-6}$alk$NR^aR^a$, —O$C_{2-6}$alkO$R^a$, —S$R^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)O$R^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$ and —$NR^aC_{2-6}$alkO$R^a$; or $R^2$ is $C_{1-6}$alk substituted by 0, 1, 2 or 3 substituents selected from $C_{1-4}$haloalk, halo, cyano, nitro, —C(=O)$R^b$, —C(=O)O$R^b$, —C(=O)$NR^aR^a$, —C(=$NR^a$)$NR^aR^a$, —O$R^a$, —OC(=O)$R^b$, —OC(=O)$NR^aR^a$, —O$C_{2-6}$alk$NR^aR^a$, —O$C_{2-6}$alkO$R^a$, —S$R^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)O$R^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$ and —$NR^aC_{2-6}$alkO$R^a$, or $R^2$ is $C^{1-6}$alk substituted by 0, 1, 2 or 3 halo substituents and additionally substituted by 0 or 1 substituents selected from $R^c$;

$R^3$ is H, $C_{1-8}$alk, $C_{1-8}$alkOH, $C_{1-4}$haloalk, halo, cyano, —C(=O)$R^b$, —C(=O)O$R^b$, —C(=O)$NR^aR^a$, —C(=$NR^a$)$NR^aR^a$, —O$R^a$, —OC(=O)$R^b$, —OC(=O)$NR^aR^a$, —O$C_{2-6}$alk$NR^aR^a$, —O$C_{2-6}$alkO$R^a$, —S$R^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)O$R^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alk$NR^aR^a$ or —$NR^aC_{2-6}$alkO$R^a$;

$R^4$ is independently, at each instance, H, $C_{1-6}$alk, —$C_{1-3}$haloalk, —O$C_{1-6}$alk, —O$C_{1-3}$haloalk, —N($C_{1-6}$alk)$C_{1-6}$alk, —NH$C_{1-6}$alk, —NC(=O)$C_{1-6}$alk, —N($C_{1-6}$alk)$C_{1-6}$alk, F, Cl, Br, CN, OH or $NH_2$; or $R^3$ and $R^4$ together form a four-atom unsaturated bridge containing 0 or 1 N atoms, wherein the bridge is substituted by 0, 1 or 2$R^5$ substituents;

$R^5$ is independently, in each instance, Cl, Br, F, $CH_3$, $CF_3$, or O$R^a$;

$R^6$ is F, $CF_3$, $C_{1-6}$alk, or O$R^a$;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —O$C_{1-4}$alk, —OH, —$NH_2$, —O$C_{1-4}$alk, —O$C_{1-4}$haloalk, —NH$C_{1-4}$alk, and —N($C_{1-4}$alk)$C_{1-4}$alk; and $R^c$ is independently, at each instance, a saturated, partially saturated or unsaturated 4-, 5- or 6-membered monocyclic ring containing 0, 1, 2, 3 or 4 heteroatoms selected from N, O and S, wherein the $C_{1-6}$alkyl and ring are substituted by 0 or 1 oxo groups substituted by 0, 1, 2 or 3 substituents selected from $C_{1-8}$alk, $C_{1-4}$haloalk, halo and cyano. In some such embodiments, Y is selected from NH or O. In some such embodiments, Y is NH whereas in other such embodiments, Y is O.

In one embodiment, the compound of Formula I has the Formula IA:

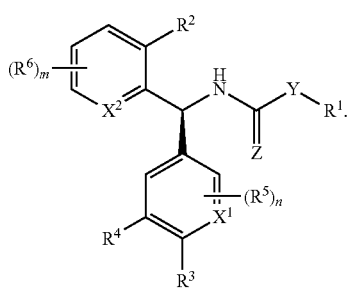

IA

In another embodiment, the compound of Formula I has the Formula IB:

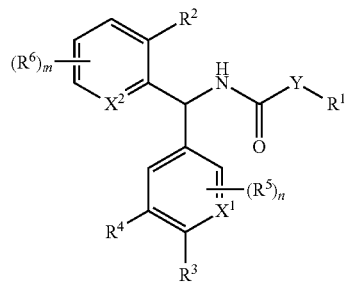

IB where Y is NH or O.

In another embodiment, the compound of Formula I has the Formula IC:

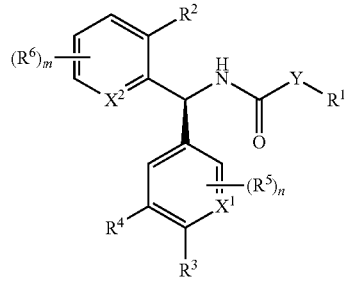

IC or any pharmaceutically-acceptable salt thereof, wherein:

m is 0, 1, 2 or 3;

n is 0 or 1;

$X^1$ is $C(R^4)$ or N;

$X^2$ is CH or N;

$R^1$ is selected from $C_{1-6}$alk or a direct-bonded, $C_{1-2}$alk-linked, $C_{1-2}$alkO-linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 heteroatoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{1-6}$alkO$R^a$, wherein the ring is additionally substituted by 0 or 1 directly bonded, SO$_2$ linked, C(=O) linked or CH$_2$ linked saturated, partially-saturated or unsaturated 3-, 4-, 5-, 6- or 7-membered monocyclic ring substituted by 0, 1, 2 or 3 groups selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —S$R^a$, —S(=O)$R^a$, —S(=O)$_2R^a$, —S(=O)$_2$N$R^aR^a$, —N$R^aR^a$, and —N($R^a$)C(=O)$R^a$;

$R^2$ is selected from H, halo, cyano, $R^c$, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$; or $R^2$ is $C_{1-6}$alk substituted by 0, 1, 2 or 3 substituents selected from $C_{1-4}$haloalk, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$, or $R^2$ is $C^{1-6}$alk substituted by 0, 1, 2 or 3 halo substituents and additionally substituted by 0 or 1 substituents selected from $R^c$;

$R^3$ is H, $C_{1-8}$alk, $C_{1-4}$haloalk, halo, cyano, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ or —N$R^aC_{2-6}$alkO$R^a$;

$R^4$ is independently, at each instance, H, $C_{1-6}$alk, —$C_{1-3}$haloalk, —OC$_{1-6}$alk, —OC$_{1-3}$haloalk, —N(C$_{1-6}$alk)C$_{1-6}$alk, —NHC$_{1-6}$alk, —NC(=O)C$_{1-6}$alk, —N(C$_{1-6}$alk)C$_{1-6}$alk, F, Cl, Br, CN, OH or NH$_2$; or $R^3$ and $R^4$ together form a four-atom unsaturated bridge containing 0 or 1 N atoms, wherein the bridge is substituted by 0, 1 or 2 $R^5$ substituents;

$R^5$ is independently, in each instance, F, CH$_3$ or CF$_3$;

$R^6$ is F;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —OC$_{1-4}$alk, —OH, —NH$_2$, —OC$_{1-4}$alk, —OC$_{1-4}$haloalk, —NHC$_{1-4}$alk, and —N(C$_{1-4}$alk)C$_{1-4}$alk; and $R^c$ is independently, at each instance, a saturated, partially saturated or unsaturated 4-, 5- or 6-membered monocyclic ring containing 0, 1, 2, 3 or 4 atoms selected from N, O and S, wherein the $C_{1-6}$alkyl and ring are substituted by 0 or 1 oxo groups substituted by 0, 1, 2 or 3 substituents selected from $C_{1-8}$alk, $C_{1-4}$haloalk, halo and cyano.

In another embodiment, the compound of Formula I has the Formula ID:

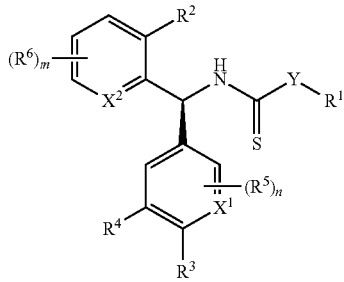

where Y is NH or O.

In some embodiments, the invention provides a compound or tautomer of any of the embodiments in a neutral form. In some such embodiments, the invention provides a compound of any of the embodiments in a neutral form.

In other embodiments, the invention provides a pharmaceutically-acceptably salt of the compound or a pharmaceutically acceptable salt of the tautomer of any one of the embodiments. In other embodiments, the invention provides a pharmaceutically-acceptably salt of the compound of any one of the embodiments. In some such embodiments, the salt is a trifluoroacetate or a bis trifluoroacetate salt.

The invention also provides pharmaceutical compositions that include the compound of any one of the embodiments or the pharmaceutically-acceptable salt thereof, the tautomer thereof, the pharmaceutically-acceptable salt of the tautomer, or the mixture thereof. Such compositions typically include a pharmaceutically-acceptable diluent or carrier.

The invention further provides methods of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders in a subject. Such methods typically include administering the compound according to any of the embodiments or the pharmaceutically-acceptable salt thereof, the tautomer thereof, the pharmaceutically-acceptable salt of the tautomer, or the mixture thereof to the subject. In some such methods the subject is suffering from neuropathic pain whereas in other such embodiments, the subject is suffering from migraine pain.

The invention also provides the use of the compound of any of the embodiments or the pharmaceutically-acceptable salt thereof, the tautomer thereof, the pharmaceutically-acceptable salt of the tautomer, or the mixture thereof in the preparation of a medicament.

The invention still further provides the use of the compound of any of the embodiments or the pharmaceutically-acceptable salt thereof, the tautomer thereof, the pharmaceutically-acceptable salt of the tautomer, or the mixture thereof for treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders in a subject. In some such embodiments, the use is for treating neuropathic pain whereas in other such embodiments, the use is for treating migraine.

The invention also provides the compound according to any of the embodiments described herein or the pharmaceutically-acceptable salt thereof, the tautomer thereof, the pharmaceutically-acceptable salt of the tautomer, or the mixture thereof for treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders in a subject. In some such embodiments, the compound of any of the embodiments or the pharmaceutically-acceptable salt thereof, the tautomer thereof, the pharmaceutically-acceptable salt of the tautomer, or the mixture thereof is for treating neuropathic pain in a subject. In other such embodiments, the compound of any of the embodiments or the pharmaceutically-acceptable salt thereof, the tautomer thereof, the pharmaceutically-acceptable salt of the tautomer, or the mixture thereof is for treating migraine pain in a subject The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION OF THE INVENTION

The compounds of this invention may have in general several asymmetric centers and are typically depicted in the form of racemic mixtures. This invention is intended to encompass racemic mixtures, partially racemic mixtures and separate enantiomers and diasteromers.

Unless otherwise specified, the following definitions apply to terms found in the specification and claims:

"$C_{\alpha-\beta}$alk" means an alkyl group comprising a minimum of α and a maximum of β carbon atoms in a branched, cyclical or linear relationship or any combination of the three, wherein α and β represent integers. The alkyl groups described in this section may also contain one or two double or triple bonds. A designation of $C_0$alk indicates a direct bond. Examples of $C_{1-6}$alkyl include, but are not limited to the following:

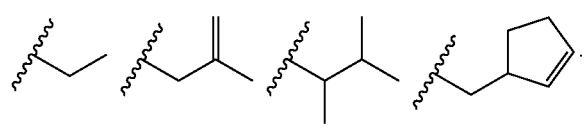

Where the term "$C_{\alpha-\beta}$alkyl" and "$C_{\alpha-\beta}$cycloalkyl" are used, they relate to acyclic saturated alkyls and cyclic saturated alkyls, respectively.

"Benzo group", alone or in combination, means the divalent radical $C_4H_4$=, one representation of which is —CH=CH—CH=CH—, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

The term "cyano" refers to a nitrile group which may be written as —C≡N. "Halo" or "halogen" means a halogen atoms selected from F, Cl, Br and I. "$C_{V-W}$haloalk" means an alk group, as described above, wherein any number—at least one—of the hydrogen atoms attached to the alk chain are replaced by F, Cl, Br or I.

The group $N(R^a)R^a$ and the like include substituents where the two $R^a$ groups together form a ring, optionally including a N, O or S atom, and include groups such as:

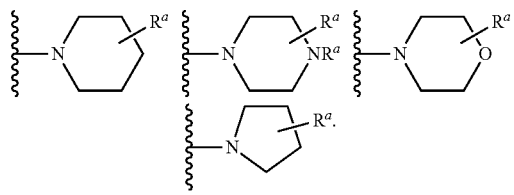

The group $N(C_{\alpha-\beta}alk)C_{\alpha-\beta}alk$, wherein α and β are as defined above, include substituents where the two $C_{\alpha-\beta}$alk groups together form a ring, optionally including a N, O or S atom, and include groups such as:

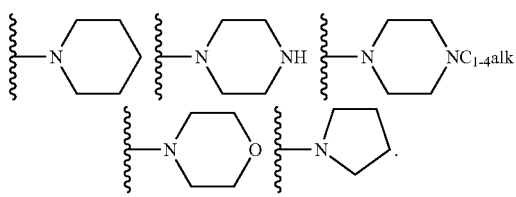

"Heterocycle" means a ring comprising at least one carbon atom and at least one other atom selected from N, O and S.

Examples of heterocycles that may be found in the claims include, but are not limited to, the following:

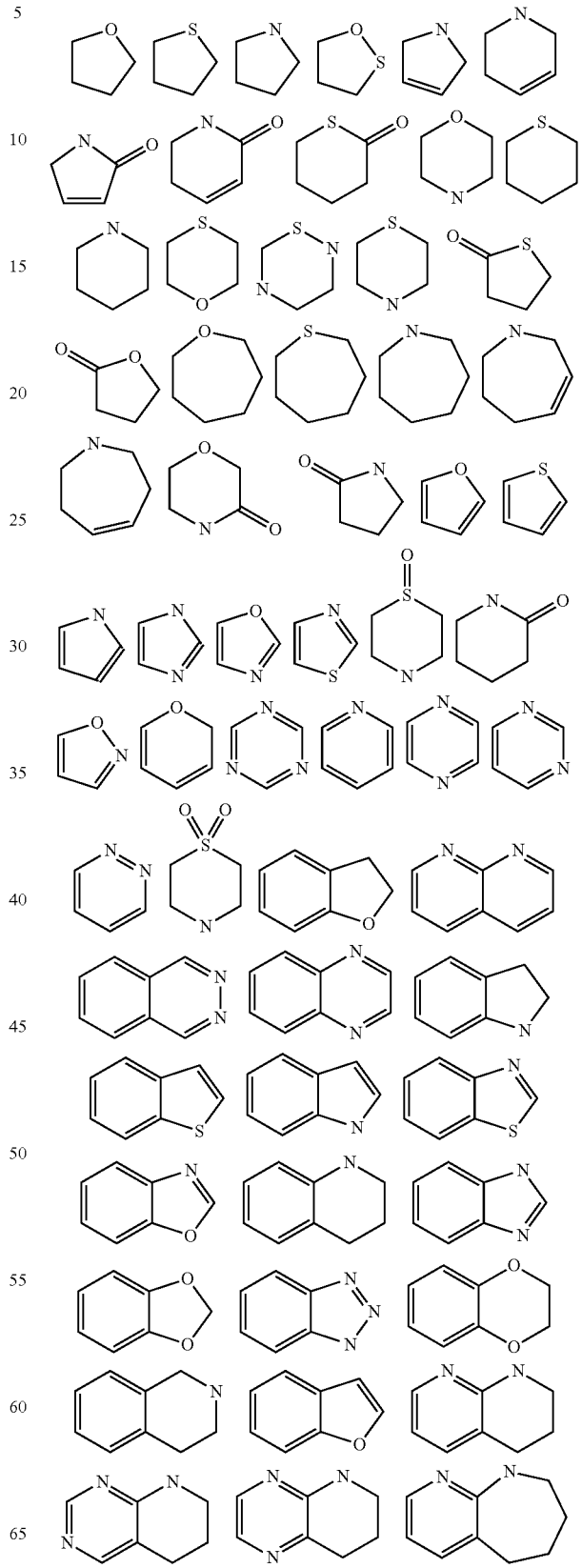

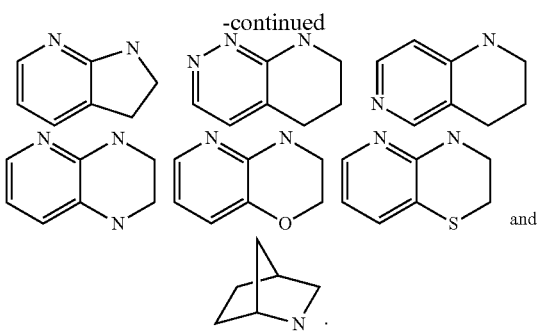

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, trifluoroacetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially-saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

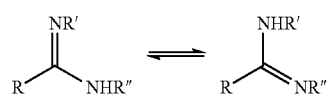

-continued

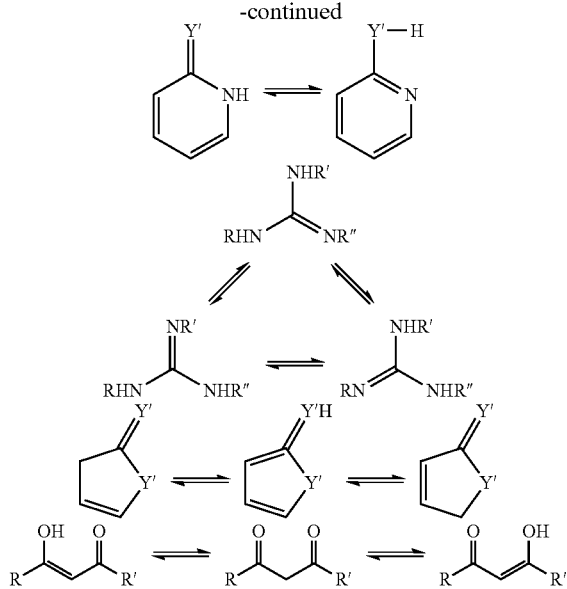

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language like "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

One aspect of the current invention relates to compounds having the general structure:

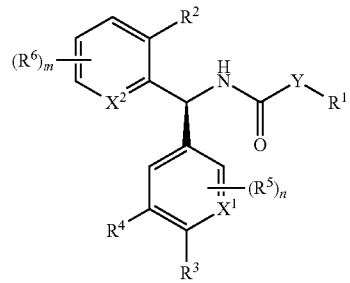

or any pharmaceutically-acceptable salt thereof, wherein:
m is 0, 1, 2 or 3;
n is 0 or 1;
$X^1$ is $C(R^4)$ or N;
$X^2$ is C or N;
Y is NH or O;
$R^1$ is selected from $C_{1-6}$alk or a direct-bonded, $C_{1-2}$alk-linked, $C_{1-2}$alkO-linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 atoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N(R$^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the ring is additionally substituted by 0 or 1 directly bonded, SO$_2$ linked, C(=O) linked or CH$_2$ linked saturated, partially-saturated or unsaturated 3-, 4-, 5-, 6- or 7-membered monocyclic ring substituted by 0, 1, 2 or 3 groups selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —S$R^a$, —S(=O)$R^a$, —S(=O)$_2R^a$, —S(=O)$_2$N$R^aR^a$, —N$R^aR^a$, and —N($R^a$)C(=O)$R^a$;
$R^2$ is selected from H, halo, cyano, $R^c$, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$; or $R^2$ is $C_{1-6}$alk substituted by 0, 1, 2 or 3 substituents selected from $C_{1-4}$haloalk, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$, or $R^2$ is $C^{1-6}$alk substituted by 0, 1, 2 or 3 halo substituents and additionally substituted by 0 or 1 substituents selected from $R^c$;

$R^3$ is H, $C_{1-8}$alk, $C_{1-4}$haloalk, halo, cyano, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ or —N$R^aC_{2-6}$alkO$R^a$;

$R^4$ is independently, at each instance, H, $C_{1-6}$alk, —$C_{1-3}$haloalk, —O$C_{1-6}$alk, —O$C_{1-3}$haloalk, —N($C_{1-6}$alk)$C_{1-6}$alk, —NH$C_{1-6}$alk, —NC(=O)$C_{1-6}$alk, —N($C_{1-6}$alk)$C_{1-6}$alk, F, Cl, Br, CN, OH or NH$_2$; or $R^3$ and $R^4$ together form a four-atom unsaturated bridge containing 0 or 1 N atoms, wherein the bridge is substituted by 0, 1 or 2 $R^5$ substituents;

$R^5$ is independently, in each instance, F, CH$_3$ or CF$_3$;

$R^6$ is F;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —O$C_{1-4}$alk, —OH, —NH$_2$, —O$C_{1-4}$alk, —O$C_{1-4}$haloalk, —NH$C_{1-4}$alk, and —N($C_{1-4}$alk)$C_{1-4}$alk; and $R^c$ is independently, at each instance, a saturated, partially saturated or unsaturated 4-, 5- or 6-membered monocyclic ring containing 0, 1, 2, 3 or 4 atoms selected from N, O and S, wherein the $C_{1-6}$alkyl and ring are substituted by 0 or 1 oxo groups substituted by 0, 1, 2 or 3 substituents selected from $C_{1-8}$alk, $C_{1-4}$haloalk, halo and cyano.

Another aspect of the current invention relates to compounds having the general structure:

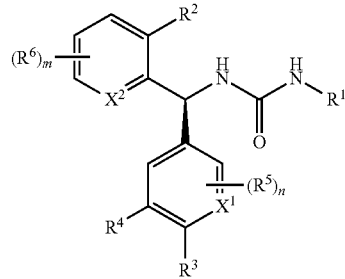

or any pharmaceutically-acceptable salt thereof, wherein:

m is 0, 1, 2 or 3;

n is 0 or 1;

$X^1$ is C($R^4$) or N;

$X^2$ is C or N;

$R^1$ is selected from $C_{1-6}$alk or a direct-bonded, $C_{1-2}$alk-linked, $C_{1-2}$alkO-linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 atoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{1-6}$alkN$R^aR^a$ and —N$R^aC_{2-6}$alkO$R^a$, wherein the ring is additionally substituted by 0 or 1 directly bonded, SO$_2$ linked, C(=O) linked or CH$_2$ linked saturated, partially-saturated or unsaturated 3-, 4-, 5-, 6- or 7-membered monocyclic ring substituted by 0, 1, 2 or 3 groups selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —S$R^a$, —S(=O)$R^a$, —S(=O)$_2R^a$, —S(=O)$_2$N$R^aR^a$, —N$R^aR^a$, and —N($R^a$)C(=O)$R^a$;

$R^2$ is selected from H, halo, cyano, $R^c$, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$; or $R^2$ is $C_{1-6}$alk substituted by 0, 1, 2 or 3 substituents selected from $C_{1-4}$haloalk, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$, or $R^2$ is $C^{1-6}$alk substituted by 0, 1, 2 or 3 halo substituents and additionally substituted by 0 or 1 substituents selected from $R^c$;

$R^3$ is H, $C_{1-8}$alk, $C_{1-4}$haloalk, halo, cyano, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ or —N$R^aC_{2-6}$alkO$R^a$;

$R^4$ is independently, at each instance, H, $C_{1-6}$alk, —$C_{1-3}$haloalk, —O$C_{1-6}$alk, —O$C_{1-3}$haloalk, —N($C_{1-6}$alk)$C_{1-6}$alk, —NH$C_{1-6}$alk, —NC(=O)$C_{1-6}$alk, —N($C_{1-6}$alk)$C_{1-6}$alk, F, Cl, Br, CN, OH or NH$_2$; or $R^3$ and $R^4$ together form a four-atom unsaturated bridge containing 0 or 1 N atoms, wherein the bridge is substituted by 0, 1 or 2 $R^5$ substituents;

$R^5$ is independently, in each instance, F, CH$_3$ or CF$_3$;

$R^a$ is F;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —O$C_{1-4}$alk, —OH, —NH$_2$, —O$C_{1-4}$alk, —O$C_{1-4}$haloalk, —NH$C_{1-4}$alk, and —N($C_{1-4}$alk)$C_{1-4}$alk; and $R^c$ is independently, at each instance, a saturated, partially saturated or unsaturated 4-, 5- or 6-membered monocyclic ring containing 0, 1, 2, 3 or 4 atoms selected from N, O and S, wherein the $C_{1-6}$alkyl and ring are substituted by 0 or 1 oxo groups substituted by 0, 1, 2 or 3 substituents selected from $C_{1-8}$alk, $C_{1-4}$haloalk, halo and cyano.

Another aspect of the current invention relates to compounds having the general structure:

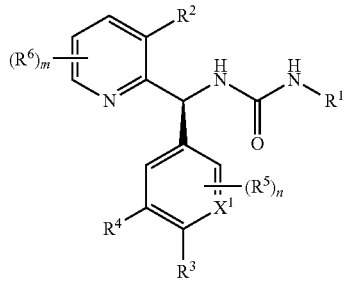

or any pharmaceutically-acceptable salt thereof, wherein:
m is 0, 1, 2 or 3;
n is 0 or 1;
$X^1$ is $C(R^4)$ or N;
$R^1$ is selected from $C_{1-6}$alk or a direct-bonded, $C_{1-2}$alk-linked, $C_{1-2}$alkO-linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 atoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{1-6}$alkO$R^a$, wherein the ring is additionally substituted by 0 or 1 directly bonded, SO$_2$ linked, C(=O) linked or CH$_2$ linked saturated, partially-saturated or unsaturated 3-, 4-, 5-, 6- or 7-membered monocyclic ring substituted by 0, 1, 2 or 3 groups selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —S$R^a$, —S(=O)$R^a$, —S(=O)$_2R^a$, —S(=O)$_2$N$R^aR^a$, —N$R^aR^a$, and —N($R^a$)C(=O)$R^a$;
$R^2$ is selected from H, halo, cyano, $R^c$, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{1-6}$alkO$R^a$; or $R^2$ is $C_{1-6}$alk substituted by 0, 1, 2 or 3 substituents selected from $C_{1-4}$haloalk, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$, or $R^2$ is $C^{1-6}$alk substituted by 0, 1, 2 or 3 halo substituents and additionally substituted by 0 or 1 substituents selected from $R^c$;
$R^3$ is H, $C_{1-8}$alk, $C_{1-4}$haloalk, halo, cyano, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ or —N$R^aC_{2-6}$alkO$R^a$;
$R^4$ is independently, at each instance, H, $C_{1-6}$alk, —$C_{1-3}$haloalk, —O$C_{1-6}$alk, —O$C_{1-3}$haloalk, —N($C_{1-6}$alk)$C_{1-6}$ alk, —NH$C_{1-6}$alk, —NC(=O)$C_{1-6}$alk, —N($C_{1-6}$alk)$C_{1-6}$ alk, F, Cl, Br, CN, OH or NH$_2$; or $R^3$ and $R^4$ together form a four-atom unsaturated bridge containing 0 or 1 N atoms, wherein the bridge is substituted by 0, 1 or 2 $R^5$ substituents;
$R^5$ is independently, in each instance, F, CH$_3$ or CF$_3$;
$R^6$ is F;
$R^a$ is independently, at each instance, H or $R^b$;
$R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —O$C_{1-4}$alk, —OH, —NH$_2$, —O$C_{1-4}$alk, —O$C_{1-4}$haloalk, —NH$C_{1-4}$alk, and —N($C_{1-4}$alk)$C_{1-4}$alk; and
$R^c$ is independently, at each instance, a saturated, partially saturated or unsaturated 4-, 5- or 6-membered monocyclic ring containing 0, 1, 2, 3 or 4 atoms selected from N, O and S, wherein the $C_{1-6}$alkyl and ring are substituted by 0 or 1 oxo groups substituted by 0, 1, 2 or 3 substituents selected from $C_{1-8}$alk, $C_{1-4}$haloalk, halo and cyano.

Another aspect of the current invention relates to compounds having the general structure:

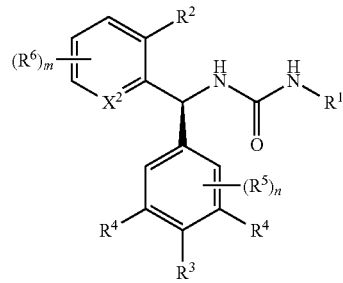

or any pharmaceutically-acceptable salt thereof, wherein:
m is 0, 1, 2 or 3;
n is 0 or 1;
$X^2$ is C or N;
$R^1$ is selected from $C_{1-6}$alk or a direct-bonded, $C_{1-2}$alk-linked, $C_{1-2}$alkO-linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 atoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the ring is additionally substituted by 0 or 1 directly bonded, SO$_2$ linked, C(=O) linked or CH$_2$ linked saturated, partially-saturated or unsaturated 3-, 4-, 5-, 6- or 7-membered monocyclic ring substituted by 0, 1, 2 or 3 groups selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —S$R^a$, —S(=O)$R^a$, —S(=O)$_2R^a$, —S(=O)$_2$N$R^aR^a$, —N$R^aR^a$, and —N($R^a$)C(=O)$R^a$;

$R^2$ is selected from H, halo, cyano, $R^c$, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —O$C_{2-6}$alkN$R^aR^a$, —O$C_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$; or $R^2$ is $C_{1-6}$alk substituted by 0, 1, 2 or 3 substituents selected from $C_{1-4}$haloalk, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —O$C_{2-6}$alkN$R^aR^a$, —O$C_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$ alkN$R^aR^a$ and —N$R^aC_{1-6}$alkO$R^a$, or $R^2$ is $C^{1-6}$alk substituted by 0, 1, 2 or 3 halo substituents and additionally substituted by 0 or 1 substituents selected from $R^c$;

$R^3$ is H, $C_{1-8}$alk, $C_{1-4}$haloalk, halo, cyano, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —O$C_{2-6}$alkN$R^aR^a$, —O$C_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ or —N$R^aC_{2-6}$alkO$R^a$;

$R^4$ is independently, at each instance, H, $C_{1-6}$alk, —$C_{1-3}$haloalk, —O$C_{1-6}$alk, —O$C_{1-3}$haloalk, —N($C_{1-6}$alk)$C_{1-6}$ alk, —NH$C_{1-6}$alk, —NC(=O)$C_{1-6}$alk, —N($C_{1-6}$alk)$C_{1-6}$ alk, F, Cl, Br, CN, OH or NH$_2$;

$R^5$ is F, CH$_3$ or CF$_3$;

$R^6$ is F;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —O$C_{1-4}$alk, —OH, —NH$_2$, —O$C_{1-4}$alk, —O$C_{1-4}$haloalk, —NH$C_{1-4}$alk, and —N($C_{1-4}$alk)$C_{1-4}$alk; and $R^c$ is independently, at each instance, a saturated, partially saturated or unsaturated 4-, 5- or 6-membered monocyclic ring containing 0, 1, 2, 3 or 4 atoms selected from N, O and S, wherein the $C_{1-6}$alkyl and ring are substituted by 0 or 1 oxo groups substituted by 0, 1, 2 or 3 substituents selected from $C_{1-8}$alk, $C_{1-4}$haloalk, halo and cyano.

Another aspect of the current invention relates to compounds having the general structure:

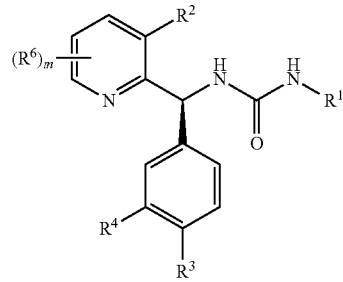

or any pharmaceutically-acceptable salt thereof, wherein:

m is 0, 1, 2 or 3;

$R^1$ is a direct-bonded, partially-saturated or unsaturated 5- or 6-membered monocyclic ring containing 1 or 2 atoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-4}$haloalk and cyano;

$R^2$ is selected from F and CF$_3$;

$R^3$ is CH$_3$, CF$_3$, F or Cl;

$R^4$ is H or F;

$R^6$ is F;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —O$C_{1-4}$alk, —OH, —NH$_2$, —O$C_{1-4}$alk, —O$C_{1-4}$haloalk, —NH$C_{1-4}$alk, and —N($C_{1-4}$alk)$C_{1-4}$alk; and $R^c$ is independently, at each instance, a saturated, partially saturated or unsaturated 4-, 5- or 6-membered monocyclic ring containing 0, 1, 2, 3 or 4 atoms selected from N, O and S, wherein the $C_{1-6}$alkyl and ring are substituted by 0 or 1 oxo groups substituted by 0, 1, 2 or 3 substituents selected from $C_{1-8}$alk, $C_{1-4}$haloalk, halo and cyano.

Another aspect of the current invention relates to compounds having the general structure:

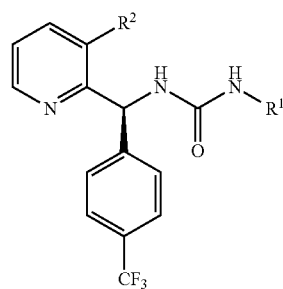

or any pharmaceutically-acceptable salt thereof, wherein:

m is 0, 1, 2 or 3;

$R^1$ is a direct-bonded, partially-saturated or unsaturated 5- or 6-membered monocyclic ring containing 1 or 2 atoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-4}$haloalk and cyano; and $R^2$ is selected from F and $CF_3$.

Another aspect of the current invention relates to compounds having the general structure:

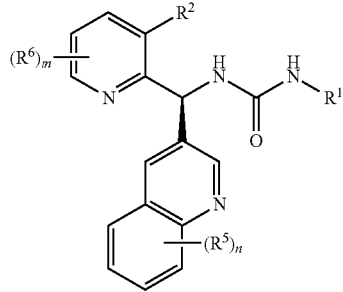

or any pharmaceutically-acceptable salt thereof, wherein:

m is 0, 1, 2 or 3;

n is 0 or 1;

$X^1$ is $C(R^4)$ or N;

$X^2$ is C or N;

Y is NH or O;

$R^1$ is selected from $C_{1-6}$alk or a direct-bonded, $C_{1-2}$alk-linked, $C_{1-2}$alkO-linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 atoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$ and —N$R^aC_{2-6}$alkN$R^aR^a$ and —N$R^aC_{2-6}$alkO$R^a$; wherein the ring is additionally substituted by 0 or 1 directly bonded, $SO_2$ linked, C(=O) linked or $CH_2$ linked saturated, partially-saturated or unsaturated 3-, 4-, 5-, 6- or 7-membered monocyclic ring substituted by 0, 1, 2 or 3 groups selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —S$R^a$, —S(=O)$R^a$, —S(=O)$_2R^a$, —S(=O)$_2$N$R^aR^a$, —N$R^aR^a$, and —N($R^a$)C(=O)$R^a$;

$R^2$ is selected from H, halo, cyano, $R^c$, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$; or $R^2$ is $C_{1-6}$alk substituted by 0, 1, 2 or 3 substituents selected from $C_{1-4}$haloalk, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$, or $R^2$ is $C^{1-6}$alk substituted by 0, 1, 2 or 3 halo substituents and additionally substituted by 0 or 1 substituents selected from $R^c$;

$R^3$ is H, $C_{1-8}$alk, $C_{1-4}$haloalk, halo, cyano, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ or —N$R^aC_{1-6}$alkO$R^a$;

$R^4$ is independently, at each instance, H, $C_{1-6}$alk, —$C_{1-3}$haloalk, —O$C_{1-6}$alk, —O$C_{1-3}$haloalk, —N($C_{1-6}$alk)$C_{1-6}$ alk, —NH$C_{1-6}$alk, —NC(=O)$C_{1-6}$alk, —N($C_{1-6}$alk)$C_{1-6}$ alk, F, Cl, Br, CN, OH or $NH_2$;

$R^5$ is F, $CH_3$ or $CF_3$;

$R^6$ is F;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —O$C_{1-4}$alk, —OH, —$NH_2$, —O$C_{1-4}$alk, —O$C_{1-4}$haloalk, —NH$C_{1-4}$alk, and —N($C_{1-4}$alk)$C_{1-4}$alk; and $R^c$ is independently, at each instance, a saturated, partially saturated or unsaturated 4-, 5- or 6-membered monocyclic ring containing 0, 1, 2, 3 or 4 atoms selected from N, O and S, wherein the $C_{1-6}$alkyl and ring are substituted by 0 or 1 oxo groups substituted by 0, 1, 2 or 3 substituents selected from $C_{1-8}$alk, $C_{1-4}$haloalk, halo and cyano.

In another embodiment, in conjunction with any above or below embodiments, $R^1$ is $C_{1-6}$alk substituted by 0, 1, 2 or 3 substituents independently selected from halo, oxo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$.

In another embodiment, in conjunction with any above or below embodiments, $R^1$ is $C_{1-2}$alk-linked saturated, partially-saturated or unsaturated 3-, 4-, 5-, 6- or 7-membered monocyclic ring containing 0, 1, 2, 3 or 4 atoms selected from N, O and S, but containing no more than one O or S atom, the ring being substituted by 0, 1, 2 or 3 substituents independently selected from halo, oxo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$.

In another embodiment, in conjunction with any above or below embodiments, $R^1$ is a direct-bonded saturated, partially-saturated or unsaturated 3-, 4-, 5-, 6- or 7-membered monocyclic or 7-, 8-, 9-, 10- or 11-membered bicyclic ring containing 0, 1, 2, 3 or 4 atoms selected from N, O and S, but containing no more than one O or S atom, the ring being substituted by 0, 1, 2 or 3 substituents independently selected from halo, oxo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2$R, —S(=O)$_2$N$R^aR^a$, —S(=O)$_2$N(R)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{1-6}$alkO$R^a$, wherein the ring is additionally substituted by 0 or 1 directly bonded, $SO_2$ linked, C(=O) linked or $CH_2$ linked saturated, partially-saturated or unsaturated 3-, 4-, 5-, 6- or 7-membered monocyclic ring substituted by 0, 1, 2 or 3 groups selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —S$R^a$, —S(=O)$R^a$, —S(=O)$_2R^a$, —S(=O)$_2$N$R^aR^a$, —N$R^aR^a$, and —N($R^a$)C(=O)$R^a$.

In another embodiment, in conjunction with any above or below embodiments, $R^1$ is a direct-bonded partially-saturated or unsaturated 5- or 6-membered monocyclic ring containing 1, 2, 3 or 4 atoms selected from N, O and S, but containing no more than one O or S atom, the ring being substituted by 0, 1, 2 or 3 substituents independently selected from halo, oxo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2$R, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$.

In another embodiment, in conjunction with any above or below embodiments, $R^1$ is a direct-bonded partially-saturated or unsaturated 6-membered monocyclic ring containing 1 or 2 N atoms, substituted by 0, 1, 2 or 3 substituents independently selected from halo, oxo, $C_{1-6}$alk, $C_{1-4}$haloalk, cyano and —O$R^a$.

In another embodiment, in conjunction with any above or below embodiments, $R^1$ is a direct-bonded unsaturated 10-membered bicyclic ring containing 1 or 2 N atoms, substituted by 0, 1, 2 or 3 substituents independently selected from halo, oxo, $C_{1-6}$alk, $C_{1-4}$haloalk, cyano and —O$R^a$.

Another aspect of the invention relates to a method of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound as described above.

Another aspect of the invention relates to a pharmaceutical composition comprising a compound according to Claim 1 and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, anxiety, depression, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

Additional Embodiments

The embodiments listed below are presented in numbered form for convenience and are in addition to the embodiments described above.

1. In a first additional embodiment, the invention provides a compound of Formula I having the structure:

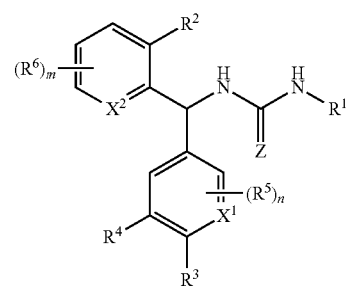

or a pharmaceutically-acceptable salt thereof, a tautomer thereof, a pharmaceutically-acceptable salt of the tautomer, a stereoisomer thereof, or a mixture thereof, wherein:

m is 0, 1, 2 or 3;
n is 0 or 1;
$X^1$ is C($R^4$) or N;
$X^2$ is CH or N;
Y is NH, N$R^{1a}$, or O;
Z is O or S;
$R^1$ is $C_{1-6}$alk, —(C=O)—O—$C_{1-6}$alk, or a direct-bonded, $C_{1-6}$alk-linked, $C_{1-2}$alkO-linked, —C(=O)—O linked, —C(=O)— linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 heteroatoms selected from N, O and S, the $C_{1-6}$alk, the $C_{1-6}$alk of the $C_{1-6}$alk-link, and the monocyclic or bicyclic ring being substituted by 0, 1, 2 or 3 substituents independently selected from halo, oxo, $C_{1-6}$alk, $C_{1-6}$alkOH, $C_{1-6}$alk-C(=O)$R^a$, $C_{1-6}$alk-C(=O)O$R^a$, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, =S, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^a$C$_{2-6}$alkN$R^aR^a$ and —N$R^a$C$_{2-6}$alkO$R^a$, wherein the ring is additionally substituted by 0 or 1 directly bonded, SO$_2$ linked, C(=O) linked or CH$_2$ linked saturated, partially-saturated or unsaturated 3-, 4-, 5-, 6- or 7-membered monocyclic ring containing 0, 1, 2, 3 or 4 heteroatoms selected from N, O and S, and substituted by 0, 1, 2 or 3 groups selected from halo, $C_{1-6}$alk, $C_{1-4}$haloalk, cyano, oxo, nitro, —C(=O)$R^a$, —C(=O)O$R^a$, —C(=O)N$R^aR^a$, —C(=N$R^a$)N$R^aR^a$, —O$R^a$, —OC(=O)$R^a$, —S$R^a$, —S(=O)$R^a$, —S(=O)$_2R^a$, —S(=O)$_2$N$R^aR^a$, —N$R^aR^a$, and —N($R^a$)C(=O)$R^a$; or $R^{1a}$ and $R^1$, together with the N atom to which they are attached, form a saturated, partially-saturated or unsaturated 4-, 5-, 6-, or 7-membered monocyclic or a 9- or 10-membered bicyclic ring containing 0, 1, or 2 additional heteroatoms independently selected from N, O, and S, wherein the ring formed by $R^{1a}$ and $R^1$ is substituted with 0, 1, or 2 substituents independently selected from halo, oxo, $C_{1-6}$alk, $C_{1-6}$alkOH, $C_{1-6}$alk-C(=O)$R^a$, $C_{1-6}$alk-C(=O)O$R^a$, $C_{1-4}$haloalk, cyano, nitro, —C(=O)$R^a$, —C(=O)O$R^a$, or —C(=O)N$R^aR^a$;

$R^2$ is H, halo, cyano, $R^c$, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$ alkN$R^aR^a$ and —N$R^a$C$_{1-6}$alkO$R^a$; or $R^2$ is $C_{1-6}$alk substituted by 0, 1, 2 or 3 substituents selected from $C_{1-4}$haloalk, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkN$R^aR^a$ and —N$R^a$C$_{2-6}$alkO$R^a$, or $R^2$ is $C^{1-6}$alk substituted by 0, 1, 2 or 3 halo substituents and additionally substituted by 0 or 1 substituents selected from $R^c$;

$R^3$ is H, $C_{1-8}$alk, $C_{1-8}$alkOH, $C_{1-4}$haloalk, halo, cyano, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O) N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkN$R^aR^a$ or —N$R^a$C$_{2-6}$ alkO$R^a$;

$R^4$ is independently, at each instance, H, $C_{1-6}$alk, —$C_{1-3}$haloalk, —OC$_{1-6}$alk, —OC$_{1-3}$haloalk, —N($C_{1-6}$alk)$C_{1-6}$ alk, —NHC$_{1-6}$alk, —NC(=O)$C_{1-6}$alk, —N($C_{1-6}$alk)$C_{1-6}$ alk, F, Cl, Br, CN, OH or NH$_2$; or $R^3$ and $R^4$ together form a four-atom unsaturated bridge containing 0 or 1 N atoms, wherein the bridge is substituted by 0, 1 or 2 $R^5$ substituents;

$R^5$ is independently, in each instance, Cl, Br, F, CH$_3$, CF$_3$, or O$R^a$;

$R^6$ is F, CF$_3$, $C_{1-6}$alk, or O$R^a$;

$R^a$ is independently, at each instance, H or $R^b$;

$R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —OC$_{1-4}$alk, —OH, —NH$_2$, —OC$_{1-4}$alk, —OC$_{1-4}$haloalk, —NHC$_{1-4}$alk, and —N($C_{1-4}$alk)$C_{1-4}$alk; and $R^c$ is independently, at each instance, a saturated, partially saturated or unsaturated 4-, 5- or 6-membered monocyclic ring containing 0, 1, 2, 3 or 4 heteroatoms selected from N, O and S, wherein the $C_{1-6}$alkyl and ring are substituted by 0 or 1 oxo groups substituted by 0, 1, 2 or 3 substituents selected from $C_{1-8}$alk, $C_{1-4}$haloalk, halo and cyano.

2. The compound of embodiment 1 or the pharmaceutically-acceptable salt thereof, the tautomer thereof, the pharmaceutically-acceptable salt of the tautomer, or the mixture thereof, wherein the compound of Formula I has the Formula IA:

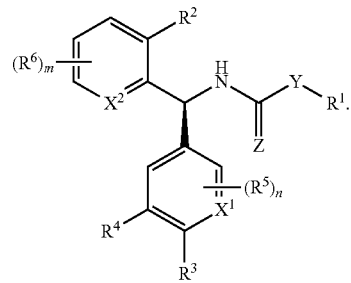

3. The compound of embodiment 1 or the pharmaceutically-acceptable salt thereof, the tautomer thereof, the pharmaceutically-acceptable salt of the tautomer, or the mixture thereof, wherein the compound of Formula I has the Formula IB:

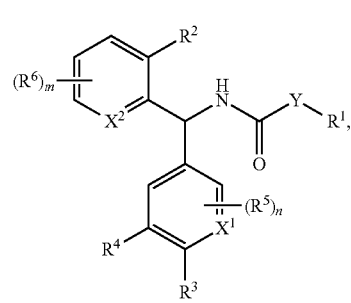

wherein Y is NH or O.

4. The compound of embodiment 3 or the pharmaceutically-acceptable salt thereof, the tautomer thereof, the pharmaceutically-acceptable salt of the tautomer, or the mixture thereof, wherein the compound of Formula I has the Formula IC:

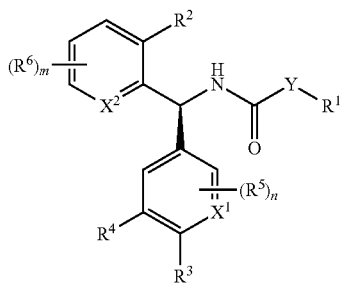

or any pharmaceutically-acceptable salt thereof, wherein:
m is 0, 1, 2 or 3;
n is 0 or 1;
$X^1$ is $C(R^4)$ or N;
$X^2$ is CH or N;
$R^1$ is selected from $C_{1-6}$alk or a direct-bonded, $C_{1-2}$alk-linked, $C_{1-2}$alkO-linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 heteroatoms selected from N, O and S, but containing no more than one O or S atom, the $C_{1-6}$alk and ring being substituted by 0, 1, 2 or 3 substituents independently selected from halo, oxo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the ring is additionally substituted by 0 or 1 directly bonded, SO$_2$ linked, C(=O) linked or CH$_2$ linked saturated, partially-saturated or unsaturated 3-, 4-, 5-, 6- or 7-membered monocyclic ring substituted by 0, 1, 2 or 3 groups selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —S$R^a$, —S(=O)$R^a$, —S(=O)$_2R^a$, —S(=O)$_2$N$R^aR^a$, —N$R^aR^a$, and —N($R^a$)C(=O)$R^a$;
$R^2$ is selected from H, halo, cyano, $R^c$, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ and —N$R^aC_{2-6}$alkO$R^a$; or $R^2$ is $C_{1-6}$alk substituted by 0, 1, 2 or 3 substituents selected from $C_{1-4}$haloalk, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkN$R^aR^a$ or —N$R^aC_{2-6}$alkO$R^a$;
$R^3$ is H, $C_{1-8}$alk, $C_{1-4}$haloalk, halo, cyano, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC$_{2-6}$alkN$R^aR^a$, —OC$_{2-6}$alkO$R^a$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)NR$^a$R$^a$, —N($R^a$)S(=O)$_2R^b$, —N($R^a$)S(=O)$_2$N$R^aR^a$, —N$R^aC_{2-6}$alkN$R^aR^a$ or —N$R^aC_{2-6}$alkO$R^a$;

$R^4$ is independently, at each instance, H, $C_{1-6}$alk, —$C_{1-3}$haloalk, —O$C_{1-6}$alk, —O$C_{1-3}$haloalk, —N($C_{1-6}$alk)$C_{1-6}$ alk, —NH$C_{1-6}$alk, —NC(=O)$C_{1-6}$alk, —N($C_{1-6}$alk)$C_{1-6}$ alk, F, Cl, Br, CN, OH or NH$_2$; or $R^3$ and $R^4$ together form a four-atom unsaturated bridge containing 0 or 1 N atoms, wherein the bridge is substituted by 0, 1 or 2 $R^5$ substituents;
$R^5$ is independently, in each instance, F, CH$_3$ or CF$_3$;
$R^6$ is F;
$R^a$ is independently, at each instance, H or $R^b$;
$R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —O$C_{1-4}$alk, —OH, —NH$_2$, —O$C_{1-4}$alk, —O$C_{1-4}$haloalk, —NH$C_{1-4}$alk, and —N($C_{1-4}$alk)$C_{1-4}$alk; and
$R^c$ is independently, at each instance, a saturated, partially saturated or unsaturated 4-, 5- or 6-membered monocyclic ring containing 0, 1, 2, 3 or 4 atoms selected from N, O and S, wherein the $C_{1-6}$alkyl and ring are substituted by 0 or 1 oxo groups substituted by 0, 1, 2 or 3 substituents selected from $C_{1-8}$alk, $C_{1-4}$haloalk, halo and cyano.

5. The compound of embodiment 4 or the pharmaceutically-acceptable salt thereof.

6. The compound of embodiment 1 or the pharmaceutically-acceptable salt thereof, the tautomer thereof, the pharmaceutically-acceptable salt of the tautomer, or the mixture thereof, wherein the compound of Formula I has the Formula ID:

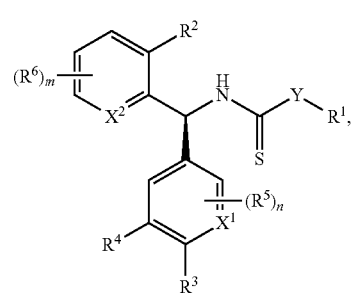

wherein Y is NH or O.

7. The compound of embodiment 1 or embodiment 2, wherein Y is N$R^{1a}$.

8. The compound of embodiment 7, wherein $R^{1a}$ and $R^1$, together with the N to which they are attached, form a 6 membered unsaturated ring.

9. The compound of embodiment 8, wherein $R^{1a}$ and $R^1$, together with the N to which they are attached, form a morpholine ring, a piperidine ring, or a piperazine ring.

10. The compound of embodiment 1 or embodiment 2 or the pharmaceutically-acceptable salt thereof, the tautomer thereof, the pharmaceutically-acceptable salt of the tautomer, or the mixture thereof, wherein $R^1$ is a saturated, partially-saturated or unsaturated 3-, 4-, 5-, 6- or 7-membered monocyclic or 7-, 8-, 9-, 10- or 11-membered bicyclic ring containing 0, 1, 2, 3 or 4 heteroatoms selected from N, O and S, wherein the monocyclic or bicyclic ring is independently substituted by 0, 1, 2 or 3 substituents.

11. The compound of embodiment 10 or the pharmaceutically-acceptable salt thereof, the tautomer thereof, the pharmaceutically-acceptable salt of the tautomer, or the mixture thereof, wherein $R^1$ is selected from phenyl, pyridyl, pyridinonyl, piperidinonyl, pyrimidinyl, tetradyrofuranyl, tetrahydropyranyl, oxetanyl, furanyl, tetrahydrothiophenyl, thiophenyl, isoxazolyl, pyrrolidinonyl, piperidinyl, cyclohexyl, cyclohexanonyl, quinolinyl, isoquinolinyl, tetrahydronaphthalenyl, dihydroindenyl, indolinonyl, indolinyl, or benzofuranyl independently substituted by 0, 1, 2, or 3 substituents.

12. The compound of embodiment 11 or the pharmaceutically-acceptable salt thereof, the tautomer thereof, the pharmaceutically-acceptable salt of the tautomer, or the mixture thereof, wherein $R^1$ is substituted with 0, 1, 2, or 3 substituents independently selected from F, Cl, Br, I, CN, $CF_3$, $NO_2$, oxo, $C_{1-6}$alk, $OCH_3$, $OCH_2CH_3$, $COCH_3$, $CO_2H$, $CO_2CH_3$, $CO_2CH_2CH_3$, $SCH_3$, $SO_2CH_3$, oxadiazolyl, a methyl-substituted oxadiazolyl, or oxadiazolonyl.

13. The compound of embodiment 1 or embodiment 2 or the pharmaceutically-acceptable salt thereof, the tautomer thereof, the pharmaceutically-acceptable salt of the tautomer, or the mixture thereof, wherein $R^1$ is $C_{1-6}$alk, wherein the $C_{1-6}$alk is independently substituted by 0, 1, 2 or 3 substituents.

14. The compound of embodiment 13 or the pharmaceutically-acceptable salt thereof, the tautomer thereof, the pharmaceutically-acceptable salt of the tautomer, or the mixture thereof, wherein $R^1$ is substituted with 0, 1, 2, or 3 substituents independently selected from F, Cl, Br, I, CN, $CF_3$, $NO_2$, oxo, $C_{1-6}$alk, $OCH_3$, $OCH_2CH_3$, $COCH_3$, $CO_2H$, $CO_2CH_3$, $CO_2CH_2CH_3$, $SCH_3$, $SO_2CH_3$, oxadiazolyl, a methyl-substituted oxadiazolyl, or oxadiazolonyl.

15. The compound of embodiment 1 or embodiment 2 or the pharmaceutically-acceptable salt thereof, the tautomer thereof, the pharmaceutically-acceptable salt of the tautomer, or the mixture thereof, wherein $R^1$ is a $C_{1-6}$alk-linked, $C_{1-2}$alkO-linked, —C(=O)—O linked, or —C(=O)— linked, saturated, partially-saturated or unsaturated 3-, 4-, 5-, 6- or 7-membered monocyclic or 7-, 8-, 9-, 10- or 11-membered bicyclic ring containing 0, 1, 2, 3 or 4 heteroatoms selected from N, O and S, wherein the monocyclic or bicyclic ring is substituted by 0, 1, 2 or 3 substituents.

16. The compound of embodiment 15 or the pharmaceutically-acceptable salt thereof, the tautomer thereof, the pharmaceutically-acceptable salt of the tautomer, or the mixture thereof, wherein $R^1$ is a —$C_{1-2}$alk-linked saturated, partially-saturated or unsaturated 3-, 4-, 5-, 6- or 7-membered monocyclic or 7-, 8-, 9-, 10- or 11-membered bicyclic ring containing 0, 1, 2, 3 or 4 heteroatoms selected from N, O and S, wherein the monocyclic or bicyclic ring is substituted by 0, 1, 2 or 3 substituents.

17. The compound of embodiment 1 or embodiment 2 or the pharmaceutically-acceptable salt thereof, the tautomer thereof, the pharmaceutically-acceptable salt of the tautomer, or the mixture thereof, wherein $R^1$ is a group of formula

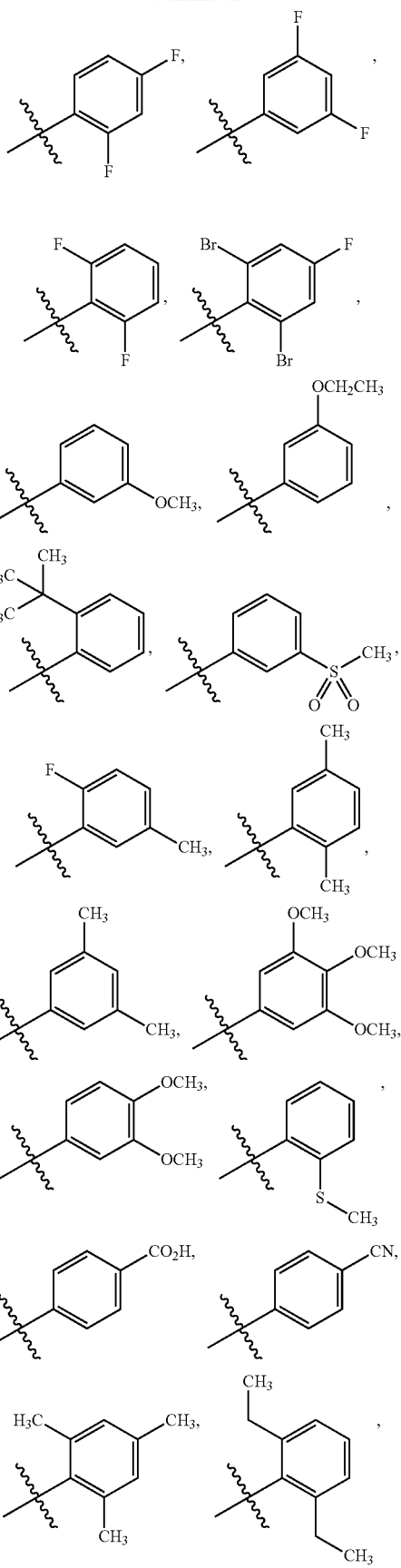

-continued
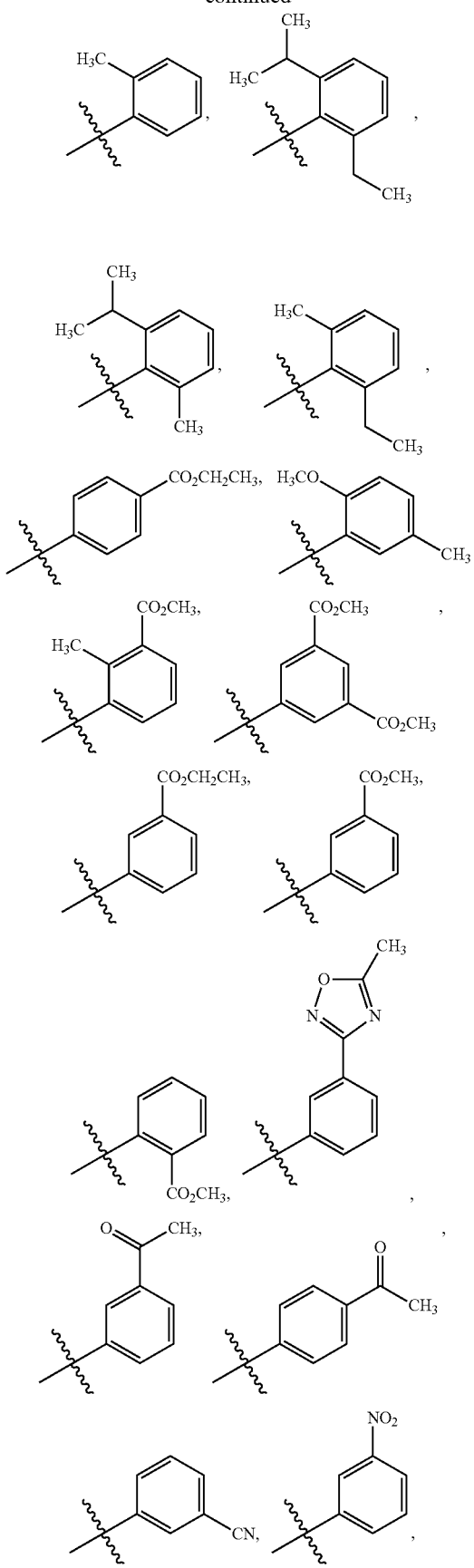
-continued
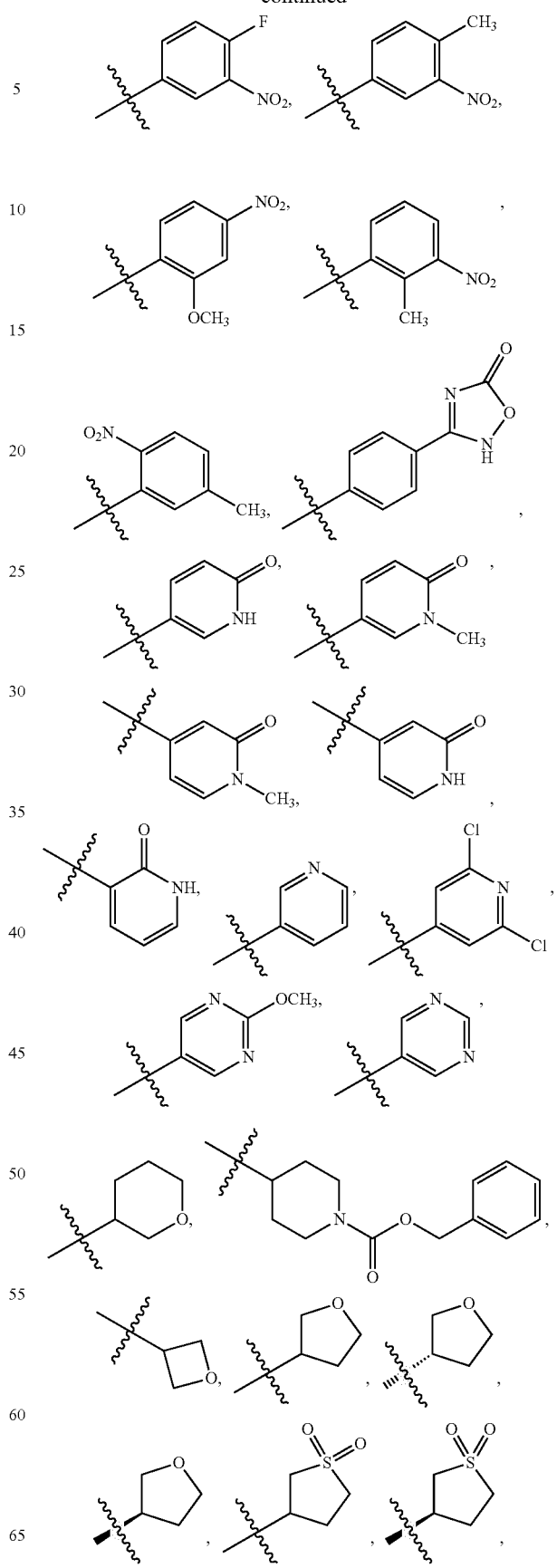

-continued
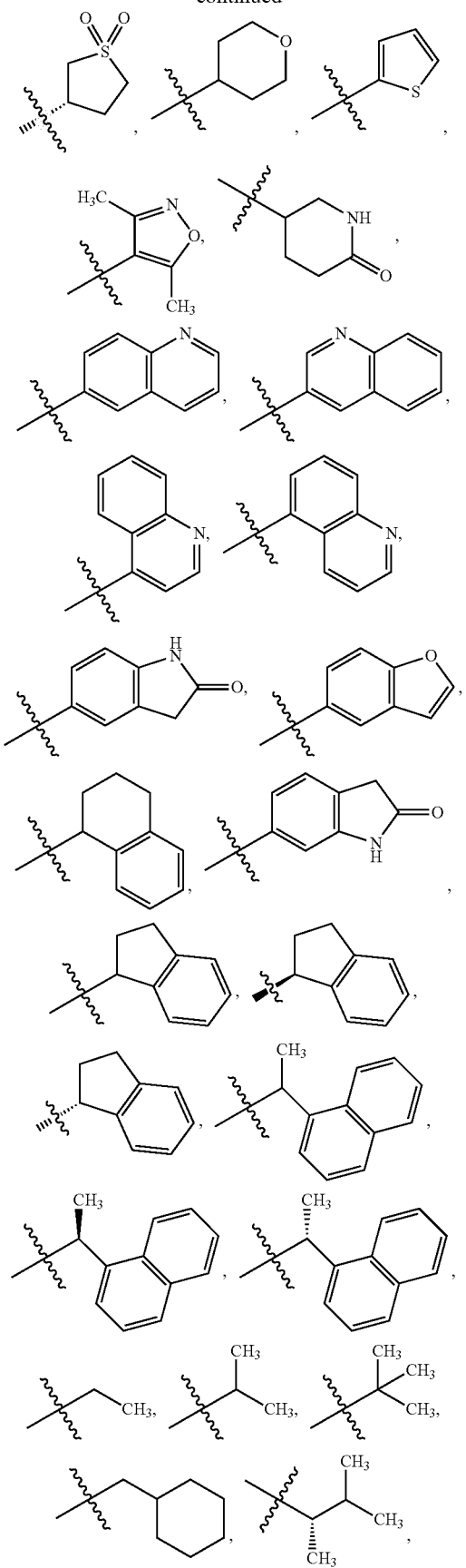
-continued
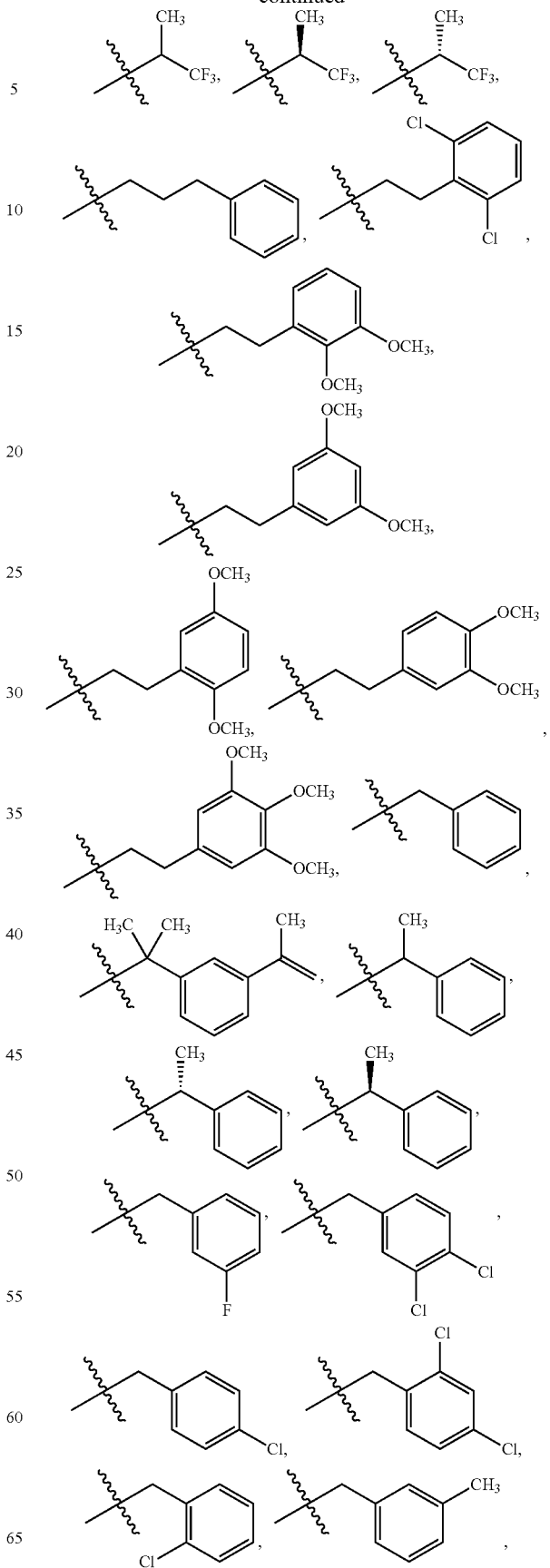

-continued
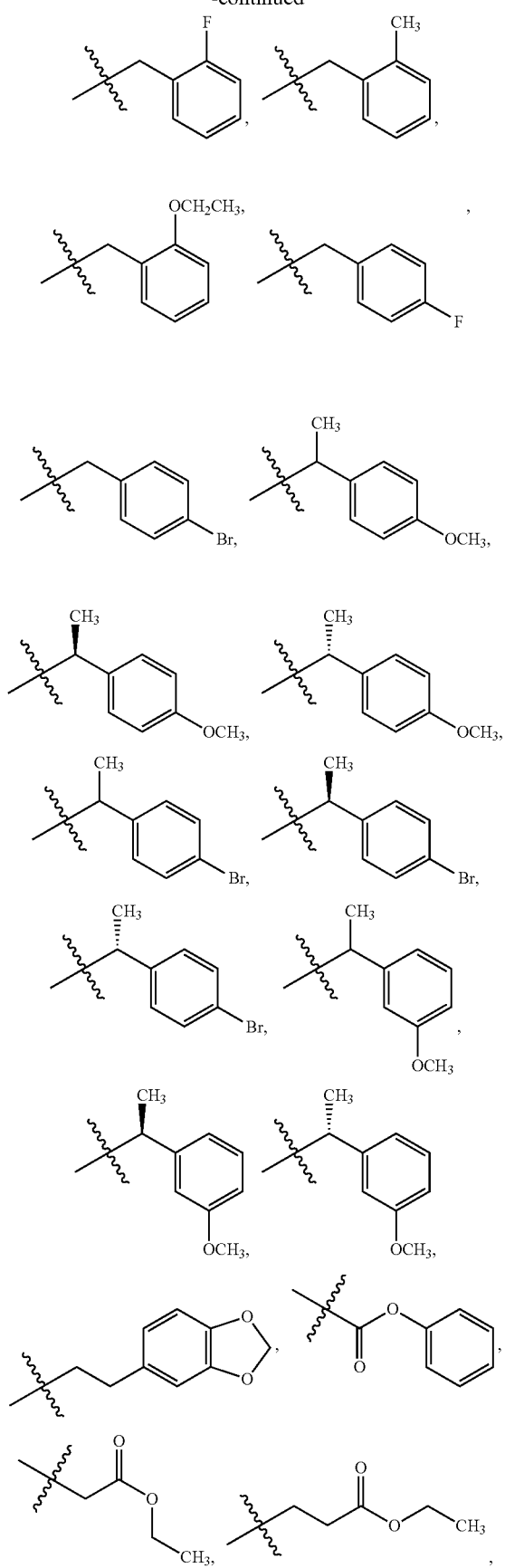
-continued
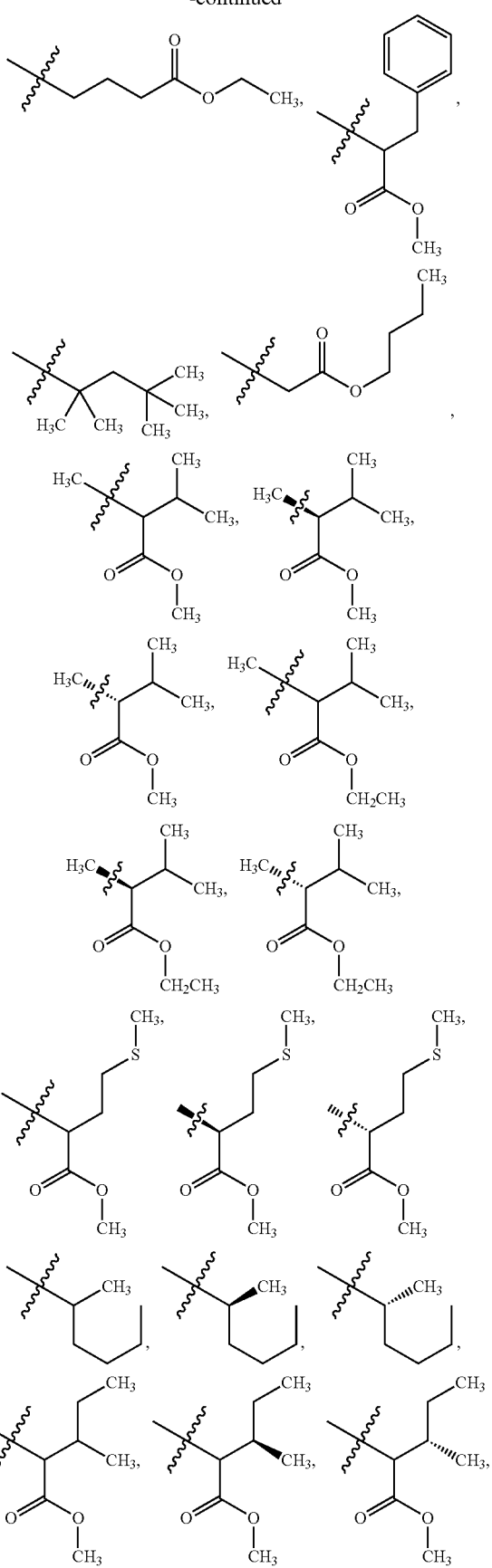

-continued

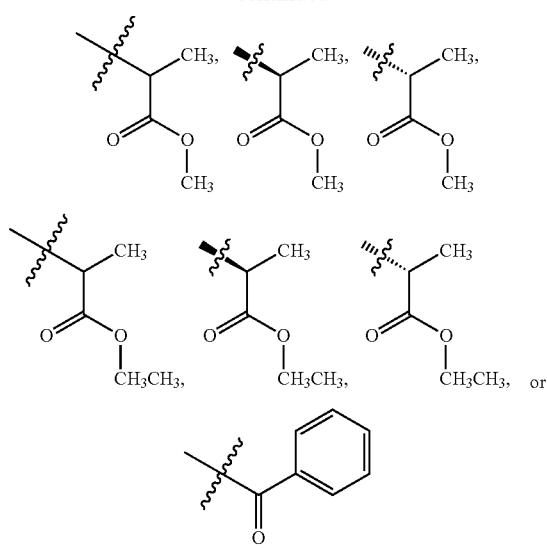

and the symbol ～, when drawn across a bond, indicates the point of attachment to the rest of the molecule.

18. The compound of embodiment 1 or clam 2 or the pharmaceutically-acceptable salt thereof, the tautomer thereof, the pharmaceutically-acceptable salt of the tautomer, or the mixture thereof, wherein $R^1$ is a group of formula

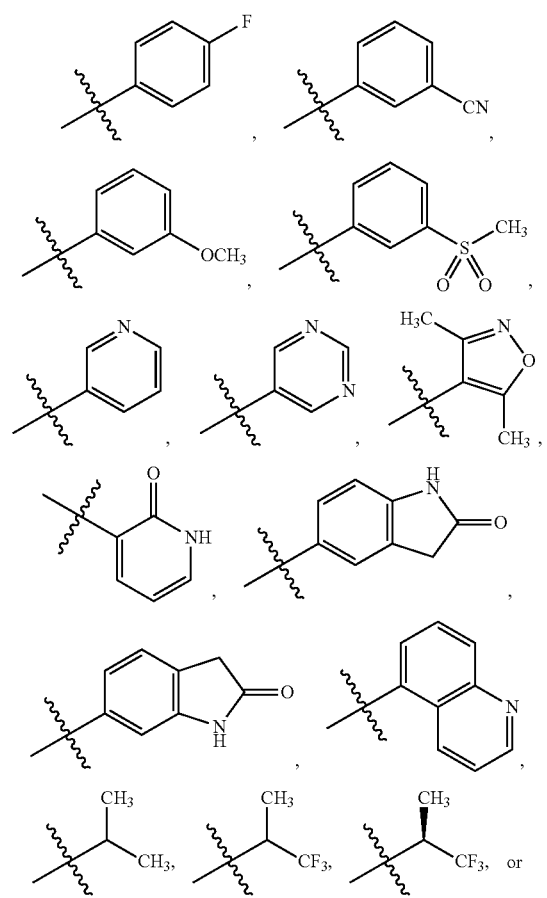

-continued

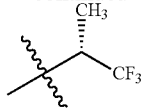

and the symbol ～, when drawn across a bond, indicates the point of attachment to the rest of the molecule.

19. The compound of embodiment 1 or embodiment 2 or the pharmaceutically-acceptable salt thereof, the tautomer thereof, the pharmaceutically-acceptable salt of the tautomer, or the mixture thereof, wherein $R^1$ is

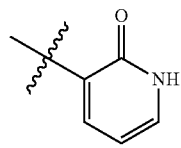 [SMILES: *c1ccc[nH]c1=O]

and the symbol ～, when drawn across a bond, indicates the point of attachment to the rest of the molecule.

20. The compound of embodiment 1 or embodiment 2 or the pharmaceutically-acceptable salt thereof, the tautomer thereof, the pharmaceutically-acceptable salt of the tautomer, or the mixture thereof, wherein $R^1$ is

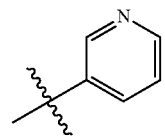 [SMILES: *c1cccnc1]

and the symbol ～, when drawn across a bond, indicates the point of attachment to the rest of the molecule.

21. The compound of embodiment 1 or embodiment 2 or the pharmaceutically-acceptable salt thereof, the tautomer thereof, the pharmaceutically-acceptable salt of the tautomer, or the mixture thereof, wherein $R^1$ is

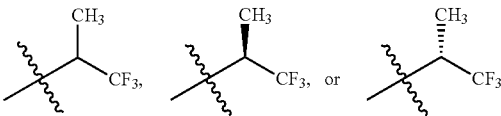

and the symbol ～, when drawn across a bond, indicates the point of attachment to the rest of the molecule.

22. The compound of any one of embodiments 1-4 or 9-21 or the pharmaceutically-acceptable salt thereof, the tautomer thereof, the pharmaceutically-acceptable salt of the tautomer, or the mixture thereof, wherein Y is NH.

23. The compound of any one of embodiments 1-4 or 9-21 or the pharmaceutically-acceptable salt thereof, the tautomer thereof, the pharmaceutically-acceptable salt of the tautomer, or the mixture thereof, wherein Y is O.

24. The compound of any one of embodiments 1-4 or 9-23 or the pharmaceutically-acceptable salt thereof, the tautomer thereof, the pharmaceutically-acceptable salt of the tautomer, or the mixture thereof, wherein $R^5$ is independently, in each instance F or $CF_3$.

25. The compound of embodiment 24 or the pharmaceutically-acceptable salt thereof, the tautomer thereof, the pharmaceutically-acceptable salt of the tautomer, or the mixture thereof, wherein $R^5$ is F.

26. The compound of any one of embodiments 1-4 or 9-25 or the pharmaceutically-acceptable salt thereof, the tautomer thereof, the pharmaceutically-acceptable salt of the tautomer, or the mixture thereof, wherein $R^6$ is F or $CF_3$.

27. The compound of embodiment 26 or the pharmaceutically-acceptable salt thereof, the tautomer thereof, the pharmaceutically-acceptable salt of the tautomer, or the mixture thereof, wherein $R^6$ is $CF_3$.

28. The compound of any one of embodiments 1-4 or 9-27 or the pharmaceutically-acceptable salt thereof, the tautomer thereof, the pharmaceutically-acceptable salt of the tautomer, or the mixture thereof, wherein n is 1.

29. The compound of any one of embodiments 1-4 or 9-27 or the pharmaceutically-acceptable salt thereof, the tautomer thereof, the pharmaceutically-acceptable salt of the tautomer, or the mixture thereof, wherein m is 0 or 1.

30. The compound of embodiment 29 or the pharmaceutically-acceptable salt thereof, the tautomer thereof, the pharmaceutically-acceptable salt of the tautomer, or the mixture thereof, wherein m is 1.

31. The compound of embodiment 29 or the pharmaceutically-acceptable salt thereof, the tautomer thereof, the pharmaceutically-acceptable salt of the tautomer, or the mixture thereof, wherein m is 0.

32. The compound of any one of embodiments 1-4 or 9-27 or the pharmaceutically-acceptable salt thereof, the tautomer thereof, the pharmaceutically-acceptable salt of the tautomer, or the mixture thereof, wherein n is 0.

33. The compound of any one of embodiments 1-4 or 9-32 or the pharmaceutically-acceptable salt thereof, the tautomer thereof, the pharmaceutically-acceptable salt of the tautomer, or the mixture thereof, wherein $R^2$ is —H, halo, or $C_{1-6}$alk substituted by 0, 1, 2 or 3 halo substituents.

34. The compound of embodiment 33 or the pharmaceutically-acceptable salt thereof, the tautomer thereof, the pharmaceutically-acceptable salt of the tautomer, or the mixture thereof, wherein $R^2$ is —H, —F, —Br, —$CF_3$, or $C_{1-6}$alk.

35. The compound of embodiment 34 or the pharmaceutically-acceptable salt thereof, the tautomer thereof, the pharmaceutically-acceptable salt of the tautomer, or the mixture thereof, wherein $R^2$ is —F, —Br, —$CF_3$, or $C_{1-6}$alk.

36. The compound of embodiment 35 or the pharmaceutically-acceptable salt thereof, the tautomer thereof, the pharmaceutically-acceptable salt of the tautomer, or the mixture thereof, wherein $R^2$ is —F.

37. The compound of embodiment 35 or the pharmaceutically-acceptable salt thereof, the tautomer thereof, the pharmaceutically-acceptable salt of the tautomer, or the mixture thereof, wherein $R^2$ is —$CF_3$.

38. The compound of any one of embodiments 1-4 or 9-32 or the pharmaceutically-acceptable salt thereof, the tautomer thereof, the pharmaceutically-acceptable salt of the tautomer, or the mixture thereof, wherein $R^2$ is —$CH_3$, —$CH_2CH_3$, —$CH_2CH_2CH_3$, —$C(CH_3)_3$, —$CH(CH_3)_2$, —$CH_2$—$C(CH_3)_3$, —CH=$CH_2$, —$CH_2$CH=$CH_2$, —C≡C—$CH_3$, or a group of formula or

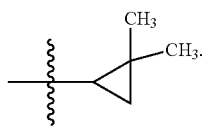

and the symbol ⌇, when drawn across a bond, indicates the point of attachment to the rest of the molecule.

39. The compound of any one of embodiments 1-4 or 9-38 or the pharmaceutically-acceptable salt thereof, the tautomer thereof, the pharmaceutically-acceptable salt of the tautomer, or the mixture thereof, wherein $R^3$ is H, $C_{1-8}$alk, $C_{1-4}$haloalk, halo, or —$OR^a$.

40. The compound of embodiment 39 or the pharmaceutically-acceptable salt thereof, the tautomer thereof, the pharmaceutically-acceptable salt of the tautomer, or the mixture thereof, wherein $R^3$ is H, —$CH_3$, —$CH_2CH_3$, F, Cl, —$OCH_3$, —$OCF_3$, or —$CF_3$.

41. The compound of embodiment 40 or the pharmaceutically-acceptable salt thereof, the tautomer thereof, the pharmaceutically-acceptable salt of the tautomer, or the mixture thereof, wherein $R^3$ is —$CH_3$, —$CH_2CH_3$, F, Cl, —$OCH_3$, —$OCF_3$, or —$CF_3$.

42. The compound of embodiment 41 or the pharmaceutically-acceptable salt thereof, the tautomer thereof, the pharmaceutically-acceptable salt of the tautomer, or the mixture thereof, wherein $R^3$ is —$OCF_3$ or —$CF_3$.

43. The compound of embodiment 42 or the pharmaceutically-acceptable salt thereof, the tautomer thereof, the pharmaceutically-acceptable salt of the tautomer, or the mixture thereof, wherein $R^3$ is —$OCF_3$.

44. The compound of embodiment 42 or the pharmaceutically-acceptable salt thereof, the tautomer thereof, the pharmaceutically-acceptable salt of the tautomer, or the mixture thereof, wherein $R^3$ is —$CF_3$.

45. The compound of embodiment 40 or the pharmaceutically-acceptable salt thereof, the tautomer thereof, the pharmaceutically-acceptable salt of the tautomer, or the mixture thereof, wherein $R^3$ is —H.

46. The compound of any one of embodiments 1-4 or 9-45 or the pharmaceutically-acceptable salt thereof, the tautomer thereof, the pharmaceutically-acceptable salt of the tautomer, or the mixture thereof, wherein $R^4$ is H.

47. The compound of any one of embodiments 1-4 or 9-45 or the pharmaceutically-acceptable salt thereof, the tautomer thereof, the pharmaceutically-acceptable salt of the tautomer, or the mixture thereof, wherein $R^4$ is F, Cl, $C_{1-6}$alk, —$OC_{1-6}$alk, or —$C_{1-3}$haloalk.

48. The compound of embodiment 47 or the pharmaceutically-acceptable salt thereof, the tautomer thereof, the pharmaceutically-acceptable salt of the tautomer, or the mixture thereof, wherein $R^4$ is F, Cl, $CF_3$, $CH_3$, or $OCH_3$.

49. The compound of embodiment 48 or the pharmaceutically-acceptable salt thereof, the tautomer thereof, the pharmaceutically-acceptable salt of the tautomer, or the mixture thereof, wherein $R^4$ is F.

50. The compound of any one of embodiments 1-4 or 9-38 or the pharmaceutically-acceptable salt thereof, the tautomer thereof, the pharmaceutically-acceptable salt of the tautomer, or the mixture thereof, wherein $R^3$ and $R^4$ together form a four-atom unsaturated bridge containing 0 or 1 N atoms, wherein the bridge is substituted by 0, 1 or 2 $R^5$ substituents.

51. The compound of any one of embodiments 1-4 or 9-50 or the pharmaceutically-acceptable salt thereof, the tautomer thereof, the pharmaceutically-acceptable salt of the tautomer, or the mixture thereof, wherein $X^2$ is N.

52. The compound of any one of embodiments 1-4 or 9-50 or the pharmaceutically-acceptable salt thereof, the tautomer thereof, the pharmaceutically-acceptable salt of the tautomer, or the mixture thereof, wherein $X^2$ is CH.

53. The compound of any one of embodiments 1-4 or 9-52 or the pharmaceutically-acceptable salt thereof, the tautomer thereof, the pharmaceutically-acceptable salt of the tautomer, or the mixture thereof, wherein $X^1$ is N.

54. The compound of any one of embodiments 1-4 or 9-52 or the pharmaceutically-acceptable salt thereof, the tautomer thereof, the pharmaceutically-acceptable salt of the tautomer, or the mixture thereof, wherein $X^1$ is $C(R^4)$.

55. The compound of embodiment 54 or the pharmaceutically-acceptable salt thereof, the tautomer thereof, the pharmaceutically-acceptable salt of the tautomer, or the mixture thereof, wherein $R^1$ is CH.

56. The compound of any one of embodiments 1-4 or 9-50 or the pharmaceutically-acceptable salt thereof, the tautomer thereof, the pharmaceutically-acceptable salt of the tautomer, or the mixture thereof, wherein $X^1$ is $C(R^4)$ and $X^2$ is N.

57. The compound of any one of embodiments 1-4 or 9-50 or the pharmaceutically-acceptable salt thereof, the tautomer thereof, the pharmaceutically-acceptable salt of the tautomer, or the mixture thereof, wherein $X^1$ is N and $X^2$ is N.

58. The compound of embodiment 1 or embodiment 2 or the pharmaceutically-acceptable salt thereof, the tautomer thereof, the pharmaceutically-acceptable salt of the tautomer, or the mixture thereof, wherein $X^2$ is N; $R^2$ is F or $CF_3$; m is 0; $X^1$ is CH; $R^4$ is F or H; $R^3$ is $CF_3$ or $OCF_3$; Y is NH; Z is O; and $R^1$ is

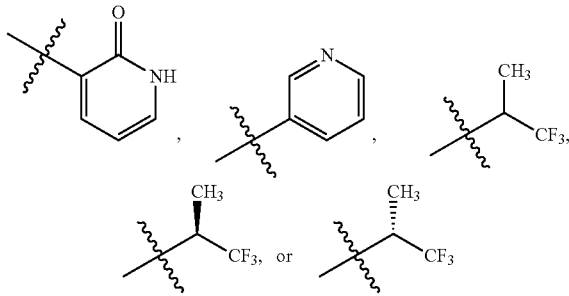

and the symbol ⁓, when drawn across a bond, indicates the point of attachment to the rest of the molecule.

59. The compound of embodiment 1, wherein the compound is
(S)-1-((3-fluoro-4-(trifluoromethyl)phenyl)(3-(trifluoromethyl)pyridin-2-yl)-methyl)-3-(pyridin-3-yl)urea;
(S)-1-((4-methoxy-phenyl)(3-(trifluoro-methyl)-pyridin-2-yl)-methyl)-3-(pyridin-3-yl)-urea;
(S)-1-((3-chlorophenyl)-(3-(trifluoro-methyl)-pyridin-2-yl)-methyl)-3-(Pyridin-3-yl)-urea;
(S)-1-((3-methoxy-phenyl)(3-(trifluoro-methyl)-pyridin-2-yl)-methyl)-3-(pyridin-3-yl)-urea;
(S)-1-((3-fluoro-4-methoxy-phenyl)(3-(trifluoro-methyl)-pyridin-2-yl)-methyl)-3-(pyridin-3-yl)-urea;
(S)-1-(pyridin-3-yl)-3-quinolin-3-yl(3-(trifluoro-methyl)-pyridin-2-yl)-methyl)urea;
(S)-1-((3-methylphenyl)-(3-(trifluoro-methyl)-pyridin-2-yl)-methyl)-3-(pyridin-3-yl)-urea;
(S)-1-((3-fluorophenyl)-(3-(trifluoro-methyl)-pyridin-2-yl)-methyl)-3-(pyridin-3-yl)-urea;
(S)-1-((3-(trifluoro-methyl)-phenyl)(3-(trifluoro-methyl)-pyridin-2-yl)-methyl)-3-(pyridin-3-yl)-urea;
(S)-1-((5-chloroquinolin-3-yl)(3-(trifluoro-methyl)-pyridin-2-yl)-methyl)-3-(pyridin-3-yl)-urea;
(S)-1-(naphthalen-2-yl(3-(trifluoro-methyl)-pyridin-2-yl)-methyl)-3-(pyridin-3-yl)-urea;
(S)-1-((8-chloroquinolin-3-yl)(3-(trifluoro-methyl)-pyridin-2-yl)-methyl)-3-(pyridin-3-yl)-urea;
(S)-1-((3,4-dichlorophenyl)(3-(trifluoro-methyl)-pyridin-2-yl)-methyl)-3-(pyridin-3-yl)-urea;
(S)-1-((8-fluoroquinolin-3-yl)(3-(trifluoro-methyl)-pyridin-2-yl)-methyl)-3-(pyridin-3-yl)-urea;
(S)-1-((3-fluoropyridin-2-yl)(4-(trifluoro-methoxy)-phenyl)-methyl)-3-(pyridin-3-yl)-urea;
(S)-1-((8-methoxy-quinolin-3-yl)-(3-(trifluoro-methyl)-pyridin-2-yl)-methyl)-3-(pyridin-3-yl)-urea;
(S)-1-(pyridin-3-yl)-3-(quinolin-6-yl(3-(trifluoro-methyl)-pyridin-2-yl)-methyl)urea;
(S)-1-((7-methoxy-quinolin-3-yl)-(3-(trifluoro-methyl)-pyridin-2-yl)-methyl)-3-(pyridin-3-yl)-urea;
(S)-1-((4-fluorophenyl)-(3-(trifluoro-methyl)-pyridin-2-yl)-methyl)-3-(pyridin-3-yl)-urea;
(S)-1-(phenyl(3-(trifluoro-methyl)-pyridin-2-yl)-methyl)-3-(pyridin-3-yl)-urea;
1-((4-fluoro-3-(trifluoro-methyl)-phenyl)(3-(trifluoro-methyl)-pyridin-2-yl)-methyl)-3-(pyridin-3-yl)-urea;
1-((4-fluoro-3-(trifluoro-methyl)-phenyl)(3-fluoropyridin-2-yl)methyl)-3-(pyridin-3-yl)-urea;
1-((3-chloro-5-fluorophenyl)-(3-(trifluoro-methyl)-pyridin-2-yl)-methyl)-3-(pyridin-3-yl)-urea;
1-((3-chloro-5-fluorophenyl)-(3-fluoro-pyridin-2-yl)-methyl)-3-(pyridin-3-yl)-urea;
1-(pyridin-3-yl)-3-((3-(trifluoro-methyl)-pyridin-2-yl)(6-(trifluoro-methyl)-pyridin-3-yl)-methyl)urea;
(S)-1-((4-chlorophenyl)-(3-(trifluoro-methyl)-pyridin-2-yl)-methyl)-3-(pyridin-3-yl)-urea;
(S)-1-((4-ethylphenyl)(3-(trifluoro-methyl)-pyridin-2-yl)-methyl)-3-(pyridin-3-yl)-urea;
(S)-1-((3-bromopyridin-2-yl)(4-(trifluoro-methyl)-phenyl)-methyl)-3-(pyridin-3-yl)-urea;
(S)-1-((3-fluoro-4-(trifluoro-methyl)-phenyl)(3-fluoropyridin-2-yl)methyl)-3-(pyridin-3-yl)-urea;
(S)-1-(pyridin-2-yl(4-(trifluoro-methyl)-phenyl)-methyl)-3-(pyridin-3-yl)-urea;
(S)-1-phenyl-3-((4-(trifluoro-methyl)-phenyl)(3-(trifluoro-methyl)-pyridin-2-yl)-methyl)urea;
(S)-1-isopropyl-3-((4-(trifluoro-methyl)-phenyl)(3-(trifluoro-methyl)-pyridin-2-yl)-methyl)urea;
1-((S)-1-(naphthalen-1-yl)ethyl)-3-((S)-(4-(trifluoro-methyl)-phenyl)(3-(trifluoro-methyl)-pyridin-2-yl)-methyl)urea;
(S)-1-(3-phenylpropyl)-3-((4-(trifluoro-methyl)-phenyl)(3-(trifluoro-methyl)-pyridin-2-yl)-methyl)urea;
(S)-1-(phenyl formate)-3-((4-(trifluoro-methyl)-phenyl)(3-(trifluoro-methyl)-pyridin-2-yl)-methyl)urea;
(S)-1-(2-(benzo[d][1,3]dioxol-5-yl)-ethyl)-3-((4-(trifluoro-methyl)-phenyl)(3-(trifluoro-methyl)-pyridin-2-yl)-methyl)urea;
(S)-1-(3-bromophenyl)-3-((4-(trifluoro-methyl)-phenyl)(3-(trifluoro-methyl)-pyridin-2-yl)-methyl)urea;
(S)-ethyl 2-(3-((4-(trifluoro-methyl)-phenyl)(3-(trifluoro-methyl)-pyridin-2-yl)-methyl)ureido)-acetate;

(S)-1-(benzofuran-5-yl)-3-((4-(trifluoro-methyl)-phenyl)(3-(trifluoro-methyl)-pyridin-2-yl)-methyl)urea;
(S)-1-(4-cyanophenyl)-3-((4-(trifluoro-methyl)-phenyl)(3-(trifluoro-methyl)-pyridin-2-yl)-methyl)urea;
(S)-1-((3-bromopyridin-2-yl)(4-(trifluoro-methyl)-phenyl)-methyl)-3-(tert-butyl)urea;
(S)-1-(tert-butyl)-3-((3-(prop-1-yn-1-yl)pyridin-2-yl)(4-(trifluoro-methyl)-phenyl)-methyl)urea;
(S)-1-((3-allylpyridin-2-yl)(4-(trifluoro-methyl)-phenyl)-methyl)-3-(pyridin-3-yl)-urea;
(S)-1-(pyridin-3-yl)-3-((4-(trifluoro-methyl)-phenyl)(3-(trifluoro-methyl)-pyridin-2-yl)-methyl)urea;
(S)-1-(tert-butyl)-3-((4-(trifluoro-methyl)-phenyl)(3-(trifluoro-methyl)-pyridin-2-yl)-methyl)urea;
(S)-1-(4-cyanophenyl)-3-((4-(trifluoro-methyl)-phenyl)(3-(trifluoro-methyl)-pyridin-2-yl)-methyl)urea;
(S)-1-(4-fluoro-phenyl)-3-((4-(trifluoro-methyl)-phenyl)(3-(trifluoro-methyl)-pyridin-2-yl)-methyl)urea;
(S)-1-(2,4-difluoro-phenyl)-3-((4-(trifluoro-methyl)-phenyl)(3-(trifluoro-methyl)-pyridin-2-yl)-methyl)urea;
(S)-1-(3,5-difluoro-phenyl)-3-((4-(trifluoro-methyl)-phenyl)(3-(trifluoro-methyl)-pyridin-2-yl)-methyl)urea;
(S)-1-(2,6-difluoro-phenyl)-3-((4-(trifluoro-methyl)-phenyl)(3-(trifluoro-methyl)-pyridin-2-yl)-methyl)urea;
(S)-1-((3-(prop-1-yn-1-yl)-pyridin-2-yl)(4-(trifluoro-methyl)-phenyl)-methyl)-3-(pyridin-3-yl)-urea;
(S)-1-(3-methoxy-phenyl)-3-((4-(trifluoro-methyl)-phenyl)(3-(trifluoro-methyl)-pyridin-2-yl)-methyl)urea;
(S)-1-(3-(methylsulfonyl)phenyl)-3-((4-(trifluoro-methyl)-phenyl)(3-(trifluoro-methyl)-pyridin-2-yl)-methyl)urea;
1-tetrahydro-2H-pyran-3-yl)-3-((S)-(4-(trifluoro-methyl)-phenyl)(3-(trifluoro-methyl)-pyridin-2-yl)-methyl)urea;
(S)-1-(3,5-dimethylisoxazol-4-yl)-3-((4-(trifluoro-methyl)-phenyl)(3-(trifluoro-methyl)-pyridin-2-yl)-methyl)urea;
1-tetrahydrofuran-3-yl)-3-((S)-(4-(trifluoro-methyl)-phenyl)(3-(trifluoro-methyl)-pyridin-2-yl)-methyl)urea;
(S)-1-(pyrimidin-5-yl)-3-((4-(trifluoro-methyl)-phenyl)(3-(trifluoro-methyl)-pyridin-2-yl)-methyl)urea;
(S)-1-(quinolin-6-yl)-3-((4-(trifluoro-methyl)-phenyl)(3-(trifluoro-methyl)-pyridin-2-yl)-methyl)urea;
(S)-1-(quinolin-3-yl)-3-((4-(trifluoro-methyl)-phenyl)(3-(trifluoro-methyl)-pyridin-2-yl)-methyl)urea;
(S)-1-(quinolin-4-yl)-3-((4-(trifluoro-methyl)-phenyl)(3-(trifluoro-methyl)-pyridin-2-yl)-methyl)urea;
1-((S)-(3-((R)-2,2-dimethylcyclopropyl)pyridin-2-yl)(4-(trifluoro-methyl)-phenyl)-methyl)-3-(pyridin-3-yl)-urea;
(S)-1-((3-neopentylpyridin-2-yl)(4-(trifluoro-methyl)-phenyl)-methyl)-3-(pyridin-3-yl)-urea;
(S)-1-(2,6-dibromo-4-fluorophenyl)-3-((4-(trifluoro-methyl)-phenyl)(3-(trifluoro-methyl)-pyridin-2-yl)-methyl)urea;
1-((3-Sulfonylcyclopentyl)methyl)-3-((S)-(4-(trifluoro-methyl)-phenyl)(3-(trifluoro-methyl)-pyridin-2-yl)-methyl)urea;
1-((S)-3-methylbutan-2-yl)-3-((S)-(4-(trifluoro-methyl)-phenyl)(3-(trifluoro-methyl)-pyridin-2-yl)-methyl)urea;
(S)-ethyl 3-(3-((4-(trifluoro-methyl)-phenyl)(3-(trifluoro-methyl)-pyridin-2-yl)-methyl)ureido)-propanoate;
(S)—N-((4-(trifluoro-methyl)-phenyl)(3-(trifluoro-methyl)-pyridin-2-yl)-methylcarbamoyl)benzamide;
(S)-ethyl 4-(3-((4-(trifluoro-methyl)-phenyl)(3-(trifluoro-methyl)-pyridin-2-yl)-methyl)ureido)-butanoate;
(S)-1-(3-methyl-5-phenylisoxazol-4-yl)-3-((4-(trifluoro-methyl)-phenyl)(3-(trifluoro-methyl)-pyridin-2-yl)-methyl)urea;
1-((R)-1-phenylethyl)-3-((S)-(4-(trifluoro-methyl)-phenyl)(3-(trifluoro-methyl)-pyridin-2-yl)-methyl)urea;
(S)-1-(2-tert-butylphenyl)-3-((4-(trifluoro-methyl)-phenyl)(3-(trifluoro-methyl)-pyridin-2-yl)-methyl)urea;
(S)-1-(3-fluoro-benzyl)-3-((4-(trifluoro-methyl)-phenyl)(3-(trifluoro-methyl)-pyridin-2-yl)-methyl)urea;
(S)-1-(2-chlorobenzyl)-3-((4-(trifluoro-methyl)-phenyl)(3-(trifluoro-methyl)-pyridin-2-yl)-methyl)urea;
(S)-1-(3,4-dimethoxy-phenyl)-3-((4-(trifluoro-methyl)-phenyl)(3-(trifluoro-methyl)-pyridin-2-yl)-methyl)urea;
(S)-benzyl 4-(3-((4-(trifluoro-methyl)-phenyl)(3-(trifluoro-methyl)-pyridin-2-yl)-methyl)ureido)-piperidine-1-carboxylate;
(S)-1-(2,6-dichloropyridin-4-yl)-3-((4-(trifluoro-methyl)-phenyl)(3-(trifluoro-methyl)-pyridin-2-yl)-methyl)urea;
(S)-1-(3-(5-methyl-1,2,4-oxadiazol-3-yl)phenyl)-3-((4-(trifluoro-methyl)-phenyl)(3-(trifluoro-methyl)-pyridin-2-yl)-methyl)urea;
(S)-methyl 4-(methylthio)-2-(3-((S)-(4-(trifluoro-methyl)-phenyl)(3-(trifluoro-methyl)-pyridin-2-yl)-methyl)ureido)-butanoate;
(S)-methyl 2-(3-((S)-(4-(trifluoro-methyl)-phenyl)(3-(trifluoro-methyl)-pyridin-2-yl)-methyl)ureido)-propanoate;
1-((S)-1-(4-methoxy-phenyl)ethyl)-3-((S)-(4-(trifluoro-methyl)-phenyl)(3-(trifluoro-methyl)-pyridin-2-yl)-methyl)urea;
(S)—N-((4-(trifluoro-methyl)-phenyl)(3-(trifluoro-methyl)-pyridin-2-yl)-methylcarbamoyl)ethylamide;
(S)-1-(2,3-dimethoxy-phenethyl)-3-((4-(trifluoro-methyl)-phenyl)(3-(trifluoro-methyl)-pyridin-2-yl)-methyl)urea;
1-((S)-hexan-2-yl)-3-((S)-(4-(trifluoro-methyl)-phenyl)(3-(trifluoro-methyl)-pyridin-2-yl)-methyl)urea;
1-((S)-1-(3-methoxy-phenyl)ethyl)-3-((S)-(4-(trifluoro-methyl)-phenyl)(3-(trifluoro-methyl)-pyridin-2-yl)-methyl)urea;
(S)-1-(2-methylbenzyl)-3-((4-(trifluoro-methyl)-phenyl)(3-(trifluoro-methyl)-pyridin-2-yl)-methyl)urea;
(S)-1-(3-acetylphenyl)-3-((4-(trifluoro-methyl)-phenyl)(3-(trifluoro-methyl)-pyridin-2-yl)-methyl)urea;
(S)-1-(2-fluoro-benzyl)-3-((4-(trifluoro-methyl)-phenyl)(3-(trifluoro-methyl)-pyridin-2-yl)-methyl)urea;
(S)-1-(2,6-diethylphenyl)-3-((4-(trifluoro-methyl)-phenyl)(3-(trifluoro-methyl)-pyridin-2-yl)-methyl)urea;
(S)-1-(2-ethyl-6-methylphenyl)-3-((4-(trifluoro-methyl)-phenyl)(3-(trifluoro-methyl)-pyridin-2-yl)-methyl)urea;
(S)-ethyl 3-(3-((4-(trifluoro-methyl)-phenyl)(3-(trifluoro-methyl)-pyridin-2-yl)-methyl)ureido)-benzoate;
(S)-1-(2-ethyl-6-isopropylphenyl)-3-((4-(trifluoro-methyl)-phenyl)(3-(trifluoro-methyl)-pyridin-2-yl)-methyl)urea;
(S)-1-(2-isopropyl-6-methylphenyl)-3-((4-(trifluoro-methyl)-phenyl)(3-(trifluoro-methyl)-pyridin-2-yl)-methyl)urea;
(S)-1-(3,5-dimethoxy-phenethyl)-3-((4-(trifluoro-methyl)-phenyl)(3-(trifluoro-methyl)-pyridin-2-yl)-methyl)urea;
(S)-ethyl 2-(3-((S)-(4-(trifluoro-methyl)-phenyl)(3-(trifluoro-methyl)-pyridin-2-yl)-methyl)ureido)-propanoate;
(S)-1-(3,4-dimethoxy-phenethyl)-3-((4-(trifluoro-methyl)-phenyl)(3-(trifluoro-methyl)-pyridin-2-yl)-methyl)urea;
(S)-methyl 3-methyl-2-(3-((S)-(4-(trifluoro-methyl)-phenyl)(3-(trifluoro-methyl)-pyridin-2-yl)-methyl)ureido)-butanoate;
(S)-1-(3-cyanophenyl)-3-((4-(trifluoro-methyl)-phenyl)(3-(trifluoro-methyl)-pyridin-2-yl)-methyl)urea;
ethyl 3-methyl-2-(3-((S)-(4-(trifluoro-methyl)-phenyl)(3-(trifluoro-methyl)-pyridin-2-yl)-methyl)ureido)-butanoate;
(3S)-methyl 3-methyl-2-(3-((S)-(4-(trifluoro-methyl)-phenyl)(3-(trifluoro-methyl)-pyridin-2-yl)-methyl)ureido)-pentanoate;

(S)-1-(3-nitrophenyl)-3-((4-(trifluoro-methyl)-phenyl)(3-(trifluoro-methyl)-pyridin-2-yl)-methyl)urea;

1-(1-(4-bromophenyl)-ethyl)-3-((S)-(4-(trifluoro-methyl)-phenyl)(3-(trifluoro-methyl)-pyridin-2-yl)-methyl)urea;

(S)-methyl 3-(3-((4-(trifluoro-methyl)-phenyl)(3-(trifluoro-methyl)-pyridin-2-yl)-methyl)ureido)-benzoate;

(S)-dimethyl 5-(3-((4-(trifluoro-methyl)-phenyl)(3-(trifluoro-methyl)-pyridin-2-yl)-methyl)ureido)-isophthalate;

(S)-butyl 2-(3-((4-(trifluoro-methyl)-phenyl)(3-(trifluoro-methyl)-pyridin-2-yl)-methyl)ureido)-acetate;

(S)-1-(2-(3-(prop-1-en-2-yl)phenyl)-propan-2-yl)-3-((4-(trifluoro-methyl)-phenyl)(3-(trifluoro-methyl)-pyridin-2-yl)-methyl)urea;

(S)-1-(3,5-dimethylphenyl)-3-((4-(trifluoro-methyl)-phenyl)(3-(trifluoro-methyl)-pyridin-2-yl)-methyl)urea;

1-((S)-1-phenylethyl)-3-((S)-(4-(trifluoro-methyl)-phenyl)(3-(trifluoro-methyl)-pyridin-2-yl)-methyl)urea;

(S)-1-(2,5-dimethylphenyl)-3-((4-(trifluoro-methyl)-phenyl)(3-(trifluoro-methyl)-pyridin-2-yl)-methyl)urea;

(S)-1-benzyl-3-((4-(trifluoro-methyl)-phenyl)(3-(trifluoro-methyl)-pyridin-2-yl)-methyl)urea;

(S)-1-(2,5-dimethoxy-phenethyl)-3-((4-(trifluoro-methyl)-phenyl)(3-(trifluoro-methyl)-pyridin-2-yl)-methyl)urea;

(S)-1-((4-(trifluoro-methyl)-phenyl)(3-(trifluoro-methyl)-pyridin-2-yl)-methyl)-3-(3,4,5-trimethoxy-benzyl)urea;

(S)-1-((4-(trifluoro-methyl)-phenyl)(3-(trifluoro-methyl)-pyridin-2-yl)-methyl)-3-(3,4,5-trimethoxy-phenyl)urea;

(S)-1-(thiophen-2-yl)-3-((4-(trifluoro-methyl)-phenyl)(3-(trifluoro-methyl)-pyridin-2-yl)-methyl)urea;

1-((2-bromopyridin-3-yl)(4-(trifluoro-methyl)-phenyl)-methyl)-3-(pyridin-3-yl)-urea;

(S)-1-((2-bromophenyl)-(4-(trifluoro-methyl)-phenyl)-methyl)-3-(pyridin-3-yl)-urea;

(S)-1-((2-bromophenyl)-(4-(trifluoro-methyl)-phenyl)-methyl)-3-tert-butylurea;

(R)-1-((3-fluoro-4-(trifluoro-methyl)-phenyl)(3-(trifluoro-methyl)-phenyl)-methyl)-3-(pyridin-3-yl)-urea;

(S)-methyl 2-(3-((3-fluoro-pyridin-2-yl)(4-(trifluoro-methyl)-phenyl)-methyl)ureido)-benzoate;

(S)-1-(pyridin-3-yl)-3-((4-(trifluoro-methyl)-phenyl)(4-(trifluoro-methyl)-pyridin-3-yl)-methyl)urea;

(S)-1-((3-fluoro-4-(trifluoro-methyl)-phenyl)(2-(trifluoro-methyl)-phenyl)-methyl)-3-(pyridin-3-yl)-urea;

(S)-1-(pyridin-3-yl)-3-((4-(trifluoro-methyl)-phenyl)(3-(trifluoro-methyl)-pyridin-2-yl)-methyl)-thiourea;

(S)-1-tert-butyl-3-((4-(trifluoro-methyl)-phenyl)(3-(trifluoro-methyl)-pyridin-2-yl)-methyl)-thiourea;

(S)-1-(3-iodophenyl)-3-((4-(trifluoro-methyl)-phenyl)(3-(trifluoro-methyl)-pyridin-2-yl)-methyl)urea;

(S)-1-(4-bromobenzyl)-3-((4-(trifluoro-methyl)-phenyl)(3-(trifluoro-methyl)-pyridin-2-yl)-methyl)urea;

(S)-1-(3-ethoxyphenyl)-3-((4-(trifluoro-methyl)-phenyl)(3-(trifluoro-methyl)-pyridin-2-yl)-methyl)urea;

(S)-1-(cyclohexylmethyl)-3-((4-(trifluoro-methyl)-phenyl)(3-(trifluoro-methyl)-pyridin-2-yl)-methyl)urea;

1-((R)-1-(3-methoxy-phenyl)ethyl)-3-((S)-(4-(trifluoro-methyl)-phenyl)(3-(trifluoro-methyl)-pyridin-2-yl)-methyl)urea;

1-((S)-2,3-dihydro-1H-inden-1-yl)-3-((S)-(4-(trifluoro-methyl)-phenyl)(3-(trifluoro-methyl)-pyridin-2-yl)-methyl)urea;

1-((R)-1-(4-methoxy-phenyl)ethyl)-3-((S)-(4-(trifluoro-methyl)-phenyl)(3-(trifluoro-methyl)-pyridin-2-yl)-methyl)urea;

(S)-1-((4-(trifluoro-methyl)-phenyl)(3-(trifluoro-methyl)-pyridin-2-yl)-methyl)-3-(2,4,4-trimethylpentan-2-yl)urea;

(S)-1-(2,6-dichlorophenethyl)-3-((4-(trifluoro-methyl)-phenyl)(3-(trifluoro-methyl)-pyridin-2-yl)-methyl)urea;

(S)-1-(2-ethoxybenzyl)-3-((4-(trifluoro-methyl)-phenyl)(3-(trifluoro-methyl)-pyridin-2-yl)-methyl)urea;

(S)-1-(4-chlorobenzyl)-3-((4-(trifluoro-methyl)-phenyl)(3-(trifluoro-methyl)-pyridin-2-yl)-methyl)urea;

(S)-1-(2,4-dichlorobenzyl)-3-((4-(trifluoro-methyl)-phenyl)(3-(trifluoro-methyl)-pyridin-2-yl)-methyl)urea;

(S)-methyl 3-phenyl-2-(3-((S)-(4-(trifluoro-methyl)-phenyl)(3-(trifluoro-methyl)-pyridin-2-yl)-methyl)ureido)-propanoate;

(S)-1-(2-(methylthio)-phenyl)-3-((4-(trifluoro-methyl)-phenyl)(3-(trifluoro-methyl)-pyridin-2-yl)-methyl)urea;

(S)-1-(4-acetylphenyl)-3-((4-(trifluoro-methyl)-phenyl)(3-(trifluoro-methyl)-pyridin-2-yl)-methyl)urea;

(S)-1-(4-fluoro-3-nitrophenyl)-3-((4-(trifluoro-methyl)-phenyl)(3-(trifluoro-methyl)-pyridin-2-yl)-methyl)urea;

(S)-1-(4-methyl-3-nitrophenyl)-3-((4-(trifluoro-methyl)-phenyl)(3-(trifluoro-methyl)-pyridin-2-yl)-methyl)urea;

(S)-1-(2-methoxy-4-nitrophenyl)-3-((4-(trifluoro-methyl)-phenyl)(3-(trifluoro-methyl)-pyridin-2-yl)-methyl)urea (S)-1-(2-methyl-3-nitrophenyl)-3-((4-(trifluoro-methyl)-phenyl)(3-(trifluoro-methyl)-pyridin-2-yl)-methyl)urea;

(S)-1-(5-methyl-2-nitrophenyl)-3-((4-(trifluoro-methyl)-phenyl)(3-(trifluoro-methyl)-pyridin-2-yl)-methyl)urea;

(S)-1-(4-fluoro-benzyl)-3-((4-(trifluoro-methyl)-phenyl)(3-(trifluoro-methyl)-pyridin-2-yl)-methyl)urea;

(S)-1-(o-tolyl)-3-((4-(trifluoro-methyl)-phenyl)(3-(trifluoro-methyl)-pyridin-2-yl)-methyl)urea;

(S)-1-(2-fluoro-5-methylphenyl)-3-((4-(trifluoro-methyl)-phenyl)(3-(trifluoro-methyl)-pyridin-2-yl)-methyl)urea;

(S)-1-(3-methylbenzyl)-3-((4-(trifluoro-methyl)-phenyl)(3-(trifluoro-methyl)-pyridin-2-yl)-methyl)urea;

(S)-1-(4-(5-oxo-4,5-dihydro-1,2,4-oxadiazol-3-yl)phenyl)-3-((4-(trifluoromethyl)-phenyl)(3-(trifluoromethyl)pyridin-2-yl)methyl)urea;

(S)-1-((3-fluoropyridin-2-yl)(4-(trifluoro-methyl)-phenyl)-methyl)-3-(2-oxoindolin-5-;

1-((S)-(3-(prop-1-yn-1-yl)-pyridin-2-yl)(4-(trifluoro-methyl)-phenyl)-methyl)-3-((S)-1,1,1-trifluoro-propan-2-yl)-urea;

1-((S)-(3-fluoro-4-(trifluoro-methyl)-phenyl)(3-(trifluoro-methyl)-pyridin-2-yl)-methyl)-3-((S)-1,1,1-trifluoro-propan-2-yl)-urea;

1-((S)-(3-fluoro-4-(trifluoro-methyl)-phenyl)(3-(trifluoro-methyl)-pyridin-2-yl)-methyl)-3-((R)-1,1,1-trifluoro-propan-2-yl)-urea;

1-((S)-(4-(trifluoro-methyl)-phenyl)(3-(trifluoro-methyl)-pyridin-2-yl)-methyl)-3-((S)-1,1,1-trifluoro-propan-2-yl)-urea;

1-((S)-(2-bromophenyl)-(4-(trifluoro-methyl)-phenyl)-methyl)-3-((S)-1,1,1-trifluoro-propan-2-yl)-urea;

(S)-1-((3-fluoro-4-(trifluoro-methyl)-phenyl)(3-(trifluoro-methyl)-pyridin-2-yl)-methyl)-3-(pyrimidin-5-yl)urea;

1-((S)-(3-fluoropyridin-2-yl)(4-(trifluoro-methyl)-phenyl)-methyl)-3-((S)-1,1,1-trifluoro-propan-2-yl)-urea;

1-((S)-(3-bromopyridin-2-yl)(4-(trifluoro-methyl)-phenyl)-methyl)-3-((S)-1,1,1-trifluoro-propan-2-yl)-urea;

1-((S)-(3-allylpyridin-2-yl)(4-(trifluoro-methyl)-phenyl)-methyl)-3-((S)-1,1,1-trifluoro-propan-2-yl)-urea;

(S)-1-(2-methoxypyrimidin-5-yl)-3-((4-(trifluoromethyl)phenyl)(3-(trifluoromethyl)pyridin-2-yl)methyl)urea;

(S)-1-((3-fluoro-pyridin-2-yl)(4-(trifluoro-methyl)phenyl)-methyl)-3-(2-methoxypyrimidin-5-yl)-urea;

(S)-1-((3-fluoro-pyridin-2-yl)(4-(trifluoro-methyl)phenyl)-methyl)-3-(1-methyl-2-oxo-1,2-dihydropyridin-4-yl)urea;

(S)-1-((3-fluoro-pyridin-2-yl)(4-(trifluoro-methyl)phenyl)-methyl)-3-(1-methyl-6-oxo-1,6-dihydropyridin-3-yl)urea;
(S)-1-((3-fluoro-pyridin-2-yl)(4-(trifluoro-methyl)phenyl)-methyl)-3-(2-oxo-1,2-dihydropyridin-3-yl)urea;
(S)-1-((3-fluoro-pyridin-2-yl)(4-(trifluoro-methyl)phenyl)-methyl)-3-(2-oxo-1,2-dihydropyridin-4-yl)urea;
(S)-1-((3-fluoro-pyridin-2-yl)(4-(trifluoro-methyl)phenyl)-methyl)-3-(6-oxo-1,6-dihydropyridin-3-yl)urea;
(S)-1-((3-fluoro-pyridin-2-yl)(4-(trifluoro-methyl)phenyl)-methyl)-3-(2-oxoindolin-6-yl)urea;
(S)-1-((3-propylpyridin-2-yl)(4-(trifluoromethyl)phenyl)methyl)-3-(pyridin-3-yl)-urea;
(S)-tert-butyl(pyridin-2-yl(4-(trifluoromethyl)phenyl)methyl)carbamate;
(S)-ethyl((4-(trifluoromethyl)phenyl)(3-(trifluoromethyl)pyridin-2-yl)methyl)-carbamate;
1-(4-fluorophenyl)-3-(phenyl(4-(trifluoromethyl)phenyl)methyl)urea;
(S)-benzyl(pyridin-2-yl(4-(trifluoromethyl)phenyl)methyl)carbamate 2,2,2-trifluoroacetate; or
(S)-tert-butyl((3-bromopyridin-2-yl)(4-(trifluoromethyl)phenyl)methyl)-carbamate; or
the pharmaceutically-acceptable salt thereof, the tautomer thereof, the pharmaceutically-acceptable salt of the tautomer, or the mixture thereof.

60. The compound of embodiment 1, wherein the compound is
(S)-tert-butyl((3-fluoro-4-(trifluoromethoxy)phenyl)(3-fluoropyridin-2-yl)methyl)carbamate;
(S)-isopropyl((3-fluoro-4-(trifluoromethoxy)phenyl)(3-fluoropyridin-2-yl)methyl)carbamate;
(S)-tetrahydro-2H-pyran-4-yl((3-fluoro-4-(trifluoromethoxy)phenyl)(3-fluoropyridin-2-yl)methyl)carbamate;
(S)-oxetan-3-yl((3-fluoro-4-(trifluoromethoxy)phenyl)(3-fluoropyridin-2-yl)methyl)carbamate;
6-oxopiperidin-3-yl((S)-(3-fluoro-4-(trifluoromethoxy)phenyl)(3-fluoropyridin-2-yl)methyl)carbamate;
(S)-1-(quinolin-5-yl)-3-((4-(trifluoromethyl)phenyl)(3-(trifluoromethyl)pyridin-2-yl)methyl)urea;
(S)-4-(3-((3-fluoro-4-(trifluoromethoxy)phenyl)(3-fluoropyridin-2-yl)methyl)ureido)benzoic acid;
(S)-1-(2-chlorophenyl)-3-((4-(trifluoromethyl)pyridin-2-yl)methyl)urea (2,2,2-trifluoro-acetate);
(S)-methyl 2-methyl-3-(3-((4-(trifluoromethyl)phenyl)(3-(trifluoromethyl)pyridin-2-yl)methyl)ureido)benzoate (2,2,2-trifluoro-acetate);
(S)-1-(2-methoxy-5-methylphenyl)-3-((4-(trifluoromethyl)phenyl)(3-(trifluoromethyl)pyridin-2-yl)methyl)urea (2,2,2-trifluoro-acetate);
(S)-1-(3,4-dichlorobenzyl)-3-((4-(trifluoromethyl)phenyl)(3-(trifluoromethyl)pyridin-2-yl)methyl)urea (2,2,2-trifluoro-acetate);
1-(1,2,3,4-tetrahydronaphthalen-1-yl)-3-((S)-(4-(trifluoromethyl)phenyl)(3-(trifluoromethyl)pyridin-2-yl)methyl)urea (2,2,2-trifluoro-acetate);
(S)-1-mesityl-3-((4-(trifluoromethyl)phenyl)(3-(trifluoromethyl)pyridin-2-yl)methyl)urea (2,2,2-trifluoro-acetate);
(S)-ethyl 4-(3-((4-(trifluoromethyl)phenyl)(3-(trifluoromethyl)pyridin-2-yl)methyl)ureido)benzoate (2,2,2-trifluoro-acetate); or
(S)-1-((3-fluoro-4-(trifluoromethoxy)phenyl)(3-fluoropyridin-2-yl)methyl)-3-(pyridin-3-yl)urea; or
the pharmaceutically-acceptable salt thereof, the tautomer thereof, the pharmaceutically-acceptable salt of the tautomer, or the mixture thereof.

61. The compound of embodiment 1, wherein the compound is
(S)-1-((3-fluoro-4-(trifluoromethyl)phenyl)(3-(trifluoromethyl)pyridin-2-yl)-methyl)-3-(pyridin-3-yl)urea;
(S)-1-(pyridin-3-yl)-3-((4-(trifluoromethyl)phenyl)(3-(trifluoromethyl)pyridin-2-yl)methyl)urea;
(S)-1-((3-(prop-1-yn-1-yl)pyridin-2-yl)(4-(trifluoromethyl)phenyl)methyl)-3-(pyridin-3-yl)urea;
1-((S)-(3-((R)-2,2-dimethylcyclopropyl)pyridin-2-yl)(4-(trifluoromethyl)phenyl)methyl)-3-(pyridin-3-yl)urea;
(S)-1-((3-fluoro-4-(trifluoromethyl)phenyl)(3-fluoropyridin-2-yl)methyl)-3-(pyridin-3-yl)urea; or
1-((S)-(3-fluoro-4-(trifluoro-methyl)phenyl)-(3-(trifluoromethyl)pyridin-2-yl)methyl)-3-((S)-1,1,1-trifluoropropan-2-yl)urea; or
the pharmaceutically-acceptable salt thereof, the tautomer thereof, the pharmaceutically-acceptable salt of the tautomer, or the mixture thereof.

62. The compound of embodiment 1, wherein the compound is (S)-1-((3-fluoro-4-(trifluoromethyl)phenyl)(3-(trifluoromethyl)pyridin-2-yl)-methyl)-3-(pyridin-3-yl)urea or the pharmaceutically-acceptable salt thereof, the tautomer thereof, the pharmaceutically-acceptable salt of the tautomer, or the mixture thereof.

63. The compound of embodiment 1, wherein the compound is (S)-1-(pyridin-3-yl)-3-((4-(trifluoromethyl)phenyl)(3-(trifluoromethyl)pyridin-2-yl)methyl)urea or the pharmaceutically-acceptable salt thereof, the tautomer thereof, the pharmaceutically-acceptable salt of the tautomer, or the mixture thereof.

64. The compound of embodiment 1, wherein the compound is (S)-1-((3-(prop-1-yn-1-yl)pyridin-2-yl)(4-(trifluoromethyl)phenyl)methyl)-3-(pyridin-3-yl)urea or the pharmaceutically-acceptable salt thereof, the tautomer thereof, the pharmaceutically-acceptable salt of the tautomer, or the mixture thereof.

65. The compound of embodiment 1, wherein the compound is 1-((S)-(3-((R)-2,2-dimethylcyclopropyl)pyridin-2-yl)(4-(trifluoromethyl)phenyl)methyl)-3-(pyridin-3-yl)urea or the pharmaceutically-acceptable salt thereof, the tautomer thereof, the pharmaceutically-acceptable salt of the tautomer, or the mixture thereof.

66. The compound of embodiment 1, wherein the compound is (S)-1-((3-fluoro-4-(trifluoromethyl)phenyl)(3-fluoropyridin-2-yl)methyl)-3-(pyridin-3-yl)urea or the pharmaceutically-acceptable salt thereof, the tautomer thereof, the pharmaceutically-acceptable salt of the tautomer, or the mixture thereof.

67. The compound of embodiment 1, wherein the compound is 1-((S)-(3-fluoro-4-(trifluoro-methyl)phenyl)-(3-(trifluoro-methyl)pyridin-2-yl)methyl)-3-((S)-1,1,1-trifluoropropan-2-yl)urea or the pharmaceutically-acceptable salt thereof, the tautomer thereof, the pharmaceutically-acceptable salt of the tautomer, or the mixture thereof.

68. The compound of embodiment 1, wherein the compound is (S)-1-((3-fluoro-4-(trifluoromethoxy)phenyl)(3-fluoropyridin-2-yl)methyl)-3-(pyridin-3-yl)urea or the pharmaceutically-acceptable salt thereof, the tautomer thereof, the pharmaceutically-acceptable salt of the tautomer, or the mixture thereof.

69. The compound of embodiment 1, wherein the compound is (S)—N-((3-fluoro-4-(trifluoromethyl)phenyl)(3-(trifluoromethyl)pyridin-2-yl)methyl)-morpholine-4-carboxamide or the pharmaceutically-acceptable salt thereof, the tautomer thereof, the pharmaceutically-acceptable salt of the tautomer, or the mixture thereof.

70. The compound or tautomer of any one of embodiments 1-4 or 9-69 in a neutral form.

71. The compound of any one of embodiments 1-4 or 9-69 in a neutral form.

72. The pharmaceutically-acceptably salt of the compound or the pharmaceutically acceptable salt of the tautomer of any one of embodiments 1-4 or 9-69.

73. The pharmaceutically-acceptably salt of the compound of any one of embodiments 1-4 or 9-69.

74. The pharmaceutically-acceptable salt of the compound of embodiment 73, wherein the salt is a trifluoroacetate or bis trifluoroacetate salt.

75. A pharmaceutical composition comprising the compound according to any one of embodiments 1-4 or 9-69 or the pharmaceutically-acceptable salt thereof, the tautomer thereof, the pharmaceutically-acceptable salt of the tautomer, or the mixture thereof, and a pharmaceutically-acceptable diluent or carrier.

76. A method of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders in a subject, the method comprising administering the compound according to any one of embodiments 1-4 or 9-69 or the pharmaceutically-acceptable salt thereof, the tautomer thereof, the pharmaceutically-acceptable salt of the tautomer, or the mixture thereof to the subject.

77. The method of embodiment 76, wherein the subject is suffering from neuropathic pain.

78. The method of embodiment 76, wherein the subject is suffering from migraine pain.

79. The use of the compound according to any one of embodiments 1-4 or 9-69 or the pharmaceutically-acceptable salt thereof, the tautomer thereof, the pharmaceutically-acceptable salt of the tautomer, or the mixture thereof in the preparation of a medicament.

80. The use of the compound according to any one of embodiments 1-4 or 9-69 or the pharmaceutically-acceptable salt thereof, the tautomer thereof, the pharmaceutically-acceptable salt of the tautomer, or the mixture thereof for treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders in a subject.

81. The use of embodiment 80, wherein the use is for treating neuropathic pain.

82. The use of embodiment 80, wherein the use is for treating migraine.

83. The compound according to any one of embodiments 1-4 or 9-69 or the pharmaceutically-acceptable salt thereof, the tautomer thereof, the pharmaceutically-acceptable salt of the tautomer, or the mixture thereof for treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, depression, anxiety, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders in a subject.

84. The compound of embodiment 83 or the pharmaceutically-acceptable salt thereof, the tautomer thereof, the pharmaceutically-acceptable salt of the tautomer, or the mixture thereof for treating neuropathic pain in a subject.

85. The compound of embodiment 83 or the pharmaceutically-acceptable salt thereof, the tautomer thereof, the pharmaceutically-acceptable salt of the tautomer, or the mixture thereof for treating migraine in a subject.

EXAMPLES

Unless otherwise noted, all materials were obtained from commercial suppliers and used without further purification. All parts are by weight and temperatures are in degrees centigrade unless otherwise indicated. All microwave assisted reactions were conducted with a Smith Synthesizer from Biotage. Mass spectral data was determined by electrospray ionization technique. All examples were purified to >90% purity as determined by high-performance liquid chromatography. Unless otherwise stated, reactions were run at room temperature.

The following abbreviations are used:
CDI—carbonyldiimidazole
DABCO—1,4-diazabicyclo[2.2.2]octane
DCM—dichloromethane
DIPEA—diisopropyl ethylamine
DMSO—dimethyl sulfoxide
DMF—N,N-dimethylformamide
DPPA—diphenylphosphoryl azide
THF—tetrahydrofuran
$Et_2O$—diethyl ether
EtOAc—ethyl acetate
EtOH—ethyl alcohol MeCN—acetonitrile
MeOH—methyl alcohol
NBS—N-bromosuccinimide
n-BuLi—n-butyllithium
t-BuLi—t-butyllithium
TFA—trifluoroacetic acid
h—hour
min—min
rt—room temperature (22-25° C.)
mL milliliters
L microliters
g grams
g micrograms
mg milligrams
μmoL micromolars General Method of Preparation The compounds described herein are prepared using techniques known to one skilled in the art through the reaction sequences depicted in schemes 1-4 as well as by other methods. Furthermore, in the following schemes, where specific acids, bases, reagents, coupling agents, solvents, etc. are mentioned, it is understood that other suitable acids, bases, reagents, coupling agents, solvents, etc. may be used and are included within the scope of the present invention.

Diarylamines used for the synthesis of compounds of the present invention were prepared as described in Scheme 1. 2-Formylpyridnes of the formula (1) were treated with 2-methylpropane-2-sulfinamide and copper sulfate in DCM to give 2-methyl-N-(pyridin-2-ylmethylene)propane-2-sulfinamides of the formula (2a). The compounds of formula (2a) were treated with aryl or heteroaryl metal halides of formula (3) at low temperature to give sulfinamides of the formula (4). Hydrolysis of sulfinamides (4) with hydrochloric acid in MeOH gives diaryl amines of formula (5a).

Scheme 1

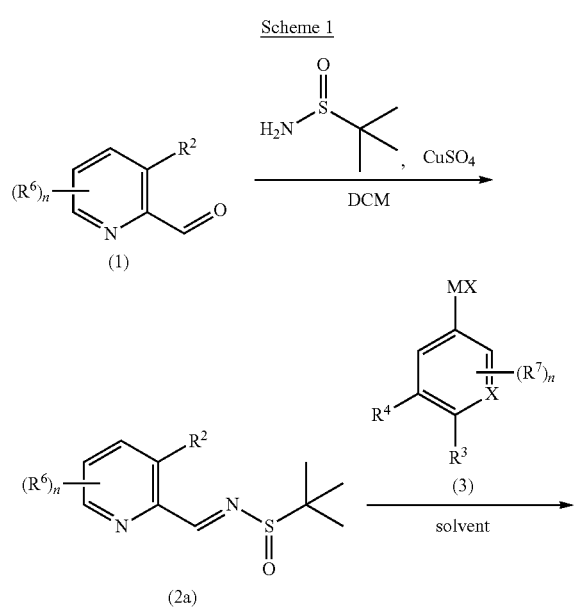

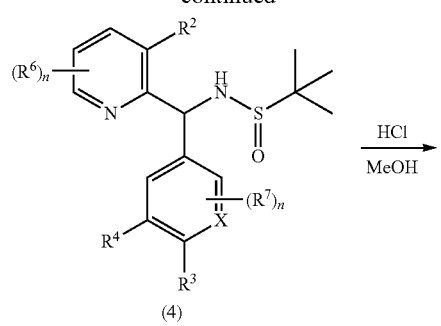

(4)

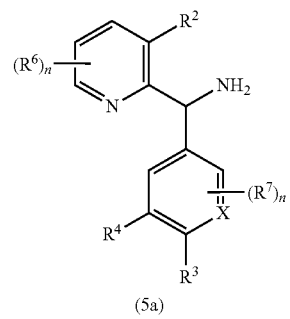

(5a)

An alternative approach to diaryl amines of formula (5a) is shown in Scheme 2. Aryl or heteroaryl aldehydes of the formula (6) were treated with 2-methylpropane-2-sulfinamide and copper sulfate in DCM to give sulfinimines of the formula (7). The compounds of formula (7) were treated with aryl or heteroaryl metal halides of formula (8) at low temperature to give sulfinamides of the formula (4). Hydrolysis of sulfinamides (4) with hydrochloric acid in MeOH gives diaryl amines of formula (5a).

Scheme 2

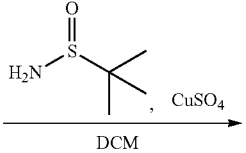

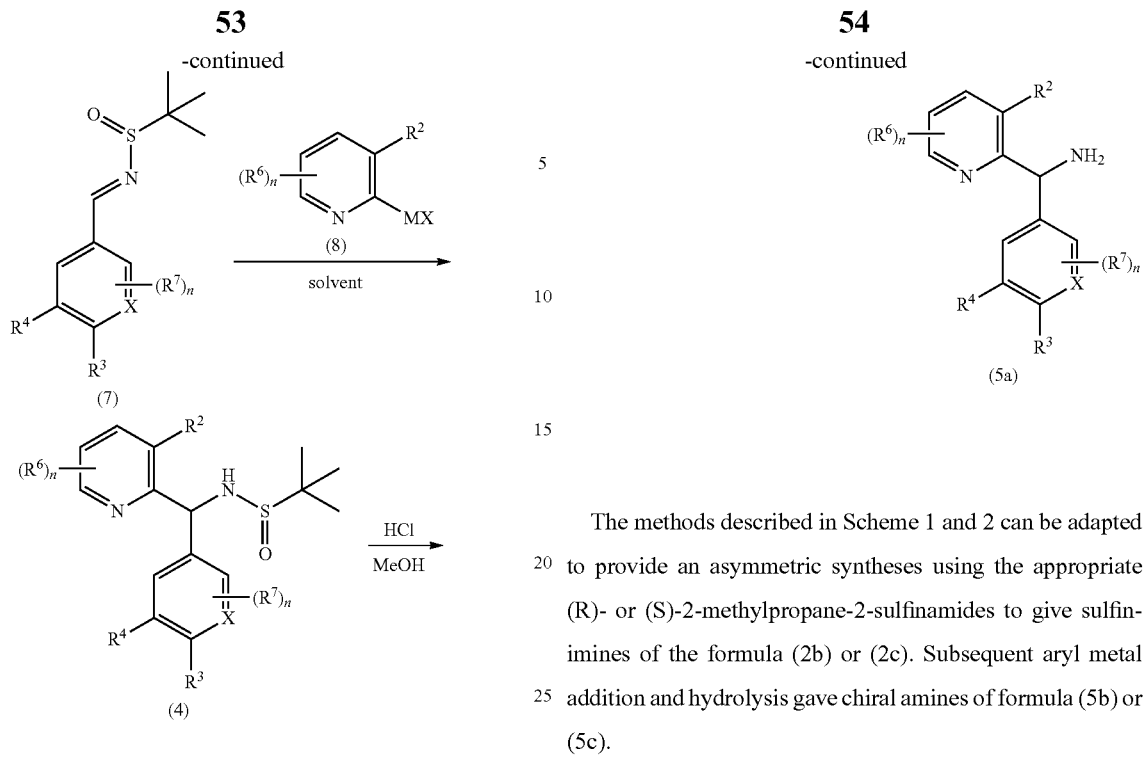
The methods described in Scheme 1 and 2 can be adapted to provide an asymmetric syntheses using the appropriate (R)- or (S)-2-methylpropane-2-sulfinamides to give sulfinimines of the formula (2b) or (2c). Subsequent aryl metal addition and hydrolysis gave chiral amines of formula (5b) or (5c).
Scheme 3
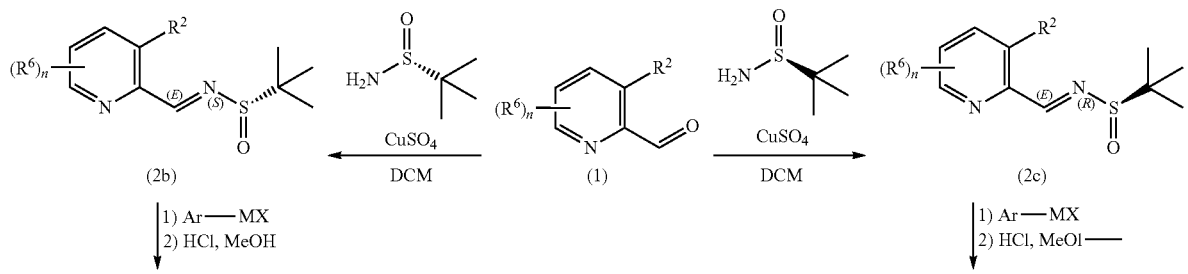

The coupling reaction of diarylamines of formula (5a-c) with the various isocyanates (9) or amines (10) can be performed as shown in Scheme 4 to afford compounds of the present invention (Formula (I)).

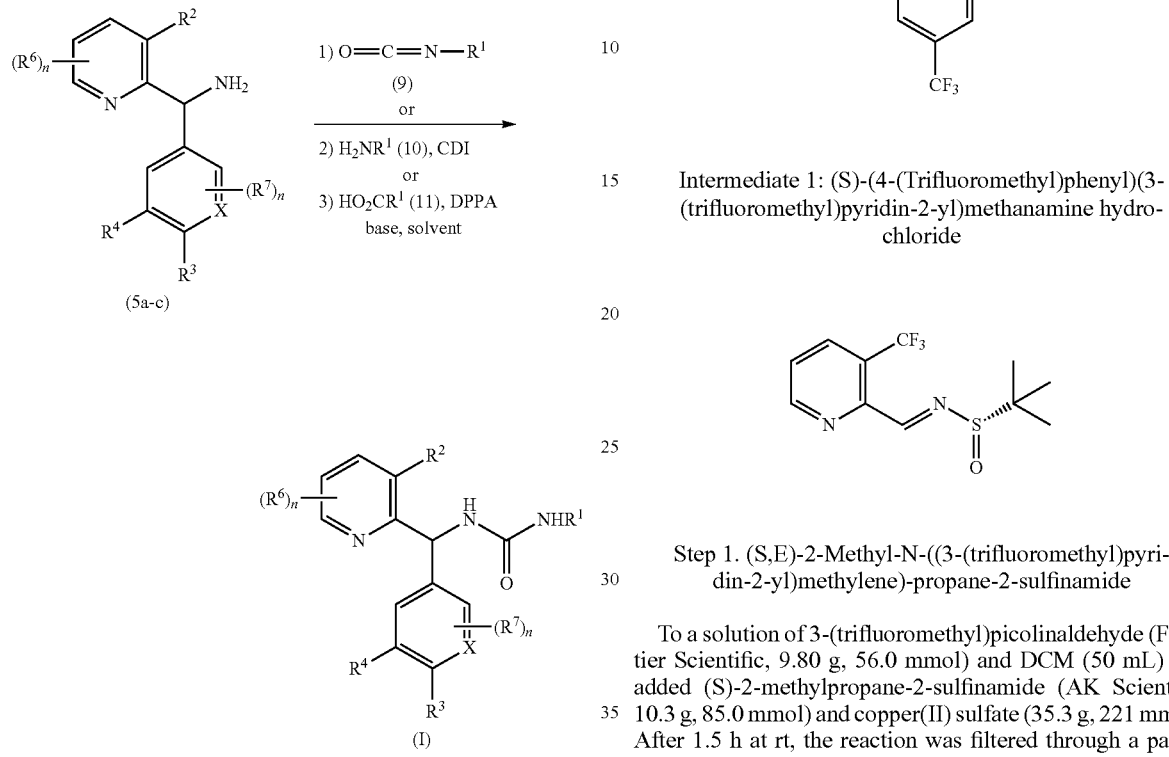

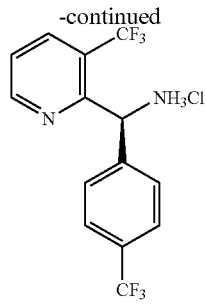

Intermediate 1: (S)-(4-(Trifluoromethyl)phenyl)(3-(trifluoromethyl)pyridin-2-yl)methanamine hydrochloride

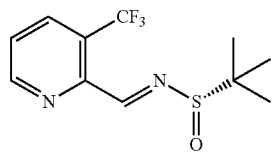 [SMILES: CC(C)(C)[S@](=O)/N=C/c1ncccc1C(F)(F)F]

Step 1. (S,E)-2-Methyl-N-((3-(trifluoromethyl)pyridin-2-yl)methylene)-propane-2-sulfinamide To a solution of 3-(trifluoromethyl)picolinaldehyde (Frontier Scientific, 9.80 g, 56.0 mmol) and DCM (50 mL) was added (S)-2-methylpropane-2-sulfinamide (AK Scientific, 10.3 g, 85.0 mmol) and copper(II) sulfate (35.3 g, 221 mmol). After 1.5 h at rt, the reaction was filtered through a pad of Celite® brand filter agent and the pad of Celite® filter agent was rinsed with DCM. The filtrate was concentrated in vacuo to give a dark green oil. The oil thus obtained was loaded onto a silica gel column and eluted with 30% EtOAc in hexanes to give (S,E)-2-methyl-N-((3-(trifluoromethyl)pyridin-2-yl)methylene)propane-2-sulfinamide (13.2 g, 47.5 mmol, 85.0% yield), as a golden oil. $^1$H NMR (300 MHz, CDCl$_3$) δ ppm 9.02 (d, J=4.3 Hz, 1H), 8.70 (d, J=1.3 Hz, 1H), 8.38 (d, J=7.7 Hz, 1H), 7.79 (dd, J=7.9, 4.8 Hz, 1H), 1.18 (s, 9H). MS (ESI pos. ion) m/z: 279.1 (M+H).

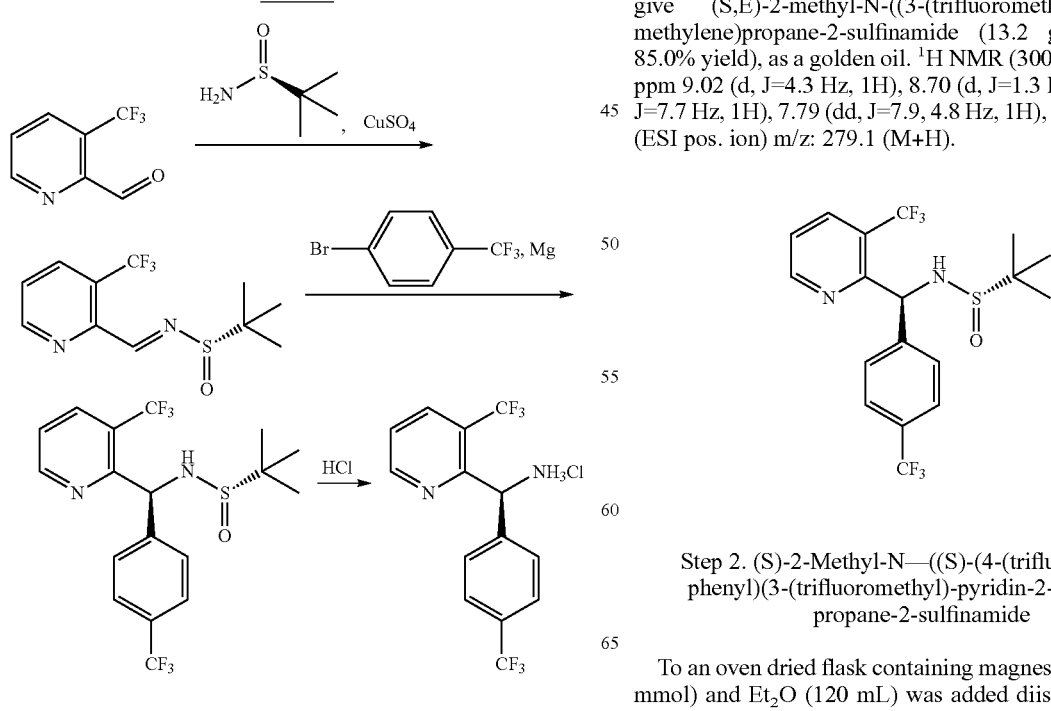

Step 2. (S)-2-Methyl-N—((S)-(4-(trifluoromethyl)phenyl)(3-(trifluoromethyl)-pyridin-2-yl)methyl)propane-2-sulfinamide To an oven dried flask containing magnesium (3.46 g, 143 mmol) and Et$_2$O (120 mL) was added diisobutylaluminum hydride (0.950 mL, 0.950 mmol), and 1-bromo-4-(trifluoromethyl)benzene (1.0 mL, 7.3 mmol) was added dropwise. The solution was allowed to stir for ~20 min during which time the reaction mixture changed from clear to a brownish tint. The reaction was placed in an ice bath and the remaining 1-bromo-4-(trifluoromethyl)benzene (11.5 mL, 83.7 mmol) was added dropwise over 20 minutes. In a separate flask, a solution of (S,E)-2-methyl-N-((3-(trifluoromethyl)pyridin-2-yl)methylene)propane-2-sulfinamide (13.22 g, 47.5 mmol) and THF (80 mL) was cooled to –78° C. for 10 min, and the Grignard solution was added to the solution of sulfinamide over 30 min. After 1 h, the reaction was quenched with saturated aqueous potassium sodium tartrate (10 mL). The reaction was poured into H₂O (150 mL). The entire solution was filtered through a pad of Celite® brand filter agent and the Celite® filter agent was rinsed liberally with THF and EtOAc. The resulting filtrate was separated and the organic layers were concentrated in vacuo to give the product as a dark orange oil. The resulting oil was adsorbed onto a plug of silica gel and chromatographed through a Redi-Sep® pre-packed silica gel column (120 g), eluting with 0% to 40% EtOAc in hexanes, to provide (S)-2-methyl-N—((S)-(4-(trifluoromethyl)phenyl)(3-(trifluoromethyl)pyridin-2-yl)methyl)propane-2-sulfinamide (14.83 g, 34.9 mmol, 77% yield) as a golden oil. ¹H NMR (600 MHz, DMSO-d₆) δ ppm 8.93 (d, J=4.8 Hz, 1H), 7.25 (d, J=7.8 Hz, 1H), 7.71-7.67 (m, 2H), 7.61-7.59 (m, 1H), 7.54 (d, J=8.4 Hz, 2H), 6.08 (d, J=9 Hz, 1H), 5.90 (d, J=9 Hz, 1H), 1.20 (s, 9H). MS (ESI pos. ion) m/z: 425.1 (M+H).

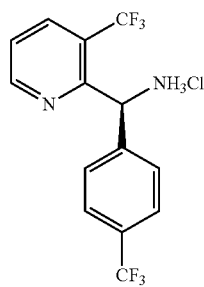

Step 3. (S)-(4-(Trifluoromethyl)phenyl)(3-(trifluoromethyl)pyridin-2-yl)-methanamine hydrochloride To a cooled (0° C.) stirring solution of ((S)-2-methyl-N—((S)-(4-(trifluoro-methyl)phenyl)(3-(trifluoromethyl)pyridin-2-yl)methyl)propane-2-sulfonamide (27 g, 63 mmol) in Et₂O (270 mL) was added 4.0 M HCl in 1,4-dioxane (157 mL, 630 mmol, 10 equiv.) at 0° C. The reaction mixture was then stirred for 30 min at the same temperature. The reaction progress was monitored by TLC (50% EtOAc in petroleum ether). After completion of the reaction, the reaction mixture was concentrated under reduced pressure and triturated with Et₂O to get a white solid which was filtered and dried to give (S)-(4-(trifluoromethyl)phenyl)(3-(trifluoromethyl)pyridin-2-yl)methanamine hydrochloride (14 g, 39 mmol, 70% yield) as a white solid. 1H NMR (600 MHz, DMSO-d₆) δ ppm 9.26 (s, 3H), 9.08 (d, J=4.2 Hz, 1H), 8.35 (d, J=7.8 Hz, 1H), 7.82-7.77 (m, 3H), 7.67 (d, J=8.4 Hz, 2H), 5.94 (s, 1H). MS (ESI pos. ion) m/z: 321.1 (M+H) for free base.

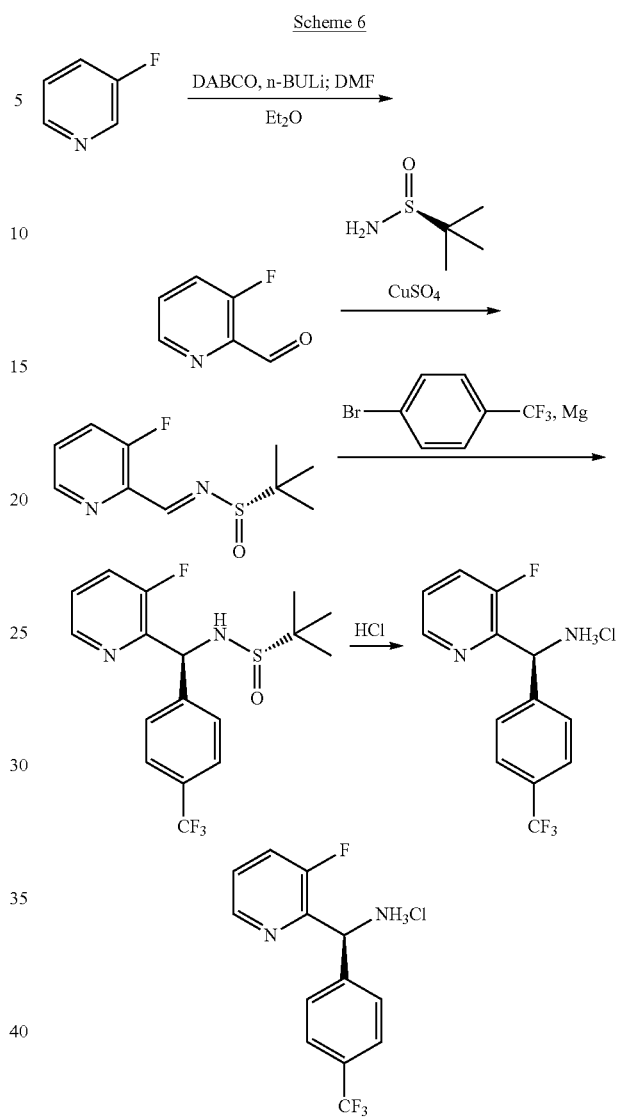

Scheme 6

Intermediate 2: (S)-(4-(Trifluoromethyl)phenyl)(3-(trifluoromethyl)pyridin-2-yl)methanamine hydrochloride

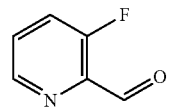

Step 1. 3-Fluoropicolinaldehyde

To a stirred solution of DABCO (262.4 g, 2342 mmol) in anhydrous Et₂O (2.1 L) at –25° C. in a 10 L 3-neck round bottom flask was added n-BuLi (2.5 M in hexane, 938 mL, 2342 mmol). The mixture was stirred between –25° C. to –10° C. for 45 min. and then cooled to –70° C. To the above solution, was added 3-fluoropyridine (206.7 g, 2129 mmol) dropwise, and the reaction mixture was stirred between –70°

C. to −60° C. for 1.5 h before DMF (344 mL, 4258 mmol) was added. The progress of reaction was monitored by TLC (5% EtOAc in Petroleum ether). After 1 h stirring at −70° C., water (800 mL) was added and the reaction was allowed to warm to rt. The layers were separated, and the aqueous layer was extracted with DCM (5×1 L). The combined organic layers were washed with brine and dried over sodium sulphate. After removal of solvent, the residue was purified by silica gel chromatography using a gradient of EtOAc in hexane to give 3-fluoropicolinaldehyde as a pale yellow oil. $^1$H-NMR (400 MHz, CDCl$_3$): δ ppm 10.21 (s, 1H), 8.63 (t, J=2.2 Hz, 1H), 7.54-7.57 (m, 2H). MS (ESI pos. ion) m/z: 126.0 (M+H).

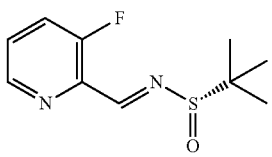

Step 2. (S,E)-N-((3-Fluoropyridin-2-yl)methylene)-2-methylpropane-2-sulfinamide A mixture of 3-fluoropicolinaldehyde (300 g, 2400 mmol), copper sulfate (572 g, 3600 mmol) and (S)-2-methylpropane-2-sulfinamide (319 g, 2640 mmol) in DCM (3 L) in a 10 L 3-neck round bottom flask was stirred for 3 h at rt. The progress of reaction was monitored by TLC (30% EtOAc in petroleum ether). After completion of reaction, the solid was filtered off and the filtrate was concentrated under vacuum. The residue was purified by column chromatography using silica (60-120 mesh) with 20% EtOAc in n-hexane as eluent to give (S,E)-N-((3-fluoropyridin-2-yl)methylene)-2-methylpropane-2-sulfinamide as a yellow oil. $^1$H-NMR (400 MHz, CDCl$_3$): δ ppm 8.89 (s, 1H), 8.64 (s, 1H), 7.55 (t, J=8.4 Hz, 1H), 7.46 (d, J=3.6 Hz, 1H), 1.29 (s, 9H). MS (ESI pos. ion) m/z: 155.0 (M−O and t-Bu).

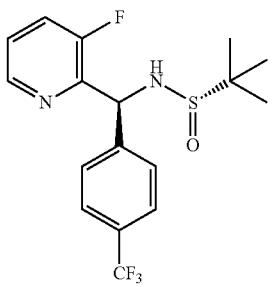 [SMILES: CC(C)(C)[S@](=O)N[C@@H](c1ccc(C(F)(F)F)cc1)c1ncccc1F]

Step-3. (S)—N—((S)-(3-Fluoropyridin-2-yl)(4-(trifluoromethyl)phenyl)methyl)-2-methylpropane-2-sulfinamide To a stirred suspension of magnesium (170 g, 2365 mmol) in THF (1.35 L), was added 4-bromobenzotrifluoride (532 g, 2365 mmol). Stirring was continued for 4 h (cautious: slightly exothermic, cooled with a water bath if needed). The solution was cannulated to a stirred solution of (S,E)-N-((3-fluoropyridin-2-yl)methylene)-2-methylpropane-2-sulfinamide (270 g, 1182 mmol) in THF (1.3 L) at −78° C. dropwise. Stirring was continued for 1 h. The progress of reaction was monitored by TLC (50% EtOAc in petroleum ether). After completion of the reaction, the reaction mixture was quenched with saturated aqueous NH$_4$Cl (2.5 L), and the solution extracted with Et$_2$O (5×500 mL). The organic layers were combined, dried over Na$_2$SO$_4$, concentrated, and purified by column chromatography using silica (100-200 mesh) with 25-30% EtOAc in petroleum ether as eluent to give (S)—N—((S)-(3-fluoropyridin-2-yl)(4(trifluoro-methyl)phenyl)methyl)-2-methylpropane-2-sulfinamide as a brown oil. $^1$H-NMR (400 MHz, CDCl$_3$): δ ppm 8.45 (d, J=3.6 Hz, 1H), 7.73-7.78 (m, 1H), 7.71 (d, J=8.4 Hz, 2H), 7.63 (m, 2H), 7.43-7.48 (m, 1H), 6.23 (d, J=6.8 Hz, 1H), 5.99 (d, J=6.8 Hz, 1H), 1.36 (s, 9H). MS (ESI pos. ion) m/z: 375.1 (M−O and t-Bu).

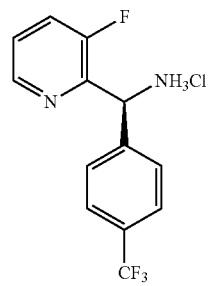

Step 4. (S)-(3-Fluoropyridin-2-yl)(4-(trifluoromethyl)phenyl)methanamine

To a cooled (0° C.) stirring solution of (S)—N—((S)-(3-fluoropyridin-2-yl)(4-(trifluoromethyl)phenyl)methyl)-2-methylpropane-2-sulfinamide (108 g, 288.8 mmol) in DCM:EtOH (1:1, 1080 mL), was added saturated HCl in 1,4-dioxane (216 mL). Stirring was continued for 2 h at 0° C. The progress of reaction was monitored by TLC (100% EtOAc). After completion of the reaction, the reaction mixture was concentrated and triturated with Et$_2$O to give a white solid which was filtered and dried to give (S)-(3-fluoropyridin-2-yl)(4-(trifluoromethyl)phenyl) methanamine hydrochloride as a white solid. $^1$H-NMR (400 MHz, CDCl$_3$) δ ppm 9.23 (s, 3H), 8.60 (d, J=4.8 Hz, 1H), 7.87 (d, J=1.2 Hz, 1H), 7.84 (d, J=8.4 Hz, 2H), 7.72 (d, J=8.4 Hz, 2H), 7.59-7.63 (m, 1H), 6.09 (s, 1H). MS (ESI pos. ion) m/z: 270.1 (M+H).

General Procedure for Preparation of Diarylmethanamines (Intermediates 3-40)

Additional diarylmethanamines were prepared as described in Scheme 5, Steps 2-3; substituting the appropriate starting materials. Variations in methods applied in Scheme 5, Step 2 of the various intermediate syntheses are elaborated below. The amine intermediates were isolated as either the hydrochloride salts or as the free bases.

Method A:

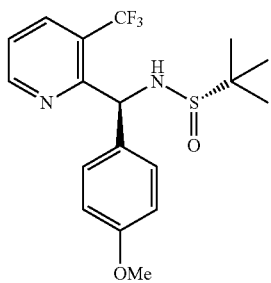 [SMILES: COc1ccc([C@H](N[S@@](=O)C(C)(C)C)c2ncccc2C(F)(F)F)cc1]

Intermediate 3: (S)—N—((S)-(4-Methoxyphenyl)(3-(trifluoromethyl)pyridin-2-yl)methyl)-2-methylpropane-2-sulfinamide Magnesium metal (0.095 g, 3.91 mmol) was activated using a crystal of iodine prior to addition of THF (1 mL). 1-Bromo-4-methoxybenzene (0.400 g, 2.139 mmol) was added, and the reaction was left without stirring for 5 minutes after which initiation was observed. Additional THF (15 mL) was added, and the resulting mixture was stirred for 2 hours. Next, (S,E)-2-methyl-N-((3-(trifluoromethyl)pyridin-2-yl)methylene)propane-2-sulfinamide (0.500 g, 1.797 mmol) was added, and the mixture was stirred for 10 minutes. The reaction was quenched by addition of saturated aqueous NH$_4$Cl (10 mL). H$_2$O (100 mL) and EtOAc (150 mL) were added, and the phases were mixed and separated. The organic layer was dried with magnesium sulfate and evaporated to dryness under reduced pressure. Purification using silica chromatography (hexane to EtOAc gradient) gave (S)—N—((S)-(4-methoxyphenyl)(3-(trifluoromethyl)pyridin-2-yl)methyl)-2-methylpropane-2-sulfinamide.

The sulfinamide prepared as described above was then subjected to hydrolysis conditions similar to those described above in Scheme 5, Step 3 to give Intermediate 3 in Table 1 below.

Method B:

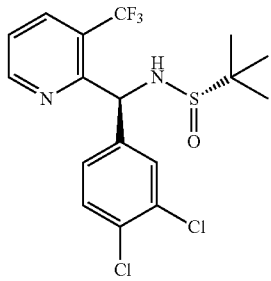 [SMILES: CC(C)(C)[S@](=O)N[C@@H](c1ccc(Cl)c(Cl)c1)c1ncccc1C(F)(F)F]

Intermediate 4: (S)—N—((S)-(3,4-Dichlorophenyl)(3-(trifluoromethyl)pyridin-2-yl)methyl)-2-methylpropane-2-sulfinamide (S,E)-2-Methyl-N-((3-(trifluoromethyl)pyridin-2-yl)methylene)propane-2-sulfinamide (0.493 g, 1.772 mmol) was dissolved in dry THF (10 mL) and cooled in an ice bath. 3,4-Dichlorophenylmagnesium bromide (Aldrich, 0.5 M solution in THF, 4.0 mL, 2.0 mmol) was added, and the reaction mixture was stirred for 5 minutes. Saturated aqueous NH$_4$Cl (10 mL), H$_2$O (100 mL) and EtOAc (100 mL) were added, and the phases were mixed and separated. The organic layer was dried with magnesium sulfate and evaporated to dryness under reduced pressure. Purification using silica chromatography (hexane to EtOAc gradient) gave (S)—N—((S)-(3,4-dichlorophenyl)(3-(trifluoromethyl)pyridin-2-yl)methyl)-2-methylpropane-2-sulfinamide.

The sulfinamide prepared as described above was then subjected to hydrolysis conditions similar to those described above in Scheme 5, Step 3 to give Intermediate 4 in Table 1 below.

Method C:

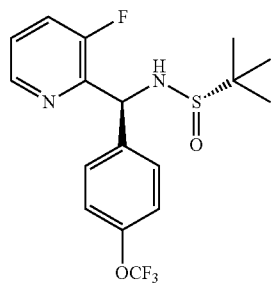 [SMILES: CC(C)(C)[S@](=O)N[C@@H](c1ccc(OC(F)(F)F)cc1)c1ncccc1F]

Intermediate 8: (S)—N—((S)-(3-Fluoropyridin-2-yl)(4-(trifluoromethoxy)-phenyl)methyl)-2-methylpropane-2-sulfinamide 1-Iodo-4-(trifluoromethoxy)benzene (1.00 g, 3.47 mmol) was dissolved in dry THF (10 mL) and cooled in an ice bath. Isopropylmagnesium chloride, lithium chloride complex (14% solution in THF, Aldrich, 3.07 mL, 2.82 mmol) was added, and the mixture was stirred for 10 min. A solution of (S,E)-N-((3-fluoropyridin-2-yl)methylene)-2-methylpropane-2-sulfinamide (0.643 g, 2.82 mmol) in dry THF (10 mL) was added, and the reaction was stirred. After 50 minutes, the reaction was quenched by addition of saturated aqueous NH$_4$Cl (10 mL). H$_2$O (100 mL) and EtOAc (150 mL) were added, and the phases were mixed and separated. The organic layer was dried with magnesium sulfate and evaporated to dryness under reduced pressure. Purification using silica chromatography (hexane to EtOAc gradient) gave the desired (S)—N—((S)-(3-fluoropyridin-2-yl)(4-(trifluoromethoxy)phenyl)methyl)-2-methylpropane-2-sulfinamide.

The sulfinamide was then subjected to hydrolysis conditions similar to those described above in Scheme 6, Step 4 to give Intermediate 8 in Table 1 below.

TABLE 1

Diarylmethanamines prepared analogous to Scheme 5 and 6
(Intermediates 3-39).

| Intermediate | Method | Aryl Halide or Grignard in Step 2 | Structure | Name | Mol. Formula (Mol. Wt.) |
|---|---|---|---|---|---|
| 3 | A | 4-bromoanisole (Br, OMe) | 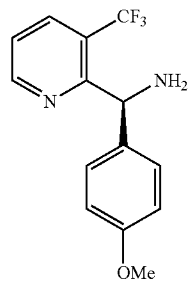 [SMILES: COc1ccc([C@H](N)c2ncccc2C(F)(F)F)cc1] | (S)-(4-methoxyphenyl)(3-(trifluoromethyl)-pyridin-2-yl)-methanamine hydrochloride | $C_{14}H_{13}F_3N_2O$ (282.26) |
| 4 | B | 3,4-dichlorophenylmagnesium bromide (MgBr, Cl, Cl) | 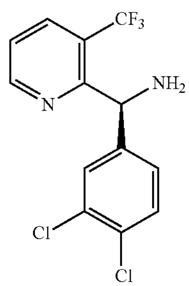 [SMILES: N[C@@H](c1ccc(Cl)c(Cl)c1)c1ncccc1C(F)(F)F] | (S)-(3,4-dichlorophenyl)(3-(trifluoromethyl)-pyridin-2-yl)-methanamine | $C_{13}H_9Cl_2F_3N_2$ (321.13) |
| 5 | A | 4-bromo-2-fluoroanisole (Br, F, OMe) | 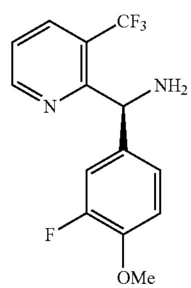 [SMILES: COc1ccc([C@H](N)c2ncccc2C(F)(F)F)cc1F] | (S)-(3-fluoro-4-methoxyphenyl)(3-(trifluoromethyl)-pyridin-2-yl)-methanamine | $C_{14}H_{12}F_4N_2O$ (330.25) |
| 6[2] | A | (Br, F$_3$C, F) | 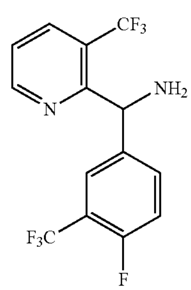 [SMILES: NC(c1ccc(F)c(C(F)(F)F)c1)c1ncccc1C(F)(F)F] | (4-fluoro-3-(trifluoromethyl)-phenyl)(3-(trifluoromethyl)-pyridin-2-yl)-methanamine | $C_{14}H_9F_7N_2$ (338.22) |
| 7 | A | (Br, F, CF$_3$) | 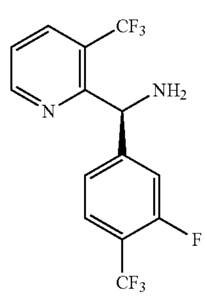 [SMILES: N[C@@H](c1ccc(C(F)(F)F)c(F)c1)c1ncccc1C(F)(F)F] | (S)-(3-fluoro-4-(trifluoromethyl)-phenyl)(3-(trifluoromethyl)-pyridin-2-yl)-methanamine | $C_{14}H_9F_7N_2$ (338.22) |

TABLE 1-continued

Diarylmethanamines prepared analogous to Scheme 5 and 6 (Intermediates 3-39).

| Intermediate | Method | Aryl Halide or Grignard in Step 2 | Structure | Name | Mol. Formula (Mol. Wt.) |
|---|---|---|---|---|---|
| 8 | C | 4-iodo-(trifluoromethoxy)benzene | 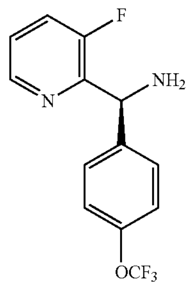 [SMILES: N[C@@H](c1ccc(OC(F)(F)F)cc1)c1ncccc1F] | (S)-(3-fluoropyridin-2-yl)-(4-(trifluoromethoxy)phenyl)-methanamine | $C_{14}H_{10}F_4N_2O$ (286.22) |
| 9[2] | A | 4-bromo-1-fluoro-2-(trifluoromethyl)benzene | 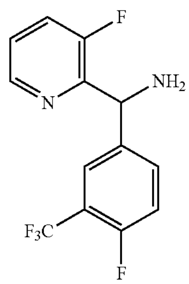 [SMILES: NC(c1ccc(F)c(C(F)(F)F)c1)c1ncccc1F] | (4-fluoro-3-(trifluoromethyl)phenyl)(3-fluoropyridin-2-yl)-methanamine | $C_{14}H_9F_7N_2$ (338.22) |
| 10 | C | 4-iodochlorobenzene | 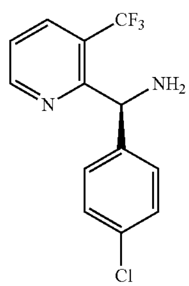 [SMILES: N[C@@H](c1ccc(Cl)cc1)c1ncccc1C(F)(F)F] | (S)-(4-chlorophenyl)(3-(trifluoromethyl)-pyridin-2-yl)-methanamine | $C_{13}H_{10}ClF_3N_2$ (286.68) |
| 11 | C | 8-chloro-3-iodoquinoline | 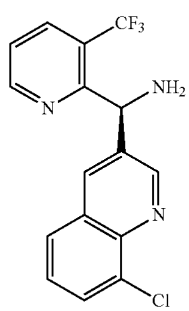 [SMILES: N[C@@H](c1cnc2c(Cl)cccc2c1)c1ncccc1C(F)(F)F] | (S)-(8-chloroquinolin-3-yl)(3-(trifluoromethyl)-pyridin-2-yl)-methanamine | $C_{16}H_{11}ClF_3N_3$ (337.73) |
| 12 | C | 3-iodo-7-methoxyquinoline | 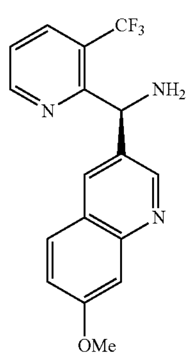 [SMILES: COc1ccc2cc([C@H](N)c3ncccc3C(F)(F)F)cnc2c1] | (S)-(7-methoxyquinolin-3-yl)(3-(trifluoromethyl)-pyridin-2-yl)-methanamine | $C_{17}H_{14}F_3N_3O$ (333.31) |

TABLE 1-continued

Diarylmethanamines prepared analogous to Scheme 5 and 6
(Intermediates 3-39).

| Intermediate | Method | Aryl Halide or Grignard in Step 2 | Structure | Name | Mol. Formula (Mol. Wt.) |
|---|---|---|---|---|---|
| 13 | C | 5-chloro-3-iodoquinoline | (S)-(3-(trifluoromethyl)pyridin-2-yl)(5-chloroquinolin-3-yl)methanamine structure | (S)-(5-chloroquinolin-3-yl)(3-(trifluoromethyl)-pyridin-2-yl)-methanamine | $C_{16}H_{11}ClF_3N_3$ (337.73) |
| 14 | C | 3-iodoquinoline | (S)-quinolin-3-yl(3-(trifluoromethyl)pyridin-2-yl)methanamine structure | (S)-quinolin-3-yl(3-(trifluoromethyl)-pyridin-2-yl)-methanamine | $C_{16}H_{12}F_3N_3$ (303.28) |
| 15 | A | 1-bromo-3-chlorobenzene | (S)-(3-chlorophenyl)(3-(trifluoromethyl)pyridin-2-yl)methanamine structure | (S)-(3-chlorophenyl)(3-(trifluoromethyl)-pyridin-2-yl)-methanamine | $C_{13}H_{10}ClF_3N_2$ (286.68) |
| 16[2] | A | 1-bromo-3-chloro-5-fluorobenzene | (3-chloro-5-fluorophenyl)(3-(trifluoromethyl)pyridin-2-yl)methanamine structure | (3-chloro-5-fluoro-phenyl)(3-(trifluoromethyl)-pyridin-2-yl)-methanamine | $C_{13}H_9ClF_4N_2$ (304.67) |
| 17 | A | 2-bromonaphthalene | (S)-naphthalen-2-yl(3-(trifluoromethyl)pyridin-2-yl)methanamine structure | (S)-naphthalen-2-yl(3-(trifluoromethyl)-pyridin-2-yl)-methanamine | $C_{17}H_{13}F_3N_2$ (302.29) |

TABLE 1-continued

Diarylmethanamines prepared analogous to Scheme 5 and 6
(Intermediates 3-39).

| Inter-mediate | Method | Aryl Halide or Grignard in Step 2 | Structure | Name | Mol. Formula (Mol. Wt.) |
|---|---|---|---|---|---|
| 18 | B | 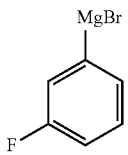 | 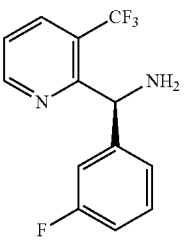 [SMILES: N[C@@H](c1cccc(F)c1)c1ncccc1C(F)(F)F] | (S)-(3-fluoro-phenyl)(3-(trifluoro-methyl)-pyridin-2-yl)-methanamine | $C_{13}H_{10}F_4N_2$ (270.23) |
| 19 | A | 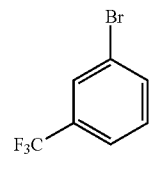 | 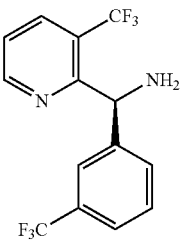 [SMILES: N[C@@H](c1cccc(C(F)(F)F)c1)c1ncccc1C(F)(F)F] | (S)-(3-(trifluoro-methyl)-phenyl)(3-(trifluoro-methyl)-pyridin-2-yl)-methanamine | $C_{14}H_{10}F_6N_2$ (320.23) |
| 20 | C | 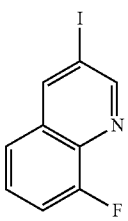 | 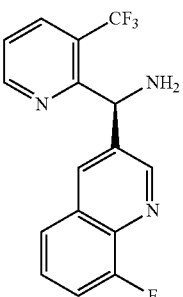 | (S)-(8-fluoro-quinolin-3-yl)(3-(trifluoro-methyl)-pyridin-2-yl)-methanamine | $C_{16}H_{11}F_4N_3$ (321.27) |
| 21 | B | 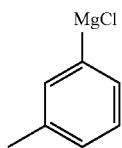 | 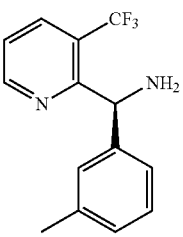 [SMILES: Cc1cccc([C@H](N)c2ncccc2C(F)(F)F)c1] | (S)-m-tolyl(3-(trifluoro-methyl)-pyridin-2-yl)-methanamine | $C_{14}H_{13}F_3N_2$ (266.26) |
| 22 | C | 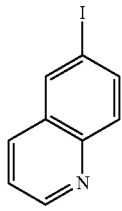 | 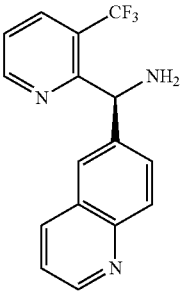 [SMILES: N[C@@H](c1ccc2ncccc2c1)c1ncccc1C(F)(F)F] | (S)-quinolin-6-yl(3-(trifluoro-methyl)-pyridin-2-yl)methanamine | $C_{16}H_{12}F_3N_3$ (303.28) |

TABLE 1-continued

Diarylmethanamines prepared analogous to Scheme 5 and 6
(Intermediates 3-39).

| Intermediate | Method | Aryl Halide or Grignard in Step 2 | Structure | Name | Mol. Formula (Mol. Wt.) |
|---|---|---|---|---|---|
| 23 | C | 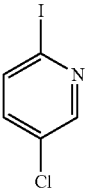 | 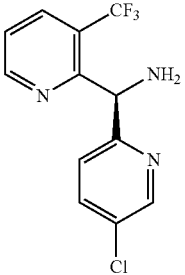 [SMILES: N[C@@H](c1ccc(Cl)cn1)c1ncccc1C(F)(F)F] | (S)-(5-chloropyridin-2-yl)(3-(trifluoromethyl)-pyridin-2-yl)methanamine | $C_{12}H_9ClF_3N_3$ (287.67) |
| 24 | C | 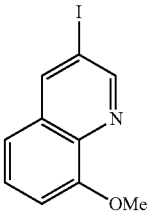 [SMILES: COc1cccc2cc(I)cnc12] | 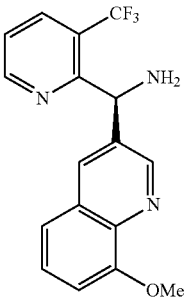 [SMILES: COc1cccc2cc([C@H](N)c3ncccc3C(F)(F)F)cnc12] | (S)-(8-methoxyquinolin-3-yl)(3-(trifluoromethyl)-pyridin-2-yl)-methanamine | $C_{14}H_{10}F_6N_2$ (333.31) |
| 25 | B | 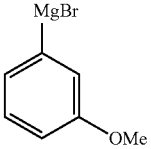 | 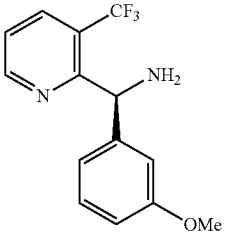 [SMILES: COc1cccc([C@H](N)c2ncccc2C(F)(F)F)c1] | (S)-(3-methoxyphenyl)(3-(trifluoromethyl)-pyridin-2-yl)-methanamine | $C_{14}H_{13}F_3N_2O$ (282.26) |
| 26[2] | A | 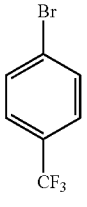 | 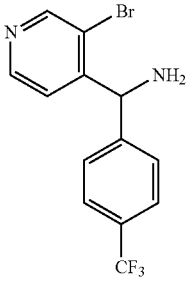 [SMILES: NC(c1ccc(C(F)(F)F)cc1)c1ccncc1Br] | (3-bromopyridin-4-yl)(4-(trifluoromethyl)-phenyl)-methanamine | $C_{13}H_{10}BrF_3N_2$ (331.13) |
| 27 | B | 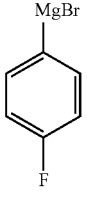 | 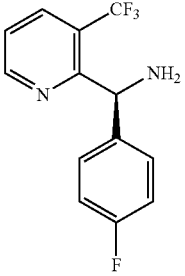 [SMILES: N[C@@H](c1ccc(F)cc1)c1ncccc1C(F)(F)F] | (S)-(4-fluorophenyl)(3-(trifluoromethyl)-pyridin-2-yl)-methanamine | $C_{13}H_{10}F_4N_2$ (270.23) |

TABLE 1-continued

Diarylmethanamines prepared analogous to Scheme 5 and 6
(Intermediates 3-39).

| Intermediate | Method | Aryl Halide or Grignard in Step 2 | Structure | Name | Mol. Formula (Mol. Wt.) |
|---|---|---|---|---|---|
| 28 | B | PhMgBr | 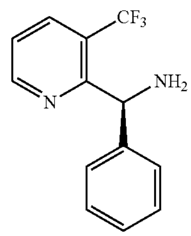 [SMILES: N[C@@H](c1ccccc1)c1ncccc1C(F)(F)F] | (S)-phenyl(3-(trifluoromethyl)-pyridin-2-yl)-methanamine | $C_{13}H_{11}F_3N_2$ (252.24) |
| 29 | B | 4-ethylphenyl-MgBr | 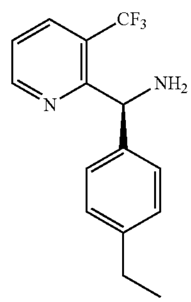 [SMILES: CCc1ccc([C@H](N)c2ncccc2C(F)(F)F)cc1] | (S)-(4-ethylphenyl)-(3-(trifluoromethyl)-pyridin-2-yl)-methanamine | $C_{15}H_{15}F_3N_2$ (280.29) |
| 30 | A | 3-bromo-(trifluoromethyl)benzene | 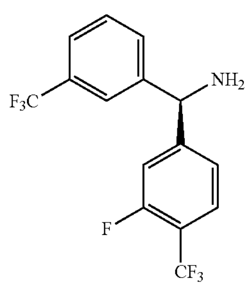 [SMILES: N[C@H](c1cccc(C(F)(F)F)c1)c1ccc(C(F)(F)F)c(F)c1] | (R)-(3-fluoro-4-(trifluoromethyl)-phenyl)(3-(trifluoromethyl)-phenyl)-methanamine | $C_{15}H_{10}F_7N$ (337.24) |
| 31[2] | A | 4-bromo-(trifluoromethyl)benzene | 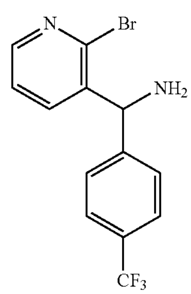 [SMILES: NC(c1ccc(C(F)(F)F)cc1)c1cccnc1Br] | (2-bromopyridin-3-yl)(4-(trifluoromethyl)-phenyl)-methanamine | $C_{13}H_{10}BrF_3N_2$ (331.13) |
| 32 | A | 4-bromo-2-fluoro-1-(trifluoromethyl)benzene | 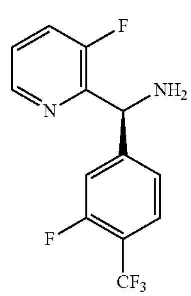 [SMILES: N[C@@H](c1ccc(C(F)(F)F)c(F)c1)c1ncccc1F] | (S)-(3-fluoro-4-(trifluoromethyl)-phenyl)(3-fluoropyridin-2-yl)-methanamine | $C_{13}H_9F_5N_2$ (288.22) |

TABLE 1-continued

Diarylmethanamines prepared analogous to Scheme 5 and 6
(Intermediates 3-39).

| Inter-mediate | Method | Aryl Halide or Grignard in Step 2 | Structure | Name | Mol. Formula (Mol. Wt.) |
|---|---|---|---|---|---|
| 33[2] | A | 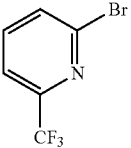 | 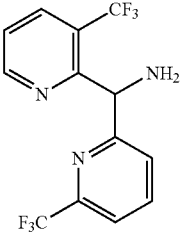 [SMILES: NC(c1cccc(C(F)(F)F)n1)c1ncccc1C(F)(F)F] | (3-(trifluoro-methyl)-pyridin-2-yl)-(6-(trifluoro-methyl)-pyridin-2-yl)-methanamine | $C_{13}H_9F_6N_3$ (321.22) |
| 34[2] | A | 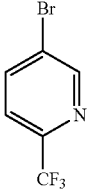 | 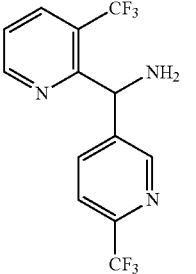 [SMILES: NC(c1ccc(C(F)(F)F)nc1)c1ncccc1C(F)(F)F] | (3-(trifluoro-methyl)-pyridin-2-yl)-(6-(trifluoro-methyl)-pyridin-3-yl)-methanamine | $C_{13}H_9F_6N_3$ (321.22) |
| 35[2] | A | 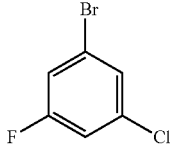 | 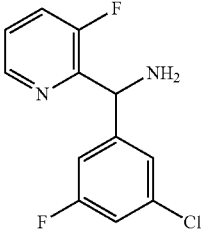 [SMILES: NC(c1cc(F)cc(Cl)c1)c1ncccc1F] | (3-chloro-5-fluoro-phenyl)(3-fluoropyridin-2-yl)-methanamine | $C_{12}H_9ClF_2N$ (254.66) |
| 36[1] | A | 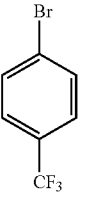 | 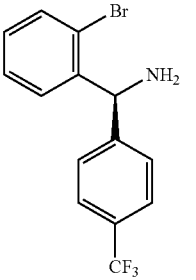 [SMILES: N[C@@H](c1ccc(C(F)(F)F)cc1)c1ccccc1Br] | (S)-(2-bromophenyl)(4-(trifluoro-methyl)-phenyl)-methanamine | $C_{14}H_{11}BrF_3N$ (330.14) |
| 37[1] | A | 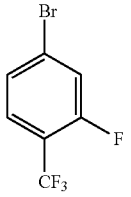 | 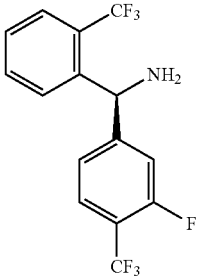 [SMILES: N[C@@H](c1ccc(C(F)(F)F)c(F)c1)c1ccccc1C(F)(F)F] | (S)-(3-fluoro-4-(trifluoro-methyl)-phenyl)(2-(trifluoro-methyl)-phenyl)-methanamine | $C_{15}H_{10}F_7N$ (337.24) |

TABLE 1-continued

Diarylmethanamines prepared analogous to Scheme 5 and 6 (Intermediates 3-39).

| Inter-mediate | Method | Aryl Halide or Grignard in Step 2 | Structure | Name | Mol. Formula (Mol. Wt.) |
|---|---|---|---|---|---|
| 38[1] | A |  | 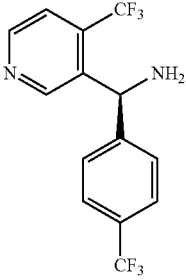 [SMILES: N[C@@H](c1ccc(C(F)(F)F)cc1)c1cnccc1C(F)(F)F] | (S)-(4-(trifluoro-methyl)-phenyl)(4-(trifluoro-methyl)-pyridin-3-yl)-methanamine | $C_{14}H_{10}F_6N_2$ (230.23) |
| 39 | A | 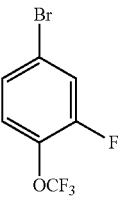 | 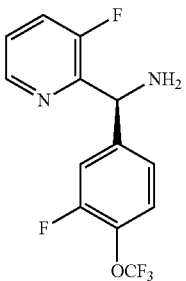 [SMILES: N[C@@H](c1ccc(OC(F)(F)F)c(F)c1)c1ncccc1F] | (S)-(3-fluoro-4-(trifluoromethoxy)phenyl)(3-fluoropyridin-2-yl)methanamine | C13H9F5N2O (304.22) |

[1] These amines were prepared employing (R)-2-methylpropane-2-sulfinamide in the first step (Scheme 5). For reversal of stereochemistry observed in the Ellman sulfonylimine chemistry observed with 2-pyridyl substrates, see Kuduk, S.D.; DiPardo, R. M.; Chang, R. K.; Ng, C.; Bock, M. G. Tetrahedron Lett. 2004, 45, 6641-6643.
[2] Prepared employing racemic 2-methylpropane-2-sulfinamide in the first step (Scheme 5)

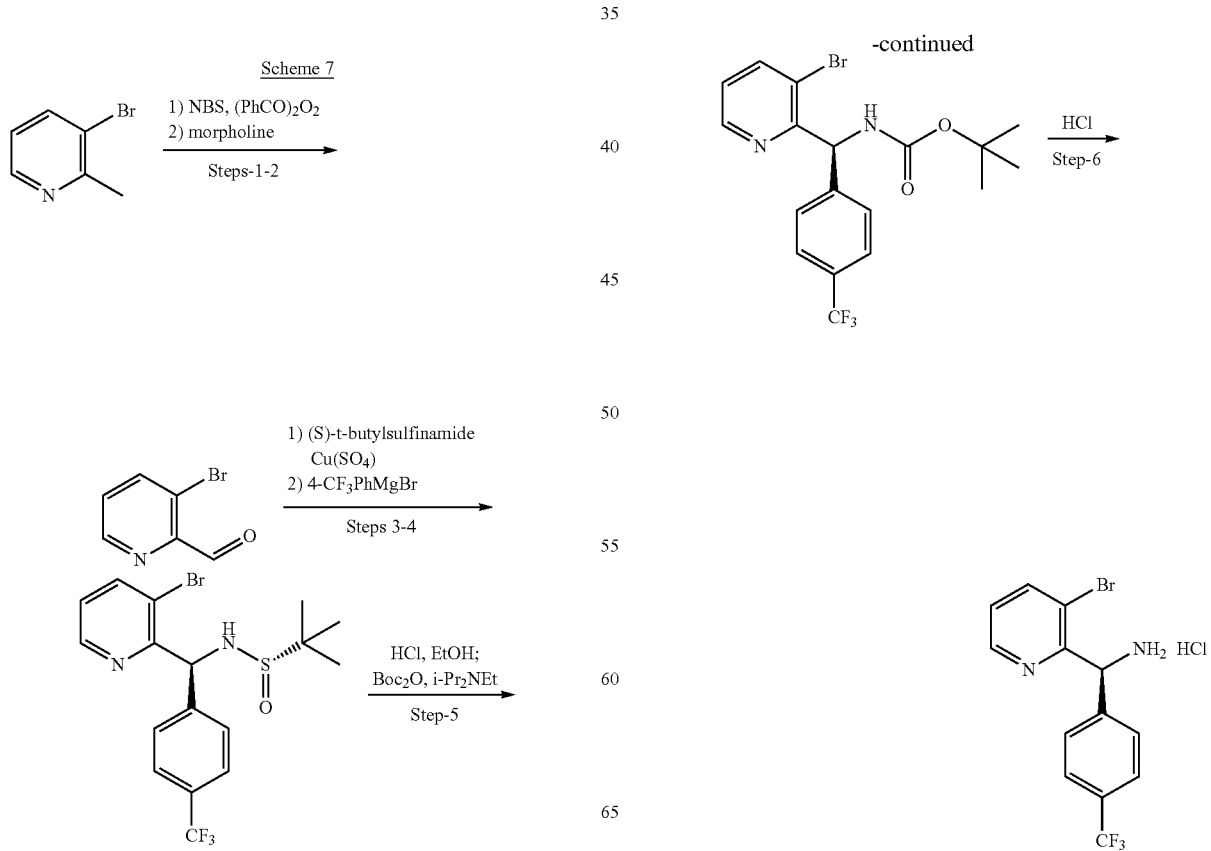

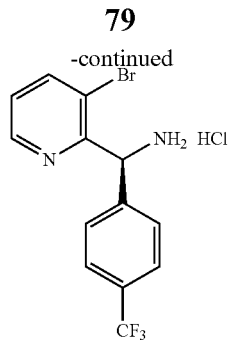

Intermediate 40: (S)-(3-(Prop-1-yn-1-yl)pyridin-2-yl)(4-(trifluoromethyl)-phenyl)methanamine hydrochloride

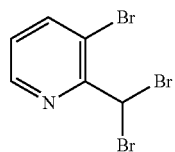

Step-1. 3-Bromo-2-dibromethyl-pyridine

To a solution of 3-bromo-picoline (25 g, 0.145 mol) in CCl$_4$ was added NBS (51.66 g, 0.29 mol) and benzoylperoxide (2.5 g, 0.018 mol). The resulting mixture was then gradually heated to reflux for 30 h. The reaction mixture was cooled to rt, the succinamide was filtered off, and the filtrate was concentrated under reduced pressure. The resulting residue was purified by flash column chromatography using silica (100-200 mesh) with EtOAc:hexane (1:9) as eluent to furnish 40.0 g pure 3-bromo-2-dibromomethyl-pyridine. $^1$H-NMR (400 MHz, CDCl$_3$) δ ppm 7.67 (d, 1H), 7.86 (d, 1H), 7.15 (t, 2H).

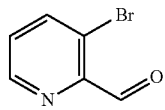

Step-2. 3-Bromo-pyridine-2-carbaldehyde

A suspension of 3-bromo-2-dibromomethyl-pyridine (10.0 g, 30.32 mmol) in morpholine (30.0 mL) was heated at 60° C. for 1 h. The reaction mixture was then cooled to rt and diluted with EtOAc (200 mL) followed by adjustment to pH 4 by adding citric acid (40.0 g). The reaction mixture was extracted with EtOAc (3×200 mL). The combined organic layers were dried over Na$_2$SO$_4$ and concentrated under reduced pressure. The resulting residue was purified by column chromatography using silica (100-200 mesh) and 3% EtOAc in hexane as eluent to give 3-bromo-pyridine-2-carbaldehyde. $^1$H-NMR (400 MHz, CDCl$_3$) δ ppm 10.23 (s, 1H), 8.75 (d, 1H), 8.03 (d, 1H), 7.32 (t, 1H).

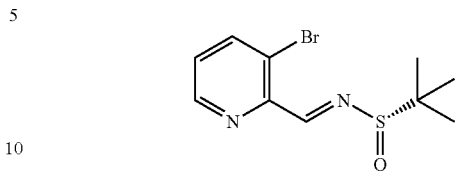

Step 3. (S,E)-N-((3-Bromopyridin-2-yl)methylene)-2-methylpropane-2-sulfinamide

A mixture of 3-bromo piconaldehyde (10 g, 53.8 mmol), copper sulfate (3.98 mL, 81 mmol) and (S)-2-methylpropane-2-sulfinamide (6.84 g, 56.4 mmol) in DCM (100 mL) was stirred at rt overnight. The solid was filtered off and the filtrate concentrated under vacuum. The residue thus obtained was purified by column chromatography using silica (100-200 mesh) with 20% EtOAc in n-hexane as eluent to give (S,E)-N-((3-bromopyridin-2-yl)methylene)-2-methylpropane-2-sulfinamide as yellow oil. $^1$H-NMR (400 MHz, CDCl$_3$): δ ppm 9.0 (s, 1H), 8.75 (d, 1H), 7.97 (d, 1H), 7.32 (t, 1H), 5.2 (d, 1H), 1.3 (s, 9H).

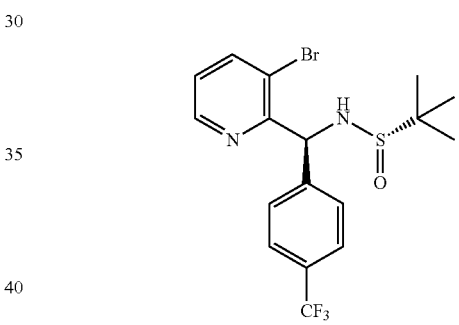

Step 4. 2-Methyl-propane-2-sulfinic acid ((3-bromo-pyridin-2yl)-(4-trifluoro-methyl-phenyl)-methyl)-amide To a stirred suspension of magnesium, (2.143 g, 88 mmol) in THF (50 mL) was added 4-bromobenzotrifluoride (5.06 mL, 36.2 mmol). Stirring was continued for 4 h (cautious: slightly exothermic, cooled with an water bath if needed). The solution was decanted from the resulting mixture and added to a stirred solution of N-(3-bromopyridin-2-yl)methylene)-2-methylpropane-2-sulfonamide(5.1 g, 17.64 mmol) in THF (100 mL) at −78° C. dropwise. Stirring was continued for another hour after the addition, and then the reaction was quenched with saturated aqueous NH$_4$Cl, extracted with ether (3×20 mL), dried over Na$_2$SO$_4$, concentrated, and purified by column chromatography using silica (100-200 mesh) with 5% EtOAc in hexane as eluent to give the title compound as a brown oil.

81

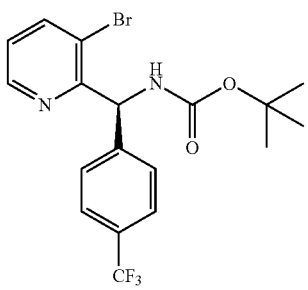 [SMILES: CC(C)(C)OC(=O)N[C@@H](c1ccc(C(F)(F)F)cc1)c1ncccc1Br]

Step 5. (S)-tert-Butyl((3-bromopyridin-2-yl)(4-(trifluoromethyl)phenyl)methyl)carbamate To a cooled (0° C.) stirring solution of 2-methyl-propane-2-sulfinic acid ((3-bromo-pyridin-2yl)-(4-trifluoromethyl-phenyl)-methyl)-amide (5.0 g, 11.49 mmol) in DCM/EtOH (1:1, 60 mL), was added 4.0 M HCl in 1,4-dioxane (14.36 mL, 57.4 mmol). Stirring was continued for 2 h and then DIPEA (10.00 mL, 57.4 mmol) was added, followed by di-tert-butyl dicarbonate (4.00 mL, 17.23 mmol) addition. The resulting mixture was stirred at rt overnight, taken up in H$_2$O, extracted in DCM (3×100 mL), dried over Na$_2$SO$_4$ and concentrated under reduced pressure. The residue thus obtained was purified by silica gel (100-200 mesh) column chromatography using 5% EtOAc in hexane as eluent to give the title compound as a white solid. $^1$H-NMR (400 MHz, DMSO-d$_6$) δ ppm 8.5 (dd, 1H), 7.81 (dd, 1H), 7.52 (s, 4H), 7.2 (dd, 1H) 6.51 (d, 1H), 6.32 (d. 1H), 1.41 (s, 9H). MS (ESI pos. ion) m/z: 431.2, 433.2 (M+H).

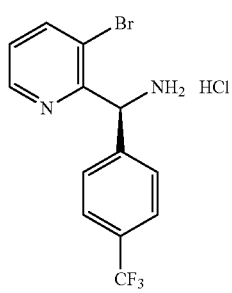 [SMILES: N[C@@H](c1ccc(C(F)(F)F)cc1)c1ncccc1Br ; Cl]

Step 6. (S)-(3-Bromopyridin-2-yl)(4-(trifluoromethyl)phenyl)methanamine hydrochloride To a solution of (S)-tert-butyl((3-bromopyridin-2-yl)(4-(trifluoromethyl)-phenyl)methyl)carbamate (2.0 g, 4.64 mmol) in MeOH (10 mL) was added hydrogen chloride (3.48 mL, 13.91 mmol) (4.0 M in 1,4-dioxane). The reaction was then stirred for 27 h at rt under N$_2$ and then the reaction was concentrated in vacuo to give the amine (1.7 g) as a white solid which was used without further purification in subsequent steps. MS (ESI pos. ion) m/z: 331.0, 332.9 (M+H).

82

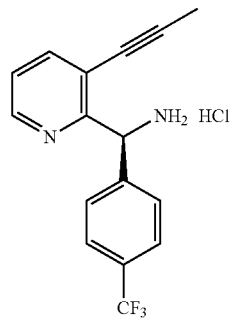 [SMILES: CC#Cc1cccnc1[C@@H](N)c1ccc(C(F)(F)F)cc1 ; Cl]

Intermediate 41: (S)-(3-(Prop-1-yn-1-yl)pyridin-2-yl)(4-(trifluoromethyl)-phenyl)methanamine hydrochloride

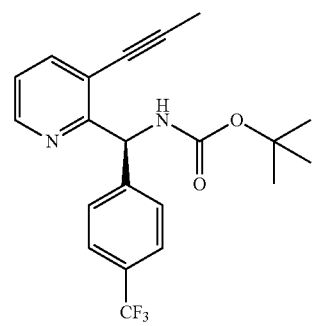

Step 1. (S)-tert-Butyl((3-(prop-1-yn-1-yl)pyridin-2-yl)(4-(trifluoromethyl)-phenyl)methyl)carbamate To a microwave vial containing (S)-tert-butyl((3-bromopyridin-2-yl)(4-(trifluoromethyl)phenyl)methyl)carbamate (500 mg, 1.159 mmol) and a stir bar was added 1,4-dioxane (6 mL). To this solution was added tetrakis(triphenylphosphine)palladium(0) (67.0 mg, 0.058 mmol, 0.05 equiv.) and tributyl(prop-1-yn-1-yl)stannane (458 mg, 1.391 mmol, 1.2 equiv.). The vial was capped and irradiated in a microwave at 120° C. for 20 min. The vial was allowed to cool, diluted with hexanes (5 mL) and loaded directly to a normal phase silica gel column (80 g ISCO, 0 to 40% EtOAc in hexanes) to provide (S)-tert-butyl((3-(prop-1-yn-1-yl)pyridin-2-yl)(4-(trifluoromethyl)phenyl)methyl)carbamate as a white solid.

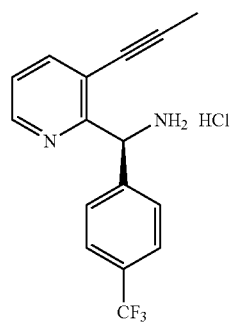 [SMILES: CC#Cc1cccnc1[C@@H](N)c1ccc(C(F)(F)F)cc1 ; Cl]

Step 2. (S)-(3-(Prop-1-yn-1-yl)pyridin-2-yl)(4-(trifluoromethyl)phenyl)-methanamine hydrochloride To a round bottom flask containing (S)-tert-butyl((3-(prop-1-yn-1-yl)-pyridin-2-yl)(4-(trifluoromethyl)phenyl)methyl)carbamate (400 mg, 1.025 mmol) was added DCM (8 mL). The resulting mixture was stirred at 23° C. for 2 min. Hydrogen chloride (4 mL, 4 N in 1,4-dioxane) was then added via syringe. The reaction was then stirred for 3 h and then the volatiles were removed via rotary evaporator. The solid was placed on high vacuum overnight to give (S)-(3-(prop-1-yn-1-yl)pyridin-2-yl)(4-(trifluoromethyl)phenyl)methanamine hydrochloride as a white solid.

mmol), allylboronic acid pinacol ester (0.507 mL, 3.01 mmol), cesium fluoride (0.171 mL, 4.64 mmol), and $(Ph_3P)_4Pd$ (0.536 g, 0.464 mmol) in 1,4-dioxane (10 mL) was heated by microwave at 125° C. in 30 min. The mixture was then cooled, taken up in $H_2O$, extracted with $Et_2O$ (3×), dried over $MgSO_4$, concentrated and purified by ISCO (0-50% EtOAc/hexanes). The residue was dissolved in DCM (10 mL) and HCl in 4 M 1,4-dioxane (4.64 mL, 18.55 mmol) was added. Stirring was continued for 2 h, and the solution was then concentrated to dryness to give the title compound as a white solid. MS (ESI pos. ion) m/z: 293.0 (M+H).

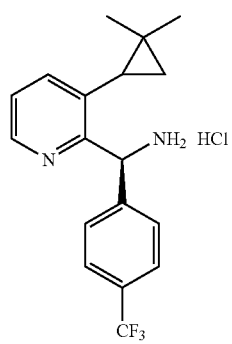 [SMILES: CC1(C)CC1c1cccnc1[C@@H](N)c1ccc(C(F)(F)F)cc1 ; Cl]

Intermediate 42: (1S)-(3-(2,2-Dimethylcyclopropyl)pyridin-2-yl)(4-(trifluoromethyl)phenyl)methanamine hydrochloride A mixture of (S)-tert-butyl(3-bromopyridin-2-yl)(4-(trifluoromethyl)-phenyl)methylcarbamate (1.50 g, 3.48 mmol), potassium (2,2-dimethylcyclopropyl)trifluoroborate (0.857 g, 4.87 mmol), potassium phosphate (2.58 g, 12.17 mmol), dicyclohexyl(2',6'-dimethoxybiphenyl-2-yl)phosphine (0.314 g, 0.765 mmol), and palladium acetate (0.094 g, 0.417 mmol) in toluene/$H_2O$ (10:1, 11 mL) was heated at 100° C. for 24 h. The reaction mixture was then cooled, diluted with $H_2O$, and extracted with EtOAc (3×). The combined extracts were dried over $MgSO_4$, concentrated and purified by ISCO (silica gel, 10% EtOAc/hexanes) to give a colorless oil which was dissolved in DCM (3 mL) and then 4 mL of 4 M HCl in 1,4-dioxane was added. The solution was stirred at rt overnight and concentrated to dryness to give the title compound as an off white solid. MS (ESI pos. ion) m/z: 321.0 (M+H).

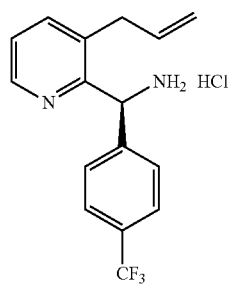 [SMILES: C=CCc1cccnc1[C@@H](N)c1ccc(C(F)(F)F)cc1 ; Cl]

Intermediate 43: (S)-(3-Allylpyridin-2-yl)(4-(trifluoromethyl)phenyl) methanamine hydrochloride A mixture of (S)-tert-butyl(3-bromopyridin-2-yl)(4-(trifluoromethyl)-phenyl)methylcarbamate (1.00 g, 2.319

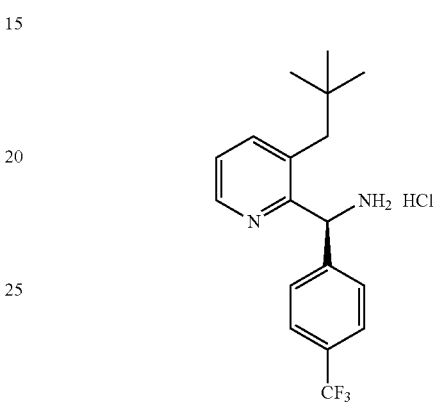

Intermediate 44: (S)-(3-Neopentylpyridin-2-yl)(4-(trifluoromethyl)phenyl)-methanamine hydrochloride A mixture of (S)-tert-butyl(3-bromopyridin-2-yl)(4-(trifluoromethyl)-phenyl)methylcarbamate (0.500 g, 1.159 mmol), bis(tri-t-butylphosphine)-palladium (0) (0.119 g, 0.232 mmol), and neopentylzinc(II) bromide (4.75 mL, 2.377 mmol) in THF (5 mL) was heated to 135° C. by microwave and stirred for 30 min. The reaction mixture was cooled, quenched with saturated aqueous $NH_4Cl$, and extracted with EtOAc (3×). The extracts were dried over $MgSO_4$, concentrated, and purified by ISCO (0-40% EtOAc/hyexanes) to give the carbamate intermediate. The carbamate was dissolved in DCM (5 mL) and 4 M HCl in 1,4-dioxane (2 mL) was added. The reaction mixture was then stirred at rt overnight and concentrated to dryness to give the title compound as a white solid. MS (ESI pos. ion) m/z: 323.0 (M+H).

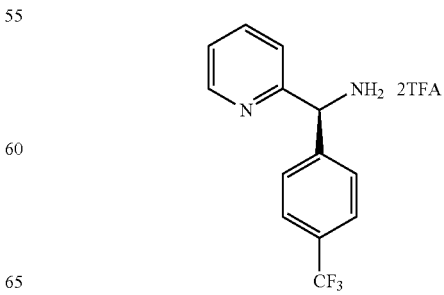

Intermediate 45: (S)-Pyridin-2-yl(4-(trifluoromethyl)phenyl)methanamine bis(2,2,2-trifluoroacetate)

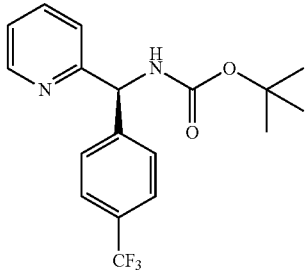 [SMILES: CC(C)(C)OC(=O)N[C@@H](c1ccc(C(F)(F)F)cc1)c1ccccn1]

Step 1. (S)-tert-Butyl(pyridin-2-yl(4-(trifluoromethyl)phenyl)methyl)-carbamate To a solution of (S)-tert-butyl((3-bromopyridin-2-yl)(4-(trifluoromethyl)-phenyl)methyl)carbamate (Intermediate 40, Step 5) (2.24 g, 5.19 mmol) in MeOH (20 mL) was added palladium hydroxide, (20 wt % Pd (dry basis) on carbon, wet, degussa type) (0.365 g, 2.60 mmol). The resulting mixture was then stirred at rt under H$_2$ (1 atm) overnight. The mixture was next filtered through Celite® brand filter agent and the Celite® filter agent was washed with a solution of MeOH/EtOAc (1:1, 3×20 mL). The combined filtrates were concentrated and dried to give the desired product as a yellow oil, which was used in the next step without further purification.

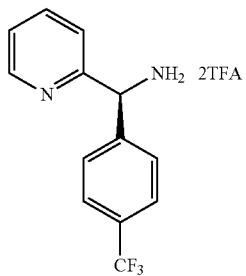 [SMILES: N[C@@H](c1ccc(C(F)(F)F)cc1)c1ccccn1 ; "2TFA"]

Step 2. (S)-Pyridin-2-yl(4-(trifluoromethyl)phenyl)methanamine bis(2,2,2-trifluoroacetate)

To a solution of(S)-tert-butyl(pyridin-2-yl(4-(trifluoromethyl)phenyl)methyl)carbamate (1.83 g, 5.19 mmol) in DCM (12 mL) was added TFA (3.86 mL, 51.9 mmol). The resulting mixture was then stirred at rt for 1 h. The mixture was then concentrated and dried to give the title compound as a yellow oil which was used without further purification in the next step.

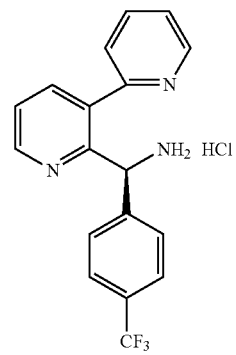 [SMILES: N[C@@H](c1ccc(C(F)(F)F)cc1)c1ncccc1-c1ccccn1 ; Cl]

Intermediate 46: (S)-[2,3'-Bipyridin]-2'-yl(4-(trifluoromethyl)phenyl)-methanaminedihydrochloride A mixture of (S)-tert-butyl(3-bromopyridin-2-yl)(4-(trifluoromethyl)-phenyl)methylcarbamate (Intermediate 40, Step 5) (0.711 g, 1.649 mmol), 2-(tributylstannyl)pyridine (0.910 g, 2.473 mmol), and (Ph$_3$P)$_4$Pd (0.381 g, 0.330 mmol) in 1,4-dioxane (10 mL) was heated by microwave at 125° C. for 30 min. The reaction mixture was then cooled, concentrated, and purified by ISCO (silica gel, 0-60% EtOAc/hexanes). The residue was dissolved in DCM (3 mL) and hydrogen chloride (3.30 mL, 13.19 mmol, 4.0 M in 1,4-dioxane) was added. After stirring for 2 h, the mixture was concentrated to dryness to give the title compound. MS (ESI pos. ion) m/z: 330.0 (M+H).

EXAMPLES

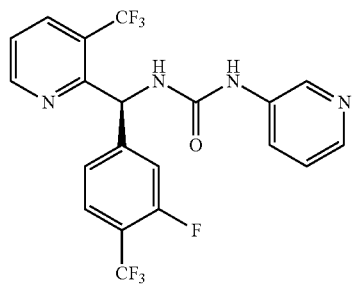

Example 1

(S)-1-((3-Fluoro-4-(trifluoromethyl)phenyl)(3-(trifluoromethyl)-pyridin-2-yl)methyl)-3-(pyridin-3-yl)urea bis(2,2,2-trifluoroacetate)

To a solution of (S)-(3-fluoro-4-(trifluoromethyl)phenyl)(3-(trifluoromethyl)pyridin-2-yl)methanamine (Intermediate 7) (566 mg, 1.673 mmol) and DIPEA (0.291 mL, 1.673 mmol) in DCM (5 mL) was added 3-isocyanatopyridine (201 mg, 1.673 mmol). The resulting mixture was stirred at rt for 1 h. The reaction was then concentrated to 1.0 mL, diluted with DMF (2.0 mL), filtered through a syringe filter, and purified by preparative reverse phase HPLC [Phenomenx Gemini Axia™-5µ C-18 column (150×30 mm), 10-100% MeCN/ 0.1% TFA in H$_2$O]. The product-containing fractions were combined and the solvent was removed by lyophilization to give (S)-1-((3-fluoro-4-(trifluoromethyl)phenyl)(3-(trifluoromethyl)pyridin-2-yl)methyl)-3-(pyridin-3-yl)urea bis(2,2,2-trifluoroacetate) as a white solid. $^1$H NMR (300 MHz, d$_4$-MeOH): δ ppm 9.15 (br. s., 1H), 8.93 (d, J=4.1 Hz, 1H), 8.37 (br. s., 1H), 8.29-8.15 (m, 2H), 7.85 (dd, J=5.6, 8.3 Hz, 1H), 7.70-7.54 (m, 2H), 7.47-7.26 (m, 2H), 6.59 (s, 1H). MS (ESI pos. ion) m/z: 458.9 (M+H).

General Urea Formation Procedure for Examples (2-147)

To a solution of amine (0.156 mol), DIPEA (0.080 mL, 0.468 mmol, 3.0 equiv.) in DCM or DMF (1 mL) at rt was added the corresponding isocyanate (0.156 mmol). The reaction was then stirred 1 h at rt. Next, the reaction was diluted with DMF (1 mL), filtered through a syringe filter, and then it was purified by silica gel chromatography to provide the title compounds. Alternatively, the compounds were purified by preparative reverse phase HPLC [Phenomenx Gemini Axia™-5µ C-18 column (150×30 mm), 10-100% MeCN/ 0.1% TFA in H$_2$O]. The product-containing fractions were combined and the solvent removed by lyophilization to provide the target compound as the TFA salts; or the product was dissolved in MeOH (1 mL) and washed through PL-HCO$_3$ MP-resin, and the resin was further washed with MeOH (2×0.4 mL). The combined filtrates were then concentrated and dried in vacuo to give the title compounds as free bases; or the product containing fractions were concentrated, the solids dissolved in DCM and the organic layer extracted with saturated aqueous NaHCO$_3$, the organic layer was dried, and concentrated to provide the title compounds as free bases. Compounds prepared using this general method are shown in Table 2.

Scheme 8

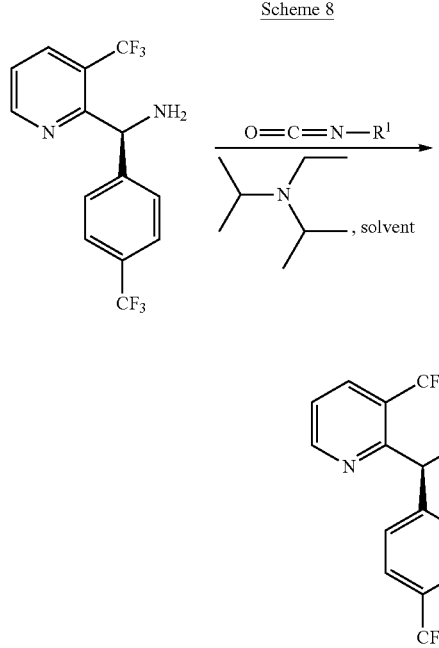

TABLE 2

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 2 | 3 | O=C=N-(pyridin-3-yl) | (structure) | (S)-1-((4-methoxyphenyl)(3-(trifluoromethyl)pyridin-2-yl)methyl)-3-(pyridin-3-yl)urea | 403.1 |
| 3 | 15 | O=C=N-(pyridin-3-yl) | (structure) | (S)-1-((3-chlorophenyl)-(3-(trifluoromethyl)-pyridin-2-yl)-methyl)-3-(pyridin-3-yl)-urea | 407.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 4 | 25 | O=C=N-(pyridin-3-yl) | | (S)-1-((3-methoxyphenyl)(3-(trifluoromethyl)-pyridin-2-yl)-methyl)-3-(pyridin-3-yl)-urea | 403.1 |
| 5 | 5 | O=C=N-(pyridin-3-yl) | | (S)-1-((3-fluoro-4-methoxyphenyl)(3-(trifluoromethyl)-pyridin-2-yl)-methyl)-3-(pyridin-3-yl)-urea | 421.1 |
| 6 | 14 | O=C=N-(pyridin-3-yl) | | (S)-1-(pyridin-3-yl)-3-(quinolin-3-yl(3-(trifluoromethyl)-pyridin-2-yl)-methyl)urea | 424.1 |
| 7 | 21 | O=C=N-(pyridin-3-yl) | | (S)-1-((3-methylphenyl)(3-(trifluoromethyl)-pyridin-2-yl)-methyl)-3-(pyridin-3-yl)-urea | 387.0 |
| 8 | 18 | O=C=N-(pyridin-3-yl) | | (S)-1-((3-fluorophenyl)-(3-(trifluoromethyl)-pyridin-2-yl)-methyl)-3-(pyridin-3-yl)-urea | 391.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 9 | 19 | | | (S)-1-((3-(trifluoromethyl)phenyl)(3-(trifluoromethyl)pyridin-2-yl)methyl)-3-(pyridin-3-yl)urea | 441.0 |
| 10 | 13 | | | (S)-1-((5-chloroquinolin-3-yl)(3-(trifluoromethyl)pyridin-2-yl)methyl)-3-(pyridin-3-yl)urea | 458.0 |
| 11 | 17 | | | (S)-1-(naphthalen-2-yl)(3-(trifluoromethyl)pyridin-2-yl)methyl)-3-(pyridin-3-yl)urea | 423.0 |
| 12 | 11 | | | (S)-1-((8-chloroquinolin-3-yl)(3-(trifluoromethyl)pyridin-2-yl)methyl)-3-(pyridin-3-yl)urea | 458.0 |
| 13 | 4 | | | (S)-1-((3,4-dichlorophenyl)(3-(trifluoromethyl)pyridin-2-yl)methyl)-3-(pyridin-3-yl)urea | 440.9 |

//

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 14 | 20 | O=C=N-(3-pyridyl) | | (S)-1-((8-fluoro-quinolin-3-yl)-(3-(trifluoro-methyl)-pyridin-2-yl)-methyl)-3-(pyridin-3-yl)-urea | 442.0 |
| 15 | 8 | O=C=N-(3-pyridyl) | | (S)-1-((3-fluoropyridin-2-yl)(4-(trifluoro-methoxy)-phenyl)-methyl)-3-(pyridin-3-yl)-urea | 407.0 |
| 16 | 24 | O=C=N-(3-pyridyl) | | (S)-1-((8-methoxy-quinolin-3-yl)-(3-(trifluoro-methyl)-pyridin-2-yl)-methyl)-3-(pyridin-3-yl)-urea | 454.0 |
| 17 | 22 | O=C=N-(3-pyridyl) | | (S)-1-(pyridin-3-yl)-3-(quinolin-6-yl(3-(trifluoro-methyl)-pyridin-2-yl)-methyl)urea | 424.1 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 18 | 12 | 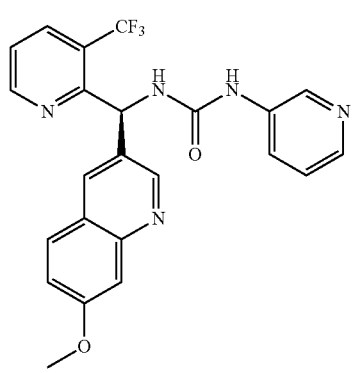 [SMILES: COc1ccc2cc([C@H](NC(=O)Nc3cccnc3)c3ncccc3C(F)(F)F)cnc2c1] | 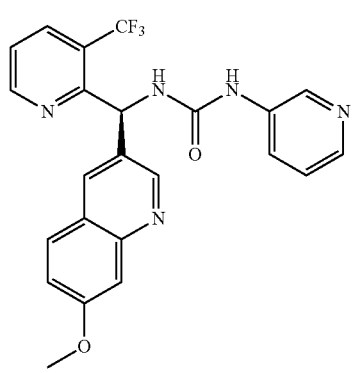 [SMILES: COc1ccc2cc([C@H](NC(=O)Nc3cccnc3)c3ncccc3C(F)(F)F)cnc2c1] | (S)-1-((7-methoxy-quinolin-3-yl)-(3-(trifluoro-methyl)-pyridin-2-yl)-methyl)-3-(pyridin-3-yl)-urea | 454.0 |
| 19 | 27 | 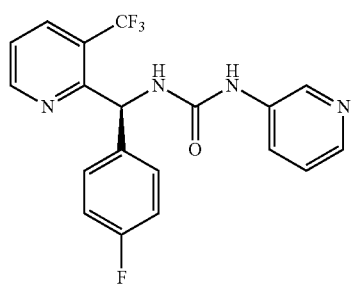 [SMILES: O=C(Nc1cccnc1)N[C@@H](c1ccc(F)cc1)c1ncccc1C(F)(F)F] | 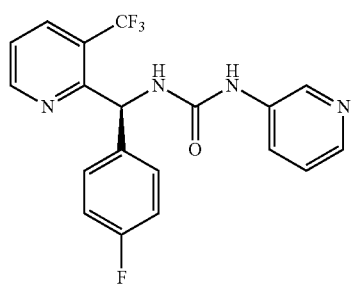 [SMILES: O=C(Nc1cccnc1)N[C@@H](c1ccc(F)cc1)c1ncccc1C(F)(F)F] | (S)-((4-fluorophenyl)-(3-(trifluoro-methyl)-pyridin-2-yl)-methyl)-3-(pyridin-3-yl)-urea | 391.0 |
| 20 | 28 | 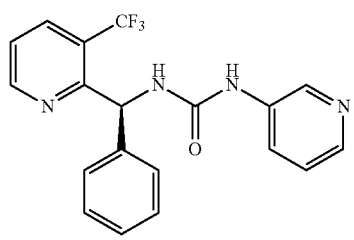 [SMILES: O=C(Nc1cccnc1)N[C@@H](c1ccccc1)c1ncccc1C(F)(F)F] | 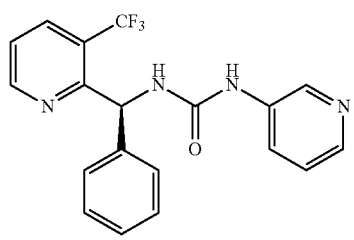 [SMILES: O=C(Nc1cccnc1)N[C@@H](c1ccccc1)c1ncccc1C(F)(F)F] | (S)-1-(phenyl(3-(trifluoro-methyl)-pyridin-2-yl)-methyl)-3-(pyridin-3-yl)-urea | 373.1 |
| 21 | 6 | 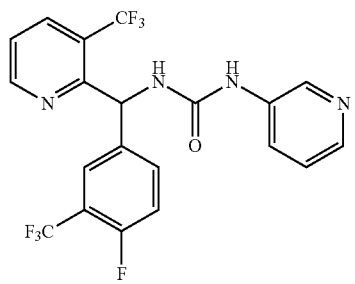 [SMILES: O=C(Nc1cccnc1)NC(c1ccc(F)c(C(F)(F)F)c1)c1ncccc1C(F)(F)F] | 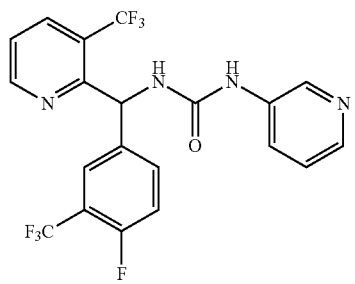 [SMILES: O=C(Nc1cccnc1)NC(c1ccc(F)c(C(F)(F)F)c1)c1ncccc1C(F)(F)F] | 1-((4-fluoro-3-(trifluoro-methyl)-phenyl)(3-(trifluoro-methyl)-pyridin-2-yl)-methyl)-3-(pyridin-3-yl)-urea (2,2,2-trifluoro-acetate) | 459.0 |
| 22 | 9 | 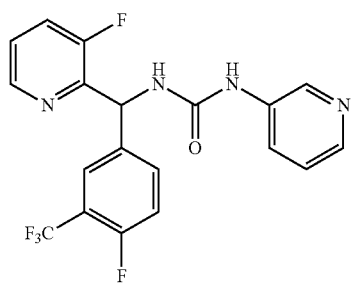 [SMILES: O=C(Nc1cccnc1)NC(c1ccc(F)c(C(F)(F)F)c1)c1ncccc1F] | 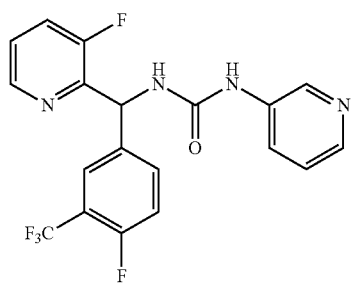 [SMILES: O=C(Nc1cccnc1)NC(c1ccc(F)c(C(F)(F)F)c1)c1ncccc1F] | 1-((4-fluoro-3-(trifluoro-methyl)-phenyl)(3-fluoropyridin-2-yl)methyl)-3-(pyridin-3-yl)urea (2,2,2-trifluoro-acetate) | 409.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 23 | 16 | | | 1-((3-chloro-5-fluoro-phenyl)(3-(trifluoro-methyl)-pyridin-2-yl)-methyl)-3-(pyridin-3-yl)-urea (2,2,2-trifluoro-acetate) | 424.8 |
| 24 | 35 | | | 1-((3-chloro-5-fluoro-phenyl)(3-fluoropyridin-2-yl)methyl)-3-(pyridin-3-yl)urea (2,2,2-trifluoro-acetate) | 374.9 |
| 25 | 34 | | | 1-(pyridin-3-yl)-3-((3-(trifluoro-methyl)-pyridin-2-yl)-(6-(trifluoro-methyl)-pyridin-3-yl)-methyl)urea (2,2,2-trifluoro-acetate) | 441.9 |
| 26 | 10 | | | (S)-1-((4-chlorophenyl)-(3-(trifluoro-methyl)-pyridin-2-yl)-methyl)-3-(pyridin-3-yl)-urea | 407.0 |
| 27 | 29 | | | (S)-1-((4-ethylphenyl)-(3-(trifluoro-methyl)-pyridin-2-yl)-methyl)-3-(pyridin-3-yl)-urea | 401.1 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 28 | 40 | O=C=N-(pyridin-3-yl) | | (S)-1-((3-bromopyridin-2-yl)(4-(trifluoromethyl)phenyl)methyl)-3-(pyridin-3-yl)urea | 452.0 |
| 29 | 32 | O=C=N-(pyridin-3-yl) | | (S)-1-((3-fluoro-4-(trifluoromethyl)phenyl)(3-fluoropyridin-2-yl)methyl)-3-(pyridin-3-yl)urea | 409.0 |
| 30 | 45 | O=C=N-(pyridin-3-yl) | | (S)-1-(pyridin-2-yl(4-(trifluoromethyl)phenyl)methyl)-3-(pyridin-3-yl)urea | 373.0 |
| 31 | 1 | O=C=N-phenyl | | (S)-1-phenyl-3-((4-(trifluoromethyl)phenyl)(3-(trifluoromethyl)pyridin-2-yl)methyl)urea | 440.0 |
| 32 | 1 | O=C=N-isopropyl | | (S)-1-isopropyl-3-((4-(trifluoromethyl)phenyl)(3-(trifluoromethyl)pyridin-2-yl)methyl)urea | 406.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 33 | 1 | | | 1-((S)-1-(naphthalen-1-yl)ethyl)-3-((S)-(4-(trifluoromethyl)phenyl)(3-(trifluoromethyl)pyridin-2-yl)methyl)urea (2,2,2-trifluoroacetate) | 518.0 |
| 34 | 1 | | | (S)-1-(3-phenylpropyl)-3-((4-(trifluoromethyl)phenyl)(3-(trifluoromethyl)pyridin-2-yl)methyl)urea (2,2,2-trifluoroacetate) | 482.0 |
| 35 | 1 | | | (S)-1-(phenylformate)-3-((4-(trifluoromethyl)phenyl)(3-(trifluoromethyl)pyridin-2-yl)methyl)urea (2,2,2-trifluoroacetate) | 484.0 |
| 36 | 1 | | | (S)-1-(2-(benzo[d][1,3]dioxol-5-yl)ethyl)-3-((4-(trifluoromethyl)phenyl)(3-(trifluoromethyl)pyridin-2-yl)methyl)urea (2,2,2-trifluoroacetate) | 512.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 37 | 1 | | | (S)-1-(3-bromophenyl)-3-((4-(trifluoromethyl)phenyl)(3-(trifluoromethyl)pyridin-2-yl)methyl)urea (2,2,2-trifluoroacetate) | 519.9 |
| 38 | 1 | | | (S)-ethyl 2-(3-((4-(trifluoromethyl)phenyl)(3-(trifluoromethyl)pyridin-2-yl)methyl)ureido)acetate (2,2,2-trifluoroacetate) | 450.0 |
| 39 | 1 | | | (S)-1-(benzofuran-5-yl)-3-((4-(trifluoromethyl)phenyl)(3-(trifluoromethyl)pyridin-2-yl)methyl)urea (2,2,2-trifluoroacetate) | 480.0 |
| 40 | 40 | | | (S)-1-(4-cyanophenyl)-3-((4-(trifluoromethyl)phenyl)(3-(trifluoromethyl)pyridin-2-yl)methyl)urea | 476.0 |
| 41 | 40 | | | (S)-1-((3-bromopyridin-2-yl)(4-(trifluoromethyl)phenyl)methyl)-3-(tert-butyl)urea | 430.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 42 | 41 | O=C=N-tBu | | (S)-1-(tert-butyl)-3-((3-(prop-1-yn-1-yl)pyridin-2-yl)(4-(trifluoromethyl)phenyl)methyl)urea | 390.0 |
| 43 | 43 | O=C=N-(pyridin-3-yl) | | (S)-1-((3-allylpyridin-2-yl)(4-(trifluoromethyl)phenyl)methyl)-3-(pyridin-3-yl)urea | 413.0 |
| 44 | 1 | O=C=N-(pyridin-3-yl) | | (S)-1-(pyridin-3-yl)-3-((4-(trifluoromethyl)phenyl)(3-(trifluoromethyl)pyridin-2-yl)methyl)urea | 441.0 |
| 45 | 1 | O=C=N-tBu | | (S)-1-(tert-butyl)-3-((4-(trifluoromethyl)phenyl)(3-(trifluoromethyl)pyridin-2-yl)methyl)urea | 420.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 46 | 1 | O=C=N-C6H4-CN (4-CN) | | (S)-1-(4-cyanophenyl)-3-((4-(trifluoromethyl)phenyl)(3-(trifluoromethyl)pyridin-2-yl)methyl)urea | 465.0 |
| 47 | 1 | O=C=N-C6H4-F (4-F) | | (S)-1-(4-fluorophenyl)-3-((4-(trifluoromethyl)phenyl)(3-(trifluoromethyl)pyridin-2-yl)methyl)urea | 458.0 |
| 48 | 1 | O=C=N-C6H3-2,4-F2 | | (S)-1-(2,4-difluorophenyl)-3-((4-(trifluoromethyl)phenyl)(3-(trifluoromethyl)pyridin-2-yl)methyl)urea | 476.0 |
| 49 | 1 | O=C=N-C6H3-3,5-F2 | | (S)-1-(3,5-difluorophenyl)-3-((4-(trifluoromethyl)phenyl)(3-(trifluoromethyl)pyridin-2-yul)methyl)urea | 476.0 |
| 50 | 1 | O=C=N-C6H3-2,6-F2 | | (S)-1-(2,6-difluorophenyl)-3-((4-(trifluoromethyl)phenyl)(3-(trifluoromethyl)pyridin-2-yl)methyl)urea | 476.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 51 | 41 | | | (S)-1-((3-(prop-1-yn-1-yl)pyridin-2-yl)(4-(trifluoromethyl)phenyl)methyl)-3-(pyridin-3-yl)-urea | 411.0 |
| 52 | 1 | | | (S)-1-(3-methoxyphenyl)-3-((4-(trifluoromethyl)phenyl)(3-(trifluoromethyl)pyridin-2-yl)methyl)urea (2,2,2-trifluoroacetate) | 470.0 |
| 53 | 1 | | | (S)-1-(3-(methylsulfonyl)phenyl)-3-((4-(trifluoromethyl)phenyl)(3-(trifluoromethyl)pyridin-2-yl)methyl)urea | 518.0 |
| 54 | 1 | | | 1-(tetrahydro-2H-pyran-3-yl)-3-((S)-(4-(trifluoromethyl)phenyl)(3-(trifluoromethyl)pyridin-2-yl)methyl)urea | 448.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 55 | 1 | | | (S)-1-(3,5-dimethylisoxazol-4-yl)-3-((4-(trifluoromethyl)phenyl)(3-(trifluoromethyl)pyridin-2-yl)metyl)urea | 459.0 |
| 56 | 1 | | | 1-(tetrahydrofuran-3-yl)-3-((S)-(4-(trifluoromethyl)phenyl)(3-(trifluoromethyl)pyridin-2-yl)methyl)urea | 434.0 |
| 57 | 1 | | | (S)-1-(pyrimidin-5-yl)-3-((4-(trifluoromethyl)phenyl)(3-(trifluoromethyl)pyridin-2-yl)methyl)urea | 442.0 |
| 58 | 1 | | | (S)-1-(quinolin-6-yl)-3-((4-(trifluoromethyl)phenyl)(3-(trifluoromethyl)pyridin-2-yl)methyl)urea | 491.0 |
| 59 | 1 | | | (S)-1-(quinolin-3-yl)-3-((4-(trifluoromethyl)phenyl)(3-(trifluoromethyl)pyridin-2-yl)methyl)urea | 491.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 60 | 1 | | | (S)-1-(quinolin-4-yl)-3-((4-(trifluoromethyl)phenyl)(3-(trifluoromethyl)pyridin-2-yl)methyl)urea | 491.0 |
| 61 | 42 | | | 1-((S)-(3-((R)-2,2-dimethylcyclopropyl)-pyridin-2-yl)-(4-(trifluoromethyl)-phenyl)-methyl)-3-(pyridin-3-yl)-urea | 441.0 |
| 62 | 44 | | | (S)-1-((3-neopentylpyridin-2-yl)-4-(trifluoromethyl)-phenyl)-methyl)-3-(pyridin-3-yl)-urea | 443.0 |
| 63 | 1 | | | (S)-1-(2,6-dibromo-4-fluorophenyl)-3-((4-(trifluoromethyl)-phenyl)(3-(trifluoromethyl)-pyridin-2-yl)methyl)urea (2,2,2-trifluoroacetate) | 614.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 64 | 1 | | | 1-((3-Sulfonylcyclopentyl)-methyl)-3-((S)-(4-(trifluoromethyl)-phenyl)(3-(trifluoromethyl)-pyridin-2-yl)-methyl)urea (2,2,2-trifluoroacetate) | 496.0 |
| 65 | 1 | | | 1-((S)-3-methylbutan-2-yl)-3-((S)-(4-(trifluoromethyl)-phenyl)(3-(trifluoromethyl)-pyridin-2-yl)-methyl)urea (2,2,2-trifluoroacetate) | 434.0 |
| 66 | 1 | | | (S)-ethyl 3-(3-((4-(trifluoromethyl)-phenyl)(3-(trifluoromethyl)-pyridin-2-yl)-methyl)-ureido)-propanoate (2,2,2-trifluoroacetate) | 464.0 |
| 67 | 1 | | | (S)-N-((4-(trifluoromethyl)-phenyl)(3-(trifluoromethyl)-pyridin-2-yl)-methylcarbamoyl)benzamide (2,2,2-trifluoroacetate) | 468.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 68 | 1 | | | (S)-ethyl 4-(3-((4-(trifluoromethyl)-phenyl)(3-(trifluoromethyl)-pyridin-2-yl)-methyl)-ureido)-butanoate (2,2,2-trifluoroacetate) | 478.0 |
| 69 | 1 | | | (S)-1-(3-methyl-5-phenylisoxazol-4-yl)-3-((4-(trifluoromethyl)-phenyl)(3-(trifluoromethyl)-pyridin-2-yl)-methyl)urea (2,2,2-trifluoroacetate) | 521.0 |
| 70 | 1 | | | 1-((R)-1-phenylethyl)-3-((S)-(4-(trifluoromethyl)-phenyl)(3-(trifluoromethyl)-pyridin-2-yl)-methyl)urea (2,2,2-trifluoroacetate) | 468.0 |
| 71 | 1 | | | (S)-1-(tert-butylphenyl)-3-((4-(trifluoromethyl)-phenyl)(3-(trifluoromethyl)-pyridin-2-yl)-methyl)urea (2,2,2-trifluoroacetate) | 496.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 72 | 1 | 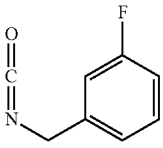 [SMILES: O=C=NCc1cccc(F)c1] | 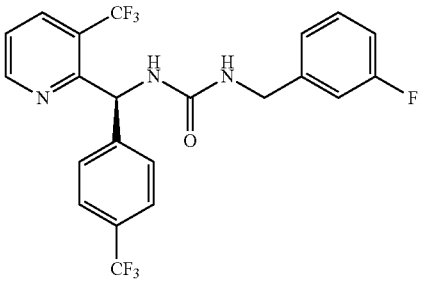 [SMILES: O=C(NCc1cccc(F)c1)N[C@@H](c1ccc(C(F)(F)F)cc1)c1ncccc1C(F)(F)F] | (S)-1-(3-fluorobenzyl)-3-((4-(trifluoromethyl)phenyl)(3-(trifluoromethyl)pyridin-2-yl)methyl)urea (2,2,2-trifluoroacetate) | 472.0 |
| 73 | 1 | 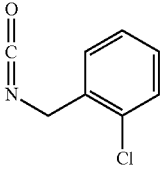 [SMILES: O=C=NCc1ccccc1Cl] | 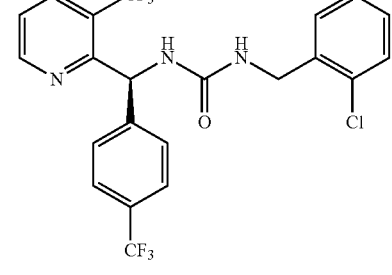 | (S)-1-(2-chlorobenzyl)-3-((4-(trifluoromethyl)phenyl)(3-(trifluoromethyl)pyridin-2-yl)methyl)urea (2,2,2-trifluoroacetate) | 488.0 |
| 74 | 1 | 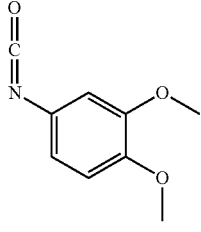 | 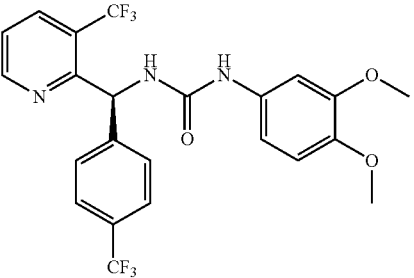 [SMILES: COc1ccc(NC(=O)N[C@@H](c2ccc(C(F)(F)F)cc2)c2ncccc2C(F)(F)F)cc1OC] | (S)-1-(3,4-dimethoxyphenyl)-3-((4-(trifluoromethyl)phenyl)(3-(trifluoromethyl)pyridin-2-yl)methyl)urea (2,2,2-trifluoroacetate) | 500.0 |
| 75 | 1 | 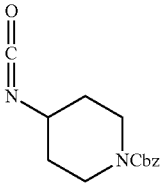 | 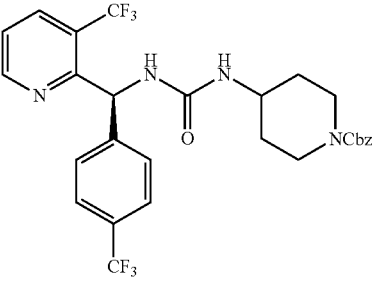 [SMILES: O=C(NC1CCN(C(=O)OCc2ccccc2)CC1)N[C@@H](c1ccc(C(F)(F)F)cc1)c1ncccc1C(F)(F)F] | (S)-benzyl 4-(3-((4-(trifluoromethyl)phenyl)(3-(trifluoromethyl)pyridin-2-yl)methyl)ureido)piperidine-1-carboxylate (2,2,2-trifluoroacetate) | 581.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 76 | 1 | | | (S)-1-(2,6-dichloropyridin-4-yl)-3-((4-(trifluoromethyl)phenyl)(3-(trifluoromethyl)pyridin-2-yl)methyl)urea (2,2,2-trifluoroacetate) | 509.0 |
| 77 | 1 | | | (S)-1-(3-(5-methyl-1,2,4-oxadiazol-3-yl)phenyl)-3-((4-(trifluoromethyl)phenyl)(3-(trifluoromethyl)pyridin-2-yl)methyl)urea (2,2,2-trifluoroacetate) | 522.0 |
| 78 | 1 | | | (S)-methyl 4-(methylthio)-2-(3-((S)-(4-(trifluoromethyl)phenyl)(3-(trifluoromethyl)pyridin-2-yl)methyl)-ureido)-butanoate (2,2,2-trifluoroacetate) | 510.0 |
| 79 | 1 | | | (S)-methyl-2-(3-((S)-(4-(trifluoromethyl)phenyl)(3-(trifluoromethyl)pyridin-2-yl)methyl)-ureido)-propanoate (2,2,2-trifluoroacetate) | 450.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 80 | 1 | | | 1-((S)-1-(4-methoxy-phenyl)ethyl)-3-((S)-(4-(trifluoro-methyl)-phenyl)(3-(trifluoro-methyl)-pyridin-2-yl)-methyl)urea (2,2,2-trifluoro-acetate) | 498.0 |
| 81 | 1 | | | (S)-N-((4-(trifluoro-methyl)-phenyl)(3-(trifluoro-methyl)-pyridin-2-yl)-methylcarbamoyl)-ethylamide (2,2,2-trifluoro-acetate) | 436.0 |
| 82 | 1 | | | (S)-1-(2,3-dimethoxy-phenethyl)-3-((4-(trifluoro-methyl)-phenyl)(3-(trifluoro-methyl)-pyridin-2-yl)-methyl)urea (2,2,2-trifluoro-acetate) | 528.0 |
| 83 | 1 | | | 1-((S)-hexan-2-yl)-3-((S)-(4-(trifluoro-methyl)-phenyl)(3-(trifluoro-methyl)-pyridin-2-yl)-methyl)urea (2,2,2-trifluoro-acetate) | 448.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 84 | 1 | | | 1-((S)-1-(3-methoxyphenyl)ethyl)-3-((S)-(4-(trifluoromethyl)phenyl)(3-(trifluoromethyl)pyridin-2-yl)methyl)urea (2,2,2-trifluoroacetate) | 498.0 |
| 85 | 1 | | | (S)-1-(2-methylbenzyl)-3-((4-(trifluoromethyl)phenyl)(3-(trifluoromethyl)pyridin-2-yl)methyl)urea (2,2,2-trifluoroacetate) | 468.0 |
| 86 | 1 | | | (S)-1-(3-acetylphenyl)-3-((4-(trifluoromethyl)phenyl)(3-(trifluoromethyl)pyridin-2-yl)methyl)urea (2,2,2-trifluoroacetate) | 482.0 |
| 87 | 1 | | | (S)-1-(2-fluorobenzyl)-3-((4-(trifluoromethyl)phenyl)(3-(trifluoromethyl)pyridin-2-yl)methyl)urea (2,2,2-trifluoroacetate) | 472.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 88 | 1 | | | (S)-1-(2,6-diethylphenyl)-3-((4-(trifluoromethyl)phenyl)(3-(trifluoromethyl)pyridin-2-yl)methyl)urea (2,2,2-trifluoroacetate) | 496.0 |
| 89 | 1 | | | (S)-1-(2-ethyl-6-methylphenyl)-3-((4-(trifluoromethyl)phenyl)(3-(trifluoromethyl)pyridin-2-yl)methyl)urea (2,2,2-trifluoroacetate) | 482.0 |
| 90 | 1 | | | (S)-ethyl 3-(3-((4-(trifluoromethyl)phenyl)(3-(trifluoromethyl)pyridin-2-yl)methyl)-ureido)-benzoate (2,2,2-trifluoroacetate) | 512.0 |
| 91 | 1 | | | (S)-1-(2-ethyl-6-isopropylphenyl)-3-((4-(trifluoromethyl)phenyl)(3-(trifluoromethyl)pyridin-2-yl)methyl)urea (2,2,2-trifluoroacetate) | 510.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 92 | 1 | | | (S)-1-(2-isopropyl-6-methylphenyl)-3-((4-(trifluoromethyl)phenyl)(3-(trifluoromethyl)pyridin-2-yl)methyl)urea (2,2,2-trifluoroacetate) | 496.0 |
| 93 | 1 | | | (S)-1-(3,5-dimethoxyphenethyl)-3-((4-(trifluoromethyl)phenyl)(3-(trifluoromethyl)pyridin-2-yl)methyl)urea (2,2,2-trifluoroacetate) | 528.0 |
| 94 | 1 | | | (S)-ethyl 2-(3-((S)-(4-(trifluoromethyl)phenyl)(3-(trifluoromethyl)pyridin-2-yl)ureido)propanoate (2,2,2-trifluoroacetate) | 464.0 |
| 95 | 1 | | | (S)-1-(3,4-dimethoxyphenethyl)-3-((4-(trifluoromethyl)phenyl)(3-(trifluoromethyl)pyridin-2-yl)methyyl)urea (2,2,2-trifluoroacetate) | 528.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 96 | 1 | | | (S)-methyl 3-(methyl-2-(3-((S)-(4-(trifluoromethyl)-phenyl)(3-(trifluoromethyl)-pyridin-2-yl)-methyl)-ureido)-butanoate (2,2,2-trifluoroacetate) | 478.0 |
| 97 | 1 | | | (S)-1-(3-cyanophenyl)-3-((4-(trifluoromethyl)-phenyl)(3-(trifluoromethyl)-pyridin-2-yl)-methyl)urea (2,2,2-trifluoroacetate) | 465.0 |
| 98 | 1 | | | ethyl 3-methyl-2-(3-((S)-(4-(trifluoromethyl)-phenyl)(3-(trifluoromethyl)-pyridin-2-yl)-methyl)-ureido)-butanoate (2,2,2-trifluoroacetate) | 492.0 |
| 99 | 1 | | | (3S)-methyl 3-methyl-2-(3-((S)-(4-(trifluoromethyl)-phenyl)(3-(trifluoromethyl)-pyridin-2-yl)-methyl)-ureido)-pentanoate (2,2,2-trifluoroacetate) | 492.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 100 | 1 | | | (S)-1-(3-nitrophenyl)-3-((4-(trifluoromethyl)phenyl)(3-(trifluoromethyl)pyridin-2-yl)methyl)urea (2,2,2-trifluoroacetate) | 485.0 |
| 101 | 1 | | | 1-(1-(4-bromophenyl)ethyl)-3-((S)-(4-(trifluoromethyl)phenyl)(3-(trifluoromethyl)pyridin-2-yl)methyl)urea (2,2,2-trifluoroacetate) | 546.0 |
| 102 | 1 | | | (S)-methyl 3-(3-((4-(trifluoromethyl)phenyl)(3-(trifluoromethyl)pyridin-2-yl)methyl)ureido)benzoate (2,2,2-trifluoroacetate) | 498.0 |
| 103 | 1 | | | (S)-dimethyl 5-(3-((4-(trifluoromethyl)phenyl)(3-(trifluoromethyl)pyridin-2-yl)methyl)ureido)isophthalate (2,2,2-trifluoroacetate) | 556.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 104 | 1 | | | (S)-butyl 2-(3-((4-(trifluoromethyl)phenyl)(3-(trifluoromethyl)pyridin-2-yl)methyl)ureido)acetate (2,2,2-trifluoroacetate) | 478.0 |
| 105 | 1 | | | (S)-1-(2-(3-(prop-1-en-2-yl)phenyl)propan-2-yl)-3-((4-(trifluoromethyl)phenyl)(3-(trifluoromethyl)pyridin-2-yl)methyl)urea (2,2,2-trifluoroacetate) | 522.0 |
| 106 | 1 | | | (S)-1-(3,5-dimethylphenyl)-3-((4-(trifluoromethyl)phenyl)(3-(trifluoromethyl)pyridin-2-yl)methyl)urea (2,2,2-trifluoroacetate) | 468.0 |
| 107 | 1 | | | 1-((S)-1-phenylethyl)-3-((S)-(4-(trifluoromethyl)phenyl)(3-(trifluoromethyl)pyridin-2-yl)methyl)urea (2,2,2-trifluoroacetate) | 468.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 108 | 1 | | | (S)-1-(2,5-dimethylphenyl)-3-((4-(trifluoromethyl)-pyridin-2-yl)methyl)urea (2,2,2-trifluoroacetate) | 468.0 |
| 109 | 1 | | | (S)-1-benzyl-3-((4-(trifluoromethyl)-phenyl)(3-(trifluoromethyl)-pyridin-2-yl)methyl)urea (2,2,2-trifluoroacetate) | 454.0 |
| 110 | 1 | | | (S)-1-(2,5-dimethoxyphenethyl)-3-((4-(trifluoromethyl)-phenyl)(3-(trifluoromethyl)-pyridin-2-yl)methyl)urea (2,2,2-trifluoroacetate) | 528.0 |
| 111 | 1 | | | (S)-1-((4-(trifluoromethyl)-phenyl)(3-(trifluoromethyl)-pyridin-2-yl)methyl)-3-(3,4,5-trimethoxybenzyl)urea (2,2,2-trifluoroacetate) | 544.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 112 | 1 | 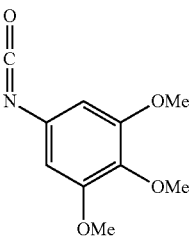 [SMILES: COc1cc(N=C=O)cc(OC)c1OC] | 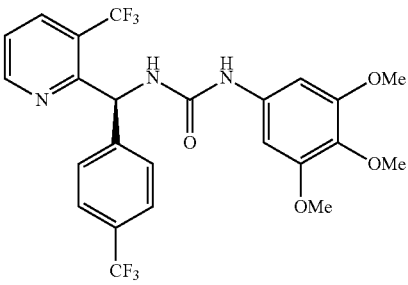 [SMILES: COc1cc(NC(=O)N[C@@H](c2ccc(C(F)(F)F)cc2)c2ncccc2C(F)(F)F)cc(OC)c1OC] | (S)-1-((4-(trifluoromethyl)-phenyl)(3-(trifluoromethyl)-pyridin-2-yl)-methyl)-3-(3,4,5-trimethoxy-phenyl)urea (2,2,2-trifluoroacetate) | 530.0 |
| 113 | 1 | 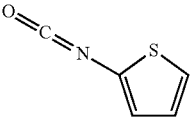 | 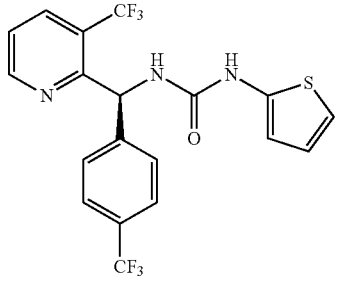 [SMILES: O=C(Nc1cccs1)N[C@@H](c1ccc(C(F)(F)F)cc1)c1ncccc1C(F)(F)F] | (S)-1-(thiophen-2-yl)-3-((4-(trifluoromethyl)-phenyl)(3-(trifluoromethyl)-pyridin-2-yl)-methyl)urea (2,2,2-trifluoroacetate) | 446.0 |
| 114 | 31 | 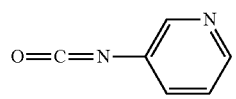 | 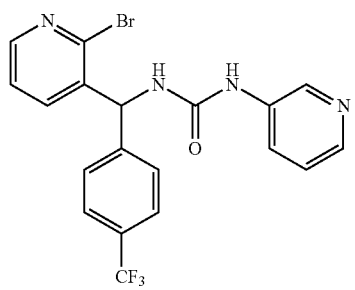 [SMILES: O=C(Nc1cccnc1)NC(c1ccc(C(F)(F)F)cc1)c1cccnc1Br] | 1-((2-bromopyridin-3-yl)(4-(trifluoromethyl)-phenyl)-methyl)-3-(pyridin-3-yl)-urea (2,2,2-trifluoroacetate) | 450.9 452.9 |
| 115 | 36 | 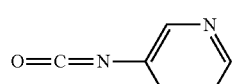 | 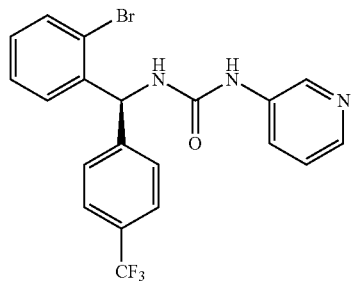 [SMILES: O=C(Nc1cccnc1)N[C@@H](c1ccc(C(F)(F)F)cc1)c1ccccc1Br] | (S)-1-((2-bromophenyl)(4-(trifluoromethyl)-phenyl)-methyl)-3-(pyridin-3-yl)-urea 2,2,2-trifluoroacetate (2,2,2-trifluoroacetate) | 449.9 451.9 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 116 | 36 | O=C=N-tBu | | (S)-1-((2-bromophenyl)(4-(trifluoromethyl)phenyl)methyl)-3-tert-butylurea | 428.9 431.0 |
| 117 | 30 | O=C=N-(3-pyridyl) | | (R)-1-((3-fluoro-4-(trifluoromethyl)phenyl)(3-(trifluoromethyl)phenyl)methyl)-3-(pyridin-3-yl)urea (2,2,2-trifluoroacetate) | 458.0 |
| 118 | 2 | | | (S)-methyl 2-(3-((3-fluoropyridin-2-yl)(4-(trifluoromethyl)phenyl)methyl)ureido)benzoate | 448.0 |
| 119 | 38 | O=C=N-(3-pyridyl) | | (S)-1-(pyridin-3-yl)-3-((4-(trifluoromethyl)phenyl)(4-(trifluoromethyl)pyridin-3-yl)methyl)urea bis(2,2,2-trifluoroacetate) | 440.9 |
| 120 | 26 | O=C=N-(3-pyridyl) | | 1-((3-bromopyridin-4-yl)(4-(trifluoromethyl)phenyl)methyl)-3-(pyridin-3-yl)urea (2,2,2-trifluoroacetate) | 450.9 452.9 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 121 | 37 | | | (S)-1-((3-fluoro-4-(trifluoromethyl)phenyl)(2-(trifluoromethyl)phenyl)methyl)-3-(pyridin-3-yl)-urea | 458.0 |
| 122 | 1 | | | (S)-1-(pyridin-3-yl)-3-((4-(trifluoromethyl)phenyl)(3-(trifluoromethyl)pyridin-2-yl)methyl)-thiourea | 457.0 |
| 123 | 1 | | | (S)-1-tert-butyl-3-((4-(trifluoromethyl)phenyl)(3-(trifluoromethyl)pyridin-2-yl)methyl)-thiourea | 436.0 |
| 124 | 1 | | | (S)-1-(3-iodophenyl)-3-((4-(trifluoromethyl)phenyl)(3-(trifluoromethyl)pyridin-2-yl)methyl)urea (2,2,2-trifluoroacetate) | 566.0 |
| 125 | 1 | | | (S)-1-(4-bromobenzyl)-3-((4-(trifluoromethyl)phenyl)(3-(trifluoromethyl)pyridin-2-yl)methyl)urea (2,2,2-trifluoroacetate) | 532.0 534.0 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 126 | 1 | | | (S)-1-(3-ethoxyphenyl)-3-((4-(trifluoromethyl)phenyl)(3-(trifluoromethyl)pyridin-2-yl)methyl)urea (2,2,2-trifluoroacetate) | 484.1 |
| 127 | 1 | | | (S)-1-(cyclohexylmethyl)-3-((4-(trifluoromethyl)phenyl)(3-(trifluoromethyl)pyridin-2-yl)methyl)urea (2,2,2-trifluoroacetate) | 460.2 |
| 128 | 1 | | | 1-((R)-1-(3-methoxyphenyl)ethyl)-3-((S)-(4-(trifluoromethyl)phenyl)(3-(trifluoromethyl)pyridin-2-yl)methyl)urea (2,2,2-trifluoroacetate) | 498.1 |
| 129 | 1 | | | 1-((S)-2,3-dihydro-1H-inden-1-yl)-3-((S)-(4-(trifluoromethyl)phenyl)(3-(trifluoromethyl)pyridin-2-yl)methyl)urea (2,2,2-trifluoroacetate) | 480.1 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 130 | 1 | | | 1-((R)-1-(4-methoxy-phenyl)ethyl)-3-((S)-(4-(trifluoro-methyl)-phenyl)(3-(trifluoro-methyl)-pyridin-2-yl)-methyl)urea (2,2,2-trifluoro-acetate) | 498.1 |
| 131 | 1 | | | (S)-1-((4-(trifluoro-methyl)-phenyl)(3-(trifluoro-methyl)-pyridin-2-yl)-methyl)-3-(2,4,4-trimethylpentan-2-yl)urea (2,2,2-trifluoro-acetate) | 476.2 |
| 132 | 1 | | | (S)-1-(2,6-dichlorophen-ethyl)-3-((4-(trifluoro-methyl)-phenyl)(3-(trifluoro-methyl)-pyridin-2-yl)-methyl)urea (2,2,2-trifluoro-acetate) | 536.1 |
| 133 | 1 | | | (S)-1-(2-ethoxybenzyl)-3-((4-(trifluoro-methyl)-phenyl)(3-(trifluoro-methyl)-pyridin-2-yl)-methyl)urea (2,2,2-trifluoro-acetate) | 498.1 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 134 | 1 | | | (S)-1-(4-chlorobenzyl)-3-((4-(trifluoromethyl)phenyl)(3-(trifluoromethyl)pyridin-2-yl)methyl)urea (2,2,2-trifluoroacetate) | 488.1 |
| 135 | 1 | | | (S)-1-(2,4-dichlorobenzyl)-3-((4-(trifluoromethyl)phenyl)(3-(trifluoromethyl)pyridin-2-yl)methyl)urea (2,2,2-trifluoroacetate) | 522.0 |
| 136 | 1 | | | (S)-methyl 3-phenyl-2-(3-((S)-(4-(trifluoromethyl)phenyl)(3-(trifluoromethyl)pyridin-2-yl)methyl)ureido)propanoate (2,2,2-trifluoroacetate) | 526.1 |
| 137 | 1 | | | (S)-1-(2-(methylthio)phenyl)-3-((4-(trifluoromethyl)phenyl)(3-(trifluoromethyl)pyridin-2-yl)methyl)urea (2,2,2-trifluoroacetate) | 486.1 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 138 | 1 | | | (S)-1-(4-acetylphenyl)-3-((4-(trifluoromethyl)phenyl)(3-(trifluoromethyl)pyridin-2-yl)methyl)urea (2,2,2-trifluoroacetate) | 482.1 |
| 139 | 1 | | | (S)-1-(4-fluoro-3-nitrophenyl)-3-((4-(trifluoromethyl)phenyl)(3-(trifluoromethyl)pyridin-2-yl)methyl)urea (2,2,2-trifluoroacetate) | 503.1 |
| 140 | 1 | | | (S)-1-(4-methyl-3-nitrophenyl)-3-((4-(trifluoromethyl)phenyl)(3-(trifluoromethyl)pyridin-2-yl)methyl)urea (2,2,2-trifluoroacetate) | 499.1 |
| 141 | 1 | | | (S)-1-(2-methoxy-4-nitrophenyl)-3-((4-(trifluoromethyl)phenyl)(3-(trifluoromethyl)pyridin-2-yl)methyl)urea (2,2,2-trifluoroacetate) | 515.1 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 142 | 1 | | | (S)-1-(2-methyl-3-nitrophenyl)-3-((4-(trifluoromethyl)phenyl)(3-(trifluoromethyl)pyridin-2-yl)methyl)urea (2,2,2-trifluoroacetate) | 499.1 |
| 143 | 1 | | | (S)-1-(5-methyl-2-nitrophenyl)-3-((4-(trifluoromethyl)phenyl)(3-(trifluoromethyl)pyridin-2-yl)methyl)urea (2,2,2-trifluoroacetate) | 499.1 |
| 144 | 1 | | | (S)-1-(4-fluorobenzyl)-3-((4-(trifluoromethyl)phenyl)(3-(trifluoromethyl)pyridin-2-yl)methyl)urea (2,2,2-trifluoroacetate) | 472.1 |
| 145 | 1 | | | (S)-1-(o-tolyl)-3-((4-(trifluoromethyl)phenyl)(3-(trifluoromethyl)pyridin-2-yl)methyl)urea (2,2,2-trifluoroacetate) | 454.1 |

TABLE 2-continued

Examples 2-147 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 146 | 1 | (2-fluoro-5-methylphenyl isocyanate structure) | (urea product structure) | (S)-1-(2-fluoro-5-methylphenyl)-3-((4-(trifluoromethyl)phenyl)(3-(trifluoromethyl)pyridin-2-yl)methyl)urea (2,2,2-trifluoroacetate) | 472.1 |
| 147 | 1 | (3-methylbenzyl isocyanate structure) | (urea product structure) | (S)-1-(3-methylbenzyl)-3-((4-(trifluoromethyl)phenyl)(3-(trifluoromethyl)pyridin-2-yl)methyl)urea (2,2,2-trifluoroacetate) | 468.1 |

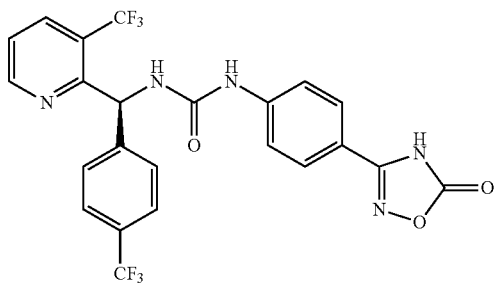 [SMILES: O=C(Nc1ccc(-c2noc(=O)[nH]2)cc1)N[C@@H](c1ccc(C(F)(F)F)cc1)c1ncccc1C(F)(F)F]

Example 148

(S)-1-(4-(5-Oxo-4,5-dihydro-1,2,4-oxadiazol-3-yl)phenyl)-3-((4-(trifluoromethyl)phenyl)(3-(trifluoromethyl)pyridin-2-yl)methyl)urea A 25 mL round-bottomed flask containing a solution of 3-(4-amino-phenyl)-1,2,4-oxadiazol-5(4H)-one 2,2,2-trifluoroacetate (0.107 g, 0.367 mmol) and CDI (0.140 g, 0.863 mmol) in anhydrous DCM (3.5 mL) was treated with DIPEA (0.200 mL, 1.150 mmol) and stirred for 3.5 h at rt. A solution of (S)-(4-(trifluoromethyl)phenyl)(3-(trifluoromethyl)pyridin-2-yl)methanamine hydrochloride (Intermediate 1) (0.118 g, 0.368 mmol) in anhydrous DCM (3.5 mL) was added followed by DIPEA (0.200 mL, 1.150 mmol), and the reaction mixture was stirred at rt for 12 h. The reaction mixture was then diluted with DCM (10 mL) and water (5 mL) and then absorbed onto a Varian Chem Elut (Diatomaceous Earth) cartridge. The organic filtrates were collected and concentrated to dryness. The resulting product was dissolved in DMSO/MeOH (1/1) (2.0 mL) and loaded on a Gilson HPLC system for purification using a MeCN/H$_2$O 0.1% TFA gradient and Phenomenx Gemini Axia-5µ C-18 column (150×30 mm). The solvent was removed from the pure fractions in the GENEVAC and the residue was dried under high vacuum to yield the title compound as an amorphous off-white solid. $^1$H NMR (400 MHz, DMSO-d$_6$): δ ppm 12.76 (s, 1H), 9.24 (s, 1H), 8.98 (d, J=3.9 Hz, 1H), 8.33-8.21 (m, 1H), 7.78-7.61 (m, 6H), 7.59-7.46 (m, 4H), 6.51 (d, J=8.4 Hz, 1H) MS (ESI pos. ion) m/z: 524.2 (M+H).

Scheme 9

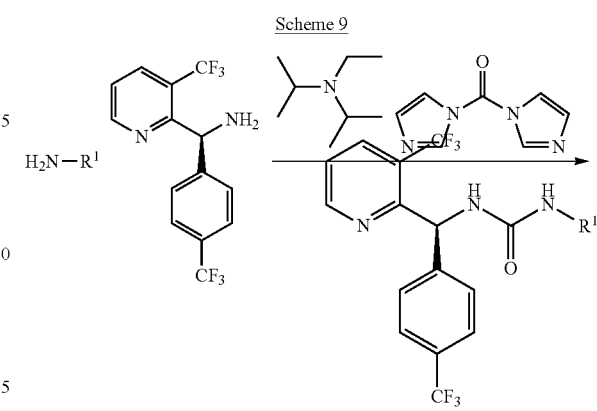

General Urea Formation Procedure for Examples

To a solution of amine (0.341 mmol) in DCM (2.0 mL) was added CDI (55.4 mg, 0.341 mmol). The solution was then stirred for 0.5 h at rt. The reaction was next treated with a solution of a second amine (selected from Intermediates 1-46) and DIPEA (0.075 mL, 0.429 mmol) in DCM (1.0 mL). After 1 h, the reaction was concentrated in vacuo. The product was then purified by either reverse phase HPLC (0-100% MeCN/(0.1% TFA in $H_2O$ ) or silica gel chromatography to provide the target compounds as either TFA salts or free bases. Compounds prepared using this general method (Scheme 9) are shown in Table 3.

TABLE 3

Examples 149-158 prepared via urea formation analogous to Scheme 9.

| Ex # | Amine Intermediate | Amine Coupling Partner Structure | Product Structure | Product Name | MS (ESI, positive ion) M + H |
|---|---|---|---|---|---|
| 149 | 2 | | | (S)-1-((3-fluoropyridin-2-yl)(4-(trifluoromethyl)-phenyl)-methyl)-3-(2-oxoindolin-5- | 445.1 |
| 150 | 41 | | | 1-((S)-(3-(prop-1-yn-1-yl)pyridin-2-yl)(4-(trifluoromethyl)-phenyl)-methyl)-3-((S)-1,1,1-trifluoropropan-2-yl)-urea | 430.1 |
| 151 | 7 | | | 1-((S)-(3-fluoro-4-(trifluoromethyl)-phenyl)(3-(trifluoromethyl)-pyridin-2-yl)-methyl)-3-((S)-1,1,1-trifluoropropan-2-yl)-urea (2,2,2-trifluoroacetate) | 478.0 |
| 152 | 7 | | | 1-((S)-(3-fluoro-4-(trifluoromethyl)-phenyl)(3-(trifluoromethyl)-pyridin-2-yl)-methyl)-3-((R)-1,1,1-trifluoropropan-2-yl)-urea (2,2,2-trifluoroacetate) | 478.0 |

TABLE 3-continued

Examples 149-158 prepared via urea formation analogous to Scheme 9.

| Ex # | Amine Intermediate | Amine Coupling Partner Structure | Product Structure | Product Name | MS (ESI, positive ion) M + H |
|---|---|---|---|---|---|
| 153 | 7 | H₂N-CH(CF₃) | (structure) | 1-((S)-(4-(trifluoro-methyl)-phenyl)(3-(trifluoro-methyl)-pyridin-2-yl)-methyl)-3-((S)-1,1,1-trifluoro-propan-2-yl)-urea (2,2,2-trifluoro-acetate) | 460.0 |
| 154 | 36 | H₂N-CH(CF₃) | (structure) | 1-((S)-(2-bromophenyl)(4-(trifluoro-methyl)-phenyl)-methyl)-3-((S)-1,1,1-trifluoro-propan-2-yl)-urea | 468.9 470.9 |
| 155 | 7 | H₂N-pyrimidin-5-yl | (structure) | (S)-1-((3-fluoro-4-(trifluoro-methyl)-phenyl)(3-(trifluoro-methyl)-pyridin-2-yl)-methyl)-3-(pyrimidin-5-yl)urea (2,2,2-trifluoro-acetate) | 460.0 |
| 156 | 2 | H₂N-CH(CF₃) | (structure) | 1-((S)-(3-fluoropyridin-2-yl)(4-(trifluoro-methyl)-phenyl)-methyl)-3-((S)-1,1,1-trifluoro-propan-2-yl)-urea | 410.0 |
| 157 | 40 | H₂N-CH(CF₃) | (structure) | 1-((S)-(3-bromopyridin-2-yl)(4-(trifluoro-methyl)-phenyl)-methyl)-3-((S)-1,1,1-trifluoro-propan-2-yl)-urea | 470.0 |

TABLE 3-continued

Examples 149-158 prepared via urea formation analogous to Scheme 9.

| Ex # | Amine Intermediate | Amine Coupling Partner Structure | Product Structure | Product Name | MS (ESI, positive ion) M + H |
|---|---|---|---|---|---|
| 158 | 43 | H₂N—CF₃ (with stereochemistry) | (structure shown) | 1-((S)-(3-allylpyridin-2-yl)(4-(trifluoromethyl)-phenyl)-methyl)-3-((S)-1,1,1-trifluoropropan-2-yl)-urea | 432.0 |

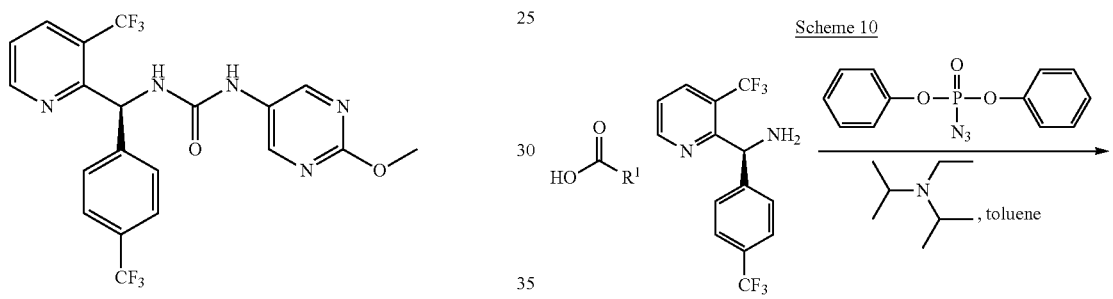

Example 159

(S)-1-(2-Methoxypyrimidin-5-yl)-3-((4-(trifluoromethyl)-phenyl)(3-(trifluoromethyl)pyridin-2-yl)methyl)urea To a solution of 2-methoxypyrimidine-5-carboxylic acid (57 mg, 0.370 mmol), DIPEA (0.161 mL, 0.925 mmol), and toluene (3 mL) was added DPPA (0.104 mL, 0.481 mmol). The reaction was stirred at 80° C. for 2 h. (S)-(4-(Trifluoromethyl)phenyl)(3-(trifluoromethyl)pyridin-2-yl)methanamine hydrochloride (Intermediate 1) (134 mg, 0.376 mmol) was then added as a solid in one portion. After 16 h, the reaction was concentrated in vacuo and the crude product was adsorbed onto a plug of silica gel and chromatographed through a Redi-Sep® pre-packed silica gel column (12 g), eluting with 0-100% EtOAc in hexane, to provide the title compound as an off-white solid. ¹H NMR (300 MHz, CDCl₃): δ ppm 8.96 (s, 2H), 8.90 (d, J=3.8 Hz, 1H), 8.22 (d, J=7.5 Hz, 1H), 8.05 (d, J=6.9 Hz, 1H), 7.63-7.45 (m, 6H), 6.85 (d, J=7.7 Hz, 1H), 4.07 (s, 3H). MS (ESI pos. ion) m/z: 472.0 (M+H).

General Urea Formation Procedure for Examples (160-166)

To a solution of a carboxylic acid (0.370 mmol), DIPEA (0.925 mmol, 2.5 equiv.) in toluene (3 mL) was added DPPA (0.104 mL, 0.481 mmol, 1.3 equiv.). The reaction was then stirred at 80° C. for 2 hours. An amine (Intermediates 1-46) (0.376 mmol, 1.0 equiv.) was then added. The resulting reaction mixture was then stirred for 16 h at rt. The reaction was then concentrated, and the product was purified by either reverse phase HPLC (0-100% MeCN/(0.1% TFA in H₂O) or silica gel chromatography to provide the target compounds as either TFA salts or free bases. Compounds prepared using this general method (Scheme 10) are shown in Table 4.

TABLE 4

Examples 160-166 prepared via urea formation analogous to Scheme 10.

| Ex # | Amine Intermediate | Acid Structure | Product Structure | Product Name | MS (ESI, positive ion) M + H |
|---|---|---|---|---|---|
| 160 | 2 | | | (S)-1-((3-fluoropyridin-2-yl)(4-(trifluoro-methyl)-phenyl)-methyl)-3-(2-methoxy-pyrimidin-5-yl)urea | 422.0 |
| 161 | 2 | | | (S)-1-((3-fluoropyridin-2-yl)(4-(trifluoro-methyl)-phenyl)-methyl)-3-(1-methyl-2-oxo-1,2-dihydropyridin-4-yl)urea | 421.1 |
| 162 | 2 | | | (S)-1-((3-fluoropyridin-2-yl)(4-(trifluoro-methyl)-phenyl)-methyl)-3-(1-methyl-6-oxo-1,6-dihydropyridin-3-yl)urea | 421.1 |
| 163 | 2 | | | (S)-1-((3-fluoropyridin-2-yl)(4-(trifluoro-methyl)-phenyl)-methyl)-3-(2-oxo-1,2-dihydropyridin-3-yl)urea | 407.1 |
| 164 | 2 | | | (S)-1-((3-fluoropyridin-2-yl)(4-(trifluoro-methyl)-phenyl)-methyl)-3-(2-oxo-1,2-dihydropyridin-4-yl)urea | 407.1 |

TABLE 4-continued

Examples 160-166 prepared via urea formation analogous to Scheme 10.

| Ex # | Amine Intermediate | Acid Structure | Product Structure | Product Name | MS (ESI, positive ion) M + H |
|---|---|---|---|---|---|
| 165 | 2 | (structure) | (structure) | (S)-1-((3-fluoropyridin-2-yl)(4-(trifluoro-methyl)-phenyl)-methyl)-3-(6-oxo-1,6-dihydropyridin-3-yl)urea | 407.1 |
| 166 | 2 | (structure) | (structure) | (S)-1-((3-fluoropyridin-2-yl)(4-(trifluoro-methyl)-phenyl)-methyl)-3-(2-oxoindolin-6-yl)urea | 445.1 |

Additional Examples

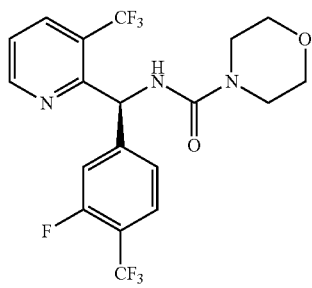 [SMILES: O=C(N[C@@H](c1ccc(C(F)(F)F)c(F)c1)c1ncccc1C(F)(F)F)N1CCOCC1]

Example 167

(S)—N-((3-Fluoro-4-(trifluoromethyl)phenyl)(3-(trifluoromethyl)pyridin-2-yl)methyl)morpholine-4-carboxamide 2,2,2-trifluoroacetate To a solution of (S)-(3-fluoro-4-(trifluoromethyl)phenyl)(3-(trifluoro-methyl)pyridin-2-yl)methanamine (Intermediate 7) (100 mg, 0.296 mmol) and DIPEA (0.101 mL, 0.591 mmol) in DCM (1.0 mL) was added morpholine-4-carbonyl chloride (66.3 mg, 0.443 mmol). The resulting reaction mixture was stirred at rt for 19 h. The reaction was then diluted with DMF (2 mL), filtered through a syringe filter, and purified by reverse phase HPLC (Phenomenx Gemini Axia™-5µ C-18 column (150×30 mm) 10-100% MeCN/0.1% TFA in $H_2O$). The product-containing fractions were combined, and the solvent was removed by lyophilization to give the title compound as a white solid. $^1$H NMR (300 MHz, $d_4$-MeOH) δ ppm 8.66-8.43 (m, 1H), 7.84 (d, J=7.9 Hz, 1H), 7.38-7.12 (m, 2H), 7.07-6.83 (m, 2H), 6.26 (s, 1H), 3.35 (peak obscured by solvent), 3.08 (br. s., 4H), 2.98 (br. s., 2H). MS (ESI pos. ion) m/z: 452.0 (M+H).

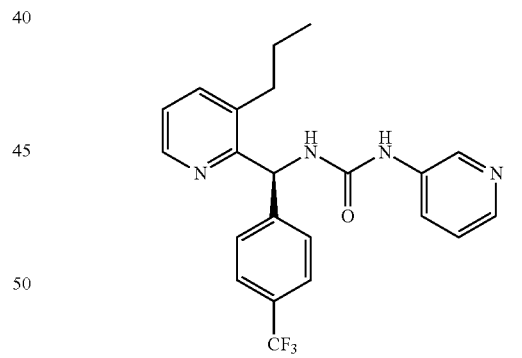

Example 168

(S)-1-((3-Propylpyridin-2-yl)(4-(trifluoromethyl)phenyl)-methyl)-3-(pyridin-3-yl)urea A solution of (S)-1-((3-allylpyridin-2-yl)(4-(trifluoromethyl)phenyl)-methyl)-3-(pyridin-3-yl)urea (Example 43) (0.055 g, 0.133 mmol) and Pd (10 wt % on carbon, 0.020 g, 0.133 mmol) in MeOH was hydrogenated under $H_2$ (1 atm) at rt for 4 h. The catalyst was filtered off, and the filtrate was concentrated to give the title compound as a white solid. $^1$H NMR (300 MHz, $d_4$-MeOH): δ ppm 8.60-8.38 (m, 2H), 8.12

(d, J=4.4 Hz, 1H), 7.93 (d, J=8.3 Hz, 1H), 7.74-7.43 (m, 5H), 7.40-7.21 (m, 2H), 6.42 (s, 1H), 2.89-2.51 (m, 2H), 1.74-1.35 (m, 2H), 0.95 (t, J=7.2 Hz, 3H). MS (ESI pos. ion) m/z: 415.0 (M+H).

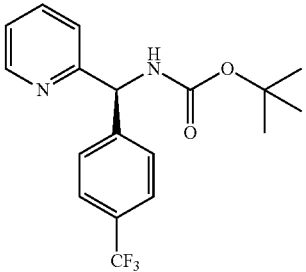 [SMILES: CC(C)(C)OC(=O)N[C@@H](c1ccc(C(F)(F)F)cc1)c1ccccn1]

Example 169

(S)-tert-Butyl(pyridin-2-yl(4-(trifluoromethyl)phenyl)methyl)-carbamate 2,2,2-trifluoroacetate To a flame-dried round bottom flask was added (S)-tert-butyl((3-bromo-pyridin-2-yl)(4-(trifluoromethyl)phenyl)methyl)carbamate (Intermediate 40, Step 5) (195 mg, 0.452 mmol) and THF (2 mL). The solution was cooled in a dry ice/acetone bath for 5 minutes and then it was treated with 1.7 M t-BuLi in pentane (0.6 mL, 1.020 mmol) and allowed to stir for 1 min. The solution was then treated dropwise with acetone (0.10 mL, 1.362 mmol). The solution was then allowed to warm to rt as the cooling bath warmed. After 5 minutes, LC-MS indicated that the major components were starting bromide and des-bromide product. The reaction was concentrated in vacuo, taken up in MeOH (3 mL) and purified by reverse-phase preparative HPLC (Shimadzu) on a Phenomenex Gemini column (10 micron, C18, 110 Å, Axia, 100×50 mm) eluting at 90 mL/min with a linear gradient of 20% to 90% MeCN (0.1% TFA) in water (0.1% TFA) over 10 minutes to give the title compound as a white solid after lyophilization. $^{1}$H NMR (300 MHz, CDCl$_{3}$) δ ppm 8.76 (d, J=5.1 Hz, 1H), 8.11-7.90 (m, 1H), 7.68-7.39 (m, 6H), 6.88-6.63 (m, 1H), 6.26-6.01 (m, 1H), 1.42 (s, 9H). MS (ESI pos. ion) m/z: 353.0 (M+H).

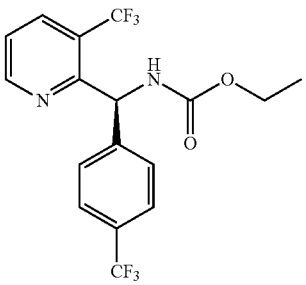 [SMILES: CCOC(=O)N[C@@H](c1ccc(C(F)(F)F)cc1)c1ncccc1C(F)(F)F]

Example 170

(S)-Ethyl((4-(trifluoromethyl)phenyl)(3-(trifluoromethyl)-pyridin-2-yl)methyl)carbamate To a mixture of (S)-(4-(trifluoromethyl)phenyl)(3-(trifluoromethyl)-pyridin-2-yl)methanamine (Intermediate 1)

(0.0610 g, 0.190 mmol) and DIPEA (0.066 mL, 0.381 mmol) in MeCN (1 mL) was added ethyl carbonochloridate (0.027 mL, 0.286 mmol). The mixture was then stirred at rt overnight. The mixture was diluted with saturated aqueous NaHCO$_{3}$ and extracted with DCM. The organic phase was dried over Na$_{2}$SO$_{4}$ and concentrated in vacuo. The resulting product was purified by silica gel chromatography: 5-50% EtOAc-hexanes to give the title compound as a colorless oil. $^{1}$H NMR (400 MHz, CDCl$_{3}$) δ ppm 8.83 (d, J=4.30 Hz, 1H), 7.99 (d, J=7.24 Hz, 1H), 7.46-7.60 (m, 4H), 7.40 (dd, J=7.73, 4.79 Hz, 1H), 6.54 (d, J=7.43 Hz, 1H), 6.41 (d, J=8.22 Hz, 1H), 4.11 (q, J=7.17 Hz, 2H), 1.17-1.30 (m, 3H). MS (ESI pos. ion) m/z: 393.0 (M+H).

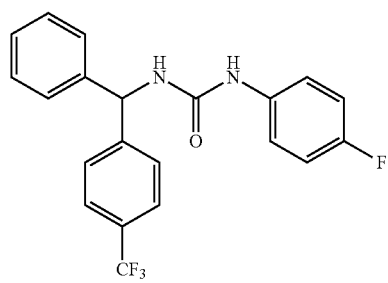 [SMILES: O=C(Nc1ccc(F)cc1)NC(c1ccccc1)c1ccc(C(F)(F)F)cc1]

Example 171

1-(4-Fluorophenyl)-3-(phenyl(4-(trifluoromethyl)phenyl)-methyl)urea

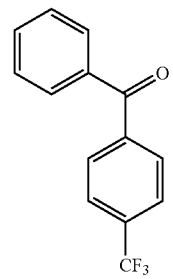

Step 1. Phenyl(4-(trifluoromethyl)phenyl)methanone

A solution of 4-(trifluoromethyl)benzhydrol (1.836 g, 7.3 mmol) in anhydrous DCM (65 mL) was treated with manganese(IV) oxide (<5 micron, activated) (5.7 g, 66 mmol). The resulting suspension was stirred at rt for 12 days. The catalyst was removed by filtration through a Celite® brand filter agent pad. The filtrate was concentrated, and the resulting solid was dried under high vacuum to afford the title compound as a white solid.

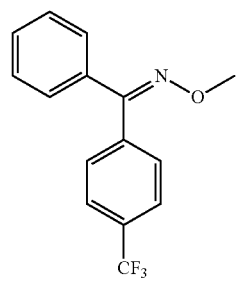 [SMILES: CO/N=C(/c1ccccc1)c1ccc(C(F)(F)F)cc1]

Step 2. Phenyl(4-(trifluoromethyl)phenyl)methanone O-methyl oxime

To a 100-mL round-bottomed flask, phenyl(4-(trifluoromethyl)phenyl)-methanone (1.0105 g, 4.039 mmol) and methoxyamine (0.4208 g, 5.038 mmol) were dissolved in pyridine (10 mL). The mixture was stirred at rt overnight. Additional methoxyamine (0.1625 g) was added, and the solution was stirred at rt for 7 h. EtOAc was added and the organic phase was washed with water, 1 N HCl (2×), water, and then with brine. The organic phase was dried over sodium sulfate, filtered and concentrated in vacuo to afford a clear oil. The oil thus obtained was purified by Biotage (EtOAc/hexanes 0-20%) to afford the title compound (1.12 g, 99.4%) as a clear oil.

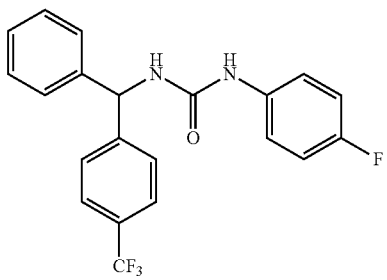 [SMILES: O=C(Nc1ccc(F)cc1)NC(c1ccccc1)c1ccc(C(F)(F)F)cc1]

Step 3. 1-(4-Fluorophenyl)-3-(phenyl(4-(trifluoromethyl)phenyl)methyl)urea

To a 5 mL microwave vial, phenyl(4-(trifluoromethyl)phenyl)methanone O-methyl oxime (0.1541 g, 0.552 mmol) and Pd/C (10 wt %, 0.0345 g, 0.324 mmol) were mixed into MeOH (2 mL). The reaction mixture was evacuated under vacuum and refilled with hydrogen (2×). The mixture was hydrogenated under balloon pressure of hydrogen at rt for 45 min. Next, 2 M $NH_3$ in MeOH (1 mL) was added and the hydrogenation was resumed under balloon pressure of hydrogen for 1 h. The Pd catalyst was removed via filtration through a pad of Celite® brand filter agent. Evaporation of solvent resulted in 0.1375 g of clear oil. The oil thus obtained was dissolved in DCM (5 mL) and 4-fluorophenyl isocyanate (0.0800 mL, 0.662 mmol) was added. The mixture was then stirred at rt for 1 h. Next, the reaction mixture was purified by Biotage™ (0-50% EtOAc/hexanes) twice to obtain the title compound as a white solid. $^1$H NMR (300 MHz, DMSO) δ ppm 8.52 (s, 1H), 7.72 (d, J=8.2 Hz, 2H), 7.54 (d, J=8.2 Hz, 2H), 7.40-7.23 (m, 8H), 7.06 (dd, J=8.6, 8.2 Hz, 2H), 6.05 (d, J=7.2 Hz, 1H). MS (ESI pos. ion) m/z: 389.0 (M+H).

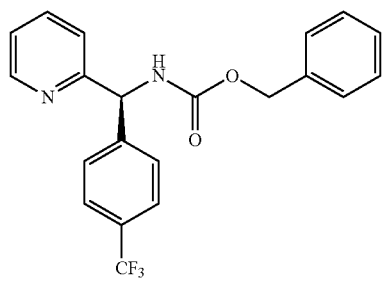 [SMILES: O=C(N[C@@H](c1ccc(C(F)(F)F)cc1)c1ccccn1)OCc1ccccc1]

Example 172

(S)-Benzyl(pyridin-2-yl(4-(trifluoromethyl)phenyl) methyl)-carbamate 2,2,2-trifluoroacetate

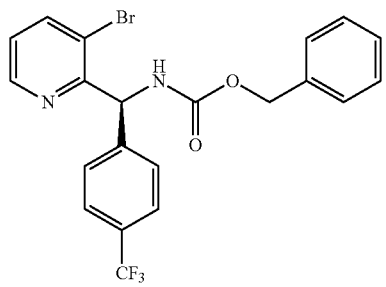 [SMILES: O=C(N[C@@H](c1ccc(C(F)(F)F)cc1)c1ncccc1Br)OCc1ccccc1]

Step 1. (S)-Benzyl((3-bromopyridin-2-yl)(4-(trifluoromethyl)phenyl)methyl)-carbamate To an ice bath cooled solution of (S)-(3-bromopyridin-2-yl)(4-(trifluoromethyl)phenyl)methanamine hydrochloride (Intermediate 40) (1.20 g, 2.2 mmol), DIPEA (1.50 mL, 8.6 mmol), and DCM (20 mL) was added benzyl chloroformate (0.40 mL, 2.8 mmol). The resulting mixture was allowed to warm to rt as the bath warmed. After 16 h, the reaction was eluted through a cartridge of silica gel (25 g) with DCM. The filtrate was concentrated in vacuo to give the title compound as a light yellow oil. MS (ESI pos. ion) m/z: 464.9, 466.9 (M+H).

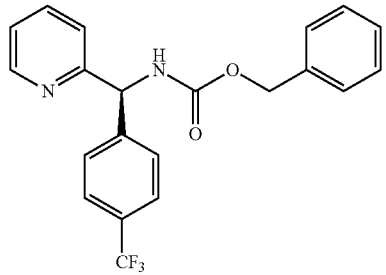 [SMILES: O=C(N[C@@H](c1ccc(C(F)(F)F)cc1)c1ccccn1)OCc1ccccc1]

Step 2. (S)-Benzyl(pyridin-2-yl(4-(trifluoromethyl) phenyl)methyl)carbamate 2,2,2-trifluoroacetate To a round bottom flask was added (S)-benzyl((3-bromopyridin-2-yl)(4-(trifluoromethyl)phenyl)methyl)carbamate (1.20 g, 1995 μmol), $Pd_2(dba)_3$ (183 mg, 200 mol), 2-dicyclohexylphosphino-2',4',6'-triisopropylbiphenyl (XPhos) (190 mg, 399 μmol), and THF (20 mL). To this mixture was added (2-(1,3-dioxolan-2-yl)ethyl)zinc(II) bromide (0.5M in $Et_2O$, 10 mL, 5 mmol). The resulting mixture was stirred at rt for 16 h. The reaction was then heated at 70° C. for 5 h. The reaction was next treated with another equivalent of catalyst, ligand and zinc reagent and heating was continued. After a further 5 days of heating, the reaction was filtered through a plug of silica gel and the plug washed with 50% EtOAc/hexanes. The filtrate was concentrated in vacuo and adsorbed onto a plug of silica gel and purified by silica gel chromatography (40 g $SiO_2$ 0-25% EtOAc/hexanes) to provide (S)-benzyl(3-((1,3-dioxolan-2-yl)methyl)pyridin-2-yl)(4-(trifluoromethyl)phenyl)methylcarbamate (175 mg, 19% yield) as a brown solid. Further purification of mixed fractions by reverse-phase preparative HPLC ((Shimadzu, Phenomenex Gemini column (5 micron, C18, 110 Å, Axia, 100×50 mm)) eluting at 90 mL/min with an linear gradient of 10-70% MeCN (0.1% TFA) in water (0.1% TFA) over 20 minutes gave the title compound as an off-white fluffy powder after lyophilization. ¹H NMR (300 MHz, CDCl₃) δ ppm 12.32 (br. s., 1H), 8.76 (d, J=4.4 Hz, 1H), 8.09 (t, J=7.0 Hz, 1H), 7.76-7.53 (m, 4H), 7.45 (d, J=8.0 Hz, 2H), 7.33 (br. s., 5H), 6.25 (d, J=6.9 Hz, 1H), 5.22-5.02 (m, 2H). MS (ESI pos. ion) m/z: 387.0 (M+H).

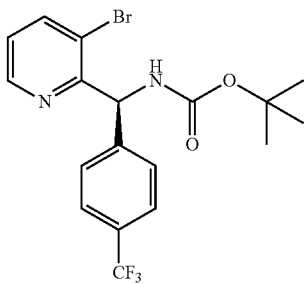 [SMILES: CC(C)(C)OC(=O)N[C@@H](c1ccc(C(F)(F)F)cc1)c1ncccc1Br]

Example 173

(S)-tert-Butyl((3-bromopyridin-2-yl)(4-(trifluoromethyl)-phenyl)methyl)carbamate The title compound was synthesized as described for Intermediate 40, Step 5. ¹H-NMR (300 MHz, DMSO-d₆): δ ppm 8.60 (d, J=3.7 Hz, 1H), 8.10 (dd, J=8.0, 1.5 Hz, 1H) 7.63-7.79 (m, 3H), 7.54 (d, J=7.5 Hz, 2H), 7.32 (dd, J=8.0, 4.5 Hz, 1H), 6.31 (d, J=8.5 Hz, 1H), 1.37 (s, 9H). MS (ESI pos. ion) m/z: 431.2, 433.2 (M+H).

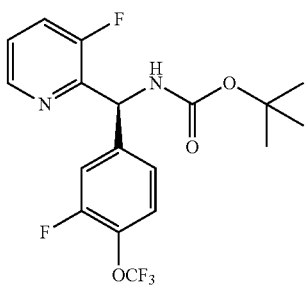 [SMILES: CC(C)(C)OC(=O)N[C@@H](c1ccc(OC(F)(F)F)c(F)c1)c1ncccc1F]

Example 174

(S)-tert-Butyl((3-fluoro-4-(trifluoromethoxy)phenyl) (3-fluoropyridin-2-yl)methyl)carbamate Di-tert-butyl dicarbonate (0.066 mL, 0.29 mmol) was added to a stirred solution of (S)-(3-fluoro-4-(trifluoromethoxy)phenyl)(3-fluoropyridin-2-yl)methanamine hydrochloride (Intermediate 39) (0.1 g, 0.29 mmol) in a 25 mL single neck rb flask in THF (5.0 mL) and saturated aqueous NaHCO₃ (2.0 mL) solution at ambient temperature. The reaction mixture was stirred at rt for 3 h. After completion of the reaction (monitored by TLC, 50% EtOAc in hexane), water (20 mL) was added to the reaction mixture, the product was extracted with Et₂O (20 mL×2), and the combined organic layers were washed with water. The organic layer was dried over anhydrous sodium sulfate and concentrated to give a residue which was purified by prep TLC using 10% EtOAc in hexane as eluent to give the title compound (0.04 g) as a sticky liquid. ¹H-NMR (400 MHz, DMSO-d₆): δ ppm 8.41 (d, J=4.4 Hz, 1H), 7.93 (d, J=8.4 Hz, 1H), 7.75-7.71 (m, 1H), 7.55-7.51 (m, 2H), 7.46-7.42 (m, 1H), 7.30 (d, J=8.0 Hz, 1H), 6.19 (d, J=8.8 Hz, 1H), 1.37 (s, 9H). MS (ESI pos. ion) m/z: 405.1 (M+H).

Scheme 11

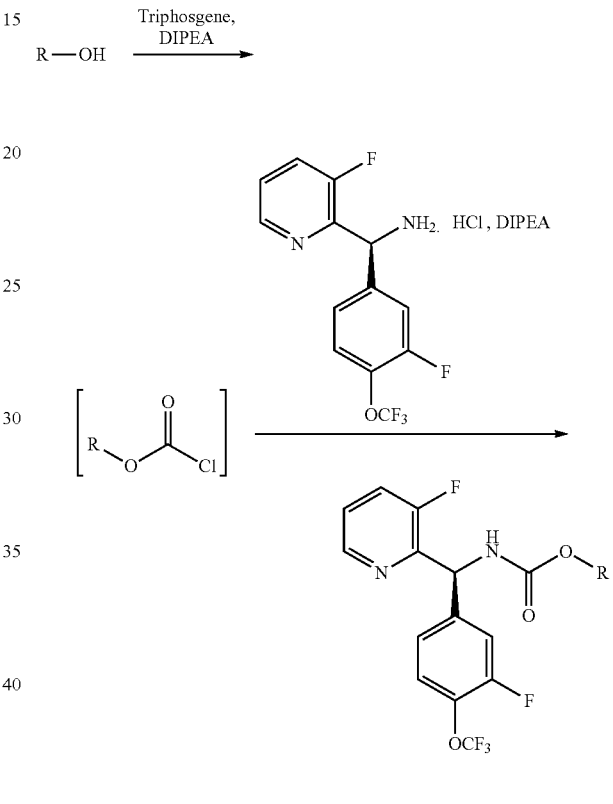

General Carbamate Formation Procedure for Examples (175-177)

To a stirred solution of an alcohol (1.0 eq) in DCM (10 volumes) at 0° C., was added DIPEA (1.5 eq) followed by triphosgene (1.0 eq). After stirring the resulting solution at the same temperature for 1 h, a solution of (S)-(3-fluoro-4-(trifluoromethoxy)phenyl) (3-fluoropyridin-2-yl) methanamine hydrochloride (1.0 eq) (Intermediate 39) in DCM (10 volumes) and DIPEA (1.5 eq) was added dropwise to the reaction. The reaction mixture was stirred at the same temperature for 0.5 h-2 h. After completion of the reaction (monitored by TLC, 50% EtOAc in hexane), water was added to the reaction mixture, and the mixture was extracted with Et₂O. The combined organic layers were washed with water. The organic layer was dried, filtered and concentrated to give a residue. The residue was purified by column chromatography over silica gel (60-120 mesh) using 5-20% EtOAc in hexane as eluent to give examples 175-177 as solids.

TABLE 5

Examples 175-177 prepared via carbamate formation analogous to Scheme 11.

| Ex # | Alcohol | Product Structure | Product Name | MS (ESI, positive ion) M + H |
|---|---|---|---|---|
| 175 | propan-2-ol | | (S)-isopropyl ((3-fluoro-4-(trifluoromethoxy)phenyl)(3-fluoropyridin-2-yl)methyl)carbamate | 391.1 |
| 176 | tetrahydro-2H-pyran-4-ol | | (S)-tetrahydro-2H-pyran-4-yl ((3-fluoro-4-(trifluoromethoxy)phenyl)(3-fluoropyridin-2-yl)methyl)carbamate | 433.1 |
| 177 | oxetan-3-ol | | (S)-oxetan-3-yl ((3-fluoro-4-(trifluoromethoxy)phenyl)(3-fluoropyridin-2-yl)methyl)carbamate | 405.0 |

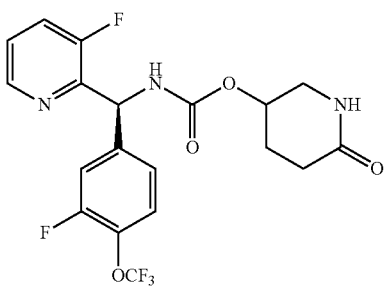 [SMILES: O=C1CCC(OC(=O)N[C@@H](c2ccc(OC(F)(F)F)c(F)c2)c2ncccc2F)CN1]

Example 178

6-Oxopiperidin-3-yl((S)-(3-fluoro-4-(trifluoromethoxy)phenyl)(3-fluoropyridin-2-yl)methyl) carbamate

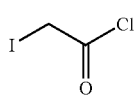

Step 1. 2-Iodoacetyl chloride

Thionyl chloride (0.1 mL, 1.32 mmol) was added dropwise to 2-iodoacetic acid (0.2 g, 1.1 mmol) at 0° C. The cooling bath was removed, and the reaction mixture was stirred at rt overnight with the exclusion of moisture and light. After completion of the reaction (monitored by TLC, 5% EtOAc in hexane), the excess thionyl chloride was evaporated under reduced pressure to give the title compound as a pink oil (0.2 g crude). The intermediate thus obtained was taken on to the next step without further purification.

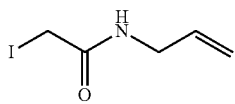

Step 2. N-Allyl-2-iodoacetamide

To a stirred solution of allyl amine (0.07 mL, 0.98 mmol) in DCM (2.0 mL) was added triethylamine (0.17 mL, 1.2 mmol) at rt. The resulting mixture was treated dropwise with a solution of 2-iodoacetyl chloride (0.2 g, 0.98 mmol) in DCM (2 mL) at 0° C. under nitrogen atmosphere. The reaction mixture was then stirred at the same temperature for an additional 2 h. After completion of the reaction (monitored by TLC, 30% EtOAc in hexane), water (20 mL) was added to the reaction mixture, and the aqueous layer extracted with DCM (20 mL×2). The combined organic layers were dried, filtered and concentrated to give a residue. The residue was purified by column chromatography over silica gel (60 120 mesh) using 15-30% EtOAc in hexane as eluent to give the title compound (0.03 g, 14%) as a white solid.

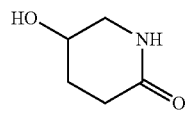

Step 3. 5-Hydroxypiperidin-2-one

Triethylborane (0.1 mL, 0.1 mmol, 1 M solution in hexane) was added to a DCM (5 mL) solution of N-allyl iodoacetamide (0.225 g, 1.0 mmol) and boron trifluoride dihydrate (0.25 g, 3.0 mmol) at rt. The resulting mixture was then stirred at this temperature for 2 h. The solution was then concentrated under reduced pressure, and the residue was refluxed gently with hydrochloric acid (20 mL, 1 N aqueous) for 3 h. The resulting mixture was then concentrated in vacuo, and the residue was dissolved in anhydrous MeOH (15 mL). Potassium carbonate (0.55 g, 4 mmol) was added, and the mixture was stirred at rt overnight. After evaporation of the solvent under reduced pressure, the resulting product was purified by flash chromatography on silica gel with chloroform-MeOH (4:1) as the eluent to afford the title compound as a white solid. $^1$H-NMR (400 MHz, CD$_3$OD): δ ppm 3.94-3.98 (m, 1H), 3.30 (dd, J=12.8, 4.0 Hz, 1H), 3.07 (dd, J=4.8, 1.2 Hz, 1H), 2.35-2.44 (m, 1H), 2.16-2.23 (m, 1H), 1.79-1.87 (m, 2H).

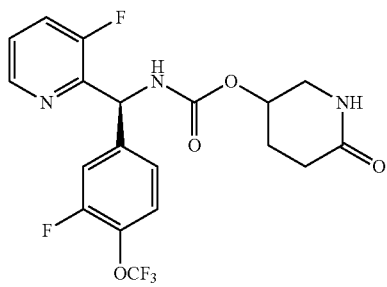 [SMILES: O=C1CCC(OC(=O)N[C@@H](c2ccc(OC(F)(F)F)c(F)c2)c2ncccc2F)CN1]

Step 4. 6-Oxopiperidin-3-yl((S)-(3-fluoro-4-(trifluoromethoxy)phenyl)(3-fluoropyridin-2-yl)methyl) carbamate To a solution of 5-hydroxypiperidin-2-one (0.2 g, 1.74 mmol) in DCM (10.0 mL) at 0° C., was added DIPEA (0.45 mL, 2.61 mmol) followed by triphosgene (0.52 g, 1.74 mmol). The reaction was then stirred for 3 h at rt and then added via cannula to a solution of (S)-(3-fluoro-4-(trifluoromethoxy)phenyl) (3-fluoropyridin-2-yl) methanamine hydrochloride (Intermediate 39) (0.59 g, 1.74 mmol) in DCM (10.0 mL) and DIPEA (0.45 mL, 2.61 mmol). The resulting reaction mixture was stirred at the same temperature for 2 h. After completion of the reaction (monitored by TLC, 50% EtOAc in hexane), saturated aqueous ammonium chloride was added to the reaction mixture, and the mixture was extracted with DCM (10 mL×2). The combined organic layers were washed with water, dried, filtered, and concentrated to give a residue. The residue was purified by prep HPLC [Agilent Zorbax XDB-C18 column (21×150 mm, 5 microns); gradient elution, 20 mL/min, 20-70% (1:1 CAN:MeOH): 0.01% TFA in H$_2$O] to give the title compound (0.04 g) as a white solid. $^1$H-NMR (400 MHz, DMSO-d$_6$): δ ppm 8.50 (d, J=4.4 Hz, 1H), 7.77-7.82 (m, 1H), 7.55-7.57 (m, 1H), 7.48-7.51 (m, 1H), 7.38-7.43 (m, 2H), 7.24 (d, J=8.4 Hz, 1H), 6.64 (d, J=7.2 Hz, 1H), 6.32 (d, J=8.4 Hz, 1H) 4.52-4.53 (m, 1H), 3.24-3.28 (m, 2H), 2.44-2.47 (m, 2H), 2.10-2.20 (m, 1H), 1.65-1.75 (m, 1H). MS (ESI pos. ion) m/z: 445.9 (M+H).

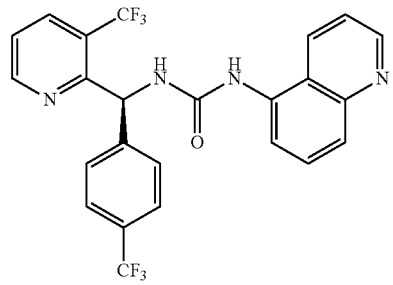 [SMILES: O=C(Nc1cccc2ncccc12)N[C@@H](c1ccc(C(F)(F)F)cc1)c1ncccc1C(F)(F)F]

Example 179

(S)-1-(Quinolin-5-yl)-3-((4-(trifluoromethyl)phenyl) (3-(trifluoromethyl)pyridin-2-yl)methyl)urea A mixture of quinoline-5-carboxylic acid (0.054 g, 0.312 mmol), DIPEA (0.054 mL, 0.312 mmol), and DPPA (0.067 mL, 0.312 mmol) in 1,4-dioxane (2 mL) was stirred at rt for 1 h. (S)-(4-(Trifluoromethyl)phenyl)(3-(trifluoromethyl)pyridin-2-yl)methanamine hydrochloride (Intermediate 1) (0.100 g, 0.312 mmol) was added, and the resulting mixture was heated at 85° C. for 24 h. The reaction mixture was cooled, concentrated, and purified by ISCO (Silica gel, 0-75% EtOAc/hexanes) to give the title compound. $^1$H-NMR (300 MHz, MeOH-d$_4$): δ ppm 8.93 (d, J=4.5 Hz, 1H), 8.82 (d, J=3.5 Hz, 1H), 8.46 (d, J=8.5 Hz, 1H), 8.18 (d, J=8.0 Hz, 1H), 7.85 (d, J=7.3 Hz, 1H), 7.75-7.83 (m, 1H), 7.71 (d, J=7.7 Hz, 1H), 7.54-7.68 (m, 5H), 7.51 (dd, J=8.6, 4.2 Hz, 1H), 6.67 (s, 1H). MS (ESI pos. ion) m/z: 491.0 (M+H).

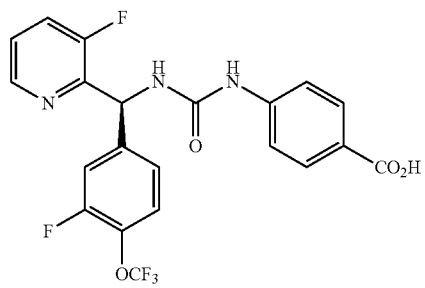 [SMILES: O=C(Nc1ccc(C(=O)O)cc1)N[C@@H](c1ccc(OC(F)(F)F)c(F)c1)c1ncccc1F]

Example 180

(S)-4-(3-((3-Fluoro-4-(trifluoromethoxy)phenyl)(3-fluoropyridin-2-yl)methyl)ureido)benzoic acid

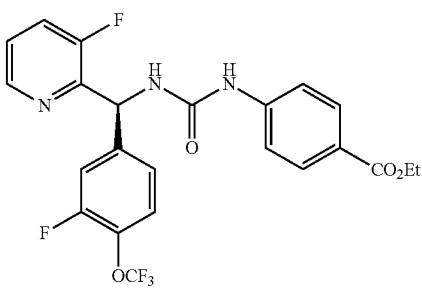 [SMILES: CCOC(=O)c1ccc(NC(=O)N[C@@H](c2ccc(OC(F)(F)F)c(F)c2)c2ncccc2F)cc1]

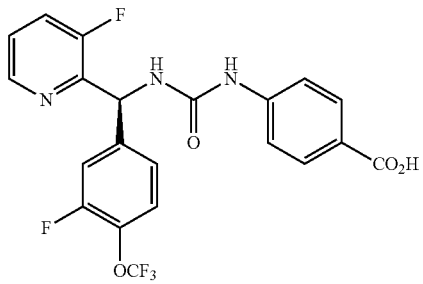 [SMILES: O=C(Nc1ccc(C(=O)O)cc1)N[C@@H](c1ccc(OC(F)(F)F)c(F)c1)c1ncccc1F]

Step 1. (S)-Ethyl 4-(3-((3-fluoro-4-(trifluoromethoxy)phenyl)(3-fluoropyridin-2-yl)methyl)ureido)benzoate To a solution of (S)-(3-fluoro-4-(trifluoromethoxy)phenyl)(3-fluoropyridin-2-yl)methanamine hydrochloride (Intermediate 39) (112 mg, 0.329 mmol) and DCM (3 mL) was added ethyl 4-isocyanatobenzoate (65 mg, 0.340 mmol) and N-ethyl-N-isopropylpropan-2-amine (0.172 mL, 0.986 mmol). The solution was stirred at rt. After 20 minutes, the reaction product was adsorbed onto a plug of silica gel and chromatographed through a Redi-Sep®pre-packed silica gel column (4 g), eluting with 70% to 90% EtOAc in hexane, to provide the title compound as a white solid.

Step 2. (S)-4-(3-((3-Fluoro-4-(trifluoromethoxy)phenyl)(3-fluoropyridin-2-yl)methyl)ureido)benzoic acid To a solution of (S)-ethyl 4-(3-((3-fluoro-4-(trifluoromethoxy)phenyl)(3-fluoropyridin-2-yl)methyl)ureido)benzoate (109 mg, 0.220 mmol) in THF (3 mL) and MeOH (1 mL) was added 1 M aqueous LiOH (4 mL, 4.00 mmol). The resulting mixture was then stirred at rt. After stirring for 24 h, the reaction was acidified with 1 N HCl to ~pH 7. The aqueous solution was extracted with DCM (3×10 mL). The combined DCM layers were washed with brine, dried over MgSO$_4$, and concentrated in vacuo to give the title compound as an off-white solid. $^1$H-NMR (300 MHz, MeOH-d$_4$): δ ppm 8.48 (d, J=4.7 Hz, 1H), 7.83-7.98 (m, 2H), 7.62 (ddd, J=9.8, 8.5, 1.3 Hz, 1H), 7.27-7.51 (m, 6H), 6.40 (d, J=1.5 Hz, 1H). MS (ESI pos. ion) m/z: 445.9 (M+H).

TABLE 6

Examples 181-187 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 181 | 1 | | | (S)-1-(2-chlorophenyl)-3-((4-(trifluoromethyl)phenyl)(3-(trifluoromethyl)pyridin-2-yl)methyl)urea (2,2,2-trifluoroacetate) | 473.8 |
| 182 | 1 | | | (S)-methyl 2-methyl-3-(3-((4-(trifluoromethyl)phenyl)(3-(trifluoromethyl)pyridin-2-yl)methyl)ureido)benzoate (2,2,2-trifluoroacetate) | 511.4 |

TABLE 6-continued

Examples 181-187 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 183 | 1 | | | (S)-1-(2-methoxy-5-methylphenyl)-3-((4-(trifluoromethyl)phenyl)(3-(trifluoromethyl)pyridin-2-yl)methyl)urea (2,2,2-trifluoroacetate) | 483.4 |
| 184 | 1 | | | (S)-1-(3,4-dichlorobenzyl)-3-((4-(trifluoromethyl)phenyl)(3-(trifluoromethyl)pyridin-2-yl)methyl)urea (2,2,2-trifluoroacetate) | 522.3 |
| 185 | 1 | | | 1-(1,2,3,4-tetrahydronaphthalen-1-yl)-3-((S)-(4-(trifluoromethyl)phenyl)(3-(trifluoromethyl)pyridin-2-yl)methyl)urea (2,2,2-trifluoroacetate) | 493.4 |
| 186 | 1 | | | (S)-1-mesityl-3-((4-(trifluoromethyl)phenyl)(3-(trifluoromethyl)pyridin-2-yl)methyl)urea (2,2,2-trifluoroacetate) | 481.4 |
| 187 | 1 | | | (S)-ethyl 4-(3-((4-(trifluoromethyl)phenyl)(3-(trifluoromethyl)pyridin-2-yl)methyl)ureido)benzoate (2,2,2-trifluoroacetate) | 511.4 |

TABLE 6-continued

Examples 181-187 prepared via urea formation analogous to Scheme 8.

| Ex. # | Amine Intermediate | Isocyanate Structure | Product Structure | Product Name | MS (ESI, positive ion) M + H |
|---|---|---|---|---|---|
| 188 | 39 | | | (S)-1-((3-fluoro-4-(trifluoromethoxy)phenyl)(3-fluoropyridin-2-yl)methyl)-3-(pyridin-3-yl)urea | 425.0 |

TABLE 7

$^1$HNMR Data for Selected Examples 1-188

| Ex. # | Freq., Solvent | $^1$HNMR Data (δ ppm) |
|---|---|---|
| 1 | 300 MHz, d$_4$-MeOH | 9.15 (br. s, 1 H), 8.93 (d, J = 4.1 Hz, 1 H), 8.37 (br. s, 1 H), 8.15-8.29 (m, 2 H), 7.85 (dd, J = 8.3, 5.6 Hz, 1 H), 7.54-7.70 (m, 2 H), 7.26-7.47 (m, 2 H), 6.59 (s, 1 H) |
| 2 | 400 MHz, CDCl$_3$ | 8.65 (br. s., 1 H), 8.14-8.32 (m, 3 H), 8.08 (d, J = 7.04 Hz, 1 H), 7.90 (d, J = 7.04 Hz, 1 H), 7.06-7.36 (m, 5 H), 6.72 (d, J = 7.43 Hz, 2 H), 6.53 (d, J = 7.24 Hz, 1 H), 3.68 (s, 3 H) |
| 3 | 400 MHz, CDCl$_3$ | 8.64 (d, J = 4.3 Hz, 1 H), 8.40 (s, 1 H), 8.27 (d, J = 2.4 Hz, 1 H), 8.2 (dd, J = 4.7, 1.0 Hz, 1 H), 8.07-8.14 (m, 1 H), 7.93 (dd, J = 8.2, 1.2 Hz, 1 H), 7.28-7.35 (m, 2 H), 7.20-7.25 (m, 1 H), 7.14-7.20 (m, 2 H), 7.07-7.14 (m, 2 H), 6.55 (d, J = 8.2 Hz, 1 H) |
| 4 | 400 MHz, CDCl$_3$ | 8.62 (d, J = 4.3 Hz, 1 H), 8.46 (br. s., 1 H), 8.27 (br. s, 1 H), 8.18 (br. s, 1 H), 8.09 (d, J = 9.0 Hz, 1 H), 7.89 (d, J = 7.4 Hz, 1 H), 7.26 (dd, J = 7.6, 5.1 Hz, 1 H), 7.05-7.21 (m, 3 H), 6.87-6.95 (m, 2 H), 6.68 (dd, J = 7.3, 1.9 Hz, 1 H), 6.57 (d, J = 8.2 Hz, 1 H), 3.66 (s, 3 H) |
| 5 | 400 MHz, CDCl$_3$ | 10.89 (br. s., 1 H), 9.19 (br. s., 1 H), 8.78 (d, J = 2.9 Hz, 1 H), 8.69 (d, J = 6.7 Hz, 1 H), 8.13 (br. s., 1 H), 7.90 (dd, J = 15.6, 7.9 Hz, 2 H), 7.63 (br. s., 1 H), 7.23-7.37 (m, 1 H), 7.04-7.20 (m, 2 H), 6.78 (t, J = 8.4 Hz, 1 H), 6.46 (d, J = 7.8 Hz, 1 H), 3.76 (s, 3 H) |
| 6 | 400 MHz, CDCl$_3$ | 8.99 (s, 1 H), 8.94 (d, J = 1.8 Hz, 1 H), 8.35 (d, J = 4.5 Hz, 1 H), 8.27 (d, J = 2.4 Hz, 1 H), 8.06 (d, J = 4.7 Hz, 1 H), 7.96-8.01 (m, 2 H), 7.86-7.97 (m, 1 H), 7.72-7.82 (m, 1 H), 7.43-7.64 (m, 3 H), 7.33-7.43 (m, 1 H), 7.12 (dd, J = 7.8, 4.7 Hz, 1 H), 7.04 (dd, J = 8.4, 4.7 Hz, 1 H), 6.71 (d, J = 8.0 Hz, 1 H) |
| 7 | 400 MHz, CDCl$_3$ | 8.70 (d, J = 4.5 Hz, 1 H), 8.14-8.28 (m, 2 H), 8.08 (d, J = 8.2 Hz, 1 H), 7.93 (d, J = 7.8 Hz, 1 H), 7.86 (s, 1 H), 7.32 (dd, J = 7.8, 4.9 Hz, 1 H), 7.06-7.20 (m, 4 H), 6.92-7.04 (m, 2 H), 6.56 (d, J = 8.2 Hz, 1 H), 2.22 (s, 3 H) |
| 8 | 400 MHz, CDCl$_3$ | 8.65 (d, J = 4.5 Hz, 1 H), 8.33 (s, 1 H), 8.28 (d, J = 2.0 Hz, 1 H), 8.19 (d, J = 4.7 Hz, 1 H), 8.10 (d, J = 8.4 Hz, 1 H), 7.93 (d, J = 7.8 Hz, 1 H), 7.31 (dd, J = 7.8, 4.9 Hz, 1 H), 7.07-7.21 (m, 4 H), 6.97-7.07 (m, 1 H), 6.78-6.88 (m, 1 H), 6.57 (d, J = 8.0 Hz, 1 H) |
| 9 | 400 MHz, CDCl$_3$ | 8.70 (d, J = 4.1 Hz, 1 H), 8.28 (br. s, 1 H), 8.18 (d, J = 3.7 Hz, 1 H), 8.01-8.11 (m, 2 H), 7.95 (d, J = 7.8 Hz, 1 H), 7.52-7.66 (m, 2 H), 7.40-7.48 (m, 1 H), 7.30-7.38 (m, 2 H), 7.08-7.21 (m, 2 H), 6.62 (d, J = 8.0 Hz, 1 H) |
| 10 | 400 MHz, CDCl$_3$ | 9.09 (d, J = 1.8 Hz, 1 H), 8.64 (d, J = 4.5 Hz, 1 H), 8.46 (br. s., 2 H), 8.35 (d, J = 2.2 Hz, 1 H), 8.17 (d, J = 4.7 Hz, 1 H), 8.11 (d, J = 8.4 Hz, 1 H), 7.88-7.99 (m, 2 H), 7.48-7.57 (m, 2 H), 7.39 (d, J = 8.0 Hz, 1 H), 7.31 (dd, J = 7.8, 4.9 Hz, 1 H), 7.17 (dd, J = 8.4, 4.7 Hz, 1 H), 6.83 (d, J = 8.0 Hz, 1 H) |
| 11 | 400 MHz d$_4$-MeOH | 8.92 (d, J = 4.3 Hz, 1 H), 8.53 (d, J = 2.2 Hz, 1 H), 8.09-8.16 (m, 2 H), 7.93-8.00 (m, 1 H), 7.72-7.84 (m, 4 H), 7.57 (dd, J = 8.6, 1.0 Hz, 1 H), 7.53 (dd, J = 7.8, 4.9 Hz, 1 H), 7.41-7.48 (m, 2 H), 7.29 (dd, J = 8.3, 4.8 Hz, 1 H), 6.74 (s, 1 H) |
| 12 | 400 MHz, CDCl$_3$ | 9.11 (d, J = 2.0 Hz, 1 H), 8.94 (s, 1 H), 8.43 (d, J = 4.1 Hz, 1 H), 8.36 (d, J = 2.4 Hz, 1 H), 8.15 (dd, J = 4.7, 1.4 Hz, 1 H), 8.03-8.11 |

TABLE 7-continued

¹HNMR Data for Selected Examples 1-188

| Ex. # | Freq., Solvent | ¹HNMR Data (δ ppm) |
|---|---|---|
| | | (m, 2 H), 7.85 (dd, J = 7.8, 1.0 Hz, 1 H), 7.76 (dd, J = 7.5, 1.1 Hz, 1 H), 7.61 (dd, J = 8.2, 1.0 Hz, 1 H), 7.55 (d, J = 8.0 Hz, 1 H), 7.40 (t, J = 7.9 Hz, 1 H), 7.23 (dd, J = 7.9, 4.8 Hz, 1 H), 7.13 (dd, J = 8.4, 4.7 Hz, 1 H), 6.77 (d, J = 8.0 Hz, 1 H) |
| 13 | 400 MHz, d₄-MeOH | 8.94 (d, J = 4.3 Hz, 1 H), 8.54 (d, J = 2.5 Hz, 1 H), 8.19 (dd, J = 8.2, 0.8 Hz, 1 H), 8.15 (dd, J = 4.7, 1.0 Hz, 1 H), 7.91-7.99 (m, 1 H), 7.59 (dd, J = 7.9, 4.8 Hz, 1 H), 7.55 (d, J = 2.0 Hz, 1 H), 7.47 (d, J = 8.4 Hz, 1 H), 7.27-7.37 (m, 2 H), 6.53 (s, 1 H) |
| 14 | 400 MHz, CDCl₃ | 9.07 (br. s, 1 H), 8.96 (s, 1 H), 8.36-8.46 (m, 2 H), 8.16 (d, J = 4.5 Hz, 1 H), 8.02-8.11 (m, 2 H), 7.86 (d, J = 8.0 Hz, 1 H), 7.55 (d, J = 8.0 Hz, 1 H), 7.46-7.51 (m, 1 H), 7.41 (td, J = 7.8, 4.9 Hz, 1 H), 7.32 (dd, J = 10.4, 7.8 Hz, 1 H), 7.23 (d, J = 7.8, 4.9 Hz, 1 H), 7.14 (dd, J = 8.3, 4.8 Hz, 1 H), 6.76 (d, J = 7.8 Hz, 1 H) |
| 15 | 400 MHz, CDCl₃ | 8.56 (s, 1 H) 8.38 (d, J = 2.4 Hz, 1 H), 8.19-8.29 (m, 2 H), 8.03-8.13 (m, 1 H), 7.46 (d, J = 7.2 Hz, 1 H), 7.29-7.42 (m, 3 H), 7.13-7.21 (m, 2 H), 7.05 (s, 1 H), 7.03 (s, 1 H), 6.44 (dd, J = 7.4, 1.2 Hz, 1 H) |
| 16 | 400 MHz, CDCl₃ | 9.33 (s, 1 H), 9.06 (d, J = 2.0 Hz, 1 H), 8.37 (d, J = 2.4 Hz, 1 H), 8.23 (d, J = 4.5 Hz, 1 H), 8.13 (dd, J = 4.7, 1.2 Hz, 1 H), 8.03-8.10 (m, 1 H), 7.91 (d, J = 1.4 Hz, 1 H), 7.82 (d, J = 7.4 Hz, 1 H), 7.61 (d, J = 8.2 Hz, 1 H), 7.37-7.44 (m, 1 H), 7.23-7.29 (m, 1 H), 7.12 (td, J = 8.6, 4.8 Hz, 2 H), 6.97 (d, J = 7.6 Hz, 1 H), 6.80 (d, J = 8.2 Hz, 1 H), 3.87 (s, 3 H) |
| 17 | 400 MHz, CDCl₃ | 8.83 (dd, J = 4.1, 1.4 Hz, 1 H), 8.60 (s, 1 H), 8.51 (d, J = 4.7 Hz, 1 H), 8.36 (d, J = 2.4 Hz, 1 H), 8.15-8.22 (m, 1 H), 8.05-8.11 (m, 1 H), 8.02 (d, J = 8.2 Hz, 1 H), 7.91 (d, J = 8.8 Hz, 1 H), 7.87 (d, J = 8.0 Hz, 1 H), 7.73 (s, 1 H), 7.68 (dd, J = 8.9, 1.5 Hz, 1 H), 7.28-7.37 (m, 2 H), 7.23 (dd, J = 7.8, 4.9 Hz, 1 H), 7.14 (dd, J = 8.4, 4.7 Hz, 1 H), 6.76 (d, J = 8.0 Hz, 1 H) |
| 18 | 400 MHz, CDCl₃ | 8.94 (s, 1 H), 8.77 (s, 1 H), 8.50 (d, J = 4.3 Hz, 1 H), 8.34 (br. s, 1 H), 8.16 (d, J = 4.5 Hz, 1 H), 8.09 (d, J = 8.0 Hz, 1 H), 7.96 (s, 1 H), 7.87 (d, J = 7.8 Hz, 1 H), 7.54 (d, J = 9.0 Hz, 1 H), 7.43 (d, J = 8.0 Hz, 1 H), 7.19-7.30 (m, 2 H), 7.08-7.17 (m, 2 H), 6.75 (d, J = 7.8 Hz, 1 H), 3.81 (s, 3 H) |
| 19 | 400 MHz, CDCl₃ | 8.71 (s, 1 H), 8.61 (d, J = 4.1 Hz, 1 H), 8.32 (d, J = 2.4 Hz, 1 H), 8.18 (dd, J = 4.7, 1.0 Hz, 1 H), 8.03-8.10 (m, 1 H), 7.90 (dd, J = 7.8, 0.8 Hz, 1 H), 7.22-7.36 (m, 4 H), 7.14 (dd, J = 8.3, 4.8 Hz, 1 H), 6.8-6.9 (m, 2 H), 6.54 (d, J = 8.0 Hz, 1 H) |
| 20 | 400 MHz, CDCl₃ | 8.74 (s, 1 H), 8.59 (d, J = 4.1 Hz, 1 H), 8.27 (br. s., 1 H), 8.17 (d, J = 3.72 Hz, 1 H), 8.03-8.10 (m, 1 H), 7.87 (dd, J = 8.0, 1.0 Hz, 1 H), 7.20-7.35 (m, 4 H), 7.04-7.19 (m, 4 H), 6.59 (d, J = 8.22 Hz, 1 H) |
| 21 | 300 MHz, d₄-MeOH | 9.14 (s, 1 H), 8.96 (d, J = 4.7 Hz, 1 H), 8.36 (d, J = 5.4 Hz, 1 H), 8.21 (d, J = 7.9 Hz, 2 H), 7.80-7.87 (m, 1 H), 7.68-7.78 (m, 2 H), 7.59-7.64 (m, 1 H), 7.31 (t, J = 9.4 Hz, 1 H), 6.58 (s, 1 H) |
| 22 | 300 MHz, d₄-MeOH | 9.21 (s, 1 H), 8.52 (d, J = 4.5 Hz, 1 H), 8.39 (d, J = 5.4 Hz, 1 H), 8.26 (d, J = 7.6 Hz, 1 H), 7.90 (dd, J = 5.6, 8.3 Hz, 1 H), 7.68-7.80 (m, 2 H), 7.64 (t, J = 9.0 Hz, 1 H), 7.44-7.50 (m, 1 H), 7.32 (t, J = 9.4 Hz, 1 H), 6.43 (s, 1 H) |
| 23 | 300 MHz, d₄-MeOH | 9.15 (br. s., 1H), 8.96 (d, J = 4.7 Hz, 1H), 8.37 (d, J = 5.4 Hz, 1H), 8.22 (d, J = 7.5 Hz, 2H), 7.84 (dd, J = 5.8, 8.4 Hz, 1H), 7.62 (dd, J = 4.8, 6.9 Hz, 1H), 7.25 (s, 1H), 7.05-7.18 (m, 2H), 6.52 (s, 1H) |
| 24 | 300 MHz, d₄-MeOH | 9.08-9.24 (m, 1 H), 8.51 (d, J = 4.2 Hz, 1 H), 8.38 (d, J = 5.3 Hz, 1 H), 8.25 (d, J = 7.9 Hz, 1 H), 7.87 (dd, J = 8.6, 5.6 Hz, 1 H), 7.57-7.76 (m, 1 H), 7.38-7.56 (m, 1 H), 7.28 (s, 1 H), 7.13 (d, J = 8.6 Hz, 2 H), 6.37 (s, 1 H) |
| 25 | 300 MHz, d₄-MeOH | 9.11 (br. s., 1 H), 8.98 (d, J = 1.2 Hz, 1 H), 8.79 (br. s., 1 H), 8.35 (dd, J = 4.0, 1.1 Hz, 1 H), 8.14-8.30 (m, 2 H), 8.01-8.12 (m, 1 H), 7.72-7.90 (m, 2 H), 7.53-7.72 (m, 1 H), 6.66 (br. s., 1 H) |
| 26 | 400 MHz, CDCl₃ | 8.77 (s, 1 H), 8.63 (d, J = 4.3 Hz, 1 H), 8.41 (d, J = 2.0 Hz, 1 H), 8.18 (d, J = 4.1 Hz, 1 H), 8.02-8.10 (m, 1 H), 7.90 (d, J = 7.8 Hz, 1 H), 7.35 (d, J = 8.2 Hz, 1 H), 7.22-7.31 (m, 3 H), 7.06-7.17 (m, 3 H), 6.54 (d, J = 8.0 Hz, 1 H) |
| 27 | 400 MHz, d₆-DMSO | 9.00 (s, 1 H), 8.96 (d, J = 4.4 Hz, 1H), 8.47 (d, J = 2.0 Hz, 1 H), 8.22 (d, J = 7.6 Hz, 1 H), 8.11 (d, J = 4.0 Hz, 1 H), 7.86 (d, J = 8.0 Hz, 1 H), 7.58-7.64 (m, 1 H), 7.49 (d, J = 8.4 Hz, 1 H), 7.14-7.26 (m, 5 H), 6.40 (d, J = 8.8 Hz, 1 H), 2.27 (q, J = 7.6 Hz, 2H), 1.13 (t, J = 7.6 Hz, 3 H) |
| 28 | 400 MHz, d₄-MeOH | 8.67 (d, J = 4.3 Hz, 1 H), 8.54 (s, 1 H), 8.14 (d, J = 4.7 Hz, 1 H), 8.06 (d, J = 8.0 Hz, 1 H), 7.96 (d, J = 8.2 Hz, 1 H), 7.63 (s, 4 H), 7.26-7.40 (m, 2 H), 6.61 (s, 1 H) |

TABLE 7-continued

¹HNMR Data for Selected Examples 1-188

| Ex. # | Freq., Solvent | ¹HNMR Data (δ ppm) |
|---|---|---|
| 29 | 300 MHz, CDCl$_3$ | 8.48 (br. s., 1 H), 8.35 (d, J = 4.1 Hz, 1 H), 8.26 (d, J = 4.1 Hz, 1 H), 8.10 (d, J = 8.2 Hz, 1 H), 7.62 (br. s., 1 H), 7.50 (t, J = 7.6 Hz, 1 H), 7.41 (t, J = 8.3 Hz, 1 H), 7.22-7.34 (m, 5 H), 6.42 (d, J = 6.3 Hz, 1 H) |
| 30 | 300 MHz, CDCl$_3$ | 8.51 (d, J = 3.7 Hz, 1 H), 8.41 (d, J = 2.2 Hz, 1 H), 8.27 (d, J = 4.0 Hz, 1 H) 7.96 (d, J = 8.2 Hz, 1 H), 7.65 (t, J = 8.5 Hz, 1 H), 7.53 (d, J = 8.3 Hz, 2 H), 7.47 (d, J = 8.3 Hz, 2 H), 7.17-7.24 (m, 3 H), 7.11 (s, 1 H), 6.11 (d, J = 6.3 Hz, 1 H) |
| 31 | 400 MHz, CDCl$_3$ | 8.65 (d, J = 3.3 Hz, 1 H), 7.91 (d, J = 7.6 Hz, 1 H), 7.35-7.49 (m, 4 H), 7.27-7.35 (m, 1 H), 7.20 (br. s, 4 H), 7.00 (br. s, 1 H), 6.73-6.86 (m, 2 H), 6.60 (d, J = 8.0 Hz, 1 H) |
| 32 | 400 MHz, CDCl$_3$ | 8.77-8.84 (m, 1 H), 7.75-8.03 (m, 1 H), 7.49-7.55 (m, 2 H), 7.43-7.48 (m, 2 H), 7.36-7.42 (m, 1 H), 6.49-6.66 (m, 1 H), 5.98-6.14 (m, 1 H), 4.02-4.22 (m, 1 H), 3.74-3.95 (m, 1 H), 1.12 (d, J = 6.5 Hz, 6 H) |
| 33 | 300 MHz d$_4$-MeOH | 8.70-8.88 (m, 1H), 8.08 (d, J = 7.7 Hz, 1H), 8.14 (d, J = 7.7 Hz, 1H), 7.86 (d, J = 6.7 Hz, 1H), 7.75 (d, J = 8.2 Hz, 1H), 7.32-7.62 (m, 9H), 6.55 (s, 1H), 5.55-5.74 (m, 1H), 1.55 (d, J = 6.7 Hz, 3H) |
| 34 | 300 MHz d$_4$-MeOH | 8.86 (d, J = 4.2 Hz, 1H), 8.14 (d, J = 7.7 Hz, 1H), 7.43-7.66 (m, 5H), 7.02-7.31 (m, 5H), 6.55 (s, 1H), 3.12 (t, J = 6.9 Hz, 2H), 2.60 (t, J = 7.7 Hz, 2H), 1.75 (quin, J = 7.3 Hz, 2H) |
| 35 | 300 MHz d$_4$-MeOH | 9.53 (d, J = 8.0 Hz, 1H), 8.88 (d, J = 4.2 Hz, 1H), 8.16 (d, J = 7.6 Hz, 1H), 7.49-7.69 (m, 5H), 7.41 (t, J = 7.7 Hz, 2H), 7.27 (t, J = 7.3 Hz, 1H), 7.18 (d, J = 7.6 Hz, 2H), 6.65 (d, J = 4.8 Hz, 1H) |
| 36 | 300 MHz d$_4$-MeOH | 8.85 (d, J = 4.2 Hz, 1H), 8.16 (d, J = 8.0 Hz, 1H), 7.39-7.67 (m, 5H), 6.58-6.76 (m, 3H), 6.55 (s, 1H), 5.89 (s, 2H), 2.67 (t, J = 6.9 Hz, 2H) |
| 37 | 300 MHz d$_4$-MeOH | 8.90 (d, J = 4.5 Hz, 1H), 8.17 (d, J = 7.5 Hz, 1H), 7.68 (s, 1H), 7.49-7.65 (m, 5H), 7.18-7.30 (m, 1H), 7.03-7.18 (m, 2H), 6.60 (s, 1H) |
| 38 | 300 MHz d$_4$-MeOH | 8.86 (br. s., 1H), 8.15 (d, J = 7.5 Hz, 1H), 7.37-7.71 (m, 5H), 6.55 (s, 1H), 4.15 (q, J = 6.7 Hz, 2H), 3.87 (br. s., 2H), 1.22 (t, J = 7.0 Hz, 3H) |
| 39 | 300 MHz d$_4$-MeOH | 8.90 (d, J = 5.3 Hz, 1H), 8.17 (d, J = 7.5 Hz, 1H), 7.49-7.74 (m, 7H), 7.37 (d, J = 9.1 Hz, 1H), 7.10-7.24 (m, 1H), 6.75 (s, 1H), 6.64 (s, 1H) |
| 40 | 300 MHz d$_4$-MeOH | 8.66 (d, J = 3.8 Hz, 1 H), 8.05 (d, J = 7.2 Hz, 1 H), 7.62 (s, 4 H), 7.58 (d, J = 2.3 Hz, 4 H), 7.30 (dd, J = 8.2, 4.7 Hz, 1 H), 6.60 (s, 1 H) |
| 41 | 300 MHz d$_4$-MeOH | 8.58 (d, J = 4.5 Hz, 1 H), 8.00 (d, J = 8.0 Hz, 1 H), 7.42-7.67 (m, 4 H), 7.23 (dd, J = 8.1, 4.6 Hz, 1 H), 6.42-6.61 (m, 1 H), 1.28 (s, 9 H) |
| 42 | 300 MHz d$_4$-MeOH | 8.47 (dd, J = 4.8, 1.6 Hz, 1 H), 7.73 (dd, J = 7.9, 1.6 Hz, 1 H), 7.56 (s, 4 H), 7.23 (dd, J = 7.7, 4.8 Hz, 1 H), 6.54 (s, 1 H), 2.14 (s, 3 H), 1.28 (s, 9 H) |
| 43 | 300 MHz d$_4$-MeOH | 8.52-8.54 (m, 2 H), 8.13 (d, J = 4.7 Hz, 1 H), 7.94 (d, J = 8.4 Hz, 1 H), 7.65 (d, J = 7.6 Hz, 1 H), 7.60 (d, J = 8.2 Hz, 2 H), 7.53 (d, J = 8.2 Hz, 2 H), 7.28-7.36 (m, 2 H), 6.42 (s, 1 H), 5.91 (ddt, J = 16.8, 10.3, 6.3 Hz, 1 H), 5.08 (d, J = 10.2 Hz, 1 H), 4.95-5.05 (m, 1 H), 3.39-3.63 (m, 2 H) |
| 44 | 400 MHz d$_4$-MeOH | 8.93 (d, J = 4.1 Hz, 1 H), 8.53 (s, 1 H), 8.19 (d, J = 8.0 Hz, 1 H), 8.14 (d, J = 4.5 Hz, 1 H), 7.96 (d, J = 8.2 Hz, 1 H), 7.63 (d, J = 8.2 Hz, 2 H), 7.58 (d, J = 8.0 Hz, 3 H), 7.27-7.37 (m, 1 H), 6.63 (s, 1 H) |
| 45 | 300 MHz d$_4$-MeOH | 8.86 (d, J = 4.5 Hz, 1 H), 8.15 (d, J = 8.0 Hz, 1 H), 7.56-7.63 (m, 2 H), 7.47-7.56 (m, 3 H), 6.53 (s, 1 H), 1.29 (s, 9 H) |
| 46 | 400 MHz d$_4$-MeOH | 8.93 (d, J = 4.1 Hz, 1 H), 8.19 (d, J = 8.0 Hz, 1 H), 7.43-7.68 (m, 9 H), 6.62 (s, 1 H) |
| 47 | 400 MHz d$_4$-MeOH | 8.92 (d, J = 4.1 Hz, 1 H), 8.18 (d, J = 8.0 Hz, 1 H), 7.62 (d, J = 8.0 Hz, 2 H), 7.57 (d, J = 8.0 Hz, 3 H), 7.29-7.39 (m, 2 H), 6.99 (t, J = 8.3 Hz, 2 H), 6.62 (s, 1 H) |
| 48 | 400 MHz d$_4$-MeOH | 8.91 (d, J = 4.3 Hz, 1 H), 8.18 (d, J = 8.0 Hz, 1 H), 7.93 (q, J = 8.0 Hz, 1 H), 7.60-7.66 (m, 2 H), 7.53-7.60 (m, 3 H), 6.92-7.02 (m, 1 H), 6.88 (t, J = 8.5 Hz, 1 H), 6.63 (s, 1 H) |
| 49 | 300 MHz d$_4$-MeOH | 8.92 (d, J = 4.4 Hz, 1 H), 8.19 (d, J = 8.0 Hz, 1 H), 7.60-7.68 (m, 2 H), 7.52-7.60 (m, 3 H), 7.03 (d, J = 7.7 Hz, 2 H), 6.61 (s, 1 H), 6.51 (t, J = 9.2 Hz, 1 H) |
| 50 | 300 MHz d$_4$-MeOH | 8.92 (d, J = 4.5 Hz, 1 H), 8.18 (d, J = 7.9 Hz, 1 H), 7.44-7.68 (m, 5 H), 7.14-7.33 (m, 1 H), 6.92-7.06 (m, 2 H), 6.62 (s, 1 H) |
| 51 | 300 MHz d$_4$-MeOH | 8.47-8.60 (m, 2 H), 8.14 (d, J = 4.4 Hz, 1 H), 7.96 (d, J = 8.3 Hz, 1 H), 7.79 (d, J = 7.9 Hz, 1 H), 7.55-7.69 (m, 4 H), 7.21-7.38 (m, 2 H), 6.61 (s, 1 H), 2.17 (s, 3 H) |
| 52 | 300 MHz d$_4$-MeOH | 8.89 (d, J = 4.4 Hz, 1 H), 8.16 (d, J = 7.9 Hz, 1 H), 7.41-7.66 (m, 5 H), 7.00-7.18 (m, 2 H), 6.80 (d, J = 8.2 Hz, 1 H), 6.61 (s, 1 H), 6.53 (d, J = 8.2 Hz, 1 H), 3.74 (s, 3 H) |

TABLE 7-continued

<sup>1</sup>HNMR Data for Selected Examples 1-188

| Ex. # | Freq., Solvent | <sup>1</sup>HNMR Data (δ ppm) |
|---|---|---|
| 53 | 300 MHz d<sub>4</sub>-MeOH | 8.91 (d, J = 4.4 Hz, 1 H), 8.17 (d, J = 7.9 Hz, 1 H), 8.09 (s, 1 H), 7.41-7.66 (m, 8 H), 6.62 (s, 1 H), 3.09 (s, 3 H) |
| 54 | 300 MHz d<sub>4</sub>-MeOH | 8.86 (d, J = 4.5 Hz, 1 H), 8.14 (d, J = 8.0 Hz, 1 H), 7.41-7.66 (m, 5 H), 6.54 (s, 1 H), 3.76 (d, J = 11.3 Hz, 1 H), 3.57-3.72 (m, 2 H), 3.41-3.57 (m, 1 H), 3.07-3.27 (m, 1 H), 1.88 (br. s., 1 H), 1.66-1.81 (m, 1 H), 1.39-1.66 (m, 2 H) |
| 55 | 300 MHz d<sub>4</sub>-MeOH | 8.90 (d, J = 4.2 Hz, 1 H), 8.17 (d, J = 8.0 Hz, 1 H), 7.47-7.69 (m, 5 H), 6.58 (s, 1 H), 2.24 (s, 3 H), 2.08 (s, 3 H) |
| 56 | 300 MHz d<sub>4</sub>-MeOH | 8.86 (d, J = 4.7 Hz, 1 H), 8.14 (d, J = 7.9 Hz, 1 H), 7.33-7.64 (m, 5 H), 6.54 (s, 1 H), 4.23 (br. s., 1 H), 3.66-3.95 (m, 3 H), 3.42-3.59 (m, 1 H), 2.04-2.31 (m, 1 H), 1.56-1.85 (m, 1 H) |
| 57 | 300 MHz d<sub>4</sub>-MeOH | 8.92 (d, J = 4.4 Hz, 1 H), 8.85 (s, 2 H), 8.73 (s, 1 H), 8.18 (d, J = 7.9 Hz, 1 H), 7.59 (q, J = 8.1 Hz, 5 H), 6.61 (s, 1 H) |
| 58 | 400 MHz d<sub>4</sub>-MeOH | 8.94 (br. s., 1 H), 8.69 (br. s., 1 H), 8.22 (t, J = 9.8 Hz, 2 H), 8.12 (s, 1 H), 7.92 (d, J = 9.0 Hz, 1 H), 7.52-7.70 (m, 6 H), 7.37-7.52 (m, 1 H), 6.68 (s, 1 H) |
| 59 | 300 MHz d<sub>4</sub>-MeOH | 8.93 (d, J = 4.4 Hz, 1 H), 8.64-8.77 (m, 1 H), 8.45 (s, 1 H), 8.18 (d, J = 7.9 Hz, 1 H), 7.92 (d, J = 8.3 Hz, 1 H), 7.81 (d, J = 7.9 Hz, 1 H), 7.47-7.68 (m, 7 H), 6.67 (s, 1 H) |
| 60 | 300 MHz d<sub>4</sub>-MeOH | 8.95 (d, J = 4.5 Hz, 1 H), 8.62 (d, J = 5.4 Hz, 1 H), 8.09-8.30 (m, 3 H), 7.96 (d, J = 8.5 Hz, 1 H), 7.74 (t, J = 7.5 Hz, 1 H), 7.50-7.69 (m, 6 H), 6.70 (s, 1 H) |
| 61 | 400 MHz d<sub>4</sub>-MeOH | 8.47-8.57 (m, 2 H), 8.13 (d, J = 4.7 Hz, 1 H), 7.95 (d, J = 8.4 Hz, 1 H), 7.46-7.67 (m, 5 H), 7.19-7.37 (m, 2 H), 6.51 (s, 1 H), 1.70 (t, J = 7.0 Hz, 1 H), 1.51 (s, 3 H), 0.90 (d, J = 7.0 Hz, 2 H), 0.81 (s, 3 H) |
| 62 | 300 MHz d<sub>4</sub>-MeOH | 8.52 (br. s., 2 H), 8.12 (d, J = 4.4 Hz, 1 H), 7.93 (d, J = 7.2 Hz, 1 H), 7.45-7.69 (m, 5 H), 7.16-7.38 (m, 2 H), 6.54 (s, 1 H), 2.93 (d, J = 13.9 Hz, 1 H), 2.54 (d, J = 14.2 Hz, 1 H), 1.00 (s, 9 H) |
| 114 | 300 MHz CDCl<sub>3</sub> | 10.66 (br. s., 1 H), 9.31 (d, J = 8.6 Hz, 1 H), 8.78 (s, 1 H), 8.32 (d, J = 4.7 Hz, 1 H), 8.01 (d, J = 4.8 Hz, 1 H), 7.71-7.77 (m, 2 H), 7.60 (d, J = 8.3 Hz, 2 H), 7.46 (d, J = 8.3 Hz, 2 H), 7.29-7.33 (m, 1 H), 6.50 (d, J = 7.5 Hz, 1 H) |
| 115 | 300 MHz d<sub>4</sub>-MeOH | 9.19 (s, 1 H), 8.40 (d, J = 5.4 Hz, 1 H), 8.31 (d, J = 8.6 Hz, 1 H), 7.90 (dd, J = 8.4, 5.8 Hz, 1 H), 7.68 (d, J = 7.7 Hz, 3 H), 7.49 (d, J = 8.0 Hz, 2 H), 7.34-7.45 (m, 2 H), 7.22-7.32 (m, 1 H), 6.56 (s, 1 H) |
| 116 | 300 MHz d<sub>4</sub>-MeOH | 7.62-7.64 (m, 3 H), 7.35-7.47 (m, 3 H), 7.28-7.35 (m, 1 H), 7.17-7.28 (m, 1 H), 6.38 (s, 1 H), 1.32 (s, 9 H) |
| 117 | 300 MHz d<sub>4</sub>-MeOH | 9.15 (d, J = 2.3 Hz, 1 H), 8.39 (d, J = 5.4 Hz, 1 H), 8.30 (ddd, J = 8.7, 2.4, 1.2 Hz, 1 H), 7.87 (dd, J = 8.7, 5.5 Hz, 1 H), 7.64-7.78 (m, 3 H), 7.56-7.64 (m, 2 H), 7.27-7.42 (m, 2 H), 6.31 (s, 1 H) |
| 118 | 300 MHz d<sub>4</sub>-MeOH | 7.16 (d, J = 4.5 Hz, 1 H), 6.89 (d, J = 9.2 Hz, 1 H), 6.67 (dd, J = 8.0, 1.5 Hz, 1 H), 6.22-6.39 (m, 5H), 6.05-6.22 (m, 2 H), 5.65-5.78 (m, 1 H), 5.22 (s, 1 H), 2.61 (s, 3 H) |
| 119 | 300 MHz d<sub>4</sub>-MeOH | 7.67 (d, J = 2.0 Hz, 1 H), 7.24-7.39 (m, 2 H), 6.90 (d, J = 5.1 Hz, 1 H), 6.79 (dd, J = 8.8, 1.2 Hz, 1 H), 6.39 (dd, J = 8.6, 5.6 Hz, 1 H), 6.31 (d, J = 5.3 Hz, 1 H), 6.22 (d, J = 8.2 Hz, 2 H), 5.98 (d, J = 8.2 Hz, 2 H), 5.13 (s, 1 H) |
| 120 | 300 MHz, CDCl<sub>3</sub> | 10.75 (s, 1 H), 9.18 (d, J = 9.2 Hz, 1 H), 8.86 (br. s., 1 H), 8.78 (br. s., 1 H), 8.62 (br. s., 1 H), 8.04 (d, J = 4.8 Hz, 1 H), 7.72 (d, J = 9.9 Hz, 1 H), 7.77 (d, J = 8.6 Hz, 1 H), 7.62 (m, J = 8.0 Hz, 2 H), 7.55 (d, J = 7.9 Hz, 1 H), 7.46 (m, J = 7.9 Hz, 2 H), 6.47 (d, J = 6.6 Hz, 1 H) |
| 121 | 400 MHz, CDCl<sub>3</sub> | 8.18 (d, J = 2.4 Hz, 1 H), 7.96-8.07 (m, 2 H), 7.87-7.92 (m, 1 H), 7.68 (d, J = 7.8 Hz, 1 H), 7.33-7.54 (m, 3 H), 7.02-7.19 (m, 4 H), 6.51 (d, J = 6.7 Hz, 1 H), 6.31 (d, J = 6.9 Hz, 1 H) |
| 122 | 300 MHz d<sub>4</sub>-MeOH | 8.94 (d, J = 4.5 Hz, 1 H), 8.64 (d, J = 1.9 Hz, 1 H), 8.28 (d, J = 4.8 Hz, 1 H), 8.18 (t, J = 9.0 Hz, 2 H), 7.55-7.70 (m, 5 H), 7.32-7.50 (m, 2 H) |
| 123 | 300 MHz d<sub>4</sub>-MeOH | 8.90 (d, J = 4.7 Hz, 1 H), 8.16 (d, J = 7.9 Hz, 1 H), 7.47-7.65 (m, 5 H), 7.43 (s, 1 H), 1.48 (s, 9 H) |
| 149 | 400 MHz, d<sub>6</sub>-DMSO | 10.16 (s, 1H), 8.75 (s, 1 H), 8.50 (d, J = 4.5 Hz, 1 H), 7.78 (t, J = 9.2 Hz, 1 H), 7.67-7.74 (m, 2 H), 7.53-7.58 (m, 2 H), 7.53-7.44 (m, 2 H), 7.30 (s, 1 H), 7.04-7.14 (m, 1 H), 6.66 (d, J = 8.4 Hz, 1 H), 6.38 (d, J = 8.2 Hz, 1 H), 3.40 (br. s., 2 H) |
| 150 | 300 MHz, CDCl<sub>3</sub> | 8.52 (dd, J = 5.1, 1.5 Hz, 1 H), 7.86 (dd, J = 7.8, 1.5 Hz, 1 H), 7.56 (d, J = 8.3 Hz, 2 H), 7.49 (d, J = 8.5 Hz, 2 H), 7.34 (dd, J = 7.9, 5.1 Hz, 1 H), 7.23 (br. s., 1 H), 6.64 (br. s., 1 H), 5.60 (br. s., 1 H), 4.48 (qd, J = 16.5, 7.2 Hz, 1 H), 2.13 (s, 3 H), 1.27 (d, J = 7.0 Hz, 3 H) |
| 151 | 300 MHz d<sub>4</sub>-MeOH | 8.87 (d, J = 4.1 Hz, 1 H), 8.05-8.30 (m, 1 H), 7.60-7.66 (m, 1 H), 7.52-7.60 (m, 1 H), 7.26 (d, J = 9.8 Hz, 2 H), 6.53 (s, 1 H), 4.42 (dt, J = 14.5, 7.3 Hz, 1 H), 1.26 (d, J = 7.0 Hz, 3 H) |

TABLE 7-continued

¹HNMR Data for Selected Examples 1-188

| Ex. # | Freq., Solvent | ¹HNMR Data (δ ppm) |
|---|---|---|
| 152 | 300 MHz, d₄-MeOH | 8.88 (d, J = 4.5 Hz, 1 H), 8.17 (d, J = 7.9 Hz, 1 H), 7.47-7.70 (m, 2 H), 7.18-7.41 (m, 2 H), 6.51 (s, 1 H), 4.40 (dt, J = 14.5, 7.3 Hz, 1 H), 1.27 (d, J = 7.0 Hz, 3 H) |
| 153 | 300 MHz, d₄-MeOH | 8.88 (dd, J = 4.8, 0.9 Hz, 1 H), 8.17 (dd, J = 8.0, 1.0 Hz, 1 H), 7.58-7.65 (m, 2 H), 7.55 (dd, J = 8.0, 4.8 Hz, 1 H), 7.45-7.52 (m, 2 H), 6.57 (s, 1 H), 4.42 (dt, J = 14.4, 7.3 Hz, 1 H), 1.27 (d, J = 6.9 Hz, 3 H) |
| 154 | 300 MHz, d₄-MeOH | 7.63 (d, J = 7.7 Hz, 3 H), 7.32-7.46 (m, 3 H), 7.17-7.32 (m, 2 H), 6.44 (s, 1 H), 4.45 (dt, J = 14.7, 7.2 Hz, 1 H), 1.29 (d, J = 7.0 Hz, 3 H) |
| 155 | 300 MHz, CDCl₃ | 9.27 (br. s., 2 H), 8.83-8.90 (m, 2 H), 8.75 (s, 1 H), 8.36 (br. s., 2 H), 8.04 (d, J = 7.9 Hz, 2 H), 7.46-7.54 (m, 2 H), 7.36-7.39 (m, 1 H), 7.22-7.30 (m, 1 H), 6.56 (s, 1 H) |
| 156 | 300 MHz, CDCl₃ | 8.33 (d, J = 4.7 Hz, 1 H), 7.52 (d, J = 8.5 Hz, 2 H), 7.46 (d, J = 8.3 Hz, 2 H), 7.38 (t, J = 8.3 Hz, 2 H), 7.23-7.29 (m, 1 H), 6.80 (d, J = 7.2 Hz, 1 H), 6.39 (dd, J = 7.2, 1.8 Hz, 1 H), 4.84 (d, J = 9.5 Hz, 1 H), 4.44-4.62 (m, 1 H), 1.25 (d, J = 6.9 Hz, 3 H) |
| 157 | 300 MHz, d₄-MeOH | 8.63 (d, J = 4.4 Hz, 1 H), 8.03 (d, J = 8.0 Hz, 1 H), 7.51-7.65 (m, 4 H), 7.28 (dd, J = 8.1, 4.6 Hz, 1 H), 6.54 (s, 1 H), 4.41 (dt, J = 14.5, 7.3 Hz, 1 H), 1.27 (d, J = 7.0 Hz, 3 H) |
| 158 | 400 MHz, d₄-MeOH | 8.37 (d, J = 4.7 Hz, 1 H), 7.52 (d, J = 7.6 Hz, 1 H), 7.47 (m, J = 8.2 Hz, 2 H), 7.27-7.39 (m, 2 H), 7.18 (dd, J = 7.8, 4.7 Hz, 1 H), 6.26 (s, 1 H), 5.79 (ddt, J = 16.8, 10.3, 6.3, 1 H), 4.86-5.04 (m, 2 H), 4.29 (dt, J = 14.5, 7.3 Hz, 1 H), 3.27-3.45 (m, 2 H), 1.14 (d, J = 7.0 Hz, 3 H) |
| 159 | 300 MHz, CDCl₃ | 8.81 (d, J = 4.1 Hz, 1 H), 8.52 (s, 2 H), 8.01 (d, J = 8.0 Hz, 1 H), 7.53 (d, J = 8.3 Hz, 1 H), 7.42-7.49 (m, 3 H), 6.67 (d, J = 8.0 Hz, 1 H), 6.61 (d, J = 8.0 Hz, 1 H), 6.23 (s, 1 H), 3.98 (s, 3 H) |
| 160 | 300 MHz, CDCl₃ | 8.55 (s, 2 H), 8.36 (d, J = 4.5 Hz, 1 H), 7.49-7.57 (m, 4 H), 7.40 (t, J = 8.0 Hz, 1 H), 7.27-7.31 (m, 1 H), 7.05 (d, J = 7.0 Hz, 1 H), 6.64 (s, 1 H), 6.44 (dd, J = 7.0, 1.9 Hz, 1 H), 3.99 (s, 3 H) |
| 161 | 400 MHz, d₆-DMSO | 9.16 (s, 1 H), 8.50 (d, J = 4.7 Hz, 1 H), 7.75-7.86 (m, 2 H), 7.72 (d, J = 8.2 Hz, 2 H), 7.46-7.57 (m, 4 H), 6.40 (d, J = 2.3 Hz, 1 H), 6.34 (d, J = 7.4 Hz, 1 H), 6.20 (dd, J = 7.4, 2.3 Hz, 1 H), 3.30 (s, 3 H) |
| 162 | 400 MHz, d₆-DMSO | 8.44-8.53 (m, 2 H), 7.81 (d, J = 2.7 Hz, 1 H), 7.74-7.78 (m, 1 H), 7.67-7.74 (m, J = 8.2 Hz, 2 H), 7.59 (d, J = 8.0 Hz, 1 H), 7.52-7.56 (m, J = 8.0 Hz, 2 H), 7.48 (td, J = 8.5, 4.4 Hz, 1 H), 7.25 (dd, J = 9.7, 2.8 Hz, 1 H), 6.29-6.38 (m, 2 H), 3.36 (s, 3 H) |
| 163 | 400 MHz, d₆-DMSO | 11.72 (br. s., 1 H), 8.80 (s, 1 H), 8.39-8.58 (m, 2 H), 7.96 (dd, J = 7.2, 1.6 Hz, 1 H), 7.64-7.81 (m, 3 H), 7.57 (d, J = 8.0 Hz, 2 H), 7.45 (dt, J = 8.5, 4.4 Hz, 1 H), 6.86-6.99 (m, 1 H), 6.41 (d, J = 8.4 Hz, 1 H), 6.12 (t, J = 6.9 Hz, 1 H) |
| 164 | 400 MHz, d₆-DMSO | 10.96 (br. s., 1 H), 9.15 (s, 1 H), 8.50 (d, J = 4.5 Hz, 1 H), 7.66-7.87 (m, 4 H), 7.42-7.59 (m, 3 H), 7.18 (d, J = 7.2 Hz, 1 H), 6.34 (d, J = 2.2 Hz, 2 H), 6.15 (dd, J = 7.2, 2.0 Hz, 1 H) |
| 165 | 400 MHz, d₆-DMSO | 11.17 (br. s., 1 H), 8.42-8.59 (m, 2 H), 7.77 (t, J = 9.2 Hz, 1 H), 7.71 (d, J = 8.2 Hz, 2 H), 7.60-7.51 (m, 4 H), 7.48 (dt, J = 8.5, 4.4 Hz, 1 H), 7.28 (dd, J = 9.6, 2.9 Hz, 1 H), 6.35 (d, J = 8.0 Hz, 1 H), 6.29 (d, J = 9.6 Hz, 1 H) |
| 166 | 400 MHz, d₆-DMSO | 10.39 (s, 1 H), 9.09 (s, 1 H), 8.64 (d, J = 4.7 Hz, 1 H), 7.92 (t, J = 9.2 Hz, 1 H), 7.85 (d, J = 8.2 Hz, 2 H), 7.56-7.76 (m, 5 H), 7.31 (d, J = 1.6 Hz, 1 H), 7.15 (d, J = 8.0 Hz, 1 H), 6.84 (dd, J = 8.0, 2.0 Hz, 1 H), 6.51 (d, J = 7.8 Hz, 1 H), 3.48 (s, 2 H) |
| 175 | 400 MHz, d₆-DMSO | 8.41 (d, J = 4.0 Hz, 1 H), 8.17 (d, J = 8.4 Hz, 1 H), 7.71-7.76 (m, 1 H), 7.52-7.56 (m, 2 H), 7.43-7.47 (m, 1 H), 7.31 (d, J = 8.4 Hz, 1 H), 6.24 (d, J = 8.4 Hz, 1 H), 4.74-4.77 (m, 1 H), 1.16 (d, J = 5.6 Hz, 6 H) |
| 176 | 400 MHz, CDCl₃ | 8.41-8.43 (d, J = 0.8 Hz, 1 H), 7.38-7.43 (m, 1 H), 7.28-7.32 (m, 1 H), 7.22-7.25 (m, 3 H), 6.87 (d, J = 7.2 Hz, 1 H), 6.19 (d, J = 6.4 Hz, 1 H), 4.82-4.84 (m, 1 H), 3.89-3.93 (m, 2 H), 3.47-3.53 (m, 2 H), 1.90-1.92 (m, 2 H), 1.70-1.64 (m, 2 H) |
| 177 | 400 MHz, d₆-DMSO | 8.61 (d, J = 8.4 Hz, 1 H), 8.43 (d, J = 4.4 Hz, 1 H), 7.72-7.74 (m, 1 H), 7.52-7.56 (m, 2 H), 7.45-7.48 (m, 1 H), 7.32 (d, J = 8.4 Hz, 1 H), 6.23 (d, J = 8.8 Hz, 1 H), 5.28-5.29 (m, 1 H), 4.72-4.75 (m, 2 H), 4.42-4.47 (m, 2 H) |
| 188 | 300 MHz, d₄-MeOH | 8.55 (d, J = 2.3 Hz, 1H), 8.50 (d, J = 4.7 Hz, 1H), 8.15 (dd, J = 4.8, 1.4 Hz, 1H), 7.96 (ddd, J = 8.4, 2.6, 1.5 Hz, 1H), 7.64 (ddd, J = 9.7, 8.5, 1.2 Hz, 1H), 7.27-7.51 (m, 5H), 6.41 (d, J = 1.6 Hz, 1H) |

Stereochemistry

Absolute stereochemistries, where noted, were determined by comparison of either (I) quantum-mechanically predicted optical rotation values (Stephens, P. J. et. al, J. Phys. Chem. A 2001, 105, 5356) or (II) VCD spectra (Stephens, P. J. et. al, Chirality 2008, 20, 643) to those measured experimentally (or, in the case of Example 28, both). A single-crystal X-ray structure of (S)-tert-butyl((3-bromopyridin-2-yl)(4-(trifluoromethyl)phenyl)methyl)carbamate (Intermediate 40 Step 5; Example 173) provided confirmation of the absolute stereochemistry.

Computed and observed optical rotation for a subset of examples in this invention are shown in Table 8. Optical rotations were measured in $CHCl_3$ at room temperature using a Perkin-Elmer digital polarimeter at 589 nm (sodium D line) in a 1.0 dm cell.

TABLE 8

Computed and Measured Optical Rotation for Absolute Stereochemistry Assignment

| Example | Computed Rotation | Measured Rotation |
|---|---|---|
| 28 | (S) = + | +105° |
| 30 | (S) = + | +62° |
| 44 | (S) = + | +87° |
| 51 | (S) = + | +32° |

Assays

Luminescence Readout Assay for Measuring Intracellular Calcium.

A stable Chinese hamster ovary cell line expressing human TRPM8 was generated using tetracycline inducible T-REx™ expression system from Invitrogen, Inc. (Carlsbad, Calif.). In order to enable a luminescence readout based on intracellular increase in calcium (Le Poul et al., 2002), the cell line was also co-transfected with pcDNA3.1 plasmid containing jelly fish aequorin cDNA. Twenty four hours before the assay, cells were seeded in 96-well plates and TRPM8 expression was induced with 0.5 μg/mL tetracycline. On the day of the assay, culture media was removed and cells were incubated with assay buffer (Ham's F12 containing 30 mM HEPES) that contained 15 μM coelenterazine (P.J.K, Germany) for 2 h. Potential antagonists were added 2.5 min prior to the addition of agonist, 1 M icilin, 100 M L-menthol, or 1 min prior to the addition of cold buffer (<10° C.). The luminescence was measured by a CCD camera based FLASH-luminometer built by Amgen, Inc. A cooling device attached to FLASH luminometer was used for cold activation. Compound activity was calculated using either GraphPad Prism 4.01 (GraphPad Software Inc, San Diego, Calif.) or Genedata Screener.

TABLE 9 hTRPM8 $IC_{50}$s for Examples 1-188

| Example | $IC_{50}$ (μM) |
|---|---|
| 1 | 0.023 |
| 2 | 0.230 |
| 3 | 0.172 |
| 4 | 1.230 |
| 5 | 0.145 |
| 6 | 0.259 |
| 7 | 0.723 |
| 8 | 0.593 |
| 9 | 0.175 |
| 10 | 0.172 |
| 11 | 0.101 |
| 12 | 0.088 |
| 13 | 0.051 |
| 14 | 0.533 |
| 15 | 0.015 |
| 16 | 2.260 |
| 17 | 0.811 |
| 18 | 0.308 |
| 19 | 0.382 |
| 20 | 1.310 |
| 21 | 0.178 |
| 22 | 0.201 |
| 23 | 0.255 |
| 24 | 0.674 |
| 25 | 0.216 |
| 26 | 0.248 |
| 27 | 0.041 |
| 28 | 0.067 |
| 29 | 0.017 |
| 30 | 0.097 |
| 31 | 0.081 |
| 32 | 0.066 |
| 33 | 1.900 |
| 34 | 0.127 |
| 35 | 1.710 |
| 36 | 0.390 |
| 37 | 4.080 |
| 38 | 1.500 |
| 39 | 4.090 |
| 40 | 2.510 |
| 41 | 0.122 |
| 42 | 0.107 |
| 43 | 0.022 |
| 44 | 0.023 |
| 45 | 0.053 |
| 46 | 3.560 |
| 47 | 0.098 |
| 48 | 2.280 |
| 49 | 0.558 |
| 50 | 0.209 |
| 51 | 0.037 |
| 52 | 0.061 |
| 53 | 0.050 |
| 54 | 0.397 |
| 55 | 0.050 |
| 56 | 0.676 |
| 57 | 0.167 |
| 58 | 0.562 |
| 59 | 0.640 |
| 60 | 0.182 |
| 61 | 0.062 |
| 62 | 1.930 |
| 63 | 0.866 |
| 64 | 5.650 |
| 65 | 0.141 |
| 66 | 0.905 |
| 67 | 0.352 |
| 68 | 0.881 |
| 69 | 0.777 |
| 70 | 0.781 |
| 71 | 5.710 |
| 72 | 0.163 |
| 73 | 0.332 |
| 74 | 0.112 |
| 75 | 0.670 |
| 76 | 0.294 |
| 77 | 0.235 |
| 78 | 1.230 |
| 79 | 1.500 |
| 80 | 0.399 |
| 81 | 0.496 |
| 82 | 0.559 |
| 83 | 0.115 |
| 84 | 0.767 |

TABLE 9-continued hTRPM8 IC$_{50}$s for Examples 1-188

| Example | IC$_{50}$ (µM) |
|---|---|
| 85 | 0.405 |
| 86 | 0.031 |
| 87 | 0.199 |
| 88 | 0.108 |
| 89 | 0.330 |
| 90 | 0.646 |
| 91 | 0.670 |
| 92 | 0.713 |
| 93 | 1.440 |
| 94 | 1.710 |
| 95 | 1.920 |
| 96 | 0.884 |
| 97 | 0.080 |
| 98 | 2.220 |
| 99 | 0.712 |
| 100 | 0.142 |
| 101 | 0.633 |
| 102 | 0.262 |
| 103 | 0.527 |
| 104 | 0.604 |
| 105 | 0.545 |
| 106 | 0.494 |
| 107 | 0.123 |
| 108 | 0.829 |
| 109 | 0.110 |
| 110 | 0.190 |
| 111 | 2.380 |
| 112 | 0.287 |
| 113 | 0.175 |
| 114 | 0.886 |
| 115 | 0.154 |
| 116 | 0.133 |
| 117 | 1.750 |
| 118 | 0.162 |
| 119 | 0.375 |
| 120 | 2.850 |
| 121 | 0.084 |
| 122 | 0.221 |
| 123 | 0.190 |
| 124 | 0.708 |
| 125 | 0.561 |
| 126 | 3.140 |
| 127 | 0.657 |
| 128 | 4.060 |
| 129 | 2.000 |
| 130 | 3.790 |
| 131 | 0.666 |
| 132 | 0.673 |
| 133 | 1.590 |
| 134 | 1.070 |
| 135 | 0.829 |
| 136 | 4.050 |
| 137 | 0.156 |
| 138 | 3.720 |
| 139 | 1.310 |
| 140 | 1.300 |
| 141 | 0.360 |
| 142 | 2.180 |
| 143 | 1.300 |
| 144 | 0.541 |
| 145 | 0.474 |
| 146 | 3.770 |
| 147 | 3.830 |
| 148 | 1.610 |
| 149 | 0.055 |
| 150 | 0.048 |
| 151 | 0.039 |
| 152 | 0.070 |
| 153 | 0.051 |
| 154 | 0.900 |
| 155 | 0.062 |
| 156 | 0.119 |
| 157 | 0.059 |
| 158 | 0.028 |
| 159 | 0.407 |
| 160 | 1.650 |
| 161 | 1.250 |
| 162 | 0.491 |
| 163 | 0.076 |
| 164 | 2.880 |
| 165 | 3.210 |
| 166 | 0.086 |
| 167 | 0.328 |
| 168 | 0.067 |
| 169 | 0.663 |
| 170 | 0.147 |
| 171 | 0.915 |
| 172 | 0.360 |
| 173 | 0.299 |
| 174 | 0.474 |
| 175 | 0.068 |
| 176 | 0.211 |
| 177 | 0.517 |
| 178 | 2.060 |
| 179 | 0.077 |
| 180 | 3.240 |
| 181 | 0.142 |
| 182 | 0.425 |
| 183 | 0.560 |
| 184 | 0.583 |
| 185 | 0.739 |
| 186 | 1.110 |
| 187 | 1.550 |
| 188 | 0.007 |

Icilin Biochemical Challenge Models

Inhibition of Icilin Induced Jumping in Mice

Example compounds at doses ranging from 0.01 to 10 mg/kg were administered to male C57BL/6 mice (18-25 g, Taconic, n=10/treatment) 1 hour before icilin to assess the ability to block the spontaneous jumps induced by icilin (i.p. suspended in 100% PEG400 at 20 mg/kg, 5 mL/kg). The total number of jumps was recorded during the 10 minutes post-icilin administration based on the number of photocell beam breaks from the vertical array of open field boxes (Kinder Scientific) while movement of the mice was restricted within a clear Plexiglas® cylinder 9.5 cm diameter×30 cm height. Resultant data is shown in Table 10.

TABLE 10

| Example | Dose (mg/kg) | % Inhibition of Mouse Jumping |
|---|---|---|
| 1 | 10 | 75 |
| 29 | 10 | 96 |
| 44 | 10 | 74 |
| 51 | 10 | 76 |
| 61 | 10 | 90 |
| 151 | 3 | 30 |

Inhibition of Icilin Induced Shaking in Rats

Example compounds at doses ranging from 0.01 to 3 mg/kg (p.o, suspended in 5% Tween80/Oralplus or suspended in 2% HPMC-1% Tween-80 pH2.2 with MSA, 5 mL/kg) were administered to male Sprague Dawley rats (200-300 g, Harlan, n=6-8/treatment) 2 hours before icilin to assess the ability to block the spontaneous wet-dog shake phenomena induced by icilin (i.p., suspended in 100% PEG400 at 0.5 mg/kg, 1 mL/kg or p.o., suspended in 2% HPMC-1% Tween-80 at 3 mg/kg, 2.5 mL/kg). Spontaneous wet-dog shakes were counted manually by two blinded observers or using LABORAS automation (Metris) for 30 minutes post-icilin dosing.

Cold Pressor Test (CPT) as a Translatable PD Model for TRPM8

The cold pressor test (CPT) was developed as a method to measure blood pressure response following exposure to a cold stimulus and has been used over 70 years in the diagnosis of hypertension and other cardiac autonomic disorders (Hines and Brown 1936). In healthy human subjects, the CPT is typically performed by immersing a subject's hand into ice water (0-5° C.) which triggers, through a vascular sympathetic activation of afferent pain and temperature neurons, an increase in blood pressure. With some modifications, this test has also been utilized in rat to delineate the medullary and spinal pathways mediating the cardio-vascular responses to cold pressor test and to identify neurotransmitters in these pathways (Sapru N et al 2008) or to characterize analgesic compounds (Koltzenburg M et al 2006 and Player M R et al 2011).

TRPM8 antagonists can be evaluated in rat CPT to determine whether TRPM8 antagonists would attenuate the increase in blood pressure resulting from exposure to cold stimulation of the paws and ventral half of the body. Male Sprague-Dawley rats weighing 350-450 g can be instrumented with a unilateral carotid artery-cannula connected to a transducer for measuring blood pressure using a Digi-Med Blood Pressure Analyzer, Model 400. Animals can be orally administered with Vehicle (2% HPMC 1% Tween 80 pH 2.2 with MSA) or test compounds at 120 minutes prior to cold challenge and anesthetized with sodium pentobarbital at 60 mg/kg ip at 100 minutes prior to cold. Blood pressure can be recorded for 5 minutes for pre-cold baseline and additional 5 minutes during immersion of the paws and ventral half of body in ice water. Percent inhibition attributed to treatment with test compound can then determined using the following formula: [1-(cold evoked change in MBP/cold evoked change in MBP post-vehicle)]×100. Plasma can be collected through artery catheter immediately after CPT for pk analysis and IC50/90 determination.

REFERENCES

Hines, E A and Brown G E. The cold pressor test for measuring the reactability of the blood pressure. Am. Heart J. 1936, 11:1-9

Nakamura T, Kawabe K, and Sapru H N. Cold pressor test in the rat: medullary and spinal pathways and neurotransmitters. Am J Physiol Heart Circ Physiol 2008, 295:H1780-H1787

Koltzenburg M, Pokorny R, Gasser U and Richarz U. Differential sensitivity of three experimental pain models in detecting the analgesic effects of transdermal fentanyl and buprenorphine. Pain 2006, 126:165-174

Parks D, Parsons W, Colburn R, Meegala S, Ballentine S, Illig C, Qin N, Liu Y, Hutchinson T, Lubin M, Stone D, Baker J, Schneider C, Ma J, Damiano B, Flores C, and Player M. Design and optimization of benzimidazole-containing transient receptor potentiate melastatin 8 (TRPM8) antagonists. J. Med. Chem. 2011, 54:233-247

CCI Model

Surgery—A chronic constriction injury (CCI) can be produced as previously described (Bennett & Xie, 1988). Under gaseous anesthesia with a mixture of isoflurane (3% for induction and 2% for maintenance) in $O_2$, the sciatic nerve can be exposed at the mid-thigh level proximal to the sciatic trifurcation. Four chromic gut ligatures (4-0) can be tied loosely around nerve, 1-2 mm apart such that the vascular supply will not be compromised.

Behavioral testing—A behavioral test can be performed to estimate cold-induced ongoing pain as previously described (Choi et al., 1994). The rat can be placed under a transparent plastic cover on an aluminum plate (IITC PE34, Woodland, Calif.) which can be kept at a cold temperature (5±0.5° C.). After 2 minutes of adaptation, the cumulative duration of time that the rat lifts its foot off the plate for the next 5 minutes can be measured. Foot lifts associated with locomotion or grooming are not counted. Seven to 9 days after the CCI surgery, baseline of the cold-induced ongoing pain can be measured. Any rat showing a cold-induced ongoing pain less than 100 sec out of 300 sec observation period can be eliminated from the study. Twenty four hours after the baseline measurement, test compound, positive control, morphine (2 mg/kg, Sigma, St. Louis) or a vehicle (saline or 2% HPMC/1% Tween 80) can be administered orally (test compound) or subcutaneously (morphine). Two hrs (test compound) or 30 mins (morphine) after the drug administration, the cold-induced ongoing pain can be measured again.

Chung Model

Surgery—Spinal nerve ligation surgery can be performed as previously described (Kim & Chung, 1992). Briefly, under gaseous anesthesia with a mixture of isoflurane (3% for induction and 2% for maintenance) in $O_2$, the spinal nerve injury can be produced by ligating the left L5 and L6 spinal nerves taking special care to avoid any possible damage to the L4 spinal nerve or surrounding area. Additional treatments can be performed to increase the development of mechanical allodynia. First, L5 spinal nerve can be cut approximately 1 mm distal to the suture as described by Li et al. (2000). Second, immediately after ligation and cut, the L4 spinal nerve can be lightly manipulated by slightly stretching it with a fine hooked glass rod and gently sliding the hook back and forth 20 times along the nerve as described by Lee et al. (2003). The whole surgery procedure from anesthesia to the clipping of the incised skin can take at most 15 minutes.

Behavioral testing—Two weeks later, mechanical sensitivity can be measured by determining the median 50% foot withdrawal threshold for von Frey filaments using the up-down method (Chaplan et al., 1994). The rats can be placed under a plastic cover (9×9×20 cm) on a metal mesh floor. The area tested consists of the middle glabrous area between the footpads of the plantar surface of the hind paw. The plantar area can be touched with a series of 9 von Frey hairs with approximately exponentially incremental bending forces (von Frey values: 3.61, 3.8, 4.0, 4.2, 4.41, 4.6, 4.8, 5.0 and 5.2; equivalent to: 0.41, 0.63, 1.0, 1.58, 2.51, 4.07, 6.31, 10 and 15.8 g). The von Frey hair can be presented perpendicular to the plantar surface with sufficient force to cause slight bending, and held for approximately 3-4 seconds. Abrupt withdrawal of the foot (paw flinching, shaking or licking for more than 1 sec.) can be recorded as a response. Any rat showing a mechanical threshold of more than 3.16 g or less than 0.7 g after surgery can be eliminated from the study. After measuring basal threshold, test compound, positive control gabapentin (Sigma, St. Louis) or a vehicle (saline or 2% HPMC/1% Tween 80) can be administered orally (test compound) or intraperitoneally (gabapentin). The measurement of the tactile threshold can be reassessed at 1.5 and 2 hrs after drug administration.

Data—Since the von Frey filament set is calibrated on a logarithmic scale by the vendor (Stoelting) and our selection of 9 filaments for the up-down method is also based on near equal logarithmic intervals (Dixon et al., 1980), data can be treated using logarithmic values in every aspect (statistical treatment as well as plotting). However, an equivalent gram value scale is labeled on the Y-axis of the figures for convenience. Data are expressed as mean±standard error of the mean (S.E.M.).

For the treatment of TRPM8-receptor-diseases, such as acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating TRPM8-receptor-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed.

Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/ or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, iso-propoxymethyl, α-methoxyethyl, groups such as α-(($C_1$-$C_4$)-alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of Formula I having the structure:

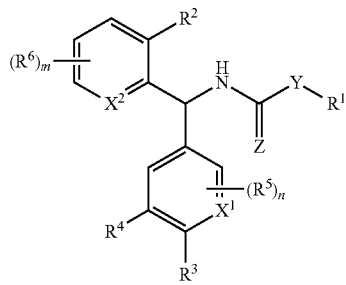

I or a pharmaceutically-acceptable salt thereof, a tautomer thereof, a pharmaceutically-acceptable salt of the tautomer, a stereoisomer thereof, or a mixture thereof, wherein:
  m is 0;
  n is 0 or 1;
  $X^1$ is CH;
  $X^2$ is N;
  Y is NH;
  Z is O;
  $R^1$ is

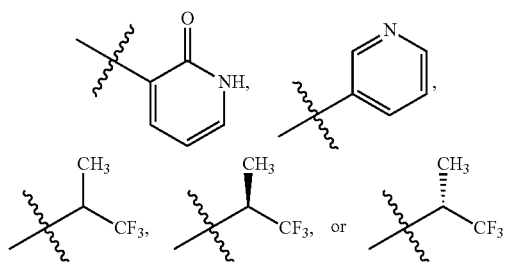

and the symbol ∿, when drawn across a bond, indicates the point of attachment to the rest of the molecule;
  $R^2$ is F or $CF_3$;
  $R^3$ is $CF_3$ or $OCF_3$;
  $R^4$ is F or H;

$R^5$ is independently, in each instance, Cl, Br, F, $CH_3$, $CF_3$, or $OR^a$;

$R^6$ is F, $CF_3$, $C_{1-6}$alk, or $OR^a$;

$R^a$ is independently, at each instance, H or $R^b$; and $R^b$ is independently, at each instance, phenyl, benzyl or $C_{1-6}$alk, the phenyl, benzyl and $C_{1-6}$alk being substituted by 0, 1, 2 or 3 substituents selected from halo, oxo, $C_{1-4}$alk, $C_{1-3}$haloalk, —$OC_{1-4}$alk, —OH, —$NH_2$, —$OC_{1-4}$alk, —$OC_{1-4}$haloalk, —$NHC_{1-4}$alk, and —$N(C_{1-4}alk)C_{1-4}$alk.

2. The compound of claim 1 or the pharmaceutically-acceptable salt thereof, the tautomer thereof, the pharmaceutically-acceptable salt of the tautomer, or the mixture thereof, wherein the compound of Formula I has the Formula IA:

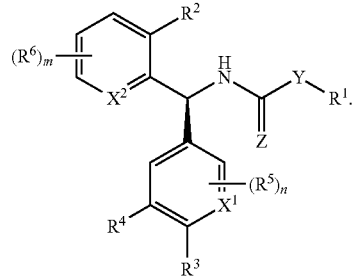

IA

3. The compound of claim 1 or the pharmaceutically-acceptable salt thereof, the tautomer thereof, the pharmaceutically-acceptable salt of the tautomer, or the mixture thereof, wherein $R^1$ is

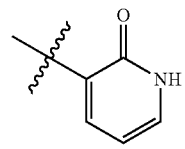 [SMILES: *c1ccc[nH]c1=O]

and the symbol ∿, when drawn across a bond, indicates the point of attachment to the rest of the molecule.

4. The compound of claim 1 or the pharmaceutically-acceptable salt thereof, the tautomer thereof, the pharmaceutically-acceptable salt of the tautomer, or the mixture thereof, wherein $R^1$ is

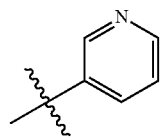 [SMILES: *c1cccnc1]

and the symbol ∿, when drawn across a bond, indicates the point of attachment to the rest of the molecule.

5. The compound of claim 1 or the pharmaceutically-acceptable salt thereof, the tautomer thereof, the pharmaceutically-acceptable salt of the tautomer, or the mixture thereof, wherein $R^1$ is

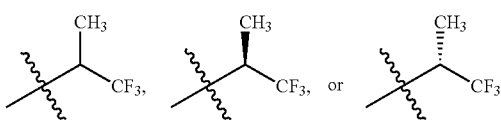

and the symbol ⌇, when drawn across a bond, indicates the point of attachment to the rest of the molecule.

6. The compound of claim 1 or the pharmaceutically-acceptable salt thereof, the tautomer thereof, the pharmaceutically-acceptable salt of the tautomer, or the mixture thereof, wherein $R^5$ is independently, in each instance F or $CF_3$.

7. The compound of claim 6 or the pharmaceutically-acceptable salt thereof, the tautomer thereof, the pharmaceutically-acceptable salt of the tautomer, or the mixture thereof, wherein $R^5$ is F.

8. The compound of claim 1 or the pharmaceutically-acceptable salt thereof, the tautomer thereof, the pharmaceutically-acceptable salt of the tautomer, or the mixture thereof, wherein n is 1.

9. The compound of claim 1 or the pharmaceutically-acceptable salt thereof, the tautomer thereof, the pharmaceutically-acceptable salt of the tautomer, or the mixture thereof, wherein n is 0.

10. The compound of claim 1 or the pharmaceutically-acceptable salt thereof, the tautomer thereof, the pharmaceutically-acceptable salt of the tautomer, or the mixture thereof, wherein $R^2$ is —F.

11. The compound of claim 1 or the pharmaceutically-acceptable salt thereof, the tautomer thereof, the pharmaceutically-acceptable salt of the tautomer, or the mixture thereof, wherein $R^2$ is —$CF_3$.

12. The compound of claim 1 or the pharmaceutically-acceptable salt thereof, the tautomer thereof, the pharmaceutically-acceptable salt of the tautomer, or the mixture thereof, wherein $R^3$ is —$OCF_3$.

13. The compound of claim 1 or the pharmaceutically-acceptable salt thereof, the tautomer thereof, the pharmaceutically-acceptable salt of the tautomer, or the mixture thereof, wherein $R^3$ is —$CF_3$.

14. The compound of claim 1 or the pharmaceutically-acceptable salt thereof, the tautomer thereof, the pharmaceutically-acceptable salt of the tautomer, or the mixture thereof, wherein $R^4$ is H.

15. The compound of claim 1 or the pharmaceutically-acceptable salt thereof, the tautomer thereof, the pharmaceutically-acceptable salt of the tautomer, or the mixture thereof, wherein $R^4$ is F.

16. A compound, wherein the compound is
(S)-1-((3-fluoro-4-(trifluoromethyl)phenyl)(3-(trifluoromethyl)pyridin-2-yl)methyl)-3-(pyridin-3-yl)urea;
(S)-1-((3-fluoropyridin-2-yl)(4-(trifluoro-methoxy)-phenyl)-methyl)-3-(pyridin-3-yl)-urea;
1-(pyridin-3-yl)-3-((3-(trifluoro-methyl)-pyridin-2-yl)(6-(trifluoro-methyl)-pyridin-3-yl)-methyl)urea;
(S)-1-((3-fluoro-4-(trifluoro-methyl)-phenyl)(3-fluoropyridin-2-yl)methyl)-3-(pyridin-3-yl)-urea;
(S)-1-(pyridin-3-yl)-3-((4-(trifluoro-methyl)-phenyl)(3-(trifluoro-methyl)-pyridin-2-yl)-methyl)urea;
(S)-1-(pyridin-3-yl)-3-((4-(trifluoro-methyl)-phenyl)(4-(trifluoro-methyl)-pyridin-3-yl)-methyl)urea;
(S)-1-((3-fluoro-4-(trifluoro-methyl)-phenyl)(2-(trifluoro-methyl)-phenyl)-methyl)-3-(pyridin-3-yl)-urea;
(S)-1-(pyridin-3-yl)-3-((4-(trifluoro-methyl)-phenyl)(3-(trifluoro-methyl)-pyridin-2-yl)-methyl)-thiourea;
1-((S)-(3-fluoro-4-(trifluoro-methyl)-phenyl)(3-(trifluoro-methyl)-pyridin-2-yl)-methyl)-3-((S)-1,1,1-trifluoro-propan-2-yl)-urea;
1-((S)-(3-fluoro-4-(trifluoro-methyl)-phenyl)(3-(trifluoro-methyl)-pyridin-2-yl)-methyl)-3-((R)-1,1,1-trifluoro-propan-2-yl)-urea;
1-((S)-(4-(trifluoro-methyl)-phenyl)(3-(trifluoro-methyl)-pyridin-2-yl)-methyl)-3-((S)-1,1,1-trifluoro-propan-2-yl)-urea;
1-((S)-(3-fluoropyridin-2-yl)(4-(trifluoro-methyl)-phenyl)-methyl)-3-((S)-1,1,1-trifluoro-propan-2-yl)-urea;
(S)-1-((3-fluoro-pyridin-2-yl)(4-(trifluoro-methyl)phenyl)-methyl)-3-(2-oxo-1,2-dihydropyridin-3-yl)urea;
(S)-1-((3-fluoro-pyridin-2-yl)(4-(trifluoro-methyl)phenyl)-methyl)-3-(2-oxo-1,2-dihydropyridin-4-yl)urea;
or
the pharmaceutically-acceptable salt thereof, the tautomer thereof, the pharmaceutically-acceptable salt of the tautomer, or the mixture thereof.

17. A compound, wherein the compound is
(S)-1-((3-fluoro-4-(trifluoromethyl)phenyl)(3-(trifluoromethyl)pyridin-2-yl)-methyl)-3-(pyridin-3-yl)urea;
(S)-1-(pyridin-3-yl)-3-((4-(trifluoromethyl)phenyl)(3-(trifluoromethyl)pyridin-2-yl)methyl)urea;
(S)-1-((3-fluoro-4-(trifluoromethyl)phenyl)(3-fluoropyridin-2-yl)methyl)-3-(pyridin-3-yl)urea; or
1-((S)-(3-fluoro-4-(trifluoro-methyl)phenyl)-(3-(trifluoro-methyl)pyridin-2-yl)methyl)-3-((S)-1,1,1-trifluoropropan-2-yl)urea; or
the pharmaceutically-acceptable salt thereof, the tautomer thereof, the pharmaceutically-acceptable salt of the tautomer, or the mixture thereof.

18. The compound of claim 17, wherein the compound is (S)-1-((3-fluoro-4-(trifluoromethyl)phenyl)(3-(trifluoromethyl)pyridin-2-yl)-methyl)-3-(pyridin-3-yl)urea or the pharmaceutically-acceptable salt thereof, the tautomer thereof, the pharmaceutically-acceptable salt of the tautomer, or the mixture thereof.

19. The compound of claim 17, wherein the compound is (S)-1-(pyridin-3-yl)-3-((4-(trifluoromethyl)phenyl)(3-(trifluoromethyl)pyridin-2-yl)methyl)urea or the pharmaceutically-acceptable salt thereof, the tautomer thereof, the pharmaceutically-acceptable salt of the tautomer, or the mixture thereof.

20. The compound of claim 17, wherein the compound is (S)-1-((3-fluoro-4-(trifluoromethyl)phenyl)(3-fluoropyridin-2-yl)methyl)-3-(pyridin-3-yl)urea or the pharmaceutically-acceptable salt thereof, the tautomer thereof, the pharmaceutically-acceptable salt of the tautomer, or the mixture thereof.

21. The compound of claim 17, wherein the compound is 1-((S)-(3-fluoro-4-(trifluoro-methyl)phenyl)-(3-(trifluoromethyl)pyridin-2-yl)methyl)-3-((S)-1,1,1-trifluoropropan-2-yl)urea or the pharmaceutically-acceptable salt thereof, the tautomer thereof, the pharmaceutically-acceptable salt of the tautomer, or the mixture thereof.

22. The compound or the tautomer of claim 1.

23. The compound of claim 1.

24. The pharmaceutically acceptable salt of the compound or the pharmaceutically acceptable salt of the tautomer of claim 1.

25. The pharmaceutically acceptable salt of the compound of claim 1.

26. The pharmaceutically-acceptable salt of the compound of claim 25, wherein the salt is a trifluoroacetate or bis trifluoroacetate salt.

27. A pharmaceutical composition comprising the compound according to claim 1 or the pharmaceutically-acceptable salt thereof, the tautomer thereof, the pharmaceutically-acceptable salt of the tautomer, or the mixture thereof, and a pharmaceutically-acceptable diluent or carrier.

28. The compound or the tautomer of claim 16.

29. The compound or the tautomer of claim 17.

30. The pharmaceutically acceptable salt of the compound or the pharmaceutically acceptable salt of the tautomer of claim 16.

31. The pharmaceutically acceptable salt of the compound or the pharmaceutically acceptable salt of the tautomer of claim 17.

32. A pharmaceutical composition comprising the compound according to claim 16 or the pharmaceutically-acceptable salt thereof, the tautomer thereof, the pharmaceutically-acceptable salt of the tautomer, or the mixture thereof, and a pharmaceutically-acceptable diluent or carrier.

33. A pharmaceutical composition comprising the compound according to claim 17 or the pharmaceutically-acceptable salt thereof, the tautomer thereof, the pharmaceutically-acceptable salt of the tautomer, or the mixture thereof, and a pharmaceutically-acceptable diluent or carrier.

\* \* \* \* \*